(12) United States Patent
Dhamankar et al.

(10) Patent No.: US 10,654,829 B2
(45) Date of Patent: May 19, 2020

(54) CRYSTALLINE FORMS AND COMPOSITIONS OF CFTR MODULATORS

(71) Applicant: Vertex Pharmaceuticals Incorporated, Boston, MA (US)

(72) Inventors: Varsha Dhamankar, Watertown, MA (US); Kirk Raymond Dinehart, Holliston, MA (US); Eleni Dokou, Cambridge, MA (US); Lori Ann Ferris, Wilmington, MA (US); Nishanth Gopinathan, Lynnfield, MA (US); Katie McCarty, Watertown, MA (US); Catherine Metzler, Medford, MA (US); Beili Zhang, San Diego, CA (US); Samuel Moskowitz, Waban, MA (US); Sarah Robertson, Somerville, MA (US); David Waltz, Waban, MA (US); Eric L. Haseltine, Melrose, MA (US); Weichao George Chen, San Diego, CA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 0 days.

(21) Appl. No.: 16/165,849

(22) Filed: Oct. 19, 2018

(65) Prior Publication Data

US 2019/0119253 A1 Apr. 25, 2019

Related U.S. Application Data

(60) Provisional application No. 62/574,670, filed on Oct. 19, 2017, provisional application No. 62/574,677, filed on Oct. 19, 2017, provisional application No. 62/650,057, filed on Mar. 29, 2018.

(51) Int. Cl.
| | | |
|---|---|---|
| *C07D 401/14* | (2006.01) | |
| *A61P 11/00* | (2006.01) | |
| *A61K 9/10* | (2006.01) | |
| *A61K 9/20* | (2006.01) | |

(52) U.S. Cl.
CPC .......... *C07D 401/14* (2013.01); *A61K 9/2013* (2013.01); *A61K 9/2054* (2013.01); *A61P 11/00* (2018.01); *A61K 9/10* (2013.01); *C07B 2200/13* (2013.01)

(58) Field of Classification Search
CPC ... C07D 401/14; A61P 11/00; C07B 2200/13; A61K 9/2013; A61K 9/2054; A61K 9/10
See application file for complete search history.

(56) References Cited

U.S. PATENT DOCUMENTS

| | | | |
|---|---|---|---|
| 5,410,061 A | 4/1995 | Gilmore et al. | |
| 6,441,004 B1 | 8/2002 | Faull et al. | |
| 6,787,651 B2 | 9/2004 | Stolle et al. | |
| 6,949,572 B2 | 9/2005 | Bertinato et al. | |
| 6,979,692 B2 | 12/2005 | Bertinato et al. | |
| 7,368,573 B2 | 5/2008 | Bertinato et al. | |
| 8,058,299 B2 | 11/2011 | Bolin et al. | |
| 9,663,508 B2 | 5/2017 | Bregman et al. | |
| 9,782,408 B2 | 10/2017 | Miller et al. | |
| 9,981,910 B2 | 5/2018 | Altenbach et al. | |
| 10,118,916 B2 | 11/2018 | Altenbach et al. | |
| 10,131,670 B2 | 11/2018 | Strohbach et al. | |
| 10,138,227 B2 | 11/2018 | Altenbach et al. | |
| 10,208,053 B2 | 2/2019 | Strohbach et al. | |
| 10,258,624 B2 | 4/2019 | Miller et al. | |
| 2002/0055631 A1 | 5/2002 | Augeri et al. | |
| 2002/0086887 A1 | 7/2002 | Augeri et al. | |
| 2005/0171185 A1 | 8/2005 | Yamasaki et al. | |
| 2005/0197376 A1 | 9/2005 | Kayakiri et al. | |
| 2011/0165118 A1 | 7/2011 | Chan et al. | |
| 2013/0267493 A1 | 10/2013 | Bhattacharya et al. | |
| 2013/0317000 A1 | 11/2013 | Chowdhury et al. | |
| 2013/0317001 A1 | 11/2013 | Andrez et al. | |
| 2015/0322002 A1 | 11/2015 | Dehnhardt et al. | |
| 2018/0093969 A1* | 4/2018 | Alcacio | C07B 59/002 |
| 2018/0099932 A1 | 4/2018 | Altenbach et al. | |

(Continued)

FOREIGN PATENT DOCUMENTS

| | | |
|---|---|---|
| CA | 2145473 A1 | 9/1995 |
| EP | 0 194 599 A2 | 9/1986 |

(Continued)

OTHER PUBLICATIONS

Anilkumar, G.N. et al. (2011) "II. Novel HCV NS5B polymerase inhibitors: Discovery of indole C2 acyl sulfonamides" *Biogranic & Medicinal Chemistry Letters*, 22(1):713-717.

(Continued)

*Primary Examiner* — Timothy R Rozof
(74) *Attorney, Agent, or Firm* — Finnegan, Henderson, Farabow, Garrett & Dunner, LLP

(57) ABSTRACT

Crystalline Forms of Compound I:

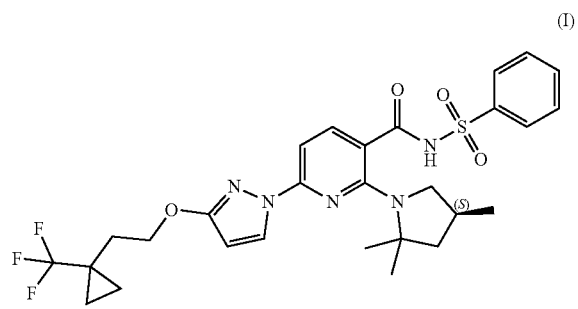

and pharmaceutically acceptable salts thereof are disclosed. Pharmaceutical compositions comprising the same, methods of treating cystic fibrosis using the same, and methods for making the same are also disclosed.

23 Claims, 36 Drawing Sheets

(56) References Cited

U.S. PATENT DOCUMENTS

| | | |
|---|---|---|
| 2018/0141954 A1 | 5/2018 | Strohbach et al. |
| 2018/0162839 A1 | 6/2018 | Abela et al. |
| 2018/0170938 A1 | 6/2018 | Strohbach et al. |
| 2018/0244611 A1 | 8/2018 | Altenbach et al. |
| 2018/0244640 A1 | 8/2018 | Altenbach et al. |
| 2019/0077784 A1 | 3/2019 | Altenbach et al. |
| 2019/0153000 A1 | 5/2019 | Munoz et al. |

FOREIGN PATENT DOCUMENTS

| | | |
|---|---|---|
| EP | 0 673 930 A1 | 9/1995 |
| EP | 1 318 978 B1 | 2/2006 |
| JP | 10-114654 A | 5/1998 |
| WO | WO 96/03380 A1 | 2/1996 |
| WO | WO 96/22022 A1 | 7/1996 |
| WO | WO 97/18712 A1 | 5/1997 |
| WO | WO 97/22586 A1 | 6/1997 |
| WO | WO 98/31226 A1 | 7/1998 |
| WO | WO 99/16744 A1 | 4/1999 |
| WO | WO 99/37153 A1 | 7/1999 |
| WO | WO 99/41238 A1 | 8/1999 |
| WO | WO 00/76969 A1 | 12/2000 |
| WO | WO 01/08487 A1 | 2/2001 |
| WO | WO 01/15533 A1 | 3/2001 |
| WO | WO 01/39597 A2 | 6/2001 |
| WO | WO 02/15902 A1 | 2/2002 |
| WO | WO 02/24636 A2 | 3/2002 |
| WO | WO 02/30895 A1 | 4/2002 |
| WO | WO 02/085120 A2 | 10/2002 |
| WO | WO 02/096883 A1 | 12/2002 |
| WO | WO 03/002533 A1 | 1/2003 |
| WO | WO 03/022050 A1 | 3/2003 |
| WO | WO 03/028458 A1 | 4/2003 |
| WO | WO 03/043423 A1 | 5/2003 |
| WO | WO 03/043655 A1 | 5/2003 |
| WO | WO 03/101959 A1 | 12/2003 |
| WO | WO 03/103394 A2 | 12/2003 |
| WO | WO 2004/021788 A1 | 3/2004 |
| WO | WO 2004/021987 A2 | 3/2004 |
| WO | WO 2004/037798 A1 | 5/2004 |
| WO | WO 2004/039753 A2 | 5/2004 |
| WO | WO 2004/043939 A1 | 5/2004 |
| WO | WO 2004/046141 A1 | 6/2004 |
| WO | WO 2004/056775 A1 | 7/2004 |
| WO | WO 2004/056777 A1 | 7/2004 |
| WO | WO 2004/078114 A2 | 9/2004 |
| WO | WO 2004/085420 A1 | 10/2004 |
| WO | WO 2005/054191 A1 | 6/2005 |
| WO | WO 2005/070006 A2 | 8/2005 |
| WO | WO 2005/080373 A1 | 9/2005 |
| WO | WO 2005/085216 A1 | 9/2005 |
| WO | WO 2005/099705 A2 | 10/2005 |
| WO | WO 2005/108369 A1 | 11/2005 |
| WO | WO 2006/030807 A1 | 3/2006 |
| WO | WO 2006/039212 A2 | 4/2006 |
| WO | WO 2006/065204 A1 | 6/2006 |
| WO | WO 2006/066968 A1 | 6/2006 |
| WO | WO 2006/067392 A2 | 6/2006 |
| WO | WO 2007/019397 A2 | 2/2007 |
| WO | WO 2007/021982 A2 | 2/2007 |
| WO | WO 2007/113327 A2 | 10/2007 |
| WO | WO 2008/005457 A2 | 1/2008 |
| WO | WO 2008/100867 A2 | 8/2008 |
| WO | WO 2008/141385 A1 | 11/2008 |
| WO | WO 2009/027730 A1 | 3/2009 |
| WO | WO 2009/032116 A1 | 3/2009 |
| WO | WO 2009/064848 A1 | 5/2009 |
| WO | WO 2009/071947 A2 | 6/2009 |
| WO | WO 2009/127822 A2 | 10/2009 |
| WO | WO 2009/138758 A2 | 11/2009 |
| WO | WO 2010/003444 A2 | 1/2010 |
| WO | WO 2010/007116 A2 | 1/2010 |
| WO | WO 2010/022307 A2 | 2/2010 |
| WO | WO 2010/025295 A2 | 3/2010 |
| WO | WO 2010/065824 A2 | 6/2010 |
| WO | WO 2010/083441 A2 | 7/2010 |
| WO | WO 2010/102758 A2 | 9/2010 |
| WO | WO 2010/110231 A1 | 9/2010 |
| WO | WO 2010/123822 A1 | 10/2010 |
| WO | WO 2010/138588 A2 | 12/2010 |
| WO | WO 2011/068560 A1 | 6/2011 |
| WO | WO 2011/102514 A1 | 8/2011 |
| WO | WO 2011/128251 A1 | 10/2011 |
| WO | WO 2011/150016 A1 | 12/2011 |
| WO | WO 2012/052540 A1 | 4/2012 |
| WO | WO 2012/087938 A1 | 6/2012 |
| WO | WO 2012/089721 A1 | 7/2012 |
| WO | WO 2012/089722 A2 | 7/2012 |
| WO | WO 2012/102297 A1 | 8/2012 |
| WO | WO 2012/110519 A1 | 8/2012 |
| WO | WO 2012/116960 A1 | 9/2012 |
| WO | WO 2012/139891 A1 | 10/2012 |
| WO | WO 2012/166415 A1 | 12/2012 |
| WO | WO 2013/033068 A1 | 3/2013 |
| WO | WO 2013/037955 A1 | 3/2013 |
| WO | WO 2013/038373 A1 | 3/2013 |
| WO | WO 2013/041602 A1 | 3/2013 |
| WO | WO 2013/082102 A1 | 6/2013 |
| WO | WO 2013/118805 A1 | 8/2013 |
| WO | WO 2013/177224 A1 | 11/2013 |
| WO | WO 2013/185202 A1 | 12/2013 |
| WO | WO 2014/008458 A2 | 1/2014 |
| WO | WO 2014/014841 A1 | 1/2014 |
| WO | WO 2014/017093 A1 | 1/2014 |
| WO | WO 2014/028381 A1 | 2/2014 |
| WO | WO 2014/028968 A1 | 2/2014 |
| WO | WO 2014/039714 A2 | 3/2014 |
| WO | WO 2014/047427 A2 | 3/2014 |
| WO | WO 2014/071122 A1 | 5/2014 |
| WO | WO 2014/071247 A1 | 5/2014 |
| WO | WO 2014/071378 A1 | 5/2014 |
| WO | WO 2014/086723 A1 | 6/2014 |
| WO | WO 2014/086739 A1 | 6/2014 |
| WO | WO 2014/086751 A1 | 6/2014 |
| WO | WO 2014/096388 A2 | 6/2014 |
| WO | WO 2014/109858 A1 | 7/2014 |
| WO | WO 2014/144100 A2 | 9/2014 |
| WO | WO 2014/152013 A1 | 9/2014 |
| WO | WO 2014/152018 A1 | 9/2014 |
| WO | WO 2014/180562 A1 | 11/2014 |
| WO | WO 2014/181287 A1 | 11/2014 |
| WO | WO 2014/190199 A1 | 11/2014 |
| WO | WO 2015/010832 A1 | 1/2015 |
| WO | WO 2015/031608 A1 | 3/2015 |
| WO | WO 2015/069287 A1 | 5/2015 |
| WO | WO 2015/160787 A1 | 10/2015 |
| WO | WO 2016/057572 A1 | 4/2016 |
| WO | WO 2016/105484 A1 | 6/2016 |
| WO | WO 2016/105485 A2 | 6/2016 |
| WO | WO 2016/160945 A1 | 10/2016 |
| WO | WO 2017/053455 A1 | 3/2017 |
| WO | WO 2017/172802 A1 | 10/2017 |
| WO | WO 2017/173274 A1 | 10/2017 |
| WO | WO 2017/177124 A1 | 10/2017 |
| WO | WO 2017/187321 A1 | 11/2017 |
| WO | WO 2017/223188 A1 | 12/2017 |
| WO | WO 2018/064632 A1 | 4/2018 |
| WO | WO 2018/081377 A1 | 5/2018 |
| WO | WO 2018/081378 A1 | 5/2018 |
| WO | WO 2018/081381 A1 | 5/2018 |
| WO | WO 2018/107100 A1 | 6/2018 |
| WO | WO 2018/116185 A1 | 6/2018 |
| WO | WO 2018/127130 A1 | 7/2018 |
| WO | WO 2018/201126 A1 | 11/2018 |
| WO | WO 2019/071078 A1 | 4/2019 |

OTHER PUBLICATIONS

Borhade, S.R. et al. (2013) "Synthesis of Novel Aryl and Heteroaryl Acyl Sulfonimidamides via Pd-Catalyzed Carbonylation Using a Nongaseous Precursor" *Organic Lett*, 15(5):1056-1059.

Chen, Y. (Jan. 26, 2016) "N-Monoacylation of Sulfonimidamides" *Synthesis*, 48(7):1019-1028.

(56) References Cited

OTHER PUBLICATIONS

Database CAPLUS, Accession No. 1965:51408. Abstract of French Patent No. FR M2868, filed Nov. 23, 1964, by Roussel-UCLAF [online]. Retrieved Jan. 6, 2017 (1 page).
Database CAPLUS, Accession No. 1965:51409. Abstract of German Patent No. DE 1182243, filed Nov. 26, 1964, by Badische Anilin & Soda-Fabrik A.G. [online]. Retrieved Jan. 6, 2017 (2 pages).
Database Pubchem, CID: 2545578. Compound Summary, T5339296. NIH, U.S. National Library of Medicine, National Center for Biotechnology Information; Modify Date: Jan. 16, 2016. [online]. Retrieved from https://pubchem.ncbi.nlm.nih.gov/compound/2545578, on Jan. 22, 2016 (9 pages).
Database Pubchem, CID: 44419393. Compound Summary, CHEMBL374189. NIH, U.S. National Library of Medicine, National Center for Biotechnology Information; Modify Date: Jan. 16, 2016. [online]. Retrieved from https://pubchem.ncbi.nlm.nih.gov/compound/44419393, on Jan. 22, 2016 (11 pages).
Database Pubchem, CID: 49774135. Compound Summary, SCHEMBL13395127. NIH, U.S. National Library of Medicine, National Center for Biotechnology Information; Modify Date: Jan. 16, 2016 [online]. Retrieved from https://pubchem.ncbi.nlm.nih.gov/compound/49774135, on Jan. 22, 2016 (10 pages).
Database Pubchem, CID: 58132855. Compound Summary, SCHEMBL831192. NIH, U.S. National Library of Medicine, National Center for Biotechnology Information, PubChem Open Chemistry Database; Modify Date: Jan. 16, 2016 [online]. Retrieved from: https://pubchem.ncbi.nlm.nih.gov/compound/58132855, on Jan. 22, 2016 (10 pages).
Dorwald, F. A. (2006) "Side Reactions in Organic Synthesis" Wiley: VCH, Weinheim p. IX of Preface p. 1-15.
Hopkins, C.R. et al. (2006) "Design and synthesis of novel N-sulfonyl-2-indole carboxamides as potent PPAR-gamma binding agents with potential application to the treatment of osteoporosis" Bioorganic & Medicinal Chemistry Letters, 16(21):5659-5663.
International Patent Application No. PCT/US2015/54316: International Search Report and Written Opinion, dated Feb. 5, 2016 (11 pages).
International Patent Application No. PCT/US2017/025381: International Search Report and Written Opinion, dated Jun. 6, 2017 (11 pages).
International Patent Application No. PCT/US2017/054611: International Search Report and Written Opinion, dated Jan. 3, 2018 (10 pages).
International Patent Application No. PCT/US2017/065425: International Search Report and Written Opinion, dated Feb. 27, 2018 (10 pages).
International Patent Application No. PCT/US2018/036610: International Search Report and Written Opinion, dated Sep. 19, 2018 (9 pages).
International Patent Application No. PCT/US2018/040427: International Search Report and Written Opinion, dated Oct. 9, 2018 (15 pages).
International Patent Application No. PCT/US2018/042415: International Search Report and Written Opinion, dated Oct. 31, 2018 (12 pages).
International Patent Application No. PCT/US2018/042486: International Search Report and Written Opinion, dated Nov. 7, 2018 (13 pages).
International Patent Application No. PCT/US2018/056772: International Search Report and Written Opinion, dated Jan. 29, 2019 (13 pages).
Kettle, J.G. et al. (2004) "N-Benzylindole-2-carboxylic acids: potent functional antagonists of the CCR2b chemokine receptor" Bioorganic & Medicinal Chemistry Letters, 14(2): 405-408.
Norman, P. (2014) "Novel picolinamide-based cystic fibrosis transmembrane regulator modulators: evaluation of WO2013038373, WO2013038376, WO2013038381, WO2013038386, and WO2013038390," Expert Opinion on Therapeutic Patents, 24(7):829-837.
Notice of Allowance and Fee(s) Due for U.S. Appl. No. 15/721,390, dated Sep. 4, 2019.
Passarella, D. et al. (2001) "Cyclodimerization of indol-2-ylacetylenes. An example of intermolecular enyne-alkyne cycloaddition" Journal of the Chemical Society, Perkin Transactions 1, 127-129.
Rosebraugh, C.J. (2015) "Highlights of Prescribing Information for Orkambi," [online] Retrieved from the Internet: https://www.accessdata.fda.gov/drugsatfda_docs/label/2015/206038Orig1s000lbl.pdf, on Aug. 24, 2017.
Silverman, R. (2004) The Organic Chemistry of Drug Design and Drug Action, Elsevier, pp. 29-32.
Tullis, E. et al. (2018) "Preliminary safety and efficacy of triple-combination CFTR modulator regimens," Respirology, 23(51):33.
U.S. Appl. No. 16/089,703, filed Sep. 28, 2018, by Bear et al.
U.S. Appl. No. 16/258,024, filed Jan. 25, 2019, by Miller et al.
U.S. Appl. No. 16/165,849, filed Oct. 19, 2018, by Dhamankar et al.
U.S. Appl. No. 16/267,222, filed Feb. 4, 2019, by Chu et al.
U.S. Appl. No. 16/267,350, filed Feb. 14, 2019, by Clemens et al.
Uttamsingh, V. et al. (2016) "WS13.6 CTP-656 tablet confirmed superiority of pharmacokinetic profile relative to Kalydeco in Phase I clinical studies" Journal of Cystic Fibrosis, 15:S22.
Wainwright, C.E. et al. (2015) "Lumacaftor-Ivacaftor in Patients with Cystic Fibrosis Homozygous for Phe508del CFTR," The New England Journal of Medicine, 373(3):220-231.
Winn, M. et al. (1993) "2-(Alkylamino)nicotinic Acid and Analogs. Potent Angiotensin II Antagonists" Journal of Medicinal Chemistry, 36(18):2676-2688.
Venkatesh, S. et al. (2000) "Role of the development scientist in compound lead selection and optimization" J. Pharm. Sci. 89(2), 145-154.
Vertex Pharmaceuticals, Inc. (Mar. 28, 2017) "Two Phase 3 Studies of the Tezacaftor/Ivacaftor Combination Treatment Met Primary Endpoints with Statistically Significant Improvements in Lung Function (FEV1) in People With Cystic Fibrosis" [online] Retrieved from the Internet: http://investors.vrtx.com/static-files/f15217ac-4a8b-436a-9215-79144ec2e59b, on Oct. 10, 2019.

\* cited by examiner

Position [°2Theta] (Copper (Cu))

Position [°2Theta] (Copper (Cu))

Position [°2Theta] (Copper (Cu))

Position [°2Theta] (Copper (Cu))

Position [°2Theta] (Copper (Cu))

Position [°2Theta] (Copper (Cu))

Position [°2Theta] (Copper (Cu))

Position [°2Theta] (Copper (Cu))

Position [°2Theta] (Copper (Cu))

Position [°2Theta] (Copper (Cu))

Position [°2Theta] (Copper (Cu))

Position [°2Theta] (Copper (Cu))

Position [°2Theta] (Copper (Cu))

Position [°2Theta] (Copper (Cu))

Position [°2Theta] (Copper (Cu))

Position [°2Theta] (Copper (Cu))

FIG. 17

| Mutation cDNA Name | Mutation Protein Name | Mutation Legacy Name |
|---|---|---|
| c.1A>G | | M1V |
| c.54-5940_273+10250del21kb | pSer18ArgfsX16 | CFTRdele2,3 |
| c.91C>T | p.Arg31Cys | R31C |
| c.115C>T | p.Gln39X | Q39X |
| c.137C>A | p.Ala46Asp | A46D |
| c.165-1G>A | No protein name | 297-1G->A |
| c.166G>A | p.Glu56Lys | E56K |
| c.174_175insA | p.Arg59LysfsX10 | 306insA |
| c.178G>T | p.Glu60X | E60X |
| c.200C>T | p.Pro67leu | P67L |
| c.220C>T | p.Arg74Trp | R74W |
| c.223C>T | p.Arg75X | R75X |
| c.224G>A | p.Arg75Gln | R75Q |
| c.254G>A | p.Gly85Glu | G85E |
| c.262_263delTT | p.Leu88IlefsX22 | 394delTT |
| c.273+1G>A | No protein name | 405+1G->A |
| c.274-1G>A | No protein name | 406-1G->A |
| c.274G>A | p.Glu92Lys | E92K |
| c.274G>T | p.Glu92X | E92X |
| c.292C>T | p.Gln98X | Q98X |
| c.313delA | p.Ile105SerfsX2 | 444delA |
| c.325_327delTATinsG | p.Tyr109GlyfsX4 | 457TAT->G |
| c.328G>C | p.Asp110His | D110H |
| c.349C>T | p.Arg117Cys | R117C |
| c.350G>A | p.Arg117His | R117H |
| c.366T>A | p.Tyr122X | Y122X |
| c.442delA | p.Ile148LeufsX5 | 574delA |
| c.443T>C | p.Ile148Thr | I148T |
| c.489+1G>T | No protein name | 621+1G->T |

FIG. 17 (continued)

| Mutation cDNA Name | Mutation Protein Name | Mutation Legacy Name |
|---|---|---|
| c.531delT | p.Ile177MetfsX12 | 663delT |
| c.532G>A | p.Gly178Glu | G178R |
| c.543_546delTAGT | p.Leu183PhefsX5 | 675del4 |
| c.579+1G>T | No protein name | 711+1G->T |
| c.579+3A>G | No protein name | 711+3A->G |
| c.579+5G>A | No protein name | 711+5G->A |
| c.580-1G>T | No protein name | 712-1G->T |
| C.59SOT | p.His199Tyr | H199Y |
| C.613CM | p.Pro205Ser | P205S |
| c.617T>G | p.Leu206Trp | L206W |
| C.658OT | p.Gln220X | Q220X |
| c.580T>G | p.Leu227Arg | L227R |
| c.720_741delAGGGAGAATGATGATGAAGTAC | p.Gly241GlufsX13 | 852del22 |
| c.828C>A | p.Cys276X | C276X |
| c.948delT | p.Phe316LeufsX12 | 1078delT |
| c.988G>T | p.Gly330X | G330X |
| c.1000C>T | p.Arg334Trp | R334W |
| c.1007T>A | p.Ile336Lys | I336K |
| c.1013C>T | p.Thr338Ile | T338I |
| c.1021T>C | p.Ser341Pro | S341P |
| c.1022_1023insTC | p.Phe342HisfsX28 | 1154insTC |
| c.1040G>A | p.Arg347His | R347H |
| c.1040G>C | p.Arg347Pro | R347P |
| c.1055G>A | p.Arg352Gln | R352Q |
| c.[1075C>A; 10799C>A] | p.[Gln359Lys;Thr360Lys] | Q359K/T360K |
| c.1081delT | p.Trp361GlyfsX8 | 1213delT |
| c.1116+1G>A | No protein name | 1248+1G->A |
| c.1127_1128insA | p.Gln378AlafsX4 | 1259insA |
| c.1153_1154insAT | p.Asn386IlefsX3 | 1288insTA |

FIG. 17 (continued)

| Mutation cDNA Name | Mutation Protein Name | Mutation Legacy Name |
|---|---|---|
| c.1202G>A or c.1203G>A | p.Trp401X | W401X |
| c.1209+1G>A | No protein name | 1341+1G->A |
| c.1210-12[5] | No protein name | 5T |
| c.1210-12(7) | No protein name | 7T |
| c.1240C>T | p.Gln414X | Q414X |
| c.1329_1330insAGAT | p.Ile444ArgfsX3 | 1461ins4 |
| c.1340delA | p.Lys447ArgfsX2 | 1471delA |
| c.1364C>A | p.Ala455Glu | A455E |
| c.1393-1G>A | No protein name | 1525-1G->A |
| c.1397C>A or c.1397C>G | p.Ser466X | S466X |
| c.1400T>C | p.Leu467Pro | L467P |
| c.1408A>G | p.Met470Val | M470V |
| c.1418delG | p.Gly473GlufsX54 | 1548delG |
| c.1466C>A | p.Ser489X | S489X |
| c.1475C>T | p.Ser492Phe | S492F |
| c.1477C>T | p.Gln493X | Q493X |
| c.1519_1521delATC | p.Ile507del | I507del |
| c.1521_1523delCTT | p.Phe508del | F508del |
| c.1545_1546delTA | p.Tyr515X | 1677delTA |
| c.1558G>T | p.Val520Phe | V520F |
| c.1573C>T | p.Gln525X | Q525X |
| c.1585-8G>A | No protein name | 1717-8G->A |
| c.1585-1G>A | No protein name | 1717-1G->A |
| c.1624G>T | p.Gly542X | G542X |
| c.1645A>C or c.1G47T>G | p.Ser549Arg | S549R |
|  |  |  |
| c.1646G>A | p.Ser549Asn | S549N |
| c.1650delA | p.Gly551ValfsX8 | 1782delA |
| c.1651G>A | p.Gly551Ser | G551S |
| c.1652G>A | p.Gly551Asp | G551D |
| c.1654C>T | p.Gln552X | Q552X |

FIG. 17 (continued)

| Mutation cDNA Name | Mutation Protein Name | Mutation Legacy Name |
|---|---|---|
| c.1657C>T | p.Arg553X | R553X |
| c.1673T>C | p.Leu558Ser | L558S |
| c.1675G>A | p.Ala559Thr | A559T |
| c.1679G>A | p.Arg560Lys | R560K |
| c.1679G>C | p.Arg560Thr | R560T |
| c.1679+1G>C | No protein name | 1811+1G->C |
| c.1679+1.6kbA>G | No protein name | 1811+1.6kbA->G |
| c.1680-1G>A | No protein name | 1812-1G->A |
| c.1682C>A | p.Ala561Glu | A561E |
| c.1692delA | p.Asp565MetfsX7 | 1824delA |
| c.1705T>G | p.Tyr569Asp | Y569D |
| c.1727G>C | p.Gly576Ala | G576A |
| c.1736A>G | p.Asp579Gly | D579G |
| c.1753G>T | p.Glu585X | E585X |
| c.1766+1G>A | No protein name | 1898+1G->A |
| c.1766+1G>C | No protein name | 1898+1G->C |
| c.1766+3A>G | No protein name | 1898+3A->G |
| c.1841A>G | p.Asp614Gly | D614G |
| c.1923_1931del9ins | pSer641ArgfsX5 | 2055del9->A |
| c.1973_1985del13insAGAAA | p.Arg658 LysfsX4 | 2105-2117del13insAGAAA |
| c.1986_1989delAACT | p.Thr663ArgfsX8 | 2118del4 |
| c.2002C>T | p.Arg668Cys | R668C |
| c.2012delT | p.Leu671X | 2143delT |
| c.2051_2052delAAinsG | p.Lys684SerfsX38 | 2183AA->G+ |
| c.2051_2052delAAinsG | p.Lys684SerfsX38 | 2183delAA->G# |
| c.2052_2053insA | p.Gln685Th rfsX4 | 2184insA |
| c.2052delA | p.Lys684AsnfsX38 | 2184delA |
| c.2125O>T | p.Arg709X | R709X |

FIG. 17 (continued)

| Mutation cDNA Name | Mutation Protein Name | Mutation Legacy Name |
|---|---|---|
| c.2128A>T | p.Lys710X | K710X |
| c.2175_2176insA | p.Glu726ArgfsX4 | 2307insA |
| c.2195T>G | p.Leu732X | L732X |
| c.2215delG | p.Val739TyrfsX16 | 2347delG |
| c.2260G>A | p.Val754Met | V754M |
| c.2290C>T | p.Arg764X | R764X |
| c.2353C>T | p.Arg785X | R785X |
| c.2374C>T | p.Arg792X | R792X |
| c.2424_2425insAT | p.Ser809IlefsX13 | 2556insAT |
| c.2453delT | p.Leu818TrpfsX3 | 2585delT |
| c.2462_2463delGT | p.Ser821ArgfsX4 | No legacy name |
| c.2464G>T | p.Glu822X | E822X |
| c.2490+1G>A | No protein name | 2622+1G->A |
| c.2491G>T | p.Glu831X | E831X |
| c.2537G>A or c.2538G>A | p.Trp846X | W846X |
| c.2547OA | p.Tyr849X | Y849X |
| c.2551C>T | p.Arg851X | R851X |
| c.2583delT | p.Phe861LeufsX3 | 2711delT |
| c.2657+2_2657+3insA | No protein name | 2789+2insA |
| c.2657+5G>A | No protein name | 2789+5G->A |
| c.2658-1G>C | No protein name | 2790-1G->C |
| c.2668C>T | p.Gln890X | Q890X |
| c.2735C>A | p.Ser912X | S912X |
| c.2737_2738insG | | 2869insG |
| c.2739T>A | p.Tyr913X | Y913X |
| c.2764_2765insAG | p.Val922GlufsX2 | 2896insAG |
| c.2780T>C | p.Leu927Pro | L927P |
| c.2834C>T | p.Ser945Leu | S945L |
| c.2875delG | p.Ala959HisfsX9 | 3007delG |
| c.2908G>C | p.Gly970Arg | G970R |
| c.2930C>T | p.Ser977Phe | S977F |
| c.2988G>A | No protein name | 3120G->A |

FIG. 17 (continued)

| Mutation cDNA Name | Mutation Protein Name | Mutation Legacy Name |
|---|---|---|
| c.2988+1G>A | No protein name | 3120+1G->A |
| c.2989-977_3367+248del | No protein name | 3121-977_3499+248del2515 |
| c.2989-1G>A | No protein name | 3121-1G->A |
| c.2991G>C | p.Leu997Phe | L997F |
| c.3002_3003delTG | p.Val1001AspfsX45 | 3132delTG |
| c.3080T>C | p.Ile1027Thr | I1027T |
| c.3140-26A>G | No protein name | 3272-26A->G |
| c.3154T>G | p.Phe1052Val | F1052V |
| c.3160C>G | p.His1054Asp | H1054D |
| c.3181G>C | p.Gly1061Arg | G1061R |
| c.3194T>C | p.Leu1065Pro | L1065P |
| c.3196C>T | p.Arg1066Cys | R1066C |
| c.3197G>A | p.Arg1066His | R1066H |
| c.3205G>A | p.Gly1069Arg | G1069R |
| c.3208C>T | p.Arg1070Trp | R1070W |
| c.3209G>A | p.Arg1070Gln | R1070Q |
| c.3222T>A | p.Phe1074Leu | F1074L |
| c.3230T>C | p.Leu1077Pro | L1077P |
| c.3266G>A | p.Trp1089X | W1089X |
| c.3276C>A or c.3276C>G | p.Tyr1092X | Y1092X |
| c.3302T>A | p.Met1101Lys | M1101K |
| c.3310G>T | p.Glu1104X | E1104X |
| c.3454G>C | p.Asp1152His | D1152H |
| c.3472C>T | p.Arg1158X | R1158X |
| c.3484C>T | p.Arg1162X | R1162X |
| c.3485G>T | p.Arg1162Leu | R1162L |
| c.3528delC | p.Lys1177SerfsX15 | 3659delC |
| c.3535_3536insTCAA | p.Thr1179IlefsX17 | 3667ins4 |
| c.3587C>G | p.Ser1196X | S1196X |

FIG. 17 (continued)

| Mutation cDNA Name | Mutation Protein Name | Mutation Legacy Name |
|---|---|---|
| c.3605delA | p.Asp1202AlafsX9 | 3737delA |
| c.3611G>A or c.3612G>A | p.Trp1204X | W1204X |
| c.3659delC | p.Thr1220LysfsX8 | 3791delC |
| c.3691delT | p.Ser1231ProfsX4 | 3821delT |
| c.3700A>G | p.Ile1234Val | I1234V |
| c.3705T>G | p.Ser1235Arg | S1235R |
| c.3717+12191C>T | No protein name | 3849+10kbC->T |
| c.371S-1G>A | No protein name | 3850-1G->A |
| c.3731G>A | p.Gly1244Glu | G1244E |
| c.3744delA | p.Lys1250ArgfsX9 | 3876delA |
| c.3752G>A | p.Ser1251Asn | S1251N |
| c.3763T>C | p.Ser1255Pro | S1255P |
| c.3764oA | p.Ser1255X | S1255X |
| c.3773_3774insT | p.Leu1258PhefsX7 | 3905insT |
| c.3808G>A | p.Asp1270Asn | D1270N |
| c.3346G>A | p.Trp12S2X | W1282X |
| c.3873+1G>A | No protein name | 4005+1G->A |
| c.3883delA | p.Ile1295PhefsX33 | 4015delA |
| c.3884_3885insT | p.Ser1297PhefsX5 | 4016insT |
| c.3909C>G | p.Asn1303Lys | N1303K |
| c.3937C>T | p.Gln1313X | Q1313X |
| c.3964-78_4242+577del | NULL | CFTRdele22,23 |
| c.4046G>A | p.Gly1349Asp | G1349D |
| c.4077_4080delTGTTinsAA | No protein name | 4209TGTT->AA |
| c.4111G>T | p.Glu1371X | E1371X |
| c.4196_4197delTC | p.Cys1400X | 4326delTC |
| c.4234C>T | p.Gln1412X | Q1412X |
| c.4242+1G>T | No protein name | 4374+1G->T |

FIG. 17 (continued)

| Mutation cDNA Name | Mutation Protein Name | Mutation Legacy Name |
|---|---|---|
| c.4251delA | p.Glu1418ArgfsX14 | 4382delA |
| c.4296_4297insGA | p.Ser1435GlyfsX14 | 4428insGA |

Compound (III) (Tablets C1 to C5); Compound (III-d) (Tablet E1)

CRYSTALLINE FORMS AND COMPOSITIONS OF CFTR MODULATORS

This application claims priority to U.S. Provisional Application No. 62/574,677, filed Oct. 19, 2017; U.S. Provisional Application No. 62/574,670, filed Oct. 19, 2017; and U.S. Provisional Application No. 62/650,057, filed Mar. 29, 2018, the entire contents of each of which are expressly incorporated herein by reference in their respective entireties.

Disclosed herein are crystalline forms of Compound I and pharmaceutically acceptable salts thereof, which are modulators of Cystic Fibrosis Transmembrane Conductance Regulator (CFTR), compositions comprising the same, methods of using the same, and processes for making the same.

Cystic fibrosis (CF) is a recessive genetic disease that affects approximately 70,000 children and adults worldwide. Despite progress in the treatment of CF, there is no cure.

In patients with CF, mutations in CFTR endogenously expressed in respiratory epithelia lead to reduced apical anion secretion causing an imbalance in ion and fluid transport. The resulting decrease in anion transport contributes to enhanced mucus accumulation in the lung and accompanying microbial infections that ultimately cause death in CF patients. In addition to respiratory disease, CF patients typically suffer from gastrointestinal problems and pancreatic insufficiency that, if left untreated, result in death. In addition, the majority of males with cystic fibrosis are infertile, and fertility is reduced among females with cystic fibrosis.

Sequence analysis of the CFTR gene has revealed a variety of disease-causing mutations (Cutting, G. R. et al. (1990) Nature 346:366-369; Dean, M. et al. (1990) Cell 61:863:870; and Kerem, B-S. et al. (1989) Science 245: 1073-1080; Kerem, B-S et al. (1990) Proc. Natl. Acad. Sci. USA 87:8447-8451). To date, greater than 2000 mutations in the CF gene have been identified; currently, the CFTR2 database contains information on only 322 of these identified mutations, with sufficient evidence to define 281 mutations as disease causing. The most prevalent disease-causing mutation is a deletion of phenylalanine at position 508 of the CFTR amino acid sequence and is commonly referred to as the F508del mutation. This mutation occurs in approximately 70% of the cases of cystic fibrosis and is associated with severe disease.

The deletion of residue 508 in CFTR prevents the nascent protein from folding correctly. This results in the inability of the mutant protein to exit the endoplasmic reticulum (ER) and traffic to the plasma membrane. As a result, the number of CFTR channels for anion transport present in the membrane is far less than observed in cells expressing wild-type CFTR, i.e., CFTR having no mutations. In addition to impaired trafficking, the mutation results in defective channel gating. Together, the reduced number of channels in the membrane and the defective gating lead to reduced anion and fluid transport across epithelia. (Quinton, P. M. (1990), FASEB J. 4: 2709-2727). The channels that are defective because of the F508del mutation are still functional, albeit less functional than wild-type CFTR channels. (Dalemans et al. (1991), Nature Lond. 354: 526-528; Pasyk and Foskett (1995), J. Cell. Biochem. 270: 12347-50). In addition to F508del, other disease-causing mutations in CFTR that result in defective trafficking, synthesis, and/or channel gating could be up- or down-regulated to alter anion secretion and modify disease progression and/or severity.

CFTR is a cAMP/ATP-mediated anion channel that is expressed in a variety of cell types, including absorptive and secretory epithelia cells, where it regulates anion flux across the membrane, as well as the activity of other ion channels and proteins. In epithelial cells, normal functioning of CFTR is critical for the maintenance of electrolyte transport throughout the body, including respiratory and digestive tissue. CFTR is composed of approximately 1480 amino acids that encode a protein which is made up of a tandem repeat of transmembrane domains, each containing six transmembrane helices and a nucleotide binding domain. The two transmembrane domains are linked by a large, polar, regulatory (R)-domain with multiple phosphorylation sites that regulate channel activity and cellular trafficking.

Chloride transport takes place by the coordinated activity of ENaC and CFTR present on the apical membrane and the $Na^+$—$K^+$-ATPase pump and Cl— channels expressed on the basolateral surface of the cell. Secondary active transport of chloride from the luminal side leads to the accumulation of intracellular chloride, which can then passively leave the cell via Cl$^-$ channels, resulting in a vectorial transport. Arrangement of $Na^+/2Cl^-/K^+$ co-transporter, $Na^+$—$K^+$-ATPase pump and the basolateral membrane $K^+$ channels on the basolateral surface and CFTR on the luminal side coordinate the secretion of chloride via CFTR on the luminal side. Because water is probably never actively transported itself, its flow across epithelia depends on tiny transepithelial osmotic gradients generated by the bulk flow of sodium and chloride.

Compound I and pharmaceutically acceptable salts thereof are potent CFTR modulators. Compound I is N-(benzenesulfonyl)-6-[3-[2-[1-(trifluoromethyl) cyclopropyl]ethoxy]pyrazol-1-yl]-2-[(4S)-2,2,4-trimethylpyrrolidin-1-yl]pyridine-3-carboxamide, and has the following structure:

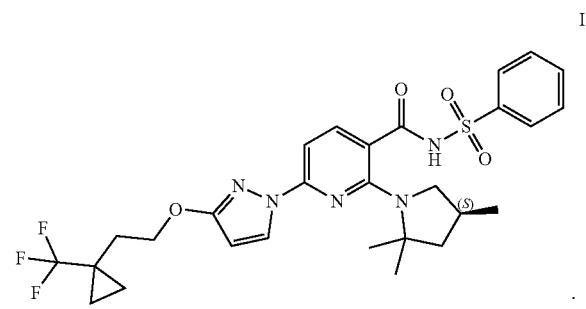

Crystalline forms are of interest in the pharmaceutical industry, where the control of the crystalline form(s) of the active ingredient may be desirable or even required. Reproducible processes for producing a compound with a particular crystalline form in high purity may be desirable for compounds intended to be used in pharmaceuticals, as different crystalline forms may possess different properties. For example, different crystalline forms may possess different chemical, physical, and/or pharmaceutical properties.

Accordingly, there is a need for novel crystalline forms of compounds useful for treatment of CFTR mediated diseases.

Disclosed herein are novel crystalline forms of Compound I and pharmaceutically acceptable salts thereof, compositions comprising the same, and methods of using and making the same.

Also, disclosed are pharmaceutical compositions comprising combinations of Compound I and/or pharmaceutically acceptable salts thereof with (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide (Compound II) and/or pharmaceutically acceptable salts thereof

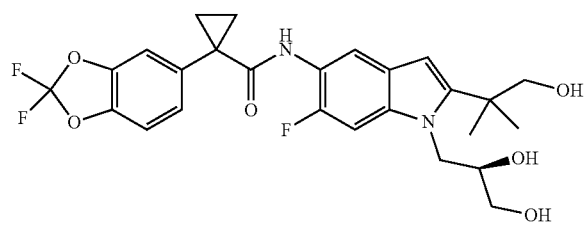

II and/or with N-(5-hydroxy-2,4-di-tert-butyl-phenyl)-4-oxo-1H-quinoline-3-carboxamide (Compound III)

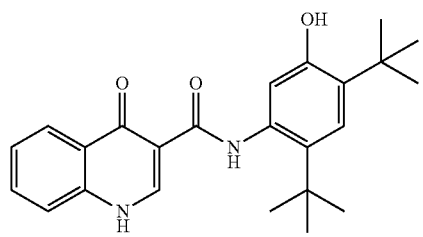

III or N-(2-(tert-butyl)-5-hydroxy-4-(2-(methyl-d3)propan-2-yl-1,1,1,3,3,3-d6)phenyl)-4-oxo-1,4-dihydroquinoline-3-carboxamide (Compound III-d)

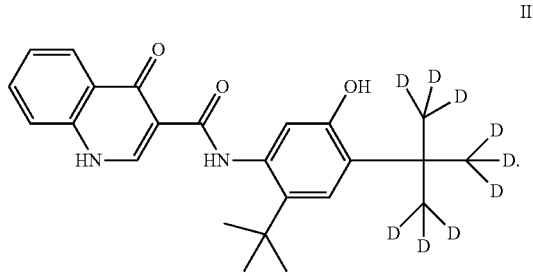

III-d

Also disclosed are methods of using a crystalline form of Compound I and/or pharmaceutically acceptable salts thereof disclosed herein alone or in combination with other CFTR modulators to treat cystic fibrosis. In certain embodiments, the crystalline form of Compound I and/or pharmaceutically acceptable salts thereof is administered with Compound II and/or Compound III or Compound III-d, either in a single pharmaceutical composition or in multiple compositions to treat cystic fibrosis.

BRIEF DESCRIPTION OF THE DRAWINGS

FIG. 17 is a representative list of CFTR genetic mutations.

DEFINITIONS

Figure 1A:
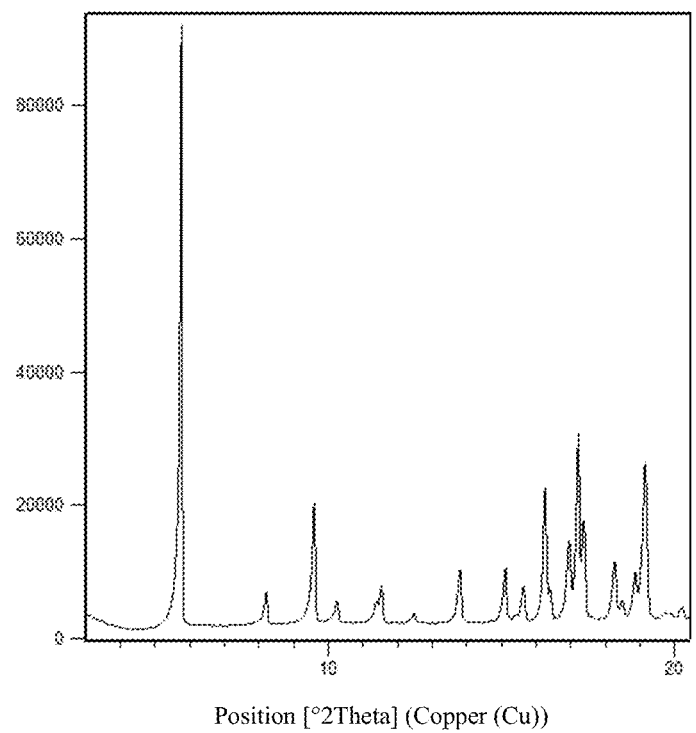
FIG. 1A shows a selection from an X-ray powder diffractogram of crystalline Form B of a potassium salt of Compound I.
Figure 1B:
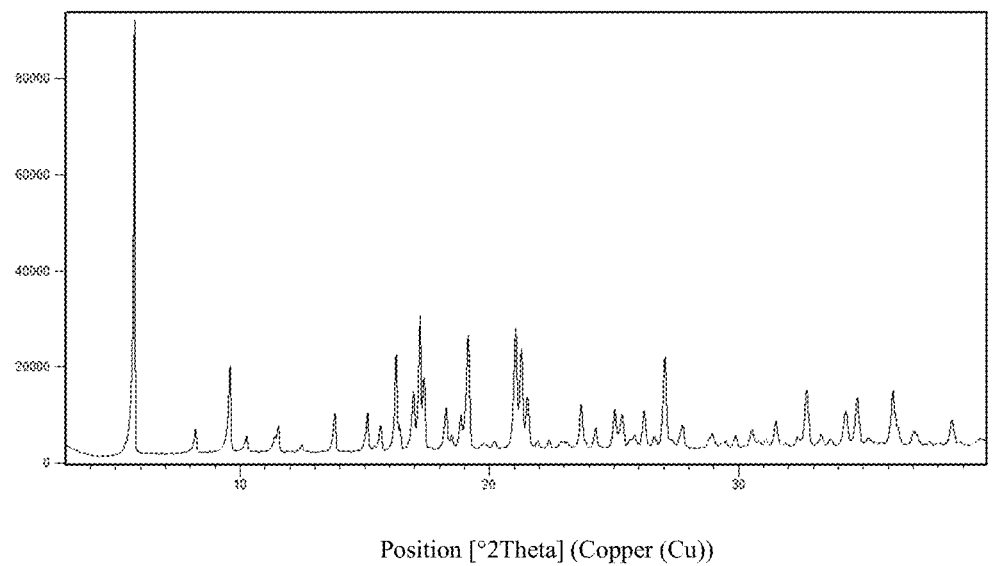
FIG. 1B shows a full scan view of an X-ray powder diffractogram of crystalline Form B of a potassium salt of Compound I.

As used herein, "Compound I" refers to a compound having a chemical name N-(benzenesulfonyl)-6-[3-[2-[1-(trifluoromethyl)cyclopropyl]ethoxy]pyrazol-1-yl]-2-[(4S)-2,2,4-trimethylpyrrolidin-1-yl]pyridine-3-carboxamide, which has the following structure:

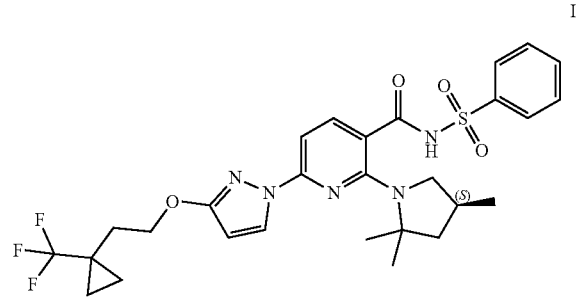

I either as an isomeric mixture or enantioenriched (e.g., >90% ee, >95% ee, or >98% ee) isomers.

As used herein, "Compound II" refers to a compound having a chemical name (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane carboxamide, which has the following structure:

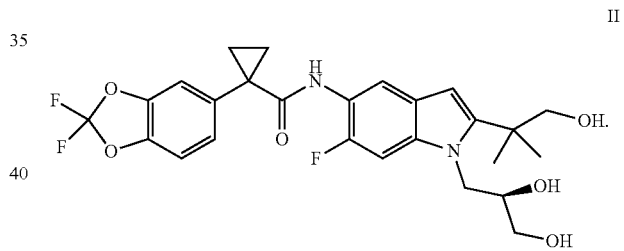

II

As used herein, "Compound III" refers to a compound having a chemical name N-(5-hydroxy-2,4-di-tert-butyl-phenyl)-4-oxo-1H-quinoline-3-carboxamide, which has the following structure:

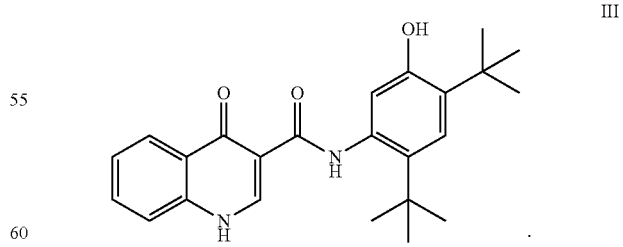

III

As used herein, "Compound III-d" refers to a compound having a chemical name N-(2-(tert-butyl)-5-hydroxy-4-(2-(methyl-d3)propan-2-yl-1,1,1,3,3,3-d6)phenyl)-4-oxo-1,4-dihydroquinoline-3-carboxamide, which has the following structure:

III-d

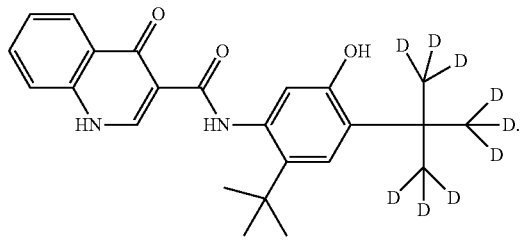

As used herein, "Compound IV" refers to a compound having a chemical name 3-(6-(1-(2,2-difluorobenzo[d][1,3]dioxol-5-yl)cyclopropanecarboxamido)-3-methylpyridin-2-yl)benzoic acid, which has the following structure:

IV

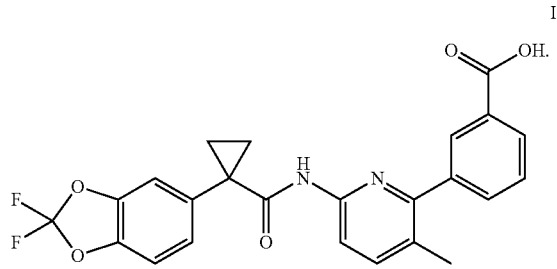

As used herein, the term "pharmaceutically acceptable salt" refers to a salt form of a compound of this disclosure wherein the salt is nontoxic. Pharmaceutically acceptable salts of Compound I, Compound II, Compound III, Compound III-d, and Compound IV of this disclosure include those derived from suitable inorganic and organic acids and bases. Pharmaceutically acceptable salts are well known in the art. For example, S. M. Berge, et al. describe pharmaceutically acceptable salts in detail in *J Pharmaceutical Sciences*, 1977, 66, 1-19.

Suitable pharmaceutically acceptable salts are, for example, those disclosed in S. M. Berge, et al. *J. Pharmaceutical Sciences*, 1977, 66, 1-19. For example, that article provides the following pharmaceutically acceptable salts:

| | | |
|---|---|---|
| Acetate | Iodide | Benzathine |
| Benzenesulfonate | Isethionate | Chloroprocaine |
| Benzoate | Lactate | Choline |
| Bicarbonate | Lactobionate | Diethanolamine |
| Bitartrate | Malate | Ethylenediamine |
| Bromide | Maleate | Meglumine |
| Calcium edetate | Mandelate | Procaine |
| Camsylate | Mesylate | Aluminum |
| Carbonate | Methylbromide | Calcium |
| Chloride | Methylnitrate | Lithium |
| Citrate | Methylsulfate | Magnesium |
| Dihydrochloride | Mucate | Potassium |
| Edetate | Napsylate | Sodium |
| Edisylate | Nitrate | Zinc |
| Estolate | Pamoate (Embonate) | |
| Esylate | Pantothenate | |
| Fumarate | Phosphate/diphosphate | |
| Gluceptate | Polygalacturonate | |
| Gluconate | Salicylate | |
| Glutamate | Stearate | |
| Glycollylarsanilate | Subacetate | |
| Hexylresorcinate | Succinate | |
| Hydrabamine | Sulfate | |
| Hydrobromide | Tannate | |
| Hydrochloride | Tartrate | |
| Hydroxynaphthoate | Teociate | |
| | Triethiodide | |

Non-limiting examples of pharmaceutically acceptable salts derived from appropriate acids include: salts formed with inorganic acids, such as hydrochloric acid, hydrobromic acid, phosphoric acid, sulfuric acid, or perchloric acid; salts formed with organic acids, such as acetic acid, oxalic acid, maleic acid, tartaric acid, citric acid, succinic acid or malonic acid; and salts formed by using other methods used in the art, such as ion exchange. Non-limiting examples of pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, and valerate salts. Pharmaceutically acceptable salts derived from appropriate bases include alkali metal, alkaline earth metal, ammonium, and $N^+(Cl^-\ 4alkyl)_4$ salts. This disclosure also envisions the quaternization of any basic nitrogen-containing groups of the compounds disclosed herein. Suitable non-limiting examples of alkali and alkaline earth metal salts include sodium, lithium, potassium, calcium, and magnesium. Further non-limiting examples of pharmaceutically acceptable salts include ammonium, quaternary ammonium, and amine cations formed using counterions such as halide, hydroxide, carboxylate, sulfate, phosphate, nitrate, lower alkyl sulfonate and aryl sulfonate. Other suitable, non-limiting examples of pharmaceutically acceptable salts include besylate and glucosamine salts.

As used herein, the term "co-crystal" is a crystalline material composed of two or more different molecules, typically the compound and co-crystal formers (or coformers), in the same crystal lattice. Co-crystals components are in a neutral state and interact nonionically.

As used herein, the term "ambient conditions" means room temperature, open air condition and uncontrolled humidity condition.

As used herein, the terms "crystal form," "crystalline form," and "Form" interchangeably refer to a crystal structure (or polymorph) having a particular molecular packing arrangement in the crystal lattice. Crystalline forms can be identified and distinguished from each other by one or more characterization techniques including, for example, X-ray powder diffraction (XRPD), single crystal X-ray diffraction, differential scanning calorimetry (DSC), dynamic vapor sorption (DVS), and/or thermogravimetric analysis (TGA). Accordingly, as used herein, the terms "crystalline Form [X] of Compound I" and "crystalline Form [C] of a [pharmaceutically acceptable]salt of Compound I" refer to unique crystalline forms that can be identified and distinguished from each other by one or more characterization techniques including, for example, X-ray powder diffraction (XRPD), single crystal X-ray diffraction, differential scanning calorimetry (DSC), dynamic vapor sorption (DVS), and/or thermogravimetric analysis (TGA). In some embodiments, the novel crystalline forms are characterized by an X-ray powder diffractogram having one or more signals at one or more specified two-theta values (° 2θ).

As used herein, the terms "solvate" and "pseudo-polymorph" interchangeably refer to a crystal form comprising one or more molecules of a compound of the present disclosure and, incorporated into the crystal lattice, one or more molecules of a solvent or solvents in stoichiometric or nonstoichiometric amounts. When the solvent is water, the solvate is referred to as a "hydrate".

As used herein, a "variable hydrate" is a crystal form comprising nonstoichiometric water in the crystal lattice. The amount of water present in a variable hydrate varies as a function of at least the relative humidity ("RH") in the environment of the variable hydrate. Since the positions of the signals in the X-ray powder diffractogram of a crystalline form correlate to the dimensions of its unit cell, a change in the size of the unit cell due to the presence (or absence) of water can be determined by comparison of X-ray diffractograms under different RH environments.

As used herein, the term "XRPD" refers to the analytical characterization method of X-ray powder diffraction. XRPD patterns can be recorded at ambient conditions in transmission or reflection geometry using a diffractometer.

As used herein, the terms "X-ray powder diffractogram," "X-ray powder diffraction pattern," "XRPD pattern" interchangeably refer to an experimentally obtained pattern plotting signal positions (on the abscissa) versus signal intensities (on the ordinate). For an amorphous material, an X-ray powder diffractogram may include one or more broad signals; and for a crystalline material, an X-ray powder diffractogram may include one or more signals, each identified by its angular value as measured in degrees 2θ (° 2θ), depicted on the abscissa of an X-ray powder diffractogram, which may be expressed as "a signal at . . . degrees two-theta," "a signal at [a] two-theta value(s) of . . ." and/or "a signal at at least . . . two-theta value(s) chosen from . . ." The term "X-ray powder diffractogram having a signal at . . . two-theta values" as used herein refers to an XRPD pattern that contains X-ray reflection positions as measured and observed in X-ray powder diffraction experiments (° 2θ).

A "signal" or "peak" as used herein refers to a point in the XRPD pattern where the intensity as measured in counts is at a local. One of ordinary skill in the art would recognize that one or more signals (or peaks) in an XRPD pattern may overlap and may, for example, not be apparent to the naked eye. Indeed, one of ordinary skill in the art would recognize that some art-recognized methods are capable of and suitable for determining whether a signal exists in a pattern, such as Rietveld refinement.

As used herein, "a signal at . . . degrees two-theta," "a signal at [a] two-theta value[s] of . . ." and/or "a signal at at least . . . two-theta value(s) chosen from . . ." refer to X-ray reflection positions as measured and observed in X-ray powder diffraction experiments (° 2θ).

The repeatability of the angular values is in the range of ±0.2° 2θ, i.e., the angular value can be at the recited angular value+0.2 degrees two-theta, the angular value−0.2 degrees two-theta, or any value between those two end points (angular value+0.2 degrees two-theta and angular value−0.2 degrees two-theta).

The terms "signal intensities" and "peak intensities" interchangeably refer to relative signal intensities within a given X-ray powder diffractogram. Factors that can affect the relative signal or peak intensities include sample thickness and preferred orientation (e.g., the crystalline particles are not distributed randomly).

As used herein, an X-ray powder diffractogram is "substantially similar to that in [a particular] Figure" when at least 90%, such as at least 95%, at least 98%, or at least 99%, of the signals in the two diffractograms overlap. In determining "substantial similarity," one of ordinary skill in the art will understand that there may be variation in the intensities and/or signal positions in XRPD diffractograms even for the same crystalline form. Thus, those of ordinary skill in the art will understand that the signal maximum values in XRPD diffractograms (in degrees two-theta (° 2θ) referred to herein) generally mean that value reported ±0.2 degrees 2θ of the reported value, an art-recognized variance.

As used herein, a crystalline form is "substantially pure" when it accounts for an amount by weight equal to or greater than 90% of the sum of all solid form(s) in a sample as determined by a method in accordance with the art, such as quantitative XRPD. In some embodiments, the solid form is "substantially pure" when it accounts for an amount by weight equal to or greater than 95% of the sum of all solid form(s) in a sample. In some embodiments, the solid form is "substantially pure" when it accounts for an amount by weight equal to or greater than 99% of the sum of all solid form(s) in a sample.

As used herein, the term "DSC" refers to the analytical method of Differential Scanning Calorimetry.

As used herein, the term "onset of decomposition" refers to the intersection point of the baseline before transition and the interflection tangent.

As used herein, the term "glass transition temperature" or "Tg" refers to the temperature above which a glassy amorphous solid becomes rubbery.

As used herein, the term "TGA" refers to the analytical method of Thermo Gravimetric (or thermogravimetric) Analysis.

As used herein, the term "solvent" refers to any liquid in which the product is at least partially soluble (solubility of product>1 g/l).

As used herein, the term "anti-solvent" refers to any liquid in which the product is insoluble or at maximum sparingly soluble (solubility of product<0.01 mol/l).

As used herein, the term "anti-solvent crystallization" refers to a process wherein supersaturation is achieved and, as a result thereof, crystallization is induced by addition of an antisolvent to the product solution.

As used herein, the term "amorphous" refers to a solid material having no long range order in the position of its molecules. Amorphous solids are generally supercooled liquids in which the molecules are arranged in a random manner so that there is no well-defined arrangement, e.g., molecular packing, and no long range order. For example, an amorphous material is a solid material having no sharp characteristic signal(s) in its X-ray power diffractogram (i.e., is not crystalline as determined by XRPD). Instead, one or more broad peaks (e.g., halos) appear in its diffractogram. Broad peaks are characteristic of an amorphous solid. See, e.g., US 2004/0006237 for a comparison of diffractograms of an amorphous material and crystalline material.

As used herein, the term "substantially amorphous" refers to a solid material having little or no long-range order in the position of its molecules. For example, substantially amorphous materials have less than 15% crystallinity (e.g., less than 10% crystallinity or less than 5% crystallinity). It is also noted that the term 'substantially amorphous' includes the descriptor, 'amorphous', which refers to materials having no (0%) crystallinity.

As used herein, the term "dispersion" refers to a disperse system in which one substance, the dispersed phase, is distributed, in discrete units, throughout a second substance (the continuous phase or vehicle). The size of the dispersed phase can vary considerably (e.g. colloidal particles of nanometer dimension, to multiple microns in size). In general, the dispersed phases can be solids, liquids, or gases. In the case of a solid dispersion, the dispersed and continuous phases are both solids. In pharmaceutical applications, a solid dispersion can include a crystalline drug (dispersed phase) in an amorphous polymer (continuous phase); or alternatively, an amorphous drug (dispersed phase) in an amorphous polymer (continuous phase). In some embodiments, a solid dispersion includes the polymer constituting the dispersed phase, and the drug constitute the continuous phase. Or, a solid dispersion includes the drug constituting the dispersed phase, and the polymer constituting the continuous phase.

As used herein, "CFTR" means cystic fibrosis transmembrane conductance regulator.

As used herein, "mutations" can refer to mutations in the CFTR gene or the CFTR protein. A "CFTR gene mutation" refers to a mutation in the CFTR gene, and a "CFTR protein mutation" refers to a mutation in the CFTR protein. A genetic defect or mutation, or a change in the nucleotides in a gene in general results in a mutation in the CFTR protein translated from that gene, or a frame shift(s).

The term "F508del" refers to a mutant CFTR protein which is lacking the amino acid phenylalanine at position 508.

As used herein, a patient who is "homozygous" for a particular gene mutation has the same mutation on each allele.

As used herein, a patient who is "heterozygous" for a particular gene mutation has this mutation on one allele, and a different mutation on the other allele.

As used herein, the term "modulator" refers to a compound that increases the activity of a biological compound such as a protein. For example, a CFTR modulator is a compound that increases the activity of CFTR. The increase in activity resulting from a CFTR modulator includes but is not limited to compounds that correct, potentiate, stabilize and/or amplify CFTR.

As used herein, the term "CFTR corrector" refers to a compound that facilitates the processing and trafficking of CFTR to increase the amount of CFTR at the cell surface. Compound I, Compound II, Compound IV, and their pharmaceutically acceptable salts thereof disclosed herein are CFTR correctors.

As used herein, the term "CFTR potentiator" refers to a compound that increases the channel activity of CFTR protein located at the cell surface, resulting in enhanced ion transport. Compound III and Compound III-d disclosed herein are CFTR potentiators.

As used herein, the term "active pharmaceutical ingredient" ("API") refers to a biologically active compound.

The terms "patient" and "subject" are used interchangeably and refer to an animal including humans.

The terms "effective dose" and "effective amount" are used interchangeably herein and refer to that amount of a compound that produces the desired effect for which it is administered (e.g., improvement in CF or a symptom of CF, or lessening the severity of CF or a symptom of CF). The exact amount of an effective dose will depend on the purpose of the treatment and will be ascertainable by one skilled in the art (see, e.g., Lloyd (1999) The Art, Science and Technology of Pharmaceutical Compounding).

As used herein, the terms "treatment," "treating," and the like generally mean the improvement of CF or a CFTR mediated disease or its symptoms or lessening the severity of CF or a CFTR mediated disease or its symptoms in a subject. "Treatment," as used herein, includes, but is not limited to, the following: increased growth of the subject, increased weight gain, reduction of mucus in the lungs, improved pancreatic and/or liver function, reduction of chest infections, and/or reductions in coughing or shortness of breath. Improvements in or lessening the severity of any of these symptoms can be readily assessed according to standard methods and techniques known in the art.

As used herein, the term "in combination with," when referring to two or more compounds, agents, or additional active pharmaceutical ingredients, means the administration of two or more compounds, agents, or active pharmaceutical ingredients to the patient prior to, concurrent with, or subsequent to each other in a single composition or in multiple compositions.

The terms "about" and "approximately", when used in connection with doses, amounts, or weight percent of ingredients of a composition or a dosage form, include the value of a specified dose, amount, or weight percent or a range of the dose, amount, or weight percent that is recognized by one of ordinary skill in the art to provide a pharmacological effect equivalent to that obtained from the specified dose, amount, or weight percent. In some embodiments, the term "about" modifies a specified number by + or −10%. In some embodiments, the term "about" modifies a specified number by + or −5%. In some embodiments, the term "about" modifies a specified number by + or −2%. In some embodiments, the term "about" modifies a specified number by + or −1%.

As used herein, the term "room temperature" or "ambient temperature" means 15° C. to 30° C.

Crystalline Form B of a Potassium Salt of Compound I

As stated above, disclosed herein are crystalline forms of Compound I:

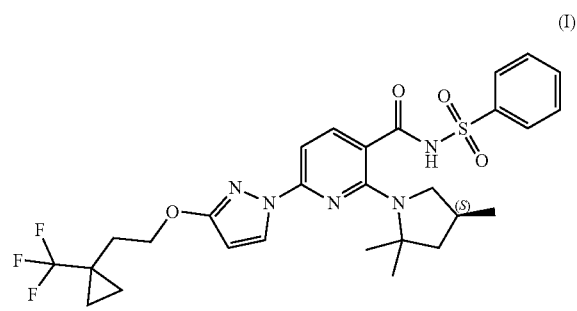

(I)

and pharmaceutically acceptable salts thereof, either as an isomeric mixture or enantioenriched (e.g., >90% ee, >95% ee, or >98% ee) isomers.

In some embodiments, the present disclosure provides crystalline Form B of a potassium salt of Compound I.

FIG. 1A shows an X-ray powder diffractogram of crystalline Form B of a potassium salt of Compound I at ambient conditions.

Figure 2:
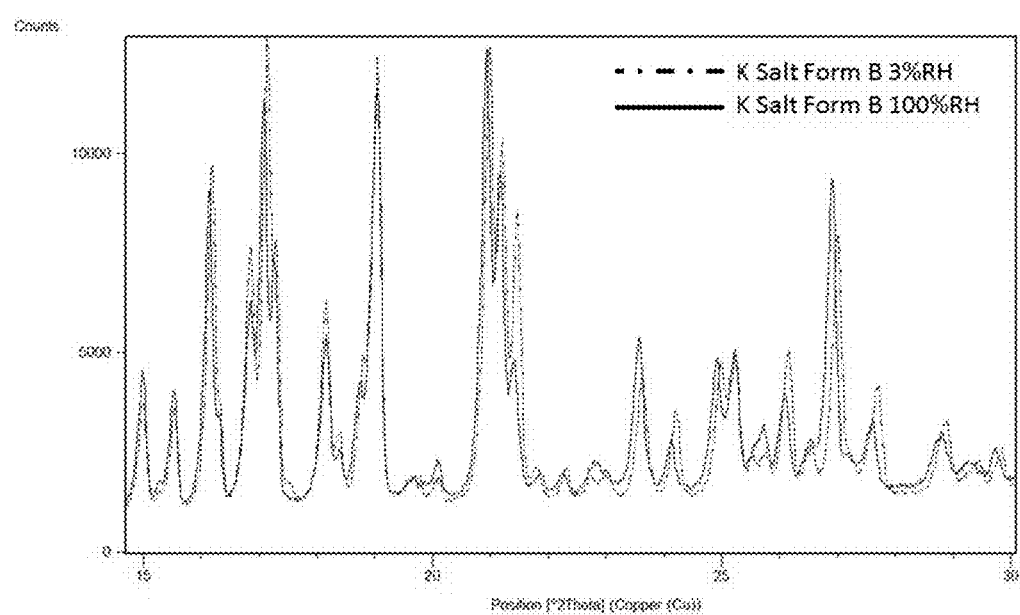
FIG. 2 shows an X-ray powder diffractogram of crystalline Form B of a potassium salt of Compound I at 3% relative humidity (RH) (red) initial and 100% RH (blue).

FIG. 2 shows an overlay of the X-ray powder diffractogram of crystalline Form B of a potassium salt of Compound I at 3% RH (red) initial and at 100% RH (blue).

Figure 3:
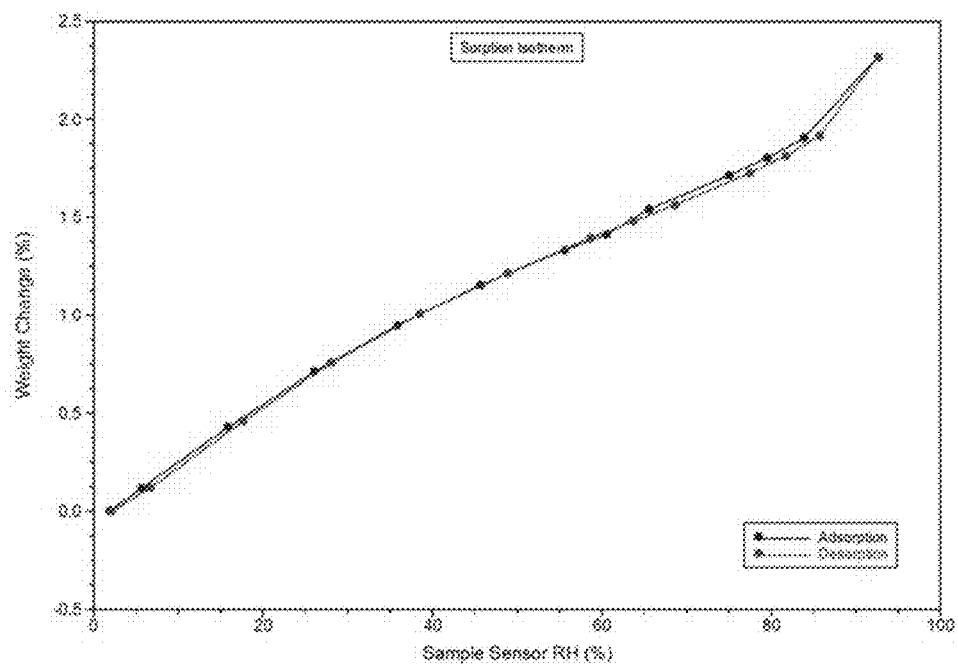
FIG. 3 shows a dynamic vapor sorption (DVS)-plot of crystalline Form B of a potassium salt of Compound I.

FIG. 3 shows the results of dynamic vapor sorption (DVS) plot of crystalline Form B of a potassium salt of Compound I. In some embodiments, the crystalline Form B of a potassium salt of Compound I is characterized by a weight change ranging from 1% to 2% or 1.5% to 1.8% in a dynamic vapor sorption experiment, while varying the relative humidity from 0-95% RH at 25° C.

Figure 4:
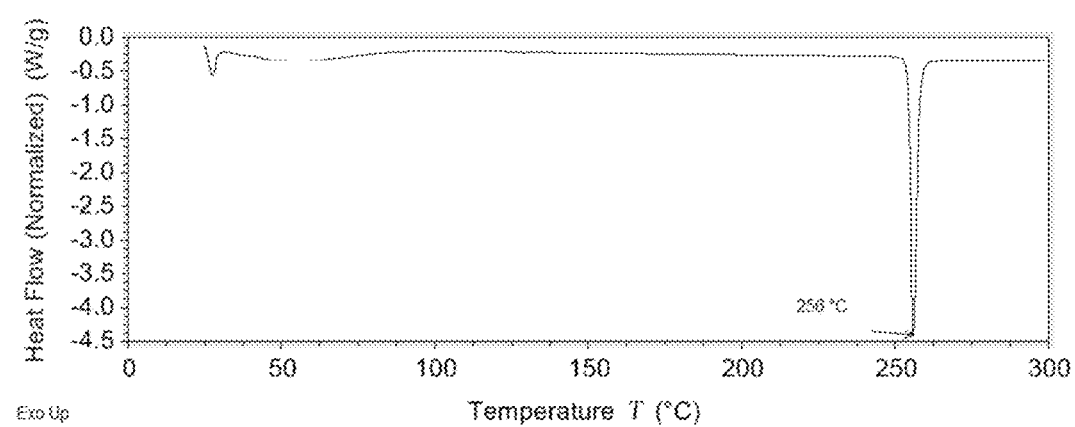
FIG. 4 shows a differential scanning calorimetry (DSC) plot of crystalline Form B of a potassium salt of Compound I.

FIG. 4 shows a DSC trace of the crystalline Form B of a potassium salt of Compound I. In some embodiments, the crystalline Form B of a potassium salt of Compound I is characterized by a DSC having an onset of decomposition temperature of 254° C. and/or a peak temperature of 256° C.

Figure 5:
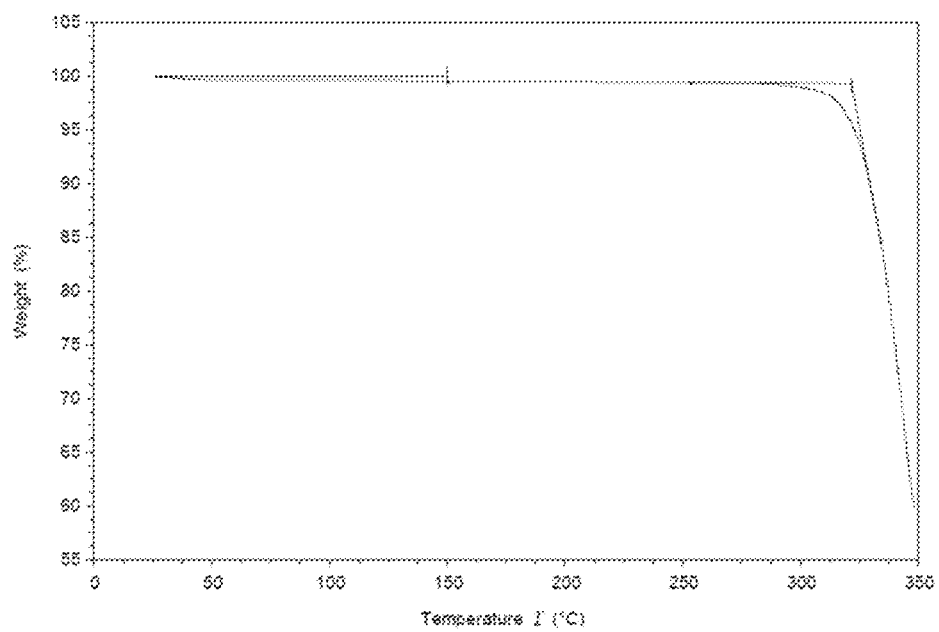
FIG. 5 shows a TGA plot of crystalline Form B of a potassium salt of Compound I.
Figure 6:
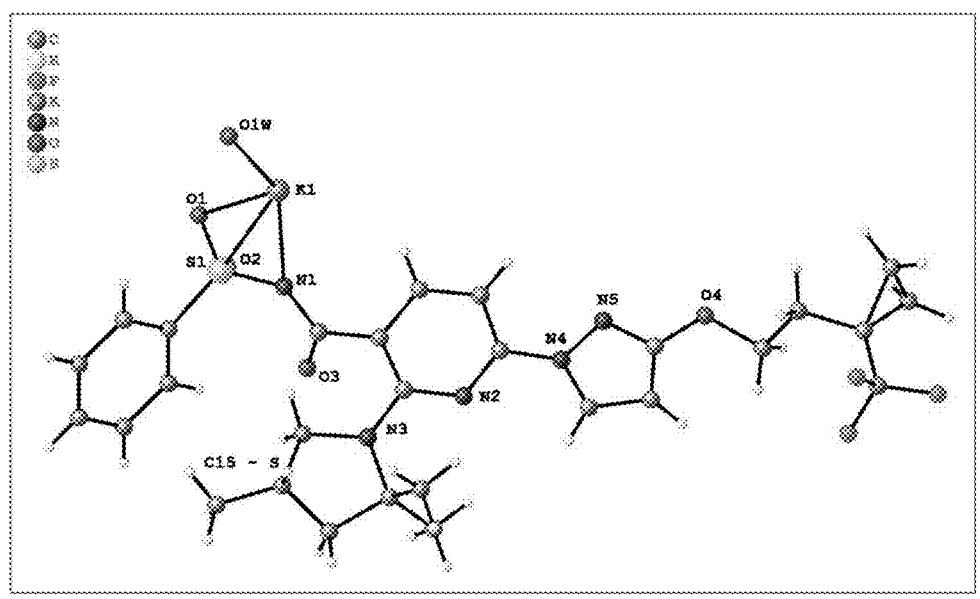
FIG. 6 shows a ball and stick plot of crystalline Form B of a potassium salt of Compound I.

FIG. 5 shows TGA results of crystalline Form B of a potassium salt of Compound I. In some embodiments, the crystalline Form B of a potassium salt of Compound I is characterized by a TGA having an onset of decomposition temperature of 322° C.

In some embodiments, the crystalline Form B of a potassium salt of Compound I is a variable hydrate. In some embodiments, the crystalline Form B of a potassium salt of Compound I comprises 71% water (molar %). In some embodiments, the crystalline Form B of a potassium salt of Compound I comprises 26% water (molar %). In some embodiments, the crystalline Form B of a potassium salt of Compound I comprises 38% water (molar %).

In some embodiments, crystalline Form B of a potassium salt of Compound I is in substantially pure form. In some embodiments, crystalline Form B of a potassium salt of Compound I is characterized by an X-ray powder diffractogram generated by an X-ray powder diffraction analysis with an incident beam of Cu Ku radiation.

In some embodiments, crystalline Form B of a potassium salt of Compound I is characterized by an X-ray powder diffractogram having a signal at 5.8±0.2 degrees two-theta. In some embodiments, crystalline Form B of a potassium salt of Compound I is characterized by an X-ray powder diffractogram having a signal at 8.2±0.2 degrees two-theta. In some embodiments, crystalline Form B of a potassium salt of Compound I is characterized by an X-ray powder diffractogram having a signal at 9.6±0.2 degrees two-theta. In some embodiments, crystalline Form B of a potassium salt of Compound I is characterized by an X-ray powder diffractogram having a signal at 10.2±0.2 degrees two-theta. In some embodiments, crystalline Form B of a potassium salt of Compound I is characterized by an X-ray powder diffractogram having a signal at 13.8±0.2 degrees two-theta. In some embodiments, crystalline Form B of a potassium salt of Compound I is characterized by an X-ray powder diffractogram having a signal at 15.1±0.2 degrees two-theta. In some embodiments, crystalline Form B of a potassium salt of Compound I is characterized by an X-ray powder diffractogram having a signal at 16.3±0.2 degrees two-theta. In some embodiments, crystalline Form B of a potassium salt of Compound I is characterized by an X-ray powder diffractogram having a signal at 17.2±0.2 degrees two-theta. In some embodiments, crystalline Form B of a potassium salt of Compound I is characterized by an X-ray powder diffractogram having a signal at 19.1±0.2 degrees two-theta.

In some embodiments, crystalline Form B of a potassium salt of Compound I is characterized by an X-ray powder diffractogram having a signal at two-theta values of 5.8±0.2, 8.2±0.2, 9.6±0.2, 10.2±0.2, 13.8±0.2, 15.1±0.2, 16.3±0.2, 17.2±0.2, and 19.1±0.2. In some embodiments, crystalline Form B of a potassium salt of Compound I is characterized by an X-ray powder diffractogram having a signal at at least eight two-theta values chosen from 5.8±0.2, 8.2±0.2, 9.6±0.2, 10.2±0.2, 13.8±0.2, 15.1±0.2, 16.3±0.2, 17.2±0.2, and 19.1±0.2. In some embodiments, crystalline Form B of a potassium salt of Compound I is characterized by an X-ray powder diffractogram having a signal at at least seven two-theta values chosen from 5.8±0.2, 8.2±0.2, 9.6±0.2, 10.2±0.2, 13.8±0.2, 15.1±0.2, 16.3±0.2, 17.2±0.2, and 19.1±0.2. In some embodiments, crystalline Form B of a potassium salt of Compound I is characterized by an X-ray powder diffractogram having a signal at at least six two-theta values chosen from 5.8±0.2, 8.2±0.2, 9.6±0.2, 10.2±0.2, 13.8±0.2, 15.1±0.2, 16.3±0.2, 17.2±0.2, and 19.1±0.2. In some embodiments, crystalline Form B of a potassium salt of Compound I is characterized by an X-ray powder diffractogram having a signal at at least five two-theta values chosen from 5.8±0.2, 8.2±0.2, 9.6±0.2, 10.2±0.2, 13.8±0.2, 15.1±0.2, 16.3±0.2, 17.2±0.2, and 19.1±0.2. In some embodiments, crystalline Form B of a potassium salt of Compound I is characterized by an X-ray powder diffractogram having a signal at at least four two-theta values chosen from 5.8±0.2, 8.2±0.2, 9.6±0.2, 10.2±0.2, 13.8±0.2, 15.1±0.2, 16.3±0.2, 17.2±0.2, and 19.1±0.2. In some embodiments, crystalline Form B of a potassium salt of Compound I is characterized by an X-ray powder diffractogram having a signal at at least three two-theta values chosen from 5.8±0.2, 8.2±0.2, 9.6±0.2, 10.2±0.2, 13.8±0.2, 15.1±0.2, 16.3±0.2, 17.2±0.2, and 19.1±0.2. In some embodiments, crystalline Form B of a potassium salt of Compound I is characterized by an X-ray powder diffractogram having a signal at at least two two-theta values chosen from 5.8±0.2, 8.2±0.2, 9.6±0.2, 10.2±0.2, 13.8±0.2, 15.1±0.2, 16.3±0.2, 17.2±0.2, and 19.1±0.2. In some embodiments, crystalline Form B of a potassium salt of Compound I is characterized by an X-ray powder diffractogram having a signal at at least one two-theta value chosen from 5.8±0.2, 8.2±0.2, 9.6±0.2, 10.2±0.2, 13.8±0.2, 15.1±0.2, 16.3±0.2, 17.2±0.2, and 19.1±0.2.

In some embodiments, crystalline Form B of a potassium salt of Compound I is characterized by an X-ray powder diffractogram having a signal at at least three two-theta values chosen from 5.8±0.2, 8.2±0.2, 10.2±0.2, 13.8±0.2, 16.3±0.2, and 19.1±0.2. In some embodiments, crystalline Form B of a potassium salt of Compound I is characterized by an X-ray powder diffractogram having a signal at at least two two-theta values chosen from 5.8±0.2, 10.2±0.2, and 19.1±0.2. In some embodiments, crystalline Form B of a potassium salt of Compound I is characterized by an X-ray powder diffractogram having a signal at two-theta values of 5.8±0.2, 10.2±0.2, and 19.1±0.2. In some embodiments, crystalline Form B of a potassium salt of Compound I is characterized by an X-ray powder diffractogram having a signal at two-theta values of 5.8±0.2, 8.2±0.2, 10.2±0.2, 13.8±0.2, 16.3±0.2, and 19.1±0.2.

In some embodiments, crystalline Form B of a potassium salt of Compound I is characterized by an X-ray powder diffractogram substantially similar to that in FIG. 1A.

In some embodiments, crystalline Form B of a potassium salt of Compound I is characterized by an orthorhombic crystal system. In some embodiments, crystalline Form B of a potassium salt of Compound I is characterized as belonging to a P212121 space group. In some embodiments, crystalline Form B of a potassium salt of Compound I is characterized by having a unit cell characterized by three edges of 9.0058±0.0009 Å, 11.5389±0.0012 Å, and 30.9399±0.003 Å. In some embodiments, crystalline Form B of a potassium salt of Compound I is characterized by having a unit cell characterized by three edges of 9.006±0.005 Å, 11.539±0.005 Å, and 30.940±0.005 Å. In some embodiments, crystalline Form B of a potassium salt of Compound I is characterized by having a unit cell characterized by three edges of 9.01±0.09 Å, 11.54±0.09 Å, and 30.9±0.2 Å. In some embodiments, crystalline Form B of a potassium salt of Compound I is characterized by having a unit cell characterized by three edges of 9.0±0.2 Å, 11.5±0.2 Å, and 31.0±0.2 Å. In some embodiments, crystalline Form B of a potassium salt of Compound I is characterized by having a unit cell of an orthorhombic crystal system characterized by three edges of 9.0±0.2 Å, 11.5±0.2 Å, and 31.0±0.2 Å.

In some embodiments, crystalline Form B of a potassium salt of Compound I is characterized by having a unit cell with the following characteristics measured at 298° K and 1.54178 Å:

| Crystal System: | Orthorhombic |
|---|---|
| Space Group: | P212121 |
| a (Å): | 9.0058(3) |
| b (Å): | 11.5389(4) |
| c (Å): | 30.9399(10) |
| α (°) | 90 |
| β (°) | 90 |
| γ (°) | 90 |
| V (Å3): | 3215.18(19) |
| Z/Z': | 4/1 |

In some embodiments, crystalline Form B of a potassium salt of Compound I is characterized by having a unit cell characterized by three angles of 90°.

In some embodiments, crystalline Form B of a potassium salt of Compound I is characterized by having a unit cell with volume of 3215 Å$^3$.

In some embodiments, the present disclosure provides crystalline Form B of a potassium salt of Compound I prepared by a process comprising reacting Compound I with a potassium base.

In some embodiments, the present disclosure provides methods of preparing crystalline Form B of a potassium salt of Compound I, comprising reacting Compound I with a potassium base. In some embodiments, the potassium base is chosen from potassium hydroxide, potassium t-butoxide, potassium acetate, potassium bicarbonate, potassium carbonate, potassium methoxide, and potassium ethoxide. In some embodiments, the potassium base is chosen from potassium hydroxide. In some embodiments, the potassium base is chosen from potassium carbonate. In some embodiments, the reaction is performed at room temperature.

Crystalline Form B of a potassium salt of Compound I, is a crystalline channel/variable-hydrate that has been found to be thermodynamically stable during development. The potassium salt Form B of Compound I is stable across a wide humidity range. In addition, it was found to be particularly amenable to scale up manufacturing processes.

Crystalline Form C of a Potassium Salt/Co-Crystal of Compound I

In some embodiments, the present disclosure provides crystalline form of a potassium salt or co-crystal of Compound I, designated as Form C.

Figure 7A:
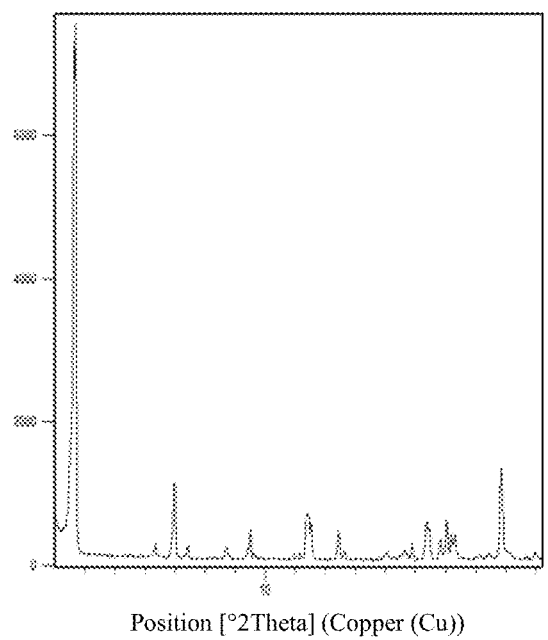
FIG. 7A shows a selection from an X-ray powder diffractogram of crystalline Form C of a potassium salt/co-crystal of Compound I.
Figure 7B:
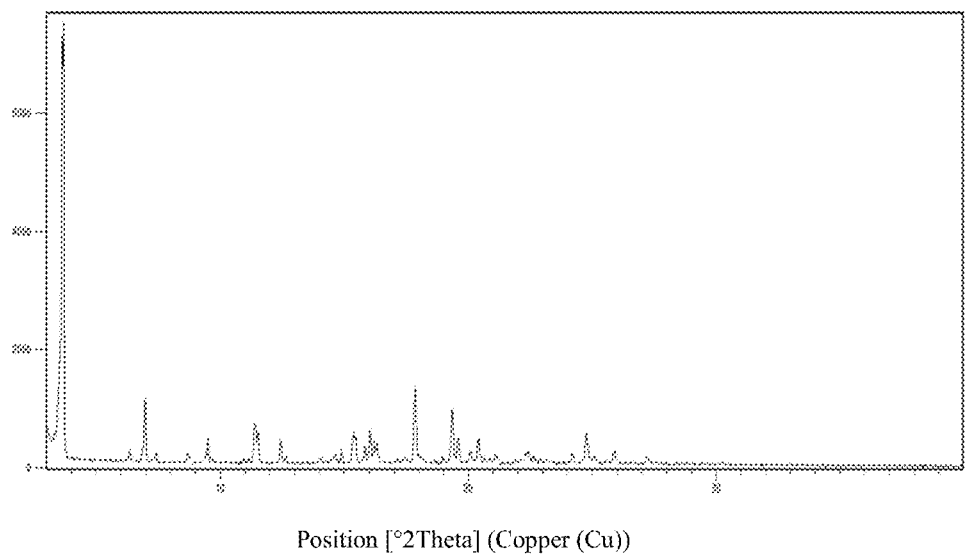
FIG. 7B shows a full scan view of an X-ray powder diffractogram of crystalline Form C of a potassium salt/co-crystal of Compound I.

FIG. 7A shows an X-ray powder diffractogram of Form C of a potassium salt/co-crystal of Compound I at ambient conditions.

In some embodiments, crystalline Form C of a potassium salt/co-crystal of Compound I is in substantially pure form. In some embodiments, crystalline Form C of a potassium salt/co-crystal of Compound I is characterized by an X-ray powder diffractogram generated by an X-ray powder diffraction analysis with an incident beam of Cu Ku radiation.

In some embodiments, crystalline Form C of a potassium salt/co-crystal of Compound I is characterized by an X-ray powder diffractogram having a signal at 3.7±0.2 degrees two-theta. In some embodiments, crystalline Form C of a potassium salt/co-crystal of Compound I is characterized by an X-ray powder diffractogram having a signal at 7.0±0.2 degrees two-theta. In some embodiments, crystalline Form C of a potassium salt/co-crystal of Compound I is characterized by an X-ray powder diffractogram having a signal at 7.4±0.2 degrees two-theta. In some embodiments, crystalline Form C of a potassium salt/co-crystal of Compound I is characterized by an X-ray powder diffractogram having a signal at 8.7±0.2 degrees two-theta. In some embodiments, crystalline Form C of a potassium salt/co-crystal of Compound I is characterized by an X-ray powder diffractogram having a signal at 9.5±0.2 degrees two-theta. In some embodiments, crystalline Form C of a potassium salt/co-crystal of Compound I is characterized by an X-ray powder diffractogram having a signal at 11.4±0.2 degrees two-theta. In some embodiments, crystalline Form C of a potassium salt/co-crystal of Compound I is characterized by an X-ray powder diffractogram having a signal at 11.5±0.2 degrees two-theta. In some embodiments, crystalline Form C of a potassium salt/co-crystal of Compound I is characterized by an X-ray powder diffractogram having a signal at 12.4±0.2 degrees two-theta. In some embodiments, crystalline Form C of a potassium salt/co-crystal of Compound I is characterized by an X-ray powder diffractogram having a signal at 16.0±0.2 degrees two-theta.

In some embodiments, crystalline Form C of a potassium salt/co-crystal of Compound I is characterized by an X-ray powder diffractogram having a signal at two-theta values 3.7±0.2, 7.0±0.2, 7.4±0.2, 8.7±0.2, 9.5±0.2, 11.4±0.2, 11.5±0.2, 12.4±0.2, and 16.0±0.2 degrees two-theta. In some embodiments, crystalline Form C of a potassium salt/co-crystal of Compound I is characterized by an X-ray powder diffractogram having a signal at at least eight two-theta values chosen from 3.7±0.2, 7.0±0.2, 7.4±0.2, 8.7±0.2, 9.5±0.2, 11.4±0.2, 11.5±0.2, 12.4±0.2, and 16.0±0.2 degrees two-theta. In some embodiments, crystalline Form C of a potassium salt/co-crystal of Compound I is characterized by an X-ray powder diffractogram having a signal at at least seven two-theta values chosen from 3.7±0.2, 7.0±0.2, 7.4±0.2, 8.7±0.2, 9.5±0.2, 11.4±0.2, 11.5±0.2, 12.4±0.2, and 16.0±0.2 degrees two-theta. In some embodiments, crystalline Form C of a potassium salt/co-crystal of Compound I is characterized by an X-ray powder diffractogram having a signal at at least six two-theta values chosen from 3.7±0.2, 7.0±0.2, 7.4±0.2, 8.7±0.2, 9.5±0.2, 11.4±0.2, 11.5±0.2, 12.4±0.2, and 16.0±0.2 degrees two-theta.

In some embodiments, crystalline Form C of a potassium salt/co-crystal of Compound I is characterized by an X-ray powder diffractogram having a signal at at least five two-theta values chosen from 3.7±0.2, 7.0±0.2, 7.4±0.2, 8.7±0.2, 9.5±0.2, 11.4±0.2, 11.5±0.2, 12.4±0.2, and 16.0±0.2 degrees two-theta. In some embodiments, crystalline Form C of a potassium salt/co-crystal of Compound I is characterized by an X-ray powder diffractogram having a signal at at least four two-theta values chosen from 3.7±0.2, 7.0±0.2, 7.4±0.2, 8.7±0.2, 9.5±0.2, 11.4±0.2, 11.5±0.2, 12.4±0.2, and 16.0±0.2 degrees two-theta. In some embodiments, crystalline Form C of a potassium salt/co-crystal of Compound I is characterized by an X-ray powder diffractogram having a signal at at least three two-theta values chosen from 3.7±0.2, 7.0±0.2, 7.4±0.2, 8.7±0.2, 9.5±0.2, 11.4±0.2, 11.5±0.2, 12.4±0.2, and 16.0±0.2 degrees two-theta. In some embodiments, crystalline Form C of a potassium salt/co-crystal of Compound I is characterized by an X-ray powder diffractogram having a signal at at least two two-theta values chosen from 3.7±0.2, 7.0±0.2, 7.4±0.2, 8.7±0.2, 9.5±0.2, 11.4±0.2, 11.5±0.2, 12.4±0.2, and 16.0±0.2 degrees two-theta. In some embodiments, crystalline Form C of a potassium salt/co-crystal of Compound I is characterized by an X-ray powder diffractogram having a signal at at least one two-theta value chosen from 3.7±0.2, 7.0±0.2, 7.4±0.2, 8.7±0.2, 9.5±0.2, 11.4±0.2, 11.5±0.2, 12.4±0.2, and 16.0±0.2 degrees two-theta.

In some embodiments, crystalline Form C of a potassium salt/co-crystal of Compound I is characterized by an X-ray powder diffractogram having a signal at at least three two-theta values chosen from 3.7±0.2, 7.0±0.2, 7.4±0.2, 9.5±0.2, 11.4±0.2, and 11.5±0.2.

In some embodiments, crystalline Form C of a potassium salt/co-crystal of Compound I is characterized by an X-ray powder diffractogram having a signal at two-theta values of 3.7±0.2, 7.0±0.2, and 11.4±0.2. In some embodiments, crystalline Form C of a potassium salt/co-crystal of Compound I is characterized by an X-ray powder diffractogram having a signal at two-theta values of 3.7±0.2, 7.0±0.2, 7.4±0.2, 9.5±0.2, 11.4±0.2, and 11.5±0.2.

In some embodiments, crystalline Form C of a potassium salt/co-crystal of Compound I is characterized by an X-ray powder diffractogram substantially similar to that in FIG. 7A.

In some embodiments, the present disclosure provides crystalline Form C of a potassium salt/co-crystal of Compound I prepared by a process comprising stirring a potassium salt of Compound I with a solvent system comprising at least one source of water. In some embodiments, the solvent system comprises water. In some embodiments, the solvent system comprises at least one organic solvent miscible with water. In some embodiments, the solvent system comprises acetonitrile. In some embodiments, the solvent system comprises at least one alcohol chosen from Cl– C4 alcohols. In some embodiments, the solvent system comprises at least one alkane chosen from C5-C alcohols. In some embodiments, the solvent system comprises at least one alkane chosen from pentane, hexane and heptane. In some embodiments, the solvent system comprises water. In some embodiments, the at least one source of water is water. In some embodiments, the at least one source of water is a hydrate of a potassium salt of Compound I. In some embodiments, stirring occurs at a temperature ranging from 20° C. to 100° C.

In some embodiments, the present disclosure provides methods of preparing crystalline Form C of a potassium salt/co-crystal Compound I comprising stirring a potassium salt of Compound I with a solvent system comprising at least one source of water. In some embodiments, the solvent system comprises water. In some embodiments, the solvent system comprises at least one organic solvent miscible with water. In some embodiments, the solvent system comprises acetonitrile. In some embodiments, the solvent system comprises at least one alcohol chosen from Cl– C4 alcohols. In some embodiments, the solvent system comprises at least one alkane chosen from C5-C alcohols. In some embodiments, the solvent system comprises at least one alkane chosen from pentane, hexane and heptane. In some embodiments, the solvent system comprises water. In some embodiments, the at least one source of water is water. In some embodiments, the solvent system is a 1:10 v/v mixture of acetonitrile and water.

In some embodiments, the at least one source of water is a hydrate of a potassium salt of Compound I. In some embodiments, stirring occurs at a temperature ranging from 20° C. to 100° C. In some embodiments, stirring occurs at a temperature ranging from 60° C. to 80° C. In some embodiments, stirring occurs in 1:10 v/v acetonitrile: water at a temperature ranging from 60° C. to 90° C. In some embodiments, stirring occurs in 1:10 v/v acetonitrile: water at a temperature ranging from 70° C. to 80° C. (e.g, at 75° C.).

Crystalline Form a of a Sodium Salt of Compound I

In some embodiments, the present disclosure provides crystalline Form A of a sodium salt of Compound I.

Figure 8A:
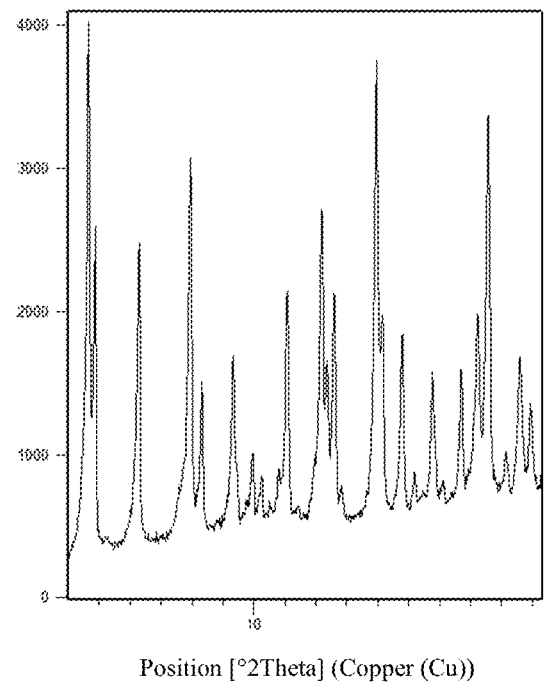
FIG. 8A shows a selection from an X-ray powder diffractogram of crystalline Form A of a sodium salt of Compound I.
Figure 8B:
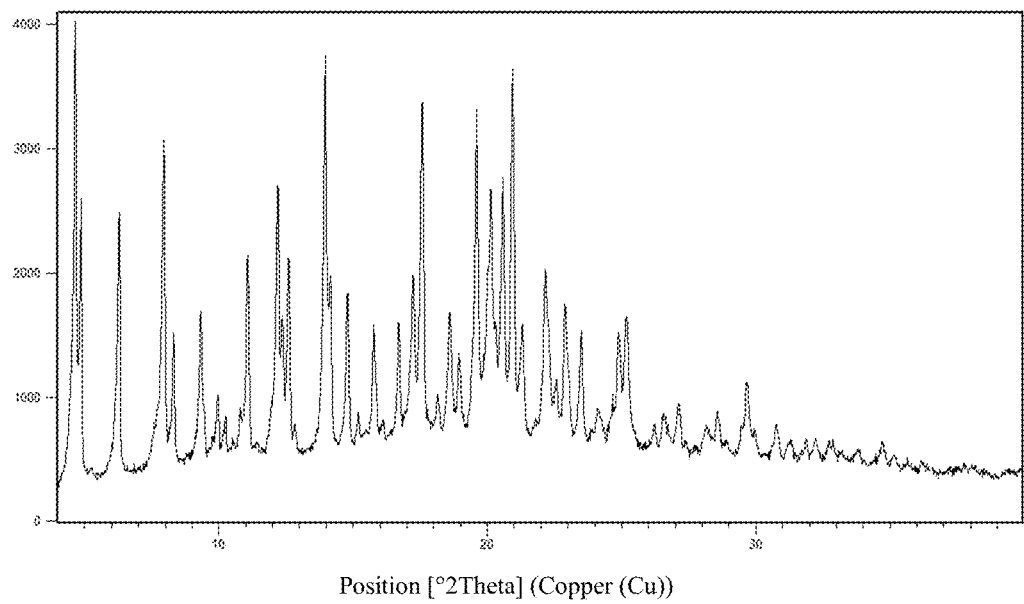
FIG. 8B shows a full scan view of an X-ray powder diffractogram of crystalline Form A of a sodium salt of Compound I.

FIG. 8A shows an X-ray powder diffractogram of crystalline Form A of a sodium salt of Compound I at ambient conditions.

In some embodiments, crystalline Form A of a sodium salt of Compound I is in substantially pure form.

In some embodiments, crystalline Form A of a sodium salt of Compound I is characterized by an X-ray powder diffractogram generated by an X-ray powder diffraction analysis with an incident beam of Cu Ku radiation.

In some embodiments, crystalline Form A of a sodium salt of Compound I is characterized by an X-ray powder diffractogram having a signal at 4.7±0.2 degrees two-theta. In some embodiments, crystalline Form A of a sodium salt of Compound I is characterized by an X-ray powder diffractogram having a signal at 4.9±0.2 degrees two-theta. In some embodiments, crystalline Form A of a sodium salt of Compound I is characterized by an X-ray powder diffractogram having a signal at 6.3±0.2 degrees two-theta. In some embodiments, crystalline Form A of a sodium salt of Compound I is characterized by an X-ray powder diffractogram having a signal at 8.0±0.2 degrees two-theta. In some embodiments, crystalline Form A of a sodium salt of Compound I is characterized by an X-ray powder diffractogram having a signal at 8.3±0.2 degrees two-theta. In some embodiments, crystalline Form A of a sodium salt of Compound I is characterized by an X-ray powder diffractogram having a signal at 11.1±0.2 degrees two-theta. In some embodiments, crystalline Form A of a sodium salt of Compound I is characterized by an X-ray powder diffractogram having a signal at 12.2±0.2 degrees two-theta. In some embodiments, crystalline Form A of a sodium salt of Compound I is characterized by an X-ray powder diffractogram having a signal at 12.6±0.2 degrees two-theta. In some embodiments, crystalline Form A of a sodium salt of Compound I is characterized by an X-ray powder diffractogram having a signal at 14.0±0.2 degrees two-theta.

In some embodiments, crystalline Form A of a sodium salt of Compound I is characterized by an X-ray powder diffractogram having a signal at 4.7±0.2, 4.9±0.2, 6.3±0.2, 8.0±0.2, 8.3±0.2, 11.1±0.2, 12.2±0.2, 12.6±0.2, and 14.0±0.2 degrees two-theta. In some embodiments, crystalline Form A of a sodium salt of Compound I is characterized by an X-ray powder diffractogram having a signal at at least eight two-theta values chosen from 4.7±0.2, 4.9±0.2, 6.3±0.2, 8.0±0.2, 8.3±0.2, 11.1±0.2, 12.2±0.2, 12.6±0.2, and 14.0±0.2. In some embodiments, crystalline Form A of a sodium salt of Compound I is characterized by an X-ray powder diffractogram having a signal at at least seven two-theta values chosen from 4.7±0.2, 4.9±0.2, 6.3±0.2, 8.0±0.2, 8.3±0.2, 11.1±0.2, 12.2±0.2, 12.6±0.2, and 14.0±0.2. In some embodiments, crystalline Form A of a sodium salt of Compound I is characterized by an X-ray powder diffractogram having a signal at at least six two-theta values chosen from 4.7±0.2, 4.9±0.2, 6.3±0.2, 8.0±0.2, 8.3±0.2, 11.1±0.2, 12.2±0.2, 12.6±0.2, and 14.0±0.2. In some embodiments, crystalline Form A of a sodium salt of Compound I is characterized by an X-ray powder diffractogram having a signal at at least five two-theta values chosen from 4.7±0.2, 4.9±0.2, 6.3±0.2, 8.0±0.2, 8.3±0.2, 11.1±0.2, 12.2±0.2, 12.6±0.2, and 14.0±0.2. In some embodiments, crystalline Form A of a sodium salt of Compound I is characterized by an X-ray powder diffractogram having a signal at at least four two-theta values chosen from 4.7±0.2, 4.9±0.2, 6.3±0.2, 8.0±0.2, 8.3±0.2, 11.1±0.2, 12.2±0.2, 12.6±0.2, and 14.0±0.2. In some embodiments, crystalline Form A of a sodium salt of Compound I is characterized by an X-ray powder diffractogram having a signal at at least three two-theta values chosen from 4.7±0.2, 4.9±0.2, 6.3±0.2, 8.0±0.2, 8.3±0.2, 11.1±0.2, 12.2±0.2, 12.6±0.2, and 14.0±0.2. In some embodiments, crystalline Form A of a sodium salt of Compound I is characterized by an X-ray powder diffractogram having a signal at at least two two-theta values chosen from 4.7±0.2, 4.9±0.2, 6.3±0.2, 8.0±0.2, 8.3±0.2, 11.1±0.2, 12.2±0.2, 12.6±0.2, and 14.0±0.2. In some embodiments, crystalline Form A of a sodium salt of Compound I is characterized by an X-ray powder diffractogram having a signal at at least one two-theta value chosen from 4.7±0.2, 4.9±0.2, 6.3±0.2, 8.0±0.2, 8.3±0.2, 11.1±0.2, 12.2±0.2, 12.6±0.2, and 14.0±0.2.

In some embodiments, crystalline Form A of a sodium salt of Compound I is characterized by an X-ray powder diffractogram having a signal at at least three two-theta values chosen from 4.7±0.2, 4.9±0.2, 6.3±0.2, 8.0±0.2, 8.3±0.2, 11.1±0.2, 12.2±0.2, 12.6±0.2, and 14.0±0.2. In some embodiments, crystalline Form A of a sodium salt of Compound I is characterized by an X-ray powder diffractogram having a signal at at least three two-theta values chosen from 4.7±0.2, 4.9±0.2, 8.0±0.2, 8.3±0.2, 12.2±0.2, and 12.6±0.2. In some embodiments, crystalline Form A of a sodium salt of Compound I is characterized by an X-ray powder diffractogram having a signal at two-theta values of 4.7±0.2, 8.0±0.2, and 12.2±0.2. In some embodiments, crystalline Form A of a sodium salt of Compound I is characterized by an X-ray powder diffractogram having a signal at two-theta values of 4.7±0.2, 4.9±0.2, 8.0±0.2, 8.3±0.2, 12.2±0.2, and 12.6±0.2.

In some embodiments, crystalline Form A of a sodium salt of Compound I is characterized by an X-ray powder diffractogram substantially similar to that in FIG. 8A.

In some embodiments, the present disclosure provides crystalline Form A of a sodium salt of Compound I prepared by a process comprising reacting Compound I with a sodium base. In some embodiments, the sodium base is chosen from sodium hydroxide, sodium t-butoxide, sodium acetate, sodium bicarbonate, sodium carbonate, sodium methoxide, and sodium ethoxide. In some embodiments, the sodium base is sodium hydroxide. In some embodiments, the sodium base is sodium methoxide. In some embodiments, the reaction is performed at room temperature. In some embodiments, Compound I in acetonitrile solution is reacted with a sodium base in solvent system comprising water. In some embodiments, Compound I in acetonitrile solution is reacted with a sodium base in solvent system comprising water at room temperature.

In some embodiments, the present disclosure provides methods for preparing crystalline Form A of a sodium salt of Compound I comprising reacting Compound I with a sodium base. In some embodiments, the sodium base is sodium hydroxide. In some embodiments, the sodium base is sodium methoxide. In some embodiments, Compound I in acetonitrile solution is reacted with a sodium base in solvent system comprising water. In some embodiments, Compound I in acetonitrile solution is reacted with a sodium base in solvent system comprising water at room temperature. In some embodiments, the reaction is performed at room temperature.

Crystalline Form D of a Sodium Salt of Compound I

In some embodiments, the present disclosure provides crystalline Form D of a sodium salt of Compound I.

Figure 9A:
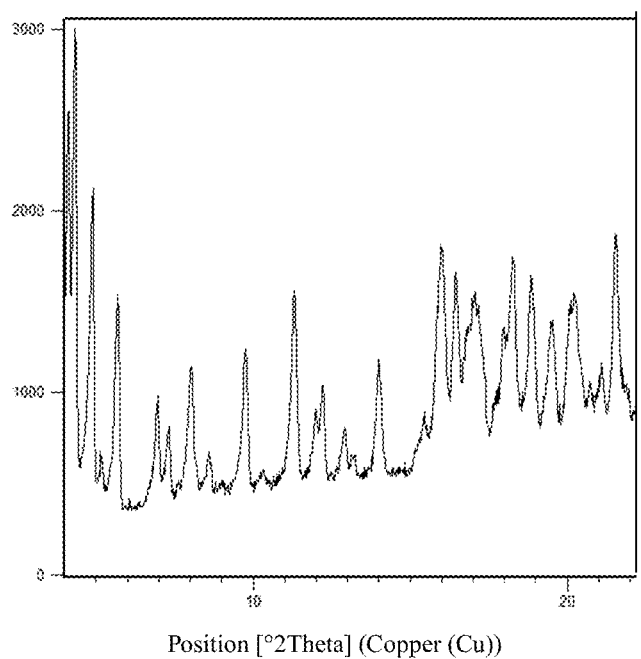
FIG. 9A shows a selection from an X-ray powder diffractogram of crystalline Form D of a sodium salt of Compound I.
Figure 9B:
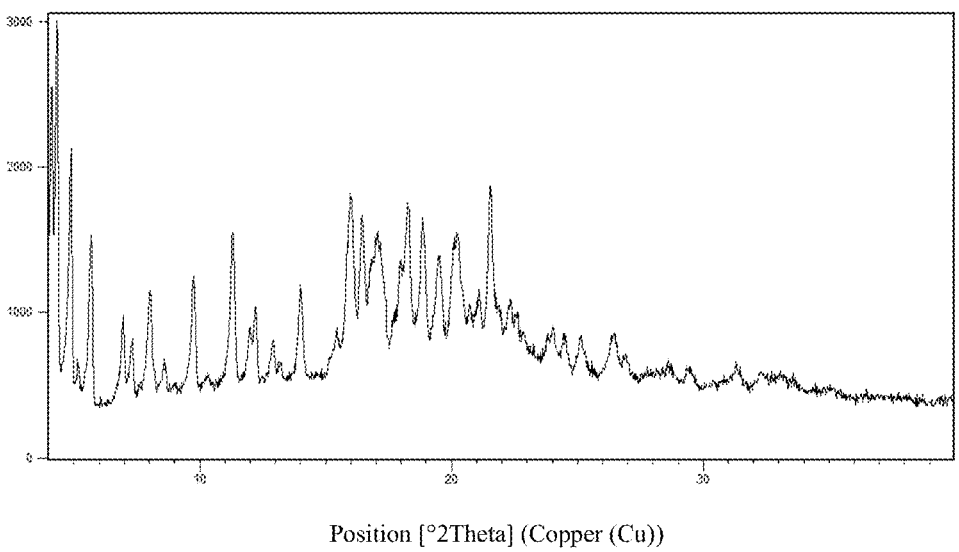
FIG. 9B shows a full scan view of an X-ray powder diffractogram of crystalline Form D of a sodium salt of Compound I.

FIG. 9A shows an X-ray powder diffractogram of crystalline Form D of a sodium salt of Compound I at ambient conditions.

In some embodiments, crystalline Form D of a sodium salt of Compound I is in substantially pure form. In some embodiments, crystalline Form D of a sodium salt of Compound I is characterized by an X-ray powder diffractogram generated by an X-ray powder diffraction analysis with an incident beam of Cu Kα radiation.

In some embodiments, crystalline Form D of a sodium salt of Compound I is characterized by an X-ray powder diffractogram having a signal at 4.9±0.2 degrees two-theta. In some embodiments, crystalline Form D of a sodium salt of Compound I is characterized by an X-ray powder diffractogram having a signal at 5.7±0.2 degrees two-theta. In some embodiments, crystalline Form D of a sodium salt of Compound I is characterized by an X-ray powder diffractogram having a signal at 7.0±0.2 degrees two-theta. In some embodiments, crystalline Form D of a sodium salt of Compound I is characterized by an X-ray powder diffractogram having a signal at 8.0±0.2 degrees two-theta. In some embodiments, crystalline Form D of a sodium salt of Compound I is characterized by an X-ray powder diffractogram having a signal at 9.8±0.2 degrees two-theta. In some embodiments, crystalline Form D of a sodium salt of Compound I is characterized by an X-ray powder diffractogram having a signal at 11.3±0.2 degrees two-theta. In some embodiments, crystalline Form D of a sodium salt of Compound I is characterized by an X-ray powder diffractogram having a signal at 12.2±0.2 degrees two-theta. In some embodiments, crystalline Form D of a sodium salt of Compound I is characterized by an X-ray powder diffractogram having a signal at 14.0±0.2 degrees two-theta. In some embodiments, crystalline Form D of a sodium salt of Compound I is characterized by an X-ray powder diffractogram having a signal at 16.0±0.2 degrees two-theta.

In some embodiments, crystalline Form D of a sodium salt of Compound I is characterized by an X-ray powder diffractogram having a signal at two-theta values 4.9±0.2, 5.7±0.2, 7.0±0.2, 8.0±0.2, 9.8±0.2, 11.3±0.2, 12.2±0.2, 14.0±0.2, and 16.0±0.2. In some embodiments, crystalline Form D of a sodium salt of Compound I is characterized by an X-ray powder diffractogram having a signal at at least eight two-theta values chosen from 4.9±0.2, 5.7±0.2, 7.0±0.2, 8.0±0.2, 9.8±0.2, 11.3±0.2, 12.2±0.2, 14.0±0.2, and 16.0±0.2. In some embodiments, crystalline Form D of a sodium salt of Compound I is characterized by an X-ray powder diffractogram having a signal at at least seven two-theta values chosen from 4.9±0.2, 5.7±0.2, 7.0±0.2, 8.0±0.2, 9.8±0.2, 11.3±0.2, 12.2±0.2, 14.0±0.2, and 16.0±0.2. In some embodiments, crystalline Form D of a sodium salt of Compound I is characterized by an X-ray powder diffractogram having a signal at at least six two-theta values chosen from 4.9±0.2, 5.7±0.2, 7.0±0.2, 8.0±0.2, 9.8±0.2, 11.3±0.2, 12.2±0.2, 14.0±0.2, and 16.0±0.2. In some embodiments, crystalline Form D of a sodium salt of Compound I is characterized by an X-ray powder diffractogram having a signal at at least five two-theta values chosen from 4.9±0.2, 5.7±0.2, 7.0±0.2, 8.0±0.2, 9.8±0.2, 11.3±0.2, 12.2±0.2, 14.0±0.2, and 16.0±0.2. In some embodiments, crystalline Form D of a sodium salt of Compound I is characterized by an X-ray powder diffractogram having a signal at at least four two-theta values chosen from 4.9±0.2, 5.7±0.2, 7.0±0.2, 8.0±0.2, 9.8±0.2, 11.3±0.2, 12.2±0.2, 14.0±0.2, and 16.0±0.2. In some embodiments, crystalline Form D of a sodium salt of Compound I is characterized by an X-ray powder diffractogram having a signal at at least three two-theta values chosen from 4.9±0.2, 5.7±0.2, 7.0±0.2, 8.0±0.2, 9.8±0.2, 11.3±0.2, 12.2±0.2, 14.0±0.2, and 16.0±0.2. In some embodiments, crystalline Form D of a sodium salt of Compound I is characterized by an X-ray powder diffractogram having a signal at at least two two-theta values chosen from 4.9±0.2, 5.7±0.2, 7.0±0.2, 8.0±0.2, 9.8±0.2, 11.3±0.2, 12.2±0.2, 14.0±0.2, and 16.0±0.2. In some embodiments, crystalline Form D of a sodium salt of Compound I is characterized by an X-ray powder diffractogram having a signal at at least one two-theta value chosen from 4.9±0.2, 5.7±0.2, 7.0±0.2, 8.0±0.2, 9.8±0.2, 11.3±0.2, 12.2±0.2, 14.0±0.2, and 16.0±0.2.

In some embodiments, crystalline Form D of a sodium salt of Compound I is characterized by an X-ray powder diffractogram having a signal at at least three two-theta values chosen from 4.9±0.2, 5.7±0.2, 8.0±0.2, 9.8±0.2, 12.2±0.2, and 14.0±0.2. In some embodiments, crystalline Form D of a sodium salt of Compound I is characterized by an X-ray powder diffractogram having a signal at two-theta values of 4.9±0.2, 8.0±0.2, and 12.2±0.2. In some embodiments, crystalline Form D of a sodium salt of Compound I is characterized by an X-ray powder diffractogram having a signal at two-theta values of 4.9±0.2, 5.7±0.2, 8.0±0.2, 9.8±0.2, 12.2±0.2, and 14.0±0.2.

In some embodiments, crystalline Form D of a sodium salt of Compound I is characterized by an X-ray powder diffractogram substantially similar to that in FIG. 9A.

In some embodiments, the present disclosure provides crystalline Form D of a sodium salt of Compound I prepared by a process comprising heating a crystalline Form M or crystalline Form E of the sodium salt of Compound I at a temperature in a range from 280° C. to 300° C. under an anhydrous condition. In some embodiments, the anhydrous condition is under dry $N_2$ or $Ar_2$. In some embodiments, the anhydrous condition is under dry $N_2$. In some embodiments, crystalline Form M or crystalline Form E is heated to a temperature ranging from 290° C. to 295° C.

In some embodiments, the present disclosure provides methods of preparing crystalline Form D of a sodium salt Compound I comprising heating an ethanol solvate of the sodium salt of Compound I at a temperature in a range from 280° C. to 300° C. under an anhydrous condition. In some embodiments, the anhydrous condition is under dry $N_2$ or $Ar_2$. In some embodiments, the anhydrous condition is under dry $N_2$. In some embodiments, the heating temperature is 290° C.-295° C. Crystalline Form D of a sodium salt of Compound I was obtained by heating either Form M of a sodium salt of Compound I or Form E of a sodium salt of Compound I at 290° C. under dry $N_2$. In one example, 8 mg of crystalline Form E of a sodium salt of Compound I was heated in a TGA pan at a 10° C./minute rate from room temperature to 290° C. and was then maintained at 290° C. for 2 minutes under dry $N_2$ (50 mL per minute).

Crystalline Form M of a Sodium Salt of Compound I

Figure 10A:
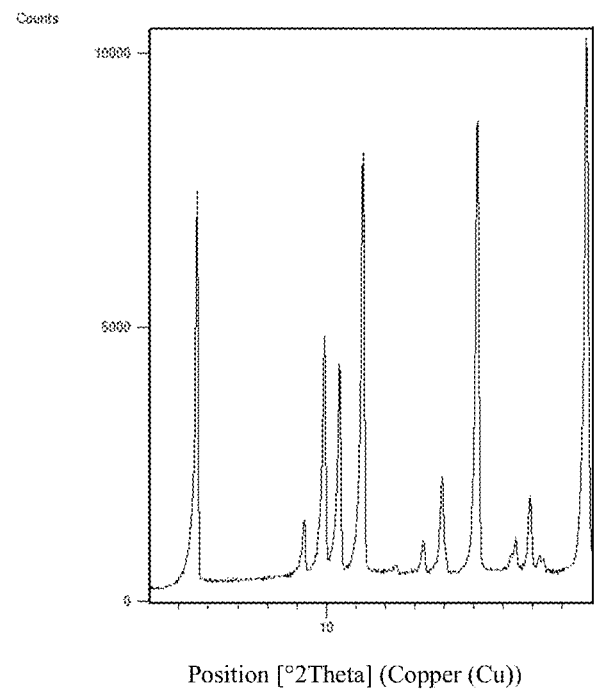
FIG. 10A shows a selection from an X-ray powder diffractogram of crystalline Form M of a sodium salt of Compound I.
Figure 10B:
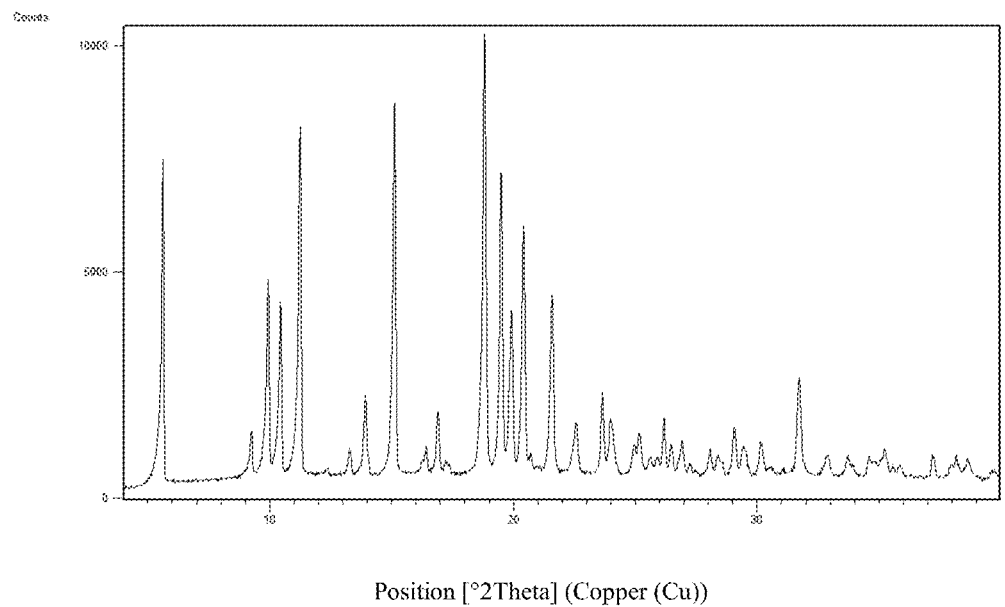
FIG. 10B shows a full scan view of an X-ray powder diffractogram of crystalline Form M of a sodium salt of Compound I.

In some embodiments, the present disclosure provides crystalline Form M of a sodium salt of Compound I:

FIG. 10A shows an X-ray powder diffractogram of crystalline Form M of a sodium salt of Compound I at ambient conditions.

Crystalline Form M is a solvate of a sodium salt of Compound I comprising up to 1 mole of solvent chosen from methanol, water, and mixtures thereof. Accordingly, crystalline Form M can comprise up to 1 mole of methanol, up to 1 mole of water, or up to 1 mole of a mixture of methanol and water.

In some embodiments, crystalline Form M of a sodium salt of Compound I is in substantially pure form. In some embodiments, crystalline Form M of a sodium salt of Compound I is characterized by an X-ray powder diffractogram generated by an X-ray powder diffraction analysis with an incident beam of Cu Kα radiation.

In some embodiments, crystalline Form M of a sodium salt of Compound I is characterized by an X-ray powder diffractogram having a signal at 9.3±0.2 degrees two-theta. In some embodiments, crystalline Form M of a sodium salt of Compound I is characterized by an X-ray powder diffractogram having a signal at 9.9±0.2 degrees two-theta. In some embodiments, crystalline Form M of a sodium salt of Compound I is characterized by an X-ray powder diffractogram having a signal at 10.5±0.2 degrees two-theta. In some embodiments, crystalline Form M of a sodium salt of Compound I is characterized by an X-ray powder diffractogram having a signal at 11.3±0.2 degrees two-theta. In some embodiments, crystalline Form M of a sodium salt of Compound I is characterized by an X-ray powder diffractogram having a signal at 13.9±0.2 degrees two-theta. In some embodiments, crystalline Form M of a sodium salt of Compound I is characterized by an X-ray powder diffractogram having a signal at 15.1±0.2 degrees two-theta. In some embodiments, crystalline Form M of a sodium salt of Compound I is characterized by an X-ray powder diffractogram having a signal at 18.8±0.2 degrees two-theta. In some embodiments, crystalline Form M of a sodium salt of Compound I is characterized by an X-ray powder diffractogram having a signal at 19.5±0.2 degrees two-theta. In some embodiments, crystalline Form M of a sodium salt of Compound I is characterized by an X-ray powder diffractogram having a signal at 19.9±0.2 degrees two-theta.

In some embodiments, crystalline Form M of a sodium salt of Compound I is characterized by an X-ray powder diffractogram having a signal at two-theta values of 9.3±0.2, 9.9±0.2, 10.5±0.2, 11.3±0.2, 13.9±0.2, 15.1±0.2, 18.8±0.2, 19.5±0.2, and 19.9±0.2. In some embodiments, crystalline Form M of a sodium salt of Compound I is characterized by an X-ray powder diffractogram having a signal at at least eight two-theta values chosen from 9.3±0.2, 9.9±0.2, 10.5±0.2, 11.3±0.2, 13.9±0.2, 15.1±0.2, 18.8±0.2, 19.5±0.2, and 19.9±0.2. In some embodiments, crystalline Form M of a sodium salt of Compound I is characterized by an X-ray powder diffractogram having a signal at at least seven two-theta values chosen from 9.3±0.2, 9.9±0.2, 10.5±0.2, 11.3±0.2, 13.9±0.2, 15.1±0.2, 18.8±0.2, 19.5±0.2, and 19.9±0.2. In some embodiments, crystalline Form M of a sodium salt of Compound I is characterized by an X-ray powder diffractogram having a signal at at least six two-theta values chosen from 9.3±0.2, 9.9±0.2, 10.5±0.2, 11.3±0.2, 13.9±0.2, 15.1±0.2, 18.8±0.2, 19.5±0.2, and 19.9±0.2. In some embodiments, crystalline Form M of a sodium salt of Compound I is characterized by an X-ray powder diffractogram having a signal at at least five two-theta values chosen from 9.3±0.2, 9.9±0.2, 10.5±0.2, 11.3±0.2, 13.9±0.2, 15.1±0.2, 18.8±0.2, 19.5±0.2, and 19.9±0.2. In some embodiments, crystalline Form M of a sodium salt of Compound I is characterized by an X-ray powder diffractogram having a signal at at least four two-theta values chosen from 9.3±0.2, 9.9±0.2, 10.5±0.2, 11.3±0.2, 13.9±0.2, 15.1±0.2, 18.8±0.2, 19.5±0.2, and 19.9±0.2. In some embodiments, crystalline Form M of a sodium salt of Compound I is characterized by an X-ray powder diffractogram having a signal at at least three two-theta values chosen from 9.3±0.2, 9.9±0.2, 10.5±0.2, 11.3±0.2, 13.9±0.2, 15.1±0.2, 18.8±0.2, 19.5±0.2, and 19.9±0.2. In some embodiments, crystalline Form M of a sodium salt of Compound I is characterized by an X-ray powder diffractogram having a signal at at least two two-theta values chosen from 9.3±0.2, 9.9±0.2, 10.5±0.2, 11.3±0.2, 13.9±0.2, 15.1±0.2, 18.8±0.2, 19.5±0.2, and 19.9±0.2. In some embodiments, crystalline Form M of a sodium salt of Compound I is characterized by an X-ray powder diffractogram having a signal at at least one two-theta value chosen from 9.3±0.2, 9.9±0.2, 10.5±0.2, 11.3±0.2, 13.9±0.2, 15.1±0.2, 18.8±0.2, 19.5±0.2, and 19.9±0.2.

In some embodiments, crystalline Form M of a sodium salt of Compound I is characterized by an X-ray powder diffractogram having a signal at at least three two-theta values chosen from 9.3±0.2, 9.9±0.2, 10.5±0.2, 11.3±0.2, 13.9±0.2, 15.1±0.2, 18.8±0.2, 19.5±0.2, and 19.9±0.2. In some embodiments, crystalline Form M of a sodium salt of Compound I is characterized by an X-ray powder diffractogram having a signal at at least three two-theta values chosen from 9.3±0.2, 9.9±0.2, 11.3±0.2, 13.9±0.2, 15.1±0.2, and 18.8±0.2.

In some embodiments, crystalline Form M of a sodium salt of Compound I is characterized by an X-ray powder diffractogram having a signal at two-theta values of 9.3±0.2, 11.3±0.2, and 15.1±0.2. In some embodiments, crystalline Form M of a sodium salt of Compound I is characterized by an X-ray powder diffractogram having a signal at two-theta values of 9.3±0.2, 9.9±0.2, 11.3±0.2, 13.9±0.2, 15.1±0.2, and 18.8±0.2.

In some embodiments, crystalline Form M of a sodium salt of Compound I is characterized by an X-ray powder diffractogram substantially similar to that in FIG. 10A.

In some embodiments, the present disclosure provides crystalline Form M of a sodium salt of Compound I prepared by a process comprising reacting Compound I with a sodium base in methanol. In some embodiments, the sodium base is chosen from sodium hydroxide, sodium t-butoxide, sodium acetate, sodium bicarbonate, sodium carbonate, sodium methoxide, and sodium ethoxide. In some embodiments, the sodium base is chosen from sodium hydroxide. In some embodiments, the sodium base is sodium methoxide. In some embodiments, Compound I in methanol is reacted with a sodium base, such as sodium hydroxide or sodium methoxide, to generate crystalline Form M of a sodium salt of Compound I. In some embodiments, the reaction is performed at room temperature.

In some embodiments, the present disclosure provides methods of preparing crystalline Form M of a sodium salt of Compound I comprising reacting Compound I with a sodium base in methanol. In some embodiments, the sodium base is chosen from sodium hydroxide, sodium t-butoxide, sodium acetate, sodium bicarbonate, sodium carbonate, sodium methoxide, and sodium ethoxide. In some embodiments, the sodium base is sodium methoxide. In some embodiments, Compound I in methanol is reacted with a sodium base, such as sodium hydroxide or sodium methoxide, to generate crystalline Form M of a sodium salt of Compound I. In some embodiments, the reaction is performed at room temperature.

Crystalline Form H of a Sodium Salt of Compound I

In some embodiments, the present disclosure provides crystalline Form H of a sodium salt of Compound I.

Figure 11A:
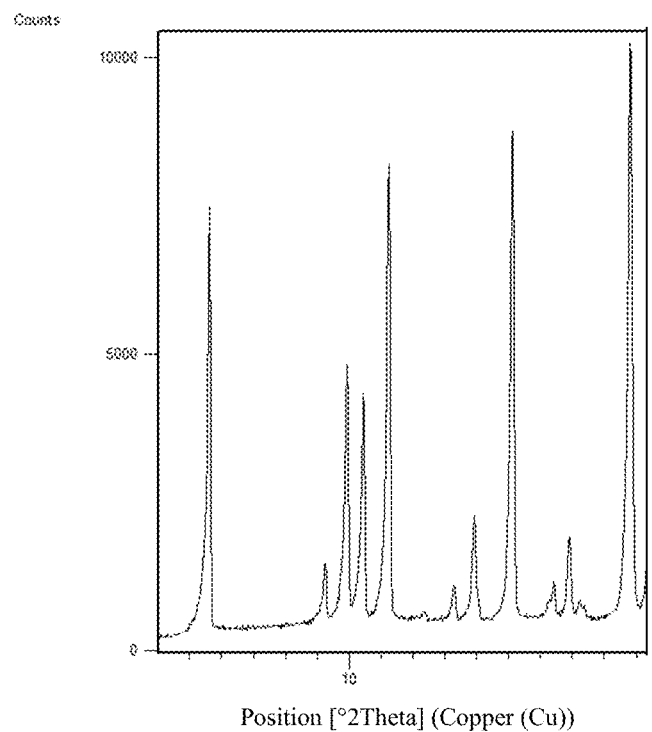
FIG. 11A shows a selection from an X-ray powder diffractogram of crystalline Form H of a sodium salt of Compound I.
Figure 11B:
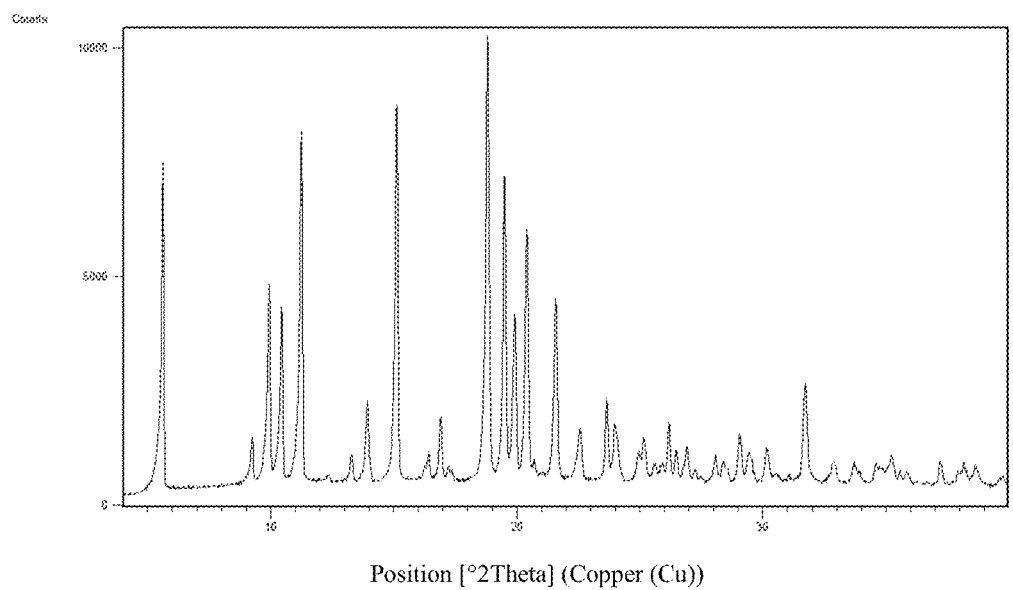
FIG. 11B shows a full-scan view of an X-ray powder diffractogram of crystalline Form H of a sodium salt of Compound I.

FIG. 11A shows an X-ray powder diffractogram of crystalline Form H of a sodium salt of Compound I at ambient conditions. In some embodiments, the present disclosure provides crystalline Form H of Compound I prepared by a process comprising de-solvating Form M of a sodium salt of Compound I disclosed herein.

In some embodiments, crystalline Form H of a sodium salt of Compound I is in substantially pure form. In some embodiments, crystalline Form H of a sodium salt of Compound I is characterized by an X-ray powder diffractogram generated by an X-ray powder diffraction analysis with an incident beam of Cu Kα radiation. In some embodiments, crystalline Form H of a sodium salt of Compound I is the methanol solvate, crystalline Form H of a sodium salt of Compound I.

In some embodiments, crystalline Form H of a sodium salt of Compound I is characterized by an X-ray powder diffractogram having a signal at 9.3±0.2 degrees two-theta. In some embodiments, crystalline Form H of a sodium salt of Compound I is characterized by an X-ray powder diffractogram having a signal at 9.9±0.2 degrees two-theta. In some embodiments, crystalline Form H of a sodium salt of Compound I is characterized by an X-ray powder diffractogram having a signal at 10.5±0.2 degrees two-theta. In some embodiments, crystalline Form H of a sodium salt of Compound I is characterized by an X-ray powder diffractogram having a signal at 11.3±0.2 degrees two-theta. In some embodiments, crystalline Form H of a sodium salt of Compound I is characterized by an X-ray powder diffractogram having a signal at 13.9±0.2 degrees two-theta. In some embodiments, crystalline Form H of a sodium salt of Compound I is characterized by an X-ray powder diffractogram having a signal at 15.1±0.2 degrees two-theta. In some embodiments, crystalline Form H of a sodium salt of Compound I is characterized by an X-ray powder diffractogram having a signal at 18.8±0.2 degrees two-theta. In some embodiments, crystalline Form H of a sodium salt of Compound I is characterized by an X-ray powder diffractogram having a signal at 19.5±0.2 degrees two-theta. In some embodiments, crystalline Form H of a sodium salt of Compound I is characterized by an X-ray powder diffractogram having a signal at 19.9±0.2 degrees two-theta.

In some embodiments, crystalline Form H of a sodium salt of Compound I is characterized by an X-ray powder diffractogram having a signal at two-theta values of 9.3±0.2, 9.9±0.2, 10.5±0.2, 11.3±0.2, 13.9±0.2, 15.1±0.2, 18.8±0.2, 19.5±0.2, and 19.9±0.2. In some embodiments, crystalline Form H of a sodium salt of Compound I is characterized by an X-ray powder diffractogram having a signal at at least eight two-theta values chosen from 9.3±0.2, 9.9±0.2, 10.5±0.2, 11.3±0.2, 13.9±0.2, 15.1±0.2, 18.8±0.2, 19.5±0.2, and 19.9±0.2. In some embodiments, crystalline Form H of a sodium salt of Compound I is characterized by an X-ray powder diffractogram having a signal at at least seven two-theta values chosen from 9.3±0.2, 9.9±0.2, 10.5±0.2, 11.3±0.2, 13.9±0.2, 15.1±0.2, 18.8±0.2, 19.5±0.2, and 19.9±0.2. In some embodiments, crystalline Form H of a sodium salt of Compound I is characterized by an X-ray powder diffractogram having a signal at at least six two-theta values chosen from 9.3±0.2, 9.9±0.2, 10.5±0.2, 11.3±0.2, 13.9±0.2, 15.1±0.2, 18.8±0.2, 19.5±0.2, and 19.9±0.2. In some embodiments, crystalline Form H of a sodium salt of Compound I is characterized by an X-ray powder diffractogram having a signal at at least five two-theta values chosen from 9.3±0.2, 9.9±0.2, 10.5±0.2, 11.3±0.2, 13.9±0.2, 15.1±0.2, 18.8±0.2, 19.5±0.2, and 19.9±0.2. In some embodiments, crystalline Form H of a sodium salt of Compound I is characterized by an X-ray powder diffractogram having a signal at at least four two-theta values chosen from 9.3±0.2, 9.9±0.2, 10.5±0.2, 11.3±0.2, 13.9±0.2, 15.1±0.2, 18.8±0.2, 19.5±0.2, and 19.9±0.2. In some embodiments, crystalline Form H of a sodium salt of Compound I is characterized by an X-ray powder diffractogram having a signal at at least three two-theta values chosen from 9.3±0.2, 9.9±0.2, 10.5±0.2, 11.3±0.2, 13.9±0.2, 15.1±0.2, 18.8±0.2, 19.5±0.2, and 19.9±0.2. In some embodiments, crystalline Form H of a sodium salt of Compound I is characterized by an X-ray powder diffractogram having a signal at at least two two-theta values chosen from 9.3±0.2, 9.9±0.2, 10.5±0.2, 11.3±0.2, 13.9±0.2, 15.1±0.2, 18.8±0.2, 19.5±0.2, and 19.9±0.2. In some embodiments, crystalline Form H of a sodium salt of Compound I is characterized by an X-ray powder diffractogram having a signal at at least one two-theta value chosen from 9.3±0.2, 9.9±0.2, 10.5±0.2, 11.3±0.2, 13.9±0.2, 15.1±0.2, 18.8±0.2, 19.5±0.2, and 19.9±0.2.

In some embodiments, crystalline Form H of a sodium salt of Compound I is characterized by an X-ray powder diffractogram having a signal at at least three two-theta values chosen from 9.3±0.2, 9.9±0.2, 10.5±0.2, 11.3±0.2, 13.9±0.2, 15.1±0.2, 18.8±0.2, 19.5±0.2, and 19.9±0.2. In some embodiments, crystalline Form H of a sodium salt of Compound I is characterized by an X-ray powder diffractogram having a signal at at least three two-theta values chosen from 9.3±0.2, 9.9±0.2, 11.3±0.2, 13.9±0.2, 15.1±0.2, and 18.8±0.2.

In some embodiments, crystalline Form H of a sodium salt of Compound I is characterized by an X-ray powder diffractogram having a signal at two-theta values of 9.3±0.2, 11.3±0.2, and 15.1±0.2. In some embodiments, crystalline Form H of a sodium salt of Compound I is characterized by an X-ray powder diffractogram having a signal at two-theta values of 9.3±0.2, 9.9±0.2, 11.3±0.2, 13.9±0.2, 15.1±0.2, and 18.8±0.2.

In some embodiments, crystalline Form H of a sodium salt of Compound I is characterized by an X-ray powder diffractogram substantially similar to that in FIG. 11A.

In some embodiments, the present disclosure provides crystalline Form H of a sodium salt of Compound I prepared by a process comprising de-solvating crystalline Form M or Form E of a sodium salt of Compound I in the presence of at least one source of water. In some embodiments, the at least one source of water is water. In some embodiments, the at least one source of water is moisture in air.

In some embodiments, the present disclosure provides methods of preparing crystalline Form H of a sodium salt of Compound I comprising de-solvating crystalline Form M or Form E of a sodium salt of Compound I in the presence of at least one source of water. In some embodiments, the at least one source of water is water. In some embodiments, the at least one source of water is moisture in air.

Crystalline Form E of a Sodium Salt of Compound I

In some embodiments, the present disclosure provides crystalline Form E of a sodium salt of Compound I.

Figure 12A:
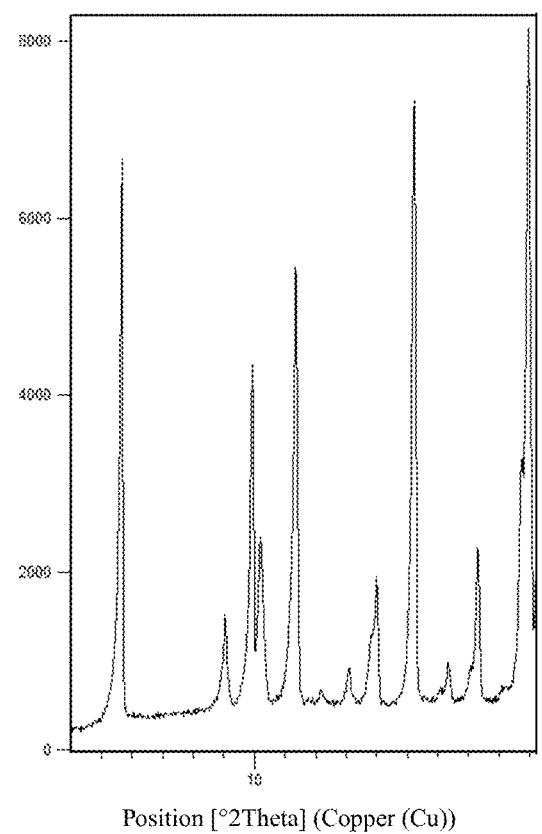
FIG. 12A shows a selection from an X-ray powder diffractogram of crystalline Form E of a sodium salt of Compound I.
Figure 12B:
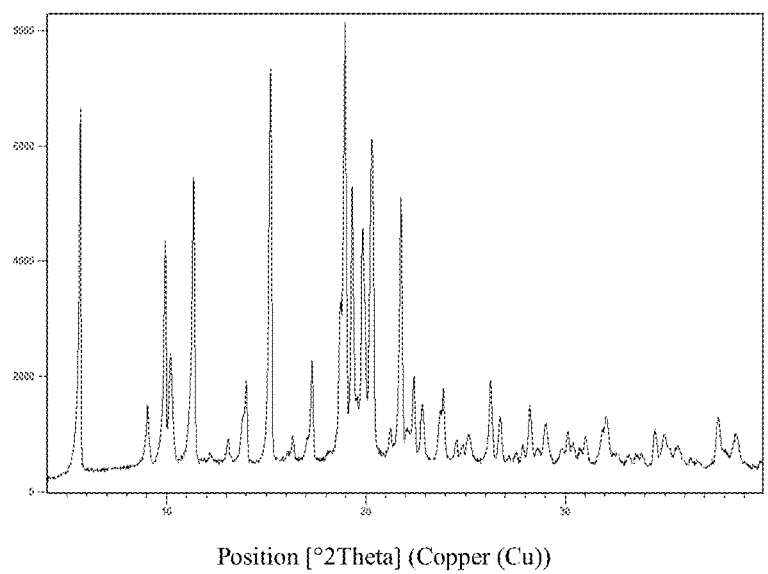
FIG. 12B shows a full scan view of an X-ray powder diffractogram of crystalline Form E of a sodium salt of Compound I.

FIG. 12A shows an X-ray powder diffractogram of crystalline Form E of a sodium salt of Compound I at ambient conditions.

Crystalline Form E is a solvate of a sodium salt of Compound I comprising up to 1 mole of solvent chosen from ethanol, water, and mixtures thereof. Accordingly, crystalline Form E can comprise up to 1 mole of ethanol, up to 1 mole of water, or up to 1 mole of a mixture of ethanol and water.

In some embodiments, crystalline Form E of a sodium salt of Compound I is in substantially pure form. In some embodiments, crystalline Form E of a sodium salt of Compound I is characterized by an X-ray powder diffractogram generated by an X-ray powder diffraction analysis with an incident beam of Cu Ku radiation.

In some embodiments, crystalline Form E of a sodium salt of Compound I is characterized by an X-ray powder diffractogram having a signal at 5.7±0.2 degrees two-theta. In some embodiments, crystalline Form E of a sodium salt of Compound I is characterized by an X-ray powder diffractogram having a signal at 9.0±0.2 degrees two-theta. In some embodiments, crystalline Form E of a sodium salt of Compound I is characterized by an X-ray powder diffractogram having a signal at 9.9±0.2 degrees two-theta. In some embodiments, crystalline Form E of a sodium salt of Compound I is characterized by an X-ray powder diffractogram having a signal at 11.4±0.2 degrees two-theta. In some embodiments, crystalline Form E of a sodium salt of Compound I is characterized by an X-ray powder diffractogram having a signal at 14.0±0.2 degrees two-theta. In some embodiments, crystalline Form E of a sodium salt of Compound I is characterized by an X-ray powder diffractogram having a signal at 15.2±0.2 degrees two-theta. In some embodiments, crystalline Form E of a sodium salt of Compound I is characterized by an X-ray powder diffractogram having a signal at 16.3±0.2 degrees two-theta. In some embodiments, crystalline Form E of a sodium salt of Compound I is characterized by an X-ray powder diffractogram having a signal at 17.3±0.2 degrees two-theta. In some embodiments, crystalline Form E of a sodium salt of Compound I is characterized by an X-ray powder diffractogram having a signal at 19.0±0.2 degrees two-theta.

In some embodiments, crystalline Form E of a sodium salt of Compound I is characterized by an X-ray powder diffractogram having a signal at 5.7±0.2 degrees two-theta. In some embodiments, crystalline Form E of a sodium salt of Compound I is characterized by an X-ray powder diffractogram having a signal at 9.0±0.2 degrees two-theta. In some embodiments, crystalline Form E of a sodium salt of Compound I is characterized by an X-ray powder diffractogram having a signal at 9.9±0.2 degrees two-theta. In some embodiments, crystalline Form E of a sodium salt of Compound I is characterized by an X-ray powder diffractogram having a signal at 10.2±0.2 degrees two-theta. In some embodiments, crystalline Form E of a sodium salt of Compound I is characterized by an X-ray powder diffractogram having a signal at 11.4±0.2 degrees two-theta. In some embodiments, crystalline Form E of a sodium salt of Compound I is characterized by an X-ray powder diffractogram having a signal at 14.0±0.2 degrees two-theta. In some embodiments, crystalline Form E of a sodium salt of Compound I is characterized by an X-ray powder diffractogram having a signal at 15.2±0.2 degrees two-theta. In some embodiments, crystalline Form E of a sodium salt of Compound I is characterized by an X-ray powder diffractogram having a signal at 16.3±0.2 degrees two-theta. In some embodiments, crystalline Form E of a sodium salt of Compound I is characterized by an X-ray powder diffractogram having a signal at 17.3±0.2 degrees two-theta. In some embodiments, crystalline Form E of a sodium salt of Compound I is characterized by an X-ray powder diffractogram having a signal at 19.0±0.2 degrees two-theta.

In some embodiments, crystalline Form E of a sodium salt of Compound I is characterized by an X-ray powder diffractogram having a signal at two-theta values of 5.7±0.2, 9.0±0.2, 9.9±0.2, 11.4±0.2, 14.0±0.2, 15.2±0.2, 16.3±0.2, 17.3±0.2, and 19.0±0.2. In some embodiments, crystalline Form E of a sodium salt of Compound I is characterized by an X-ray powder diffractogram having a signal at at least eight two-theta values chosen from 5.7±0.2, 9.0±0.2, 9.9±0.2, 11.4±0.2, 14.0±0.2, 15.2±0.2, 16.3±0.2, 17.3±0.2, and 19.0±0.2. In some embodiments, crystalline Form E of a sodium salt of Compound I is characterized by an X-ray powder diffractogram having a signal at at least seven two-theta values chosen from 5.7±0.2, 9.0±0.2, 9.9±0.2, 11.4±0.2, 14.0±0.2, 15.2±0.2, 16.3±0.2, 17.3±0.2, and 19.0±0.2. In some embodiments, crystalline Form E of a sodium salt of Compound I is characterized by an X-ray powder diffractogram having a signal at at least six two-theta values chosen from 5.7±0.2, 9.0±0.2, 9.9±0.2, 11.4±0.2, 14.0±0.2, 15.2±0.2, 16.3±0.2, 17.3±0.2, and 19.0±0.2. In some embodiments, crystalline Form E of a sodium salt of Compound I is characterized by an X-ray powder diffractogram having a signal at at least five two-theta values chosen from 5.7±0.2, 9.0±0.2, 9.9±0.2, 11.4±0.2, 14.0±0.2, 15.2±0.2, 16.3±0.2, 17.3±0.2, and 19.0±0.2. In some embodiments, crystalline Form E of a sodium salt of Compound I is characterized by an X-ray powder diffractogram having a signal at at least four two-theta values chosen from 5.7±0.2, 9.0±0.2, 9.9±0.2, 11.4±0.2, 14.0±0.2, 15.2±0.2, 16.3±0.2, 17.3±0.2, and 19.0±0.2. In some embodiments, crystalline Form E of a sodium salt of Compound I is characterized by an X-ray powder diffractogram having a signal at at least three two-theta values chosen from 5.7±0.2, 9.0±0.2, 9.9±0.2, 11.4±0.2, 14.0±0.2, 15.2±0.2, 16.3±0.2, 17.3±0.2, and 19.0±0.2. In some embodiments, crystalline Form E of a sodium salt of Compound I is characterized by an X-ray powder diffractogram having a signal at at least two two-theta values chosen from 5.7±0.2, 9.0±0.2, 9.9±0.2, 11.4±0.2, 14.0±0.2, 15.2±0.2, 16.3±0.2, 17.3±0.2, and 19.0±0.2. In some embodiments, crystalline Form E of a sodium salt of Compound I is characterized by an X-ray powder diffractogram having a signal at at least one two-theta value chosen from 5.7±0.2, 9.0±0.2, 9.9±0.2, 11.4±0.2, 14.0±0.2, 15.2±0.2, 16.3±0.2, 17.3±0.2, and 19.0±0.2.

In some embodiments, crystalline Form E of a sodium salt of Compound I is characterized by an X-ray powder diffractogram having a signal at two-theta values of 5.7±0.2, 9.0±0.2, 9.9±0.2, 10.2±0.2, 11.4±0.2, 14.0±0.2, 15.2±0.2, 16.3±0.2, 17.3±0.2, and 19.0±0.2. In some embodiments, crystalline Form E of a sodium salt of Compound I is characterized by an X-ray powder diffractogram having a signal at at least eight two-theta values chosen from 5.7±0.2, 9.0±0.2, 9.9±0.2, 10.2±0.2, 11.4±0.2, 14.0±0.2, 15.2±0.2, 16.3±0.2, 17.3±0.2, and 19.0±0.2. In some embodiments, crystalline Form E of a sodium salt of Compound I is characterized by an X-ray powder diffractogram having a signal at at least seven two-theta values chosen from 5.7±0.2, 9.0±0.2, 9.9±0.2, 10.2±0.2, 11.4±0.2, 14.0±0.2, 15.2±0.2, 16.3±0.2, 17.3±0.2, and 19.0±0.2. In some embodiments, crystalline Form E of a sodium salt of Compound I is characterized by an X-ray powder diffractogram having a signal at at least six two-theta values chosen from 5.7±0.2, 9.0±0.2, 9.9±0.2, 10.2±0.2, 11.4±0.2, 14.0±0.2, 15.2±0.2, 16.3±0.2, 17.3±0.2, and 19.0±0.2. In some embodiments, crystalline Form E of a sodium salt of Compound I is characterized by an X-ray powder diffractogram having a signal at at least five two-theta values chosen from 5.7±0.2, 9.0±0.2, 9.9±0.2, 10.2±0.2, 11.4±0.2, 14.0±0.2, 15.2±0.2, 16.3±0.2, 17.3±0.2, and 19.0±0.2. In some embodiments, crystalline Form E of a sodium salt of Compound I is characterized by an X-ray powder diffractogram having a signal at at least four two-theta values chosen from 5.7±0.2, 9.0±0.2, 9.9±0.2, 10.2±0.2, 11.4±0.2, 14.0±0.2, 15.2±0.2, 16.3±0.2, 17.3±0.2, and 19.0±0.2. In some embodiments, crystalline Form E of a sodium salt of Compound I is characterized by an X-ray powder diffractogram having a signal at at least three two-theta values chosen from 5.7±0.2, 9.0±0.2, 9.9±0.2, 10.2±0.2, 11.4±0.2, 14.0±0.2, 15.2±0.2, 16.3±0.2, 17.3±0.2, and 19.0±0.2. In some embodiments, crystalline Form E of a sodium salt of Compound I is characterized by an X-ray powder diffractogram having a signal at at least two two-theta values chosen from 5.7±0.2, 9.0±0.2, 9.9±0.2, 10.2±0.2, 11.4±0.2, 14.0±0.2, 15.2±0.2, 16.3±0.2, 17.3±0.2, and 19.0±0.2. In some embodiments, crystalline Form E of a sodium salt of Compound I is characterized by an X-ray powder diffractogram having a signal at at least one two-theta value chosen from 5.7±0.2, 9.0±0.2, 9.9±0.2, 10.2±0.2, 11.4±0.2, 14.0±0.2, 15.2±0.2, 16.3±0.2, 17.3±0.2, and 19.0±0.2. In some embodiments, crystalline Form E of a sodium salt of Compound I is characterized by an X-ray powder diffractogram having a signal at at least one two-theta value chosen from 5.7±0.2, 9.0±0.2, 10.0±0.2, 10.2±0.2, 11.4±0.2, 14.0±0.2, 15.2±0.2, 16.3±0.2, 17.3±0.2, and 19.0±0.2.

In some embodiments, crystalline Form E of a sodium salt of Compound I is characterized by an X-ray powder diffractogram having a signal at at least three two-theta values chosen from 5.7±0.2, 9.9±0.2, 11.4±0.2, 15.2±0.2, 17.3±0.2, and 19.0 ±0.2. In some embodiments, crystalline Form E of a sodium salt of Compound I is characterized by an X-ray powder diffractogram having a signal at two-theta values of 11.4±0.2, 15.2±0.2, and 19.0±0.2. In some embodiments, crystalline Form E of a sodium salt of Compound I is characterized by an X-ray powder diffractogram having a signal at two-theta values of 5.7±0.2, 9.9±0.2, 11.4±0.2, 15.2±0.2, 17.3±0.2, and 19.0±0.2.

In some embodiments, crystalline Form E of a sodium salt of Compound I is characterized by an X-ray powder diffractogram substantially similar to that in FIG. 12A.

In some embodiments, the present disclosure provides crystalline Form E of a sodium salt of Compound I prepared by a process comprising reacting Compound I with a sodium base in ethanol. In some embodiments, the sodium base is chosen from sodium hydroxide, sodium t-butoxide, sodium acetate, sodium bicarbonate, sodium carbonate, sodium methoxide, and sodium ethoxide. In some embodiments, the sodium base is sodium hydroxide. In some embodiments, the sodium base is sodium methoxide. In some embodiments, Compound I in ethanol is reacted with a sodium base, such as sodium hydroxide or sodium methoxide, to generate crystalline Form E of a sodium salt of Compound I. In some embodiments, the reaction is performed at room temperature.

In some embodiments, the present disclosure provides methods of preparing crystalline Form E of a sodium salt of Compound I comprising reacting Compound I with a sodium base in ethanol. In some embodiments, the sodium base is chosen from sodium hydroxide, sodium t-butoxide, sodium acetate, sodium bicarbonate, sodium carbonate, sodium methoxide, and sodium ethoxide. In some embodiments, the sodium base is sodium hydroxide. In some embodiments, the sodium base is sodium methoxide. In some embodiments, Compound I in ethanol is reacted with a sodium base, such as sodium hydroxide or sodium methoxide, to generate crystalline Form E of a sodium salt of Compound I. In some embodiments, the reaction is performed at room temperature.

Crystalline Form A of Compound I

In some embodiments, the present disclosure provides crystalline Form A of Compound I.

Figure 13A:
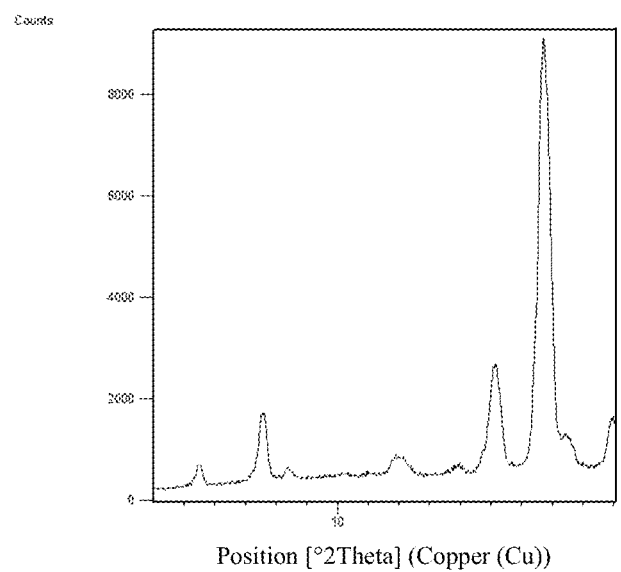
FIG. 13A shows a selection from an X-ray powder diffractogram of crystalline Form A of Compound I.
Figure 13B:
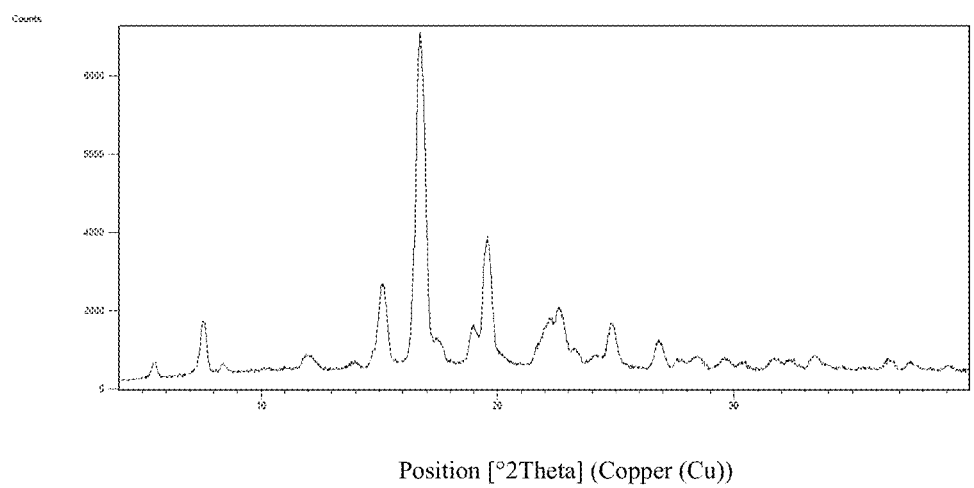
FIG. 13B shows a full scan view of an X-ray powder diffractogram of crystalline Form A of Compound I.

FIG. 13A shows an X-ray powder diffractogram of crystalline Form A of Compound I at ambient conditions.

In some embodiments, the present disclosure provides crystalline Form A of Compound I prepared by a process comprising de-solvating a methanol or ethanol solvate of crystalline Form A of Compound I. In some embodiments, the present disclosure provides crystalline Form A of Compound I prepared by a process comprising de-solvating a methanol solvate of crystalline Form A of Compound I. In some embodiments, the present disclosure provides crystalline Form A of Compound I prepared by a process comprising de-solvating an ethanol solvate of crystalline Form A of Compound I.

In some embodiments, crystalline Form A of Compound I is in substantially pure form. In some embodiments, crystalline Form A of Compound I is characterized by an X-ray powder diffractogram generated by an X-ray powder diffraction analysis with an incident beam of Cu Kα radiation.

In some embodiments, crystalline Form A of Compound I is characterized by an X-ray powder diffractogram wherein one or more of the signals may shift from batch to batch. As would be recognized by one of ordinary skill in the art, this is likely due to the collapse of the solvate structure from which crystalline Form A of Compound I is produced.

In some embodiments, crystalline Form A of Compound I is characterized by an X-ray powder diffractogram having a signal ranging from 5.3±0.2 to 5.5±0.2 degrees two-theta. In some embodiments, crystalline Form A of Compound I is characterized by an X-ray powder diffractogram having a signal ranging from 7.2±0.2 to 7.5±0.2 degrees two-theta. In some embodiments, crystalline Form A of Compound I is characterized by an X-ray powder diffractogram having a signal ranging from 11.8±0.2 to 12.2±0.2 degrees two-theta. In some embodiments, crystalline Form A of Compound I is characterized by an X-ray powder diffractogram having a signal ranging from 14.7±0.2 to 15.0±0.2 degrees two-theta. In some embodiments, crystalline Form A of Compound I is characterized by an X-ray powder diffractogram having a signal ranging from 16.7±0.2 to 17.1±0.2 degrees two-theta. In some embodiments, crystalline Form A of Compound I is characterized by an X-ray powder diffractogram having a signal ranging from 17.4±0.2 to 17.7±0.2 degrees two-theta. In some embodiments, crystalline Form A of Compound I is characterized by an X-ray powder diffractogram having a signal ranging from 18.5±0.2 to 18.8±0.2 degrees two-theta. In some embodiments, crystalline Form A of Compound I is characterized by an X-ray powder diffractogram having a signal ranging from 19.5±0.2 to 19.8±0.2 degrees two-theta.

In some embodiments, crystalline Form A of Compound I is characterized by an X-ray powder diffractogram having a signal ranging from 5.3±0.2 to 5.5±0.2, from 7.2±0.2 to 7.5±0.2, from 11.8±0.2 to 12.2±0.2, from 14.7±0.2 to 15.0±0.2, from 16.7±0.2 to 17.1±0.2, from 17.4±0.2 to 17.7±0.2, from 18.5±0.2 to 18.8±0.2, and from 19.5±0.2 to 19.8±0.2 degrees two-theta.

In some embodiments, crystalline Form A of Compound I is characterized by an X-ray powder diffractogram having a signal at at least eight of the following ranges from 5.3±0.2 to 5.5±0.2, from 7.2±0.2 to 7.5±0.2, from 11.8±0.2 to 12.2±0.2, from 14.7±0.2 to 15.0±0.2, from 16.7±0.2 to 17.1±0.2, from 17.4±0.2 to 17.7±0.2, from 18.5±0.2 to 18.8±0.2, and from 19.5±0.2 to 19.8±0.2 degrees two-theta.

In some embodiments, crystalline Form A of Compound I is characterized by an X-ray powder diffractogram having a signal at at least seven of the following ranges chosen from: from 5.3±0.2 to 5.5±0.2, from 7.2±0.2 to 7.5±0.2, from 11.8±0.2 to 12.2±0.2, from 14.7±0.2 to 15.0±0.2, from 16.7±0.2 to 17.1±0.2, from 17.4±0.2 to 17.7±0.2, from 18.5±0.2 to 18.8±0.2, and from 19.5±0.2 to 19.8±0.2 degrees two-theta. In some embodiments, crystalline Form A of Compound I is characterized by an X-ray powder diffractogram having a signal at at least six of the following ranges chosen from: from 5.3±0.2 to 5.5±0.2, from 7.2±0.2 to 7.5±0.2, from 11.8±0.2 to 12.2±0.2, from 14.7±0.2 to 15.0±0.2, from 16.7±0.2 to 17.1±0.2, from 17.4±0.2 to 17.7±0.2, from 18.5±0.2 to 18.8±0.2, and from 19.5±0.2 to 19.8±0.2 degrees two-theta.

In some embodiments, crystalline Form A of Compound I is characterized by an X-ray powder diffractogram having a signal at at least five of the following ranges chosen from: from 5.3±0.2 to 5.5±0.2, from 7.2±0.2 to 7.5±0.2, from 11.8±0.2 to 12.2±0.2, from 14.7±0.2 to 15.0±0.2, from 16.7±0.2 to 17.1±0.2, from 17.4±0.2 to 17.7±0.2, from 18.5±0.2 to 18.8±0.2, and from 19.5±0.2 to 19.8±0.2 degrees two-theta.

In some embodiments, crystalline Form A of Compound I is characterized by an X-ray powder diffractogram having a signal at at least four of the following ranges chosen from: from 5.3±0.2 to 5.5±0.2, from 7.2±0.2 to 7.5±0.2, from 11.8±0.2 to 12.2±0.2, from 14.7±0.2 to 15.0±0.2, from 16.7±0.2 to 17.1±0.2, from 17.4±0.2 to 17.7±0.2, from 18.5±0.2 to 18.8±0.2, and from 19.5±0.2 to 19.8±0.2 degrees two-theta.

In some embodiments, crystalline Form A of Compound I is characterized by an X-ray powder diffractogram having a signal at at least three of the following ranges chosen from: from 5.3±0.2 to 5.5±0.2, from 7.2±0.2 to 7.5±0.2, from 11.8±0.2 to 12.2±0.2, from 14.7±0.2 to 15.0±0.2, from 16.7±0.2 to 17.1±0.2, from 17.4±0.2 to 17.7±0.2, from 18.5±0.2 to 18.8±0.2, and from 19.5±0.2 to 19.8±0.2 degrees two-theta.

In some embodiments, crystalline Form A of Compound I is characterized by an X-ray powder diffractogram having a signal at at least two of the following ranges chosen from: from 5.3±0.2 to 5.5±0.2, from 7.2±0.2 to 7.5±0.2, from 11.8±0.2 to 12.2±0.2, from 14.7±0.2 to 15.0±0.2, from 16.7±0.2 to 17.1±0.2, from 17.4±0.2 to 17.7±0.2, from 18.5±0.2 to 18.8±0.2, and from 19.5±0.2 to 19.8±0.2 degrees two-theta.

In some embodiments, crystalline Form A of Compound I is characterized by an X-ray powder diffractogram having a signal at at least one of the following ranges chosen from: from 5.3±0.2 to 5.5±0.2, from 7.2±0.2 to 7.5±0.2, from 11.8±0.2 to 12.2±0.2, from 14.7±0.2 to 15.0±0.2, from 16.7±0.2 to 17.1±0.2, from 17.4±0.2 to 17.7±0.2, from 18.5±0.2 to 18.8±0.2, and from 19.5±0.2 to 19.8±0.2 degrees two-theta.

In some embodiments, crystalline Form A of Compound I is characterized by an X-ray powder diffractogram having a signal at at least three two-theta values chosen from 5.5±0.2, 7.6±0.2, 15.1±0.2, 16.7±0.2, 18.9±0.2, and 19.6±0.2. In some embodiments, crystalline Form A of Compound I is characterized by an X-ray powder diffractogram having a signal at three two-theta values of 7.6±0.2, 15.1±0.2, and 16.7±0.2. In some embodiments, crystalline Form A of Compound I is characterized by an X-ray powder diffractogram having a signal at two-theta values of 5.5±0.2, 7.6±0.2, 15.1±0.2, 16.7±0.2, 18.9±0.2, and 19.6±0.2.

In some embodiments, crystalline Form A of Compound I is characterized by an X-ray powder diffractogram substantially similar to that in FIG. 13A. In some embodiments, the present disclosure provides methods of preparing crystalline Form A of Compound I comprising de-solvating at least one solvate of Compound I chosen from ethanol solvates of Compound I and methanol solvates of Compound I.

Solvates

In some embodiments, the present disclosure provides at least one solvate of Compound I chosen from 1,4-dioxane solvates, 2-methyl tetrahydrofuran solvates, ethanol solvates, nitromethane solvates, 1-propanol solvates, tetrahydrofuran solvates, toluene solvates, pyridine solvates, chlorobenzene solvates, diethyl ether solvates, 2-propanol solvates, 2-butanol solvates, hexane solvates, heptane solvates, ethyl acetate solvates, methanol solvates, dichloromethane solvates, acetone solvates, methyl tert-butyl ether solvates, n-butanol solvates, N-methyl-2-pyrrolidone solvates, and t-butanol solvates of Compound I. Such solvates of Compound I can be prepared by stirring Compound I in a relevant solvent.

In some embodiments, the present disclosure provides at least one solvate of a sodium salt of Compound I chosen from ethanol solvates and methanol solvates of a sodium salt of Compound I. Such solvates of Compound I can be prepared by stirring a sodium salt of Compound I in a relevant solvent or reacting Compound I with a sodium base in a relevant solvent. In some embodiments, ethanol solvates of a sodium salt of Compound I are prepared by reacting Compound I with a sodium base in ethanol. In some embodiments, methanol solvates of a sodium salt of Compound I are prepared by reacting Compound I with a sodium base in methanol. Examples of suitable sodium bases are as described above for crystalline Form M and Form E of a sodium salt of Compound I.

In some embodiments, the present disclosure provides at least one solvate of a potassium salt of Compound I chosen from 1-pentanol solvates, isopropyl acetate solvates, 1-propanol solvates, acetone solvates, acetonitrile solvates, 2-methyl tetrahydrofuran solvates, ethyl acetate solvates, methanol solvates, ethanol solvates, methyl tert-butyl ether solvates, and methyl ethyl ketone solvates of a potassium salt of Compound I. In some embodiments, a solvate of a potassium salt of Compound I is chosen from 1-pentanol solvates, isopropyl acetate solvates, acetone solvates, acetonitrile solvates, 2-methyl tetrahydrofuran solvates, ethyl acetate solvates, methyl tert-butyl ether solvates, and methyl ethyl ketone solvates of a potassium salt of Compound I. Such solvates of Compound I can be prepared by stirring a potassium salt of Compound I in a relevant solvent or reacting Compound I with a potassium base in a relevant solvent. In some embodiments, ethanol solvates of a potassium salt of Compound I are prepared by reacting Compound I with a potassium base in ethanol. In some embodiments, methanol solvates of a potassium salt of Compound I are prepared by reacting Compound I with a potassium base in methanol. Examples of suitable potassium bases are as described above for crystalline Form B of a potassium salt of Compound I.

Isotopically Enriched Compounds

In some embodiments, the disclosure also is directed to isotope-labelled compounds of the afore-mentioned compounds, which have the same structures as disclosed herein except that one or more atoms therein have been replaced by an atom or atoms having an atomic mass or mass number which differs from the atomic mass or mass number of the atom which usually occurs naturally (isotope labelled). Examples of isotopes which are commercially available and suitable for the disclosure include isotopes of hydrogen, carbon, nitrogen, oxygen, phosphorus, fluorine and chlorine, for example $^2$H, $^3$H, $^{13}$C, $^{14}$C, $^{15}$N, $^{18}$O, $^{17}$O, $^{31}$P, $^{32}$P, $^{35}$S, $^{18}$F and $^{36}$Cl, respectively.

The isotope-labelled compounds and salts can be used in a number of beneficial ways. They can be suitable for medicaments and/or various types of assays, such as substrate tissue distribution assays. For example, tritium ($^3$H)- and/or carbon-14 ($^{14}$C)-labelled compounds are particularly useful for various types of assays, such as substrate tissue distribution assays, due to relatively simple preparation and excellent detectability. For example, deuterium ($^2$H)-labelled ones are therapeutically useful with potential therapeutic advantages over the non-$^2$H-labelled compounds. In general, deuterium ($^2$H)-labelled compounds and salts can have higher metabolic stability as compared to those that are not isotope-labelled owing to the kinetic isotope effect described below. Higher metabolic stability translates directly into an increased in vivo half-life or lower dosages, which could be desired. The isotope-labelled compounds and salts can usually be prepared by carrying out the procedures disclosed in the synthesis schemes and the related description, in the example part and in the preparation part in the present text, replacing a non-isotope-labelled reactant by a readily available isotope-labelled reactant.

In some embodiments, the isotope-labelled compounds and salts are deuterium ($^2$H)-labelled ones. In some specific embodiments, the isotope-labelled compounds and salts are deuterium ($^2$H)-labelled, wherein one or more hydrogen atoms therein have been replaced by deuterium. In chemical structures, deuterium is represented as "$^2$H" or "D."

The deuterium ($^2$H)-labelled compounds and salts can manipulate the oxidative metabolism of the compound by way of the primary kinetic isotope effect. The primary kinetic isotope effect is a change of the rate for a chemical reaction that results from exchange of isotopic nuclei, which in turn is caused by the change in ground state energies necessary for covalent bond formation after this isotopic exchange. Exchange of a heavier isotope usually results in a lowering of the ground state energy for a chemical bond and thus causes a reduction in the rate-limiting bond breakage. If the bond breakage occurs in or in the vicinity of a saddle-point region along the coordinate of a multi-product reaction, the product distribution ratios can be altered substantially. For explanation: if deuterium is bonded to a carbon atom at a non-exchangeable position, rate differences of $k_M/k_D$=2-7 are typical. For a further discussion, see S. L. Harbeson and R. D. Tung, *Deuterium In Drug Discovery and Development*, Ann. Rep. Med. Chem. 2011, 46, 403-417; and T. G. Gant "Using deuterium in drug discovery: leaving the label in the drug" J. Med. Chem. 2014, 57, 3595-3611, relevant portions of which are independently incorporated herein by reference.

The concentration of the isotope(s) (e.g., deuterium) incorporated into the isotope-labelled compounds and salt of the disclosure may be defined by the isotopic enrichment factor. The term "isotopic enrichment factor" as used herein means the ratio between the isotopic abundance and the natural abundance of a specified isotope. In some embodiments, if a substituent in a compound of the disclosure is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

When discovering and developing therapeutic agents, the person skilled in the art attempts to optimize pharmacokinetic parameters while retaining desirable in vitro properties. It may be reasonable to assume that many compounds with poor pharmacokinetic profiles are susceptible to oxidative metabolism.

One of ordinary skill in the art would understand that deuteration of one or more metabolically labile positions on a compound or active metabolite may lead to improvement of one or more superior DMPK properties while maintaining biological activity as compared to the corresponding hydrogen analogs. The superior DMPK property or properties may have an impact on the exposure, half-life, clearance, metabolism, and/or even food requirements for optimal absorption of the drug product. Deuteration may also change the metabolism at other non-deuterated positions of the deuterated compound.

In some embodiments, the pharmaceutical compositions are a tablet. In some embodiments, the tablets are suitable for oral administration. In some embodiments, the tablets can be administered concurrently with, prior to, or subsequent to, at least one active pharmaceutical ingredients or medical procedures.

Exemplary Embodiments of Crystalline Forms of Compound I

Exemplary embodiments of crystalline forms of Compound I and pharmaceutically acceptable salts and solvates thereof include:

1. Crystalline Form B of a potassium salt of Compound I:

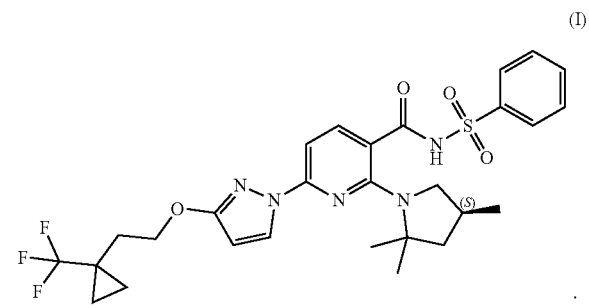

(I)

2. Crystalline Form B according to embodiment 1 in substantially pure form.
3. Crystalline Form B according to embodiment 1, characterized by an X-ray powder diffractogram having a signal at at least three two-theta values chosen from 5.8±0.2, 8.2±0.2, 9.6±0.2, 10.2±0.2, 13.8±0.2, 15.1±0.2, 16.3±0.2, 17.2±0.2, and 19.1±0.2.
4. Crystalline Form B according to embodiment 1, characterized by an X-ray powder diffractogram having a signal at at least three two-theta values chosen from 5.8±0.2, 8.2±0.2, 10.2±0.2, 13.8±0.2, 16.3±0.2, and 19.1±0.2.
5. Crystalline Form B according to embodiment 1, characterized by an X-ray powder diffractogram having a signal at three two-theta values of 5.8±0.2, 10.2±0.2, and 19.1±0.2.
6. Crystalline Form B according to embodiment 1, characterized by an X-ray powder diffractogram having a signal at six two-theta values of 5.8±0.2, 8.2±0.2, 10.2±0.2, 13.8±0.2, 16.3±0.2, and 19.1±0.2.
7. Crystalline Form B of embodiment 1, characterized by an X-ray powder diffractogram substantially similar to that in FIG. 1A.
8. Crystalline Form B of embodiment 1 having a unit cell characterized by three edges of 9.0±0.2 Å, 11.5±0.2 Å, and 31.0±0.2 Å.
9. Crystalline Form B of a potassium salt of Compound I prepared by a process comprising reacting Compound I with a potassium base.
10. A method of preparing Crystalline Form B of a potassium salt of Compound I, comprising reacting Compound I with a potassium base.
11. The method of embodiment 1, wherein said potassium base is KOH.
12. Crystalline Form C of a potassium salt/co-crystal of Compound I.
13. Crystalline Form C according to embodiment 12 in substantially pure form.
14. Crystalline Form C according to embodiment 12, characterized by an X-ray powder diffractogram having a signal at at least three two-theta values chosen from 3.7±0.2, 7.0±0.2, 7.4±0.2, 8.7±0.2, 9.5±0.2, 11.4±0.2, 11.5±0.2, 12.4±0.2, and 16.0±0.2.
15. Crystalline Form C according to embodiment 12, characterized by an X-ray powder diffractogram having a signal at at least three two-theta values chosen from 3.7±0.2, 7.0±0.2, 7.4±0.2, 9.5±0.2, 11.4±0.2, and 11.5±0.2.
16. Crystalline Form C according to embodiment 12, characterized by an X-ray powder diffractogram having a signal at three two-theta values of 3.7±0.2, 7.0±0.2, and 11.4±0.2.
17. Crystalline Form C according to embodiment 12, characterized by an X-ray powder diffractogram having a signal at six two-theta values of 3.7±0.2, 7.0±0.2, 7.4±0.2, 9.5±0.2, 11.4±0.2, and 11.5±0.2.
18. Crystalline Form C of embodiment 12, characterized by an X-ray powder diffractogram substantially similar to that in FIG. 7A.
19. Crystalline Form C of a potassium salt/co-crystal of Compound I prepared by a process comprising stirring a potassium salt of Compound I with a solvent system comprising at least one source of water.
20. A method of preparing Crystalline Form C of a potassium salt/co-crystal of Compound I, comprising stirring a potassium salt of Compound I with a solvent system comprising at least one source of water.
21. Crystalline Form A of a sodium salt of Compound I.
22. Crystalline Form A according to embodiment 21 in substantially pure form.
23. Crystalline Form A according to embodiment 21, characterized by an X-ray powder diffractogram having a signal at at least three two-theta values chosen from 4.7±0.2, 4.9±0.2, 6.3±0.2, 8.0±0.2, 8.3±0.2, 11.1±0.2, 12.2±0.2, 12.6±0.2, and 14.0±0.2.
24. Crystalline Form A according to embodiment 21, characterized by an X-ray powder diffractogram having a signal at at least three two-theta values chosen from 4.7±0.2, 4.9±0.2, 8.0±0.2, 8.3±0.2, 12.2±0.2, and 12.6±0.2.
25. Crystalline Form A according to embodiment 21, characterized by an X-ray powder diffractogram having a signal at three two-theta values of 4.7±0.2, 8.0±0.2, and 12.2±0.2.
26. Crystalline Form A according to embodiment 21, characterized by an X-ray powder diffractogram having a signal at six two-theta values of 4.7±0.2, 4.9±0.2, 8.0±0.2, 8.3±0.2, 12.2±0.2, and 12.6±0.2.
27. Crystalline Form A of embodiment 21, characterized by an X-ray powder diffractogram substantially similar to that in FIG. 8A.

28. A method of preparing crystalline Form A of a sodium salt of Compound I comprising reacting Compound I with a sodium base.

29. Crystalline Form D of a sodium salt of Compound I.

30. Crystalline Form D according to embodiment 29 in substantially pure form.

31. Crystalline Form D according to embodiment 29, characterized by an X-ray powder diffractogram having a signal at at least three two-theta values chosen from 4.9±0.2, 5.7±0.2, 7.0±0.2, 8.0±0.2, 9.8±0.2, 11.3±0.2, 12.2±0.2, 14.0±0.2, and 16.0±0.2.

32. Crystalline Form D according to embodiment 29, characterized by an X-ray powder diffractogram having a signal at at least three two-theta values chosen from 4.9±0.2, 5.7±0.2, 8.0±0.2, 9.8±0.2, 12.2±0.2, and 14.0±0.2.

33. Crystalline Form D according to embodiment 29, characterized by an X-ray powder diffractogram having a signal at three two-theta values of 4.9±0.2, 8.0±0.2, and 12.2±0.2.

34. Crystalline Form D according to embodiment 29, characterized by an X-ray powder diffractogram having a signal at six two-theta values of 4.9±0.2, 5.7±0.2, 8.0±0.2, 9.8±0.2, 12.2±0.2, and 14.0±0.2.

35. Crystalline Form D of embodiment 29, characterized by an X-ray powder diffractogram substantially similar to that in FIG. 9A.

36. A method of preparing crystalline Form D of a sodium salt Compound I, comprising heating a crystalline Form M or Form E of a sodium salt of Compound I at a temperature in a range from 280° C. to 300° C. under anhydrous conditions.

37. Crystalline Form M of a sodium salt of Compound I.

38. Crystalline Form M according to embodiment 37 in substantially pure form.

39. Crystalline Form M according to embodiment 37, characterized by an X-ray powder diffractogram having a signal at at least three two-theta values chosen from 9.3±0.2, 9.9±0.2, 10.5±0.2, 11.3±0.2, 13.9±0.2, 15.1±0.2, 18.8±0.2, 19.50±0.2, and 19.9±0.2.

40. Crystalline Form M according to embodiment 37, characterized by an X-ray powder diffractogram having a signal at at least three two-theta values chosen from 9.3±0.2, 9.9±0.2, 11.3±0.2, 13.9±0.2, 15.1±0.2, and 18.8±0.2.

41. Crystalline Form M according to embodiment 37, characterized by an X-ray powder diffractogram having a signal at three two-theta values of 9.3±0.2, 11.3±0.2, and 15.1±0.2.

42. Crystalline Form M according to embodiment 37, characterized by an X-ray powder diffractogram having a signal at six two-theta values of 9.3±0.2, 9.9±0.2, 11.3±0.2, 13.9±0.2, 15.1±0.2, and 18.8±0.2.

43. Crystalline Form M of embodiment 37, characterized by an X-ray powder diffractogram substantially similar to that in FIG. 10A.

44. A method of preparing crystalline Form M of a sodium salt of Compound I comprising reacting Compound I with a sodium base in methanol.

45. Crystalline Form A of Compound I.

46. Crystalline Form A according to embodiment 45 in substantially pure form.

47. Crystalline Form A according to embodiment 45, characterized by an X-ray powder diffractogram having a signal ranging from 5.3±0.2 to 5.5±0.2, from 7.2±0.2 to 7.5±0.2, from 11.8±0.2 to 12.2±0.2, from 14.7±0.2 to 15.0±0.2, from 16.7±0.2 to 17.1±0.2, from 17.4±0.2 to 17.7±0.2, from 18.5±0.2 to 18.8±0.2, and from 19.5±0.2 to 19.8±0.2 degrees two-theta.

48. Crystalline Form A according to embodiment 45, characterized by an X-ray powder diffractogram having at least three signals chosen from signals in the following two-theta value ranges: from 5.3±0.2 to 5.5±0.2, from 7.2±0.2 to 7.5±0.2, from 11.8±0.2 to 12.2±0.2, from 14.7±0.2 to 15.0±0.2, from 16.7±0.2 to 17.1±0.2, from 17.4±0.2 to 17.7±0.2, from 18.5±0.2 to 18.8±0.2, and from 19.5±0.2 to 19.8±0.2 degrees two-theta.

49. Crystalline Form A of embodiment 45, characterized by an X-ray powder diffractogram substantially similar to that in FIG. 13A.

50. A method of preparing crystalline Form A of Compound I comprising de-solvating at least one solvate of Compound I chosen from ethanol solvates of Compound I and methanol solvates of Compound I.

51. A crystalline form of Compound I prepared by de-solvating at least one solvate of Compound I chosen from ethanol solvates of Compound I and methanol solvates of Compound I.

52. Crystalline Form E of a sodium salt of Compound I.

53. Crystalline Form E according to embodiment 52 in substantially pure form.

54. Crystalline Form E according to embodiment 52, characterized by an X-ray powder diffractogram having a signal at at least three two-theta values chosen from 5.7±0.2, 9.1±0.2, 9.9±0.2, 11.4±0.2, 14.0±0.2, 15.2±0.2, 16.3±0.2, 17.3±0.2, and 19.0±0.2.

55. Crystalline Form E according to embodiment 52, characterized by an X-ray powder diffractogram having a signal at at least three two-theta values chosen from 5.7±0.2, 9.1±0.2, 9.9±0.2, 10.2±0.2, 11.4±0.2, 14.0±0.2, 15.2±0.2, 16.3±0.2, 17.3±0.2, and 19.0±0.2.

56. Crystalline Form E according to embodiment 52, characterized by an X-ray powder diffractogram having a signal at at least three two-theta values chosen from 5.7±0.2, 9.1±0.2, 10.0±0.2, 10.2±0.2, 11.4±0.2, 14.0±0.2, 15.2±0.2, 16.3±0.2, 17.3±0.2, and 19.0±0.2.

57. Crystalline Form E according to embodiment 52, characterized by an X-ray powder diffractogram having a signal at at least three two-theta values chosen from 5.7±0.2, 9.9±0.2, 11.4±0.2, 15.2±0.2, 17.3±0.2, and 19.0±0.2.

58. Crystalline Form E according to embodiment 52, characterized by an X-ray powder diffractogram having a signal at three two-theta values of 11.4±0.2, 15.2±0.2, and 19.0±0.2.

59. Crystalline Form E according to embodiment 52, characterized by an X-ray powder diffractogram having a signal at six two-theta values of 5.7±0.2, 9.9±0.2, 11.4±0.2, 15.2±0.2, 17.3±0.2, and 19.0±0.2.

60. Crystalline Form E of embodiment 52, characterized by an X-ray powder diffractogram substantially similar to that in FIG. 12A.

61. A method of preparing crystalline Form E of a sodium salt of Compound I comprising reacting Compound I with a sodium base in ethanol.

62. Crystalline Form H of a sodium salt of Compound I.

63. Crystalline Form H according to embodiment 62 in substantially pure form.

64. Crystalline Form H according to embodiment 62, characterized by an X-ray powder diffractogram having a signal at at least three two-theta values chosen from 9.3±0.2, 9.9±0.2, 10.5±0.2, 11.3±0.2, 13.9±0.2, 15.1±0.2, 18.8±0.2, 19.50±0.2, and 19.9±0.2.

65. Crystalline Form H according to embodiment 62, characterized by an X-ray powder diffractogram having a signal at at least three two-theta values chosen from 9.3±0.2, 9.9±0.2, 11.3±0.2, 13.9±0.2, 15.1±0.2, and 18.8±0.2.

66. Crystalline Form H according to embodiment 62, characterized by an X-ray powder diffractogram having a signal at three two-theta values of 9.3±0.2, 11.3±0.2, and 15.1±0.2.
67. Crystalline Form H according to embodiment 62, characterized by an X-ray powder diffractogram having a signal at six two-theta values of 9.3±0.2, 9.9±0.2, 11.3±0.2, 13.9±0.2, 15.1±0.2, and 18.8±0.2.
68. A method of preparing crystalline Form H of a sodium salt of Compound I comprising de-solvating crystalline Form M or Form E of a sodium salt of Compound I or crystalline Form E of a sodium salt of Compound I in the presence of one source of water.
69. A pharmaceutical formulation comprising at least one crystalline form according to any one of embodiments 1-68 and a pharmaceutically acceptable carrier.
70. A method of treating cystic fibrosis comprising administering to a patient in need thereof at least one crystalline form according to any one of embodiments 1-68 or pharmaceutical composition of embodiment 69.
71. At least one solvate of Compound I chosen from 1,4-dioxane solvates, 2-methyl tetrahydrofuran solvates, ethanol solvates, nitromethane solvates, 1-propanol solvates, tetrahydrofuran solvates, toluene solvates, pyridine solvates, chlorobenzene solvates, diethyl ether solvates, 2-propanol solvates, 2-butanol solvates, hexane solvates, heptane solvates, ethyl acetate solvates, methanol solvates, dichloromethane solvates, acetone solvates, methyl tert-butyl ether solvates, n-butanol solvates, N-methyl-2-pyrrolidone solvates, and t-butanol solvates of Compound I.
72. At least one solvate of a sodium salt Compound I chosen from ethanol solvates and methanol solvates of the sodium salt of Compound I.
73. At least one solvate of a potassium salt Compound I chosen from 1-pentanol solvates, isopropyl acetate solvates, 1-propanol solvates, acetone solvates, acetonitrile solvates, 2-methyl tetrahydrofuran solvates, ethyl acetate solvates, methanol solvates, ethanol solvates, methyl tert-butyl ether solvates, and methyl ethyl ketone solvates of a potassium salt of Compound I.

Compositions

In some embodiments, the present disclosure provides compositions comprising at least one crystalline form of Compound I and pharmaceutically acceptable salts thereof disclosed herein and a pharmaceutically acceptable carrier. In some embodiments, the compositions of the invention comprise at least one crystalline form of salt/co-crystal of Compound I disclosed herein and a pharmaceutically acceptable carrier. In some embodiments, these compositions comprise one or more additional CFTR modulating agents.

In some embodiments, the pharmaceutical compositions disclosed herein comprise a potassium salt of Compound I (in some embodiments, potassium salt crystalline Form B), either as a mixture with other forms (crystalline and/or amorphous) or a substantially pure form. In some embodiments, the pharmaceutical compositions disclosed herein comprise substantially pure crystalline Form B of a potassium salt of Compound I.

In some embodiments, the pharmaceutical compositions disclosed herein comprise crystalline Form C of a potassium salt/co-crystal of Compound I, either as a mixture with other forms (crystalline and/or amorphous) or a substantially pure form. In some embodiments, the pharmaceutical compositions disclosed herein comprise substantially pure crystalline Form C of a potassium salt/co-crystal of Compound I.

In some embodiments, the pharmaceutical compositions disclosed herein comprise a potassium salt of Compound I (in some embodiments, potassium salt crystalline Form B), either alone or in combination with one or more CFTR modulating agents. In some embodiments, the pharmaceutical composition comprises a potassium salt of Compound I (in some embodiments, potassium salt crystalline Form B), in combination with Compound II and optionally one or more additional CFTR modulating agents. In some embodiments, the pharmaceutical composition comprises a potassium salt of Compound I (in some embodiments, potassium salt crystalline Form B) in combination with Compound III and optionally one or more additional CFTR modulating agents. In some embodiments, the pharmaceutical compositions disclosed herein comprise a potassium salt of Compound I (in some embodiments, potassium salt crystalline Form B) in combination with Compound II and/or Compound III or III-d.

Solid Dispersions

In some embodiments, the pharmaceutical compositions disclosed herein comprise a potassium salt of Compound I (in some embodiments, potassium salt crystalline Form B), either as a mixture with other forms (crystalline and/or amorphous) or a substantially pure form together with a first solid dispersion and/or a second solid dispersion. In some embodiments, the first solid dispersion is a spray dried dispersion comprising Compound II. In some embodiments, the second solid dispersion is selected from a spray-dried dispersion comprising Compound III or Compound III-d. In some embodiments, the first solid dispersion is a spray dried dispersion comprising Compound II and the second solid dispersion is a spray dried dispersion comprising Compound III or Compound III-d.

In some embodiments, each of the first and second solid dispersions, such as the first and second spray dried dispersions, independently comprises a plurality of particles having a mean particle diameter of 5 to 100 microns. In some embodiments, each of the first and second solid dispersions, such as the first and second spray dried dispersions, independently comprises a plurality of particles having a mean particle diameter of 5 to 30 microns. In some embodiments, each of the first and second solid dispersions, such as the first and second spray dried dispersions, independently comprises a plurality of particles having a mean particle diameter of 15 microns.

In some embodiments, the first solid dispersions and the first spray dried dispersions of the disclosure independently comprises substantially amorphous Compound II. In some embodiments, the second solid dispersions and the second spray dried dispersions of the disclosure independently comprises substantially amorphous Compound III or Compound III-d.

In some embodiments, the solid dispersions and the spray dried dispersions of the disclosure can comprise other excipients, such as polymers and/or surfactants. Any suitable polymers and surfactants known in the art can be used in the disclosure. Certain exemplary polymers and surfactants are as described below.

Solid dispersions of any one of Compounds II, Compound III and Compound III-d may be prepared by any suitable method know in the art, e.g., spray drying, lyophilizing, hot melting, or cyrogrounding/cryomilling techniques. For example, see WO2015/160787. Typically such spray drying, lyophilizing, hot melting or cyrogrounding/cryomilling techniques generates an amorphous form of API (e.g., Compound II or Compound III, or Compound III-d).

Spray drying is a process that converts a liquid feed to a dried particulate form. Optionally, a secondary drying process such as fluidized bed drying or vacuum drying may be used to reduce residual solvents to pharmaceutically acceptable levels. Typically, spray drying involves contacting a highly dispersed liquid suspension or solution, and a sufficient volume of hot gas to produce evaporation and drying of the liquid droplets. The preparation to be spray dried can be any solution, coarse suspension, slurry, colloidal dispersion, or paste that may be atomized using the selected spray drying apparatus. In one procedure, the preparation is sprayed into a current of warm filtered gas that evaporates the solvent and conveys the dried product to a collector (e.g. a cyclone). The spent gas is then exhausted with the solvent, or alternatively the spent air is sent to a condenser to capture and potentially recycle the solvent. Commercially available types of apparatus may be used to conduct the spray drying. For example, commercial spray dryers are manufactured by Buchi Ltd. And Niro (e.g., the PSD line of spray driers manufactured by Niro) (see, US 2004/0105820; US 2003/0144257).

Techniques and methods for spray drying may be found in Perry's Chemical Engineering Handbook, 6th Ed., R. H. Perry, D. W. Green & J. O. Maloney, eds.), McGraw-Hill book co. (1984); and Marshall "Atomization and Spray-Drying" 50, Chem. Eng. Prog. Monogr. Series 2 (1954).

Removal of the solvent may require a subsequent drying step, such as tray drying, fluid bed drying, vacuum drying, microwave drying, rotary drum drying or biconical vacuum drying.

In one embodiment, the solid dispersions and the spray dried dispersions of the disclosure are fluid bed dried.

In one process, the solvent includes a volatile solvent, for example a solvent having a boiling point of less than 100° C. In some embodiments, the solvent includes a mixture of solvents, for example a mixture of volatile solvents or a mixture of volatile and non-volatile solvents. Where mixtures of solvents are used, the mixture can include one or more non-volatile solvents, for example, where the non-volatile solvent is present in the mixture at less than 15%, e.g., less than 12%, less than 10%, less than 8%, less than 5%, less than 3%, or less than 2%.

In some processes, solvents are those solvents where the API(s) (e.g., Compound II and/or Compound III) has solubilities of at least 10 mg/ml, (e.g., at least 15 mg/ml, 20 mg/ml, 25 mg/ml, 30 mg/ml, 35 mg/ml, 40 mg/ml, 45 mg/ml, 50 mg/ml, or greater). In other processes, solvents include those solvents where the API(s) (e.g., Compound II and/or Compound III) has a solubility of at least 20 mg/ml.

Exemplary solvents that could be tested include acetone, cyclohexane, dichloromethane or methylene chloride (DCM), N,N-dimethylacetamide (DMA), N,N-dimethylformamide (DMF), 1,3-dimethyl-2-imidazolidinone (DMI), dimethyl sulfoxide (DMSO), dioxane, ethyl acetate, ethyl ether, glacial acetic acid (HAc), methyl ethyl ketone (MEK), N-methyl-2-pyrrolidinone (NMP), methyl tert-butyl ether (MTBE), tetrahydrofuran (THF), pentane, acetonitrile, methanol, ethanol, isopropyl alcohol, isopropyl acetate, and toluene. Exemplary co-solvents include DCM/methanol, acetone/DMSO, acetone/DMF, acetone/water, MEK/water, THF/water, dioxane/water. In a two solvent system, the solvents can be present in of from 0.1% to 99.9% w/w. In some preferred embodiments, water is a co-solvent with acetone where water is present from 0.1% to 15%, for example 9% to 11%, e.g., 10%. In some preferred embodiments, water is a co-solvent with MEK where water is present from 0.1% to 15%, for example 9% to 11%, e.g., 10%. In some embodiments the solvent system includes three solvents. Certain exemplary solvents include those described above, for example, MEK, DCM, water, methanol, IPA, and mixtures thereof.

The particle size and the temperature drying range may be modified to prepare an optimal solid dispersion. As would be appreciated by skilled practitioners, a small particle size would lead to improved solvent removal. Applicants have found however, that smaller particles can lead to fluffy particles that, under some circumstances do not provide optimal solid dispersions for downstream processing such as tableting.

A solid dispersion (e.g., a spray dried dispersion) disclosed herein may optionally include a surfactant. A surfactant or surfactant mixture would generally decrease the interfacial tension between the solid dispersion and an aqueous medium. An appropriate surfactant or surfactant mixture may also enhance aqueous solubility and bioavailability of the API(s) (e.g., Compound II and/or Compound III) from a solid dispersion. The surfactants for use in connection with the disclosure include, but are not limited to, sorbitan fatty acid esters (e.g., Spans®), polyoxyethylene sorbitan fatty acid esters (e.g., Tweens®), sodium lauryl sulfate (SLS), sodium dodecylbenzene sulfonate (SDBS) dioctyl sodium sulfosuccinate (Docusate sodium), dioxycholic acid sodium salt (DOSS), Sorbitan Monostearate, Sorbitan Tristearate, hexadecyltrimethyl ammonium bromide (HTAB), Sodium N-lauroylsarcosine, Sodium Oleate, Sodium Myristate, Sodium Stearate, Sodium Palmitate, Gelucire 44/14, ethylenediamine tetraacetic acid (EDTA), Vitamin E d-alpha tocopheryl polyethylene glycol 1000 succinate (TPGS), Lecithin, MW 677-692, Glutanic acid monosodium monohydrate, Labrasol, PEG 8 caprylic/capric glycerides, Transcutol, diethylene glycol monoethyl ether, Solutol HS-15, polyethylene glycol/hydroxystearate, Taurocholic Acid, Pluronic F68, Pluronic F108, and Pluronic F127 (or any other polyoxyethylene-polyoxypropylene co-polymers (Pluronics®) or saturated polyglycolized glycerides (Gelucirs®)). Specific example of such surfactants that may be used in connection with this disclosure include, but are not limited to, Span 65, Span 25, Tween 20, Capryol 90, Pluronic F108, sodium lauryl sulfate (SLS), Vitamin E TPGS, pluronics and copolymers.

In some embodiments, SLS is used as a surfactant in the solid dispersion of Compound III.

In some embodiments, SLS is used as a surfactant in the solid dispersion of Compound III-d.

The amount of the surfactant (e.g., SLS) relative to the total weight of the solid dispersion may be between 0.1-15% w/w. For example, it is from 0.5% to 10%, such as from 0.5 to 5%, e.g., 0.5 to 4%, 0.5 to 3%, 0.5 to 2%, 0.5 to 1%, or 0.5%.

In certain embodiments, the amount of the surfactant relative to the total weight of the solid dispersion is at least 0.1% or at least 0.5%. In these embodiments, the surfactant would be present in an amount of no more than 15%, or no more than 12%, 11%, 10%, 9%, 8%, 7%, 6%, 5%, 4%, 3%, 2% or 1%. In some embodiments, the surfactant is in an amount of 0.5% by weight.

Candidate surfactants (or other components) can be tested for suitability for use in the disclosure in a manner similar to that described for testing polymers.

One aspect of the disclosure provides a method of generating a spray dried dispersion comprising (i) providing a mixture of one or more APIs and a solvent; and (ii) forcing the mixture through a nozzle and subjecting the mixture to spray drying conditions to generate the spray dried dispersion.

Another aspect of the disclosure provides a method of generating a spray dried dispersion comprising: (i) providing a mixture comprising one or more APIs and a solvent(s); and (ii) forcing the mixture out of a nozzle under spray dry drying conditions to generate a spray dried dispersion.

Another aspect of the disclosure provides a method of generating a spray dried dispersion comprising (i) spraying a mixture through a nozzle, wherein the mixture comprises one or more APIs and a solvent; and (ii) forcing the mixture through a nozzle under spray drying conditions to generate a particle that comprises the APIs.

Another aspect of the disclosure provides a spray dried dispersion comprising one or more APIs, wherein the dispersion is substantially free of a polymer, and wherein the spray dried dispersion is generated by (i) providing a mixture that consists essentially of one or more APIs and a solvent; and (ii) forcing the mixture through a nozzle under spray drying conditions to generate the spray dried dispersion.

Another aspect of the disclosure provides a spray dried dispersion comprising one or more APIs, wherein the dispersion is generated by (i) providing a mixture that comprising one or more APIs, a polymer(s), and a solvent(s); and (ii) forcing the mixture through a nozzle under spray drying conditions to generate the spray dried dispersion.

Another aspect of the disclosure provides a spray dried dispersion comprising a particle, wherein the particle comprises one or more APIs and a polymer(s), and wherein the spray dried dispersion is generated by (i) spraying a mixture through a nozzle, wherein the mixture comprises one or more APIs and a solvent; and (ii) forcing the mixture through a nozzle under spray drying conditions to generate the spray dried dispersion.

Another aspect of the disclosure provides a spray dried dispersion comprising a particle, wherein the particle comprises one or more APIs, and the particle is substantially free of a polymer, and wherein the spray dried dispersion is generated by (i) spraying a mixture through a nozzle, wherein the mixture comprises one or more APIs and a solvent; and (ii) forcing the mixture through a nozzle under spray drying conditions to generate the spray dried dispersion.

In some embodiments, the one or more APIs are selected from Compound II and Compound III. In some embodiments, the one or more APIs are selected from Compound II and Compound III-d.

Some embodiments further comprise further drying the spray dried dispersion. For example, the spray dried dispersion is dried under reduced pressure. In other examples, the spray dried dispersion is dried at a temperature of from 50° C. to 100° C.

In some embodiments, the solvent comprises a polar organic solvent. Examples of polar organic solvents include methylethyl ketone, THF, DCM, methanol, or IPA, or any combination thereof, such as, for example DCM/methanol. In other examples, the solvent further comprises water. In other examples, the solvent further comprises water. For instance, the solvent could be methylethyl ketone/water, THF/water, or methylethyl ketone/water/IPA. For example, the ratio of the polar organic solvent to water is from 70:30 to 95:5 by volume. In other instances, the ratio of the polar organic solvent to water is 90:10 by volume.

Some embodiments further comprise filtering the mixture before it is forced through the nozzle. Such filtering can be accomplished using any suitable filter media having a suitable pore size.

Some embodiments further comprise applying heat to the mixture as it enters the nozzle. This heating can be accomplished using any suitable heating element.

In some embodiments, the nozzle comprises an inlet and an outlet, and the inlet is heated to a temperature that is less than the boiling point of the solvent. For example, the inlet is heated to a temperature of from 90° C. to 150° C.

In some embodiments, the mixture is forced through the nozzle by a pressurized gas. Examples of suitable pressurized gases include those pressurized gas that are inert to the first agent, the second agent, and the solvent. In one example, the pressurized gas comprises elemental nitrogen.

In some embodiments, the pressurized gas has a positive pressure of from 90 psi to 150 psi.

Some embodiments further comprise further drying the spray dried dispersion. For example, the spray dried dispersion is dried under reduced pressure. In other examples, the spray dried dispersion is dried at a temperature of from 50° C. to 100° C.

In some embodiments, the solvent comprises a polar organic solvent. Examples of polar organic solvents include methylethyl ketone, THF, DCM, methanol, or IPA, or any combination thereof. In other examples, the solvent further comprises water. In other examples, the solvent further comprises water. For instance, the solvent could be methylethyl ketone/water, THF/water, or methylethyl ketone/water/IPA. For example, the ratio of the polar organic solvent to water is from 70:30 to 95:5 by volume. In other instances, the ratio of the polar organic solvent to water is 90:10 by volume.

In some embodiments, a pharmaceutically acceptable composition of the disclosure comprising substantially amorphous API(s) (e.g., Compound II and/or Compound III or III-d) may be prepared by non-spray drying techniques, such as, for example, cyrogrounding/cryomilling techniques. A composition comprising substantially amorphous API(s) (e.g., Compound II and/or Compound III or III-d) may also be prepared by hot melt extrusion techniques.

In some embodiments, the solid dispersions (e.g., spray dried dispersions) of the disclosure comprise a polymer(s). Any suitable polymers known in the art can be used in the disclosure. Exemplary suitable polymers include polymers selected from cellulose-based polymers, polyoxyethylene-based polymers, polyethylene-propylene glycol copolymers, vinyl-based polymers, PEO-polyvinyl caprolactam-based polymers, and polymethacrylate-based polymers.

The cellulose-based polymers include a methylcellulose, a hydroxypropyl methylcellulose (HPMC) (hypromellose), a hypromellose phthalate (HPMC-P), a hypromellose acetate succinate, and co-polymers thereof. The polyoxyethylene-based polymers include a polyethylene-propylene glycol, a polyethylene glycol, a poloxamer, and co-polymers thereof. The vinyl-based polymers include a polyvinylpyrrolidine (PVP), and PVP/VA. The PEO-polyvinyl caprolactam-based polymers include a polyethylene glycol, polyvinyl acetate and polyvinylcaprolactame-based graft copolymer (e.g., Soluplus®). The polymethacrylate-based polymers are synthetic cationic and anionic polymers of dimethylaminoethyl methacrylates, methacrylic acid, and methacrylic acid esters in varying ratios. Several types are commercially available and may be obtained as the dry powder, aqueous dispersion, or organic solution. Examples of such polymethacrylate-based polymers include a poly (methacrylic acid, ethyl acrylate) (1:1), a dimethylaminoethyl methacrylate-methylmethacrylate copolymer, and a Eudragit®.

In some embodiments, the cellulose-based polymer is a hypromellose acetate succinate (also known as hydroxypropyl methylcellulose acetate succinate or HMPCAS) and a hypromellose (also known as hydroxypropyl methylcellulose or HPMC), or a combination of hypromellose acetate succinate and a hypromellose. HPMCAS is available in various grades based on the content of acetyl and succinoyl groups (wt %) in the HPMCAS molecule and on particle size. For example, HPMCAS grades L, M, and H are available. HPMCAS-H is a grade that contains about 10-14 wt % of acetyl groups and about 4-8 wt % of succinoyl groups. Each HPMCAS grade is available in two particle sizes, F (fine) and G (granular). HPMC comes in various types (for example, HPMC E, F, J, and K-types). HPMC E type means that there are about 28-30% methoxy groups and about 7-12% hydroxpropoxy groups. There are various E grades ranging from low to high viscosity. For example, E3 means the viscosity is about 2.4-3.6 millipascal seconds (mPa·s) for HPMC measured at 2% in water at 20° C.; E15 means the viscosity is about 12-18 mPa·s for the HPMC measured at 2% in water at 20° C.; and E50 means the viscosity is about 40-60 mPa·s for the HPMC measured at 2% in water at 20° C.

In some embodiments, the cellulose-based polymer is hypromellose E15, hypromellose acetate succinate L or hypromellose acetate succinate H.

In some embodiments, the polyoxyethylene-based polymer or polyethylene-propylene glycol copolymer is a polyethylene glycol or a pluronic.

In some embodiments, the polyoxyethylene-based polymer or polyethylene-propylene glycol copolymer is polyethylene glycol 3350 or poloxamer 407.

In some embodiments, the vinyl-based polymer is a vinylpolyvinylpyrrolidine-based polymer, such as polyvinylpyrrolidine K30 or polyvinylpyrrolidine VA 64.

In some embodiments, the polymethacrylate polymer is Eudragit L100-55 or Eudragit® E PO.

In some embodiments, the polymer(s) is selected from cellulosic polymers such as HPMC and/or HPMCAS.

In one embodiment, a polymer is able to dissolve in aqueous media. The solubility of the polymers may be pH independent or pH dependent. The latter include one or more enteric polymers. The term "enteric polymer" refers to a polymer that is preferentially soluble in the less acidic environment of the intestine relative to the more acid environment of the stomach, for example, a polymer that is insoluble in acidic aqueous media but soluble when the pH is above 5-6. An appropriate polymer is chemically and biologically inert. In order to improve the physical stability of the solid dispersions, the glass transition temperature (Tg) of the polymer is as high as possible. For example, polymers have a glass transition temperature at least equal to or greater than the glass transition temperature of the API. Other polymers have a glass transition temperature that is within 10 to 15° C. of the API.

Additionally, the hygroscopicity of the polymers is as low, e.g., less than 10%. For the purpose of comparison in this application, the hygroscopicity of a polymer or composition is characterized at 60% relative humidity. In some preferred embodiments, the polymer has less than 10% water absorption, for example less than 9%, less than 8%, less than 7%, less than 6%, less than 5%, less than 4%, less than 3%, or less than 2% water absorption. The hygroscopicity can also affect the physical stability of the solid dispersions. Generally, moisture adsorbed in the polymers can greatly reduce the Tg of the polymers as well as the resulting solid dispersions, which will further reduce the physical stability of the solid dispersions as described above.

In one embodiment, the polymer is one or more water-soluble polymer(s) or partially water-soluble polymer(s). Water-soluble or partially water-soluble polymers include but are not limited to, cellulose derivatives (e.g., hydroxypropylmethylcellulose (HPMC), hydroxypropylcellulose (HPC)) or ethylcellulose; polyvinylpyrrolidones (PVP); polyethylene glycols (PEG); polyvinyl alcohols (PVA); acrylates, such as polymethacrylate (e.g., Eudragit® E); cyclodextrins (e.g., β-cyclodextin) and copolymers and derivatives thereof, including for example PVP-VA (polyvinylpyrollidone-vinyl acetate).

In some embodiments, the polymer is hydroxypropylmethylcellulose (HPMC), such as HPMC E50, HPMC E15, or HPMC E3.

As discussed herein, the polymer can be a pH-dependent enteric polymer. Such pH-dependent enteric polymers include, but are not limited to, cellulose derivatives (e.g., cellulose acetate phthalate (CAP)), hydroxypropyl methyl cellulose phthalates (HPMCP), hydroxypropyl methyl cellulose acetate succinate (HPMCAS), carboxymethylcellulose (CMC) or a salt thereof (e.g., a sodium salt such as (CMC-Na)); cellulose acetate trimellitate (CAT), hydroxypropylcellulose acetate phthalate (HPCAP), hydroxypropylmethyl-cellulose acetate phthalate (HPMCAP), and methylcellulose acetate phthalate (MCAP), or polymethacrylates (e.g., Eudragit® S). In some embodiments, the polymer is hydroxypropyl methyl cellulose acetate succinate (HPMCAS). In some embodiments, the polymer is hydroxypropyl methyl cellulose acetate succinate HG grade (HPMCAS-HG).

In yet another embodiment, the polymer is a polyvinylpyrrolidone co-polymer, for example, a vinylpyrrolidone/vinyl acetate co-polymer (PVP/VA).

In embodiments where Compound II, Compound III and/or Compound III-d forms a solid dispersion with a polymer, for example with an HPMC, HPMCAS, or PVP/VA polymer, the amount of polymer relative to the total weight of the solid dispersion ranges from 0.1% to 99% by weight. Unless otherwise specified, percentages of drug, polymer and other excipients as described within a dispersion are given in weight percentages. The amount of polymer is typically at least 20%, and preferably at least 30%, for example, at least 35%, at least 40%, at least 45%, or 0% (e.g., 49.5%). The amount is typically 99% or less, and preferably 80% or less, for example 75% or less, 70% or less, 65% or less, 60% or less, or 55% or less. In one embodiment, the polymer is in an amount of up to 50% of the total weight of the dispersion (and even more specifically, between 40% and 50%, such as 49%, 49.5%, or 50%).

In some embodiments, the API (e.g., Compound II or Compound III) and polymer are present in roughly equal amounts in weight, for example each of the polymer and the drug make up half of the percentage weight of the dispersion. For example, the polymer is present in 49.5 wt % and Compound II, Compound III, or Compound III-d is present in 50 wt %. In another embodiment Compound II, Compound III, or Compound III-d is present in an amount greater than half of the percentage weight of the dispersions. For example, the polymer is present in 20 wt % and Compound II, Compound III, or Compound III-d is present in 80 wt %. In other embodiments, the polymer is present in 19.5 wt % and Compound II, Compound III, or Compound III-d is present in 80 wt %.

In some embodiments, the API (e.g., Compound II or Compound III) and the polymer combined represent 1% to 20% w/w total solid content of the spray drying solution prior to spray drying. In some embodiments, Compound II, Compound III, or Compound III-d, and the polymer combined represent 5% to 15% w/w total solid content of the spray drying solution prior to spray drying. In some embodiments, Compound II, Compound III, or Compound III-d, and the polymer combined represent 11% w/w total solid content of the spray drying solution prior to spray drying.

In some embodiments, the dispersion further includes other minor ingredients, such as a surfactant (e.g., SLS). In some embodiments, the surfactant is present in less than 10% of the dispersion, for example less than 9%, less than 8%, less than 7%, less than 6%, less than 5%, less than 4%, less than 3%, less than 2%, 1%, or 0.5%.

In embodiments including a polymer, the polymer is present in an amount effective for stabilizing the solid dispersion. Stabilizing includes inhibiting or preventing, the crystallization of an API (e.g., Compound II or Compound III). Such stabilizing would inhibit the conversion of the API from amorphous to crystalline form. For example, the polymer would prevent at least a portion (e.g., 5%, 10%, 15%, 20%, 25%, 30%, 35%, 40%, 45%, 50%, 55%, 60%, 65%, 70%, 75%, or greater) of the API from converting from an amorphous to a crystalline form. Stabilization can be measured, for example, by measuring the glass transition temperature of the solid dispersion, measuring the amount of crystalline material, measuring the rate of relaxation of the amorphous material, or by measuring the solubility or bioavailability of the API.

In some embodiments, the polymers for use in the disclosure have a glass transition temperature of no less than 10-15° C. lower than the glass transition temperature of API. In some instances, the glass transition temperature of the polymer is greater than the glass transition temperature of API, and in general at least 50° C. higher than the desired storage temperature of the drug product. For example, at least 100° C., at least 105° C., at least 105° C., at least 110° C., at least 120° C., at least 130° C., at least 140° C., at least 150° C., at least 160° C., at least 160° C., or greater.

In some embodiments, the polymers for use in the disclosure have similar or better solubility in solvents suitable for spray drying processes relative to that of an API (e.g., Compound II or Compound III). In some embodiments, the polymer will dissolve in one or more of the same solvents or solvent systems as the API.

In some embodiments, the polymers for use in the disclosure can increase the solubility of an API (e.g., Compound II or Compound III) in aqueous and physiologically relative media either relative to the solubility of the API in the absence of polymer or relative to the solubility of the API when combined with a reference polymer. For example, the polymers can increase the solubility of Compound II, Compound III, or Compound III-d by reducing the amount of amorphous Compound II, Compound III, or Compound III-d that converts to a crystalline form(s), either from a solid amorphous dispersion or from a liquid suspension.

In some embodiments, the polymers for use in the disclosure can decrease the relaxation rate of the amorphous substance.

In some embodiments, the polymers for use in the disclosure can increase the physical and/or chemical stability of an API (e.g., Compound II or Compound III).

In some embodiments, the polymers for use in the disclosure can improve the manufacturability of an API (e.g., Compound II or Compound III).

In some embodiments, the polymers for use in the disclosure can improve one or more of the handling, administration or storage properties of an API (e.g., Compound II or Compound III).

In some embodiments, the polymers for use in the disclosure have little or no unfavorable interaction with other pharmaceutical components, for example excipients.

The suitability of a candidate polymer (or other component) can be tested using the spray drying methods (or other methods) described herein to form an amorphous composition. The candidate composition can be compared in terms of stability, resistance to the formation of crystals, or other properties, and compared to a reference preparation, e.g., a preparation of neat amorphous Compound II, Compound III, or Compound III-d. For example, a candidate composition could be tested to determine whether it inhibits the time to onset of solvent mediated crystallization, or the percent conversion at a given time under controlled conditions, by at least 50%, 75%, or 100% as well as the reference preparation, or a candidate composition could be tested to determine if it has improved bioavailability or solubility relative to crystalline Compound II, Compound III, or Compound III-d.

In one aspect, the disclosure provides pharmaceutical compositions comprising neat Compound I-potassium salt (in some embodiments, potassium salt crystalline Form B), a first solid dispersion comprising Compound II, and a second solid dispersion comprising Compound III.

In another aspect, the disclosure provides pharmaceutical compositions comprising neat Compound I-potassium salt (in some embodiments, potassium salt crystalline Form B), a first solid dispersion comprising Compound II, and a second solid dispersion comprising Compound III-d.

In some embodiments, the first solid dispersion comprises a cellulose polymer. For example, the first solid dispersion comprises a hydroxypropyl methylcellulose (HPMC). In some embodiments, the first solid dispersion comprises a weight ratio of HPMC to Compound II ranging from 1:10 to 1:1. In some instances, the ratio of HPMC to Compound II is from 1:3 to 1:5.

In some embodiments, the second solid dispersion comprises a cellulose polymer. For example, the second solid dispersion comprises a hydroxypropyl methylcellulose acetate succinate (HPMCAS).

In some embodiments, each of the first and second solid dispersions comprises a plurality of particles having a mean particle diameter of 5 to 100 microns. In some embodiments, the particles have a mean particle diameter of 5 to 30 microns. In some embodiments, the particles have a mean particle diameter of 15 microns.

In some embodiments, the first solid dispersion comprises from 70 wt % to 90 wt % (e.g., from 75 wt % to 85 wt %) of Compound II.

In some embodiments, the second solid dispersion comprises from 70 wt % to 90 wt % (e.g., from 75 wt % to 85 wt %) of Compound III.

In some embodiments, the second solid dispersion comprises from 70 wt % to 90 wt % (e.g., from 75 wt % to 85 wt %) of Compound III-d.

In some embodiments, each of the first and second solid dispersions is a spray dried dispersion.

In some embodiments, the compositions of the invention comprise 100 to 260 mg of a potassium salt of Compound I (in some embodiments, potassium salt crystalline Form B), and optionally comprise one or more additional CFTR modulating agents. In some embodiments, the compositions comprise about 128 mg or about 255-256 mg of a potassium salt of Compound I (in some embodiments, potassium salt crystalline Form B), and optionally comprise one or more additional CFTR modulating agents. In some embodiments, the compositions comprise about 128 mg or about 255-256 mg of a potassium salt of Compound I (in some embodiments, potassium salt crystalline Form B), together with 100 mg of Compound II and 150 mg of Compound III or 200 mg of Compound III-d. In some embodiments the compositions comprise about 128 mg of a potassium salt of Compound I (in some embodiments, potassium salt crystalline Form B), 50 mg of Compound II, and 75 mg of Compound III. In some embodiments the compositions comprise about 64 mg of a potassium salt of Compound I (in some embodiments, potassium salt crystalline Form B), about 25 mg of Compound II, and about 35 mg to 40 mg of Compound III.

Exemplary Formulations

In some embodiments, the pharmaceutical compositions disclosed herein further comprise one or more pharmaceutically acceptable excipients, such as pharmaceutically acceptable vehicles, adjuvants, or carriers.

Remington: *The Science and Practice of Pharmacy*, 21st edition, 2005, ed. D. B. Troy, Lippincott Williams & Wilkins, Philadelphia, and *Encyclopedia of Pharmaceutical Technology*, eds. J. Swarbrick and J. C. Boylan, 1988-1999, Marcel Dekker, New York, the contents of each of which is incorporated by reference herein, disclose various carriers used in formulating pharmaceutically acceptable compositions and known techniques for the preparation thereof. Except insofar as any conventional carrier medium is incompatible with the compounds of the disclosure, such as by producing any undesirable biological effect or otherwise interacting in a deleterious manner with any other component(s) of the pharmaceutically acceptable composition, its use is contemplated to be within the scope of this disclosure.

In one embodiment, the pharmaceutical compositions of the disclosure comprise one or more fillers, a disintegrant, and a lubricant.

Fillers suitable for the pharmaceutical compositions disclosed herein are compatible with the other ingredients of the pharmaceutical compositions, i.e., they do not substantially reduce the solubility, the hardness, the chemical stability, the physical stability, or the biological activity of the pharmaceutical compositions. Exemplary fillers include: celluloses, modified celluloses, (e.g. sodium carboxymethyl cellulose, ethyl cellulose hydroxymethyl cellulose, hydroxypropylcellulose), cellulose acetate, microcrystalline cellulose, calcium phosphates, dibasic calcium phosphate, starches (e.g. corn starch, potato starch), sugars (e.g., mannitol, lactose, sucrose, or the like), or any combination thereof. In one embodiment, the filler is microcrystalline cellulose.

In some embodiments, the pharmaceutical compositions comprises one or more fillers in an amount of at least 5 wt % (e.g., at least 20 wt %, at least 30 wt %, or at least 40 wt %) by weight of the pharmaceutical composition. For example, the pharmaceutical compositions comprise from 10 wt % to 60 wt % (e.g., from 20 wt % to 55 wt %, from 25 wt % to 50 wt %, or from 27 wt % to 45 wt %) of filler, by weight of the tablet. In another example, the pharmaceutical compositions comprise at least 20 wt % (e.g., at least 30 wt % or at least 40 wt %) of microcrystalline cellulose, for example MCC Avicel PH102 or Avicel PH101, by weight of the pharmaceutical composition. In yet another example, the pharmaceutical compositions comprise from 10 wt % to 60 wt % (e.g., from 20 wt % to 55 wt % or from 25 wt % to 45 wt %) of microcellulose, by weight of the pharmaceutical composition.

Disintegrants suitable for the pharmaceutical compositions disclosed herein can enhance the dispersal of the pharmaceutical compositions and are compatible with the other ingredients of the pharmaceutical compositions, i.e., they do not substantially reduce the chemical stability, the physical stability, the hardness, or the biological activity of the pharmaceutical compositions. Exemplary disintegrants include croscarmellose sodium, sodium starch glycolate, crospovidone or a combination thereof. In one embodiment, the disintegrant is croscarmellose sodium.

In some embodiments, the pharmaceutical compositions disclosed herein comprise disintegrant in an amount of 10 wt % or less (e.g., 7 wt % or less, 6 wt % or less, or 5 wt % or less) by weight of the pharmaceutical composition. For example, the pharmaceutical compositions comprise from 1 wt % to 10 wt % (e.g., from 1.5 wt % to 7.5 wt % or from 2.5 wt % to 6 wt %) of disintegrant, by weight of the pharmaceutical composition. In another example, the pharmaceutical compositions comprise 10 wt % or less (e.g., 7 wt % or less, 6 wt % or less, or 5 wt % or less) of croscarmellose sodium, by weight of the pharmaceutical composition. In yet another example, the pharmaceutical compositions comprise from 1 wt % to 10 wt % (e.g., from 1.5 wt % to 7.5 wt % or from 2.5 wt % to 6 wt %) of croscarmellose sodium, by weight of the pharmaceutical composition. In some examples, the pharmaceutical compositions comprise from 0.1% to 10 wt % (e.g., from 0.5 wt % to 7.5 wt % or from 1.5 wt % to 6 wt %) of disintegrant, by weight of the pharmaceutical composition. In still other embodiments, the pharmaceutical compositions comprise from 0.5% to 10 wt % (e.g., from 1.5 wt % to 7.5 wt % or from 2.5 wt % to 6 wt %) of disintegrant, by weight of the pharmaceutical composition.

In some embodiments, the pharmaceutical compositions disclosed herein comprise a lubricant. A lubricant can prevent adhesion of a mixture component to a surface (e.g., a surface of a mixing bowl, a granulation roll, a compression die and/or punch). A lubricant can also reduce interparticle friction within the granulate and improve the compression and ejection of compressed pharmaceutical compositions from a granulator and/or die press. A suitable lubricant for the pharmaceutical compositions disclosed herein is compatible with the other ingredients of the pharmaceutical compositions, i.e., they do not substantially reduce the solubility, the hardness, or the biological activity of the pharmaceutical compositions. Exemplary lubricants include magnesium stearate, sodium stearyl fumarate, calcium stearate, zinc stearate, sodium stearate, stearic acid, aluminum stearate, leucine, glyceryl behenate, hydrogenated vegetable oil or any combination thereof. In embodiment, the lubricant is magnesium stearate.

In one embodiment, the pharmaceutical compositions comprise a lubricant in an amount of 5 wt % or less (e.g., 4.75 wt %, 4.0 wt % or less, or 3.00 wt % or less, or 2.0 wt % or less) by weight of the pharmaceutical composition. For example, the pharmaceutical compositions comprise from 5 wt % to 0.10 wt % (e.g., from 4.5 wt % to 0.5 wt % or from 3 wt % to 1 wt %) of lubricant, by weight of the pharmaceutical composition. In another example, the pharmaceutical compositions comprise 5 wt % or less (e.g., 4.0 wt % or less, 3.0 wt % or less, or 2.0 wt % or less, or 1.0 wt % or less) of magnesium stearate, by weight of the pharmaceutical composition. In yet another example, the pharmaceutical compositions comprise from 5 wt % to 0.10 wt % (e.g., from 4.5 wt % to 0.15 wt % or from 3.0 wt % to 0.50 wt %) of magnesium stearate, by weight of the pharmaceutical composition.

Any suitable spray dried dispersions of Compound II, Compound III, and Compound III-d can be used for the pharmaceutical compositions disclosed herein. Some examples for Compound II and its pharmaceutically acceptable salts can be found in WO 2011/119984 and WO 2014/015841, all of which are incorporated herein by reference. Some examples for Compound III and its pharmaceutically acceptable salts can be found in WO 2007/134279, WO 2010/019239, WO 2011/019413, WO 2012/027731, and WO 2013/130669, all of which are incorporated herein by reference. Spray dried dispersions of Compound III-d can be prepared as those of Compound III as described in WO 2007/134279, WO 2010/019239, WO 2011/019413, WO 2012/027731, and WO 2013/130669.

Pharmaceutical compositions comprising Compound II and Compound III are disclosed in PCT Publication No. WO 2015/160787, incorporated herein by reference. An exemplary embodiment is shown in the following Table 1 for administration with crystalline Form B of the potassium salt of Compound I.

TABLE 1

Exemplary Tablet Comprising 100 mg of Compound II and 150 mg of Compound III

| | Ingredient | Amount per tablet (mg) |
|---|---|---|
| Intra-granular | Compound II SDD (spray dried dispersion) (80 wt % Compound II; 20 wt % HPMC) | 125 |
| | Compound III SDD (80 wt % Compound III; 19.5 wt % HPMCAS-HG; 0.5 wt % sodium lauryl sulfate) | 187.5 |
| | Microcrystalline cellulose | 131.4 |
| | Croscarmellose Sodium | 29.6 |
| | Total | 473.5 |
| Extra-granular | Microcrystalline cellulose | 112.5 |
| | Magnesium Stearate | 5.9 |
| | Total | 118.4 |
| Total uncoated Tablet | | 591.9 |
| Film coat | Opadry | 17.7 |
| Total coated Tablet | | 609.6 |

Pharmaceutical compositions comprising Compound III are disclosed in PCT Publication No. WO 2010/019239, incorporated herein by reference. An exemplary embodiment is shown in the following Table 2 for administration with crystalline Form B of the potassium salt of Compound I alone or in combination with Compound II.

TABLE 2

Ingredients for Exemplary Tablet of Compound III

| Tablet Formulation | Percent Dose % Wt./Wt | Dose (mg) | Batch (g) |
|---|---|---|---|
| Compound III SDD (80 wt % Compound III; 19.5 wt % HPMCAS-HG; 0.5 wt % sodium lauryl sulfate) | 34.09% | 187.5 | 23.86 |
| Microcrystalline cellulose | 30.51% | 167.8 | 21.36 |
| Lactose | 30.40% | 167.2 | 21.28 |

TABLE 2-continued

Ingredients for Exemplary Tablet of Compound III

| Tablet Formulation | Percent Dose % Wt./Wt | Dose (mg) | Batch (g) |
|---|---|---|---|
| Sodium croscarmellose | 3.000% | 16.50 | 2.100 |
| SLS | 0.500% | 2.750 | 0.3500 |
| Colloidal silicon dioxide | 0.500% | 2.750 | 0.3500 |
| Magnesium stearate | 1.000% | 5.500 | 0.7000 |
| Total | 100% | 550 | 70 |

Additional pharmaceutical compositions comprising Compound III are disclosed in PCT Publication No. WO 2013/130669, incorporated herein by reference. Exemplary mini-tablets (~2 mm diameter, ~2 mm thickness, each mini-tablet weighing 6.9 mg) was formulated to have 50 mg of Compound III per 26 mini-tablets and 75 mg of Compound III per 39 mini-tablets using the amounts of ingredients recited in Table 3, below for administration with crystalline Form B of the potassium salt of Compound I alone or in combination with Compound II.

TABLE 3

Ingredients for mini-tablets for 50 mg and 75 mg potency

| Tablet Formulation | Percent Dose % Wt./Wt. | Dose (mg) 50 mg potency | Dose (mg) 75 mg potency | Batch (g) |
|---|---|---|---|---|
| Compound III SDD (80 wt % Compound III; 19.5 wt % HPMCAS-HG; 0.5 wt % sodium lauryl sulfate) | 35 | 62.5 | 93.8 | 1753.4 |
| Mannitol | 13.5 | 24.1 | 36.2 | 675.2 |
| Lactose | 41 | 73.2 | 109.8 | 2050.2 |
| Sucralose | 2.0 | 3.6 | 5.4 | 100.06 |
| Croscarmellose sodium | 6.0 | 10.7 | 16.1 | 300.1 |
| Colloidal silicon dioxide | 1.0 | 1.8 | 2.7 | 50.0 |
| Magnesium stearate | 1.5 | 2.7 | 4.0 | 74.19 |
| Total | 100 | 178.6 | 268 | 5003.15 |

In some embodiments, the pharmaceutical compositions disclosed herein comprise one of the following formulations:

TABLE 4

| Component | Amount (mg) per composition |
|---|---|
| potassium salt of Compound I (in some embodiments, potassium salt crystalline Form B) | 200 mg to 215 mg |
| solid dispersion containing 80% Compound II, 20% hypromellose | 60 mg to 65 mg |
| solid dispersion containing 80% Compound III, 19.5% hypromellose acetate succinate, and 0.5% sodium lauryl sulfate | 90 mg to 95 mg |
| microcrystalline cellulose | 175 mg to 215 mg |
| croscarmellose sodium (CCS) | 15 mg to 30 mg |
| magnesium stearate | 3 mg to 7 mg |

TABLE 5

| Component | Amount (mg) per composition |
| --- | --- |
| potassium salt of Compound I (in some embodiments, potassium salt crystalline Form B) | 212.9 mg |
| solid dispersion containing 80% Compound II, 20% hypromellose | 62.5 mg |
| solid dispersion containing 80% Compound III, 19.5% hypromellose acetate succinate, and 0.5% sodium lauryl sulfate | 93.8 mg |
| microcrystalline cellulose | 196.7 mg |
| croscarmellose sodium | 24.7 mg |
| magnesium stearate | 5.3 mg |

TABLE 6

| Component | Amount (mg) per composition |
| --- | --- |
| potassium salt of Compound I (in some embodiments, potassium salt crystalline Form B) | 115 mg to 140 mg |
| solid dispersion containing 80% Compound II, 20% hypromellose | 60 mg to 65 mg |
| solid dispersion containing 80% Compound III, 19.5% hypromellose acetate succinate, and 0.5% sodium lauryl sulfate | 90 mg to 95 mg |
| microcrystalline cellulose | 120 mg to 135 mg |
| croscarmellose sodium | 15 mg to 25 mg |
| magnesium stearate | 2 mg to 7 mg |

TABLE 7

| Component | Amount (mg) per composition |
| --- | --- |
| potassium salt of Compound I (in some embodiments, potassium salt crystalline Form B) | 127.7 mg |
| solid dispersion containing 80% Compound II, 20% hypromellose | 62.5 mg |
| solid dispersion containing 80% Compound III, 19.5% hypromellose acetate succinate, and 0.5% sodium lauryl sulfate | 93.8 mg |
| microcrystalline cellulose | 130.6 mg |
| croscarmellose sodium | 18.1 mg |
| magnesium stearate | 3.9 mg |

In some embodiments, the pharmaceutical compositions disclosed herein comprise an intra-granular part and an extragranular part, and the intra-granular part and the extra-granular part comprise components as shown in the tables below:

TABLE 8

| | Component | Amount (mg) per composition |
| --- | --- | --- |
| Intra-granular part | potassium salt of Compound I (in some embodiments, potassium salt crystalline Form B) | 200 mg to 215 mg |
| | solid dispersion containing 80% Compound II, 20% hypromellose | 60 mg to 65 mg |
| | solid dispersion containing 80% Compound III, 19.5% hypromellose acetate succinate, and 0.5% sodium lauryl sulfate | 90 mg to 95 mg |
| | microcrystalline cellulose (e.g., PH101) | 120 mg to 150 mg |
| | croscarmellose sodium (CCS) | 10 mg to 20 mg |
| | magnesium stearate | 3 mg to 7 mg |
| Extra-granular part | microcrystalline cellulose (e.g., PH102) | 55 mg to 65 mg |
| | croscarmellose sodium | 5 mg to 10 mg |

TABLE 9

| | Component | Amount (mg) per composition |
| --- | --- | --- |
| Intra-granular part | potassium salt of Compound I (in some embodiments, potassium salt crystalline Form B) | 115 mg to 140 mg |
| | solid dispersion containing 80% Compound II, 20% hypromellose | 60 mg to 65 mg |
| | solid dispersion containing 80% Compound III, 19.5% hypromellose acetate succinate, and 0.5% sodium lauryl sulfate | 90 mg to 95 mg |
| | microcrystalline cellulose (e.g., PH101) | 80 mg to 90 mg |
| | croscarmellose sodium | 10 mg to 15 mg |
| | magnesium stearate | 2 mg to 7 mg |
| Extra-granular part | microcrystalline cellulose (e.g., PH102) | 40 mg to 45 mg |
| | croscarmellose sodium | 5 mg to 10 mg |

TABLE 10

| | Component | Amount (mg) per composition |
| --- | --- | --- |
| Intra-granular part | potassium salt of Compound I (in some embodiments, potassium salt crystalline Form B) | 115 mg to 140 mg |
| | solid dispersion containing 80% Compound II, 20% hypromellose | 60 mg to 65 mg |
| | solid dispersion containing 80% Compound III, 19.5% hypromellose acetate succinate, and 0.5% sodium lauryl sulfate | 90 mg to 95 mg |
| | microcrystalline cellulose (e.g., PH101) | 80 mg to 90 mg |
| | croscarmellose sodium | 10 mg to 15 mg |
| | magnesium stearate | 1 mg to 3 mg |
| Extra-granular part | microcrystalline cellulose (e.g., PH102) | 40 mg to 45 mg |
| | croscarmellose sodium | 5 mg to 10 mg |
| | magnesium stearate | 1 mg to 3 mg |

TABLE 11

| | Component | Amount (mg) per composition |
| --- | --- | --- |
| Intra-granular part | potassium salt of Compound I (in some embodiments, potassium salt crystalline Form B) | 115 mg to 140 mg |
| | solid dispersion containing 80% Compound II, 20% hypromellose | 60 mg to 65 mg |
| | solid dispersion containing 80% Compound III, 19.5% hypromellose acetate succinate, and 0.5% sodium lauryl sulfate | 90 mg to 95 mg |
| | microcrystalline cellulose (e.g., PH101) | 80 mg to 90 mg |
| | croscarmellose sodium | 8 mg to 15 mg |
| | magnesium stearate | 0.5 mg to 5 mg |
| Extra-granular part | microcrystalline cellulose (e.g., PH102) | 35 mg to 50 mg |
| | croscarmellose sodium | 5 mg to 10 mg |
| | magnesium stearate | 0.5 mg to 5 mg |

TABLE 12

| | Component | Amount (mg) per composition |
| --- | --- | --- |
| Intra-granular part | potassium salt of Compound I (in some embodiments, potassium salt crystalline Form B) | 115 mg to 140 mg |

TABLE 12-continued

| | Component | Amount (mg) per composition |
|---|---|---|
| | solid dispersion containing 80% Compound II, 20% hypromellose | 60 mg to 65 mg |
| | solid dispersion containing 80% Compound III, 19.5% hypromellose acetate succinate, and 0.5% sodium lauryl sulfate | 90 mg to 95 mg |
| | microcrystalline cellulose (e.g., PH101) | 80 mg to 90 mg |
| | croscarmellose sodium | 8 mg to 15 mg |
| | magnesium stearate | 0.5 mg to 5 mg |
| Extra-granular part | microcrystalline cellulose (e.g., PH102) | 35 mg to 50 mg |
| | croscarmellose sodium | 5 mg to 10 mg |

TABLE 13

| | Component | Amount (mg) per composition |
|---|---|---|
| Intra-granular part | potassium salt of Compound I (in some embodiments, potassium salt crystalline Form B) | 115 mg to 140 mg |
| | solid dispersion containing 80% Compound II, 20% hypromellose | 60 mg to 65 mg |
| | solid dispersion containing 80% Compound III, 19.5% hypromellose acetate succinate, and 0.5% sodium lauryl sulfate | 90 mg to 95 mg |
| | microcrystalline cellulose (e.g., PH101) | 80 mg to 90 mg |
| | croscarmellose sodium | 8 mg to 15 mg |
| Extra-granular part | microcrystalline cellulose (e.g., PH102) | 35 mg to 50 mg |
| | croscarmellose sodium | 5 mg to 10 mg |
| | magnesium stearate | 0.5 mg to 5 mg |

TABLE 14

| | Component | Amount (mg) per composition |
|---|---|---|
| Intra-granular part | potassium salt of Compound I (in some embodiments, potassium salt crystalline Form B) | 212-213 mg |
| | solid dispersion containing 80% Compound II, 20% hypromellose | 62-63 mg |
| | solid dispersion containing 80% Compound III, 19.5% hypromellose acetate succinate, and 0.5% sodium lauryl sulfate | 93-94 mg |
| | microcrystalline cellulose (e.g., PH101) | 137-138 mg |
| | croscarmellose sodium | 15-16 mg |
| | magnesium stearate | 5-6 mg |
| Extra-granular part | microcrystalline cellulose (e.g., PH102) | 59-60 mg |
| | croscarmellose sodium | 8-9 mg |

TABLE 15

| | Component | Amount (mg) per composition |
|---|---|---|
| Intra-granular part | potassium salt of Compound I (in some embodiments, potassium salt crystalline Form B) | 212.9 mg |
| | solid dispersion containing 80% Compound II, 20% hypromellose | 62.5 mg |
| | solid dispersion containing 80% Compound III, 19.5% hypromellose acetate succinate, and 0.5% sodium lauryl sulfate | 93.8 mg |

TABLE 15-continued

| | Component | Amount (mg) per composition |
|---|---|---|
| | microcrystalline cellulose (e.g., PH101) | 137.1 mg |
| | croscarmellose sodium | 15.8 mg |
| | magnesium stearate | 5.3 mg |
| Extra-granular part | microcrystalline cellulose (e.g., PH102) | 59.6 mg |
| | croscarmellose sodium | 8.9 mg |
| | Uncoated Tablet | 595.9 mg |
| | Coating | 18.4 mg |

TABLE 16

| | Component | Amount (mg) per composition |
|---|---|---|
| Intra-granular part | potassium salt of Compound I (in some embodiments, potassium salt crystalline Form B) | 127-128 mg |
| | solid dispersion containing 80% Compound II, 20% hypromellose | 62-63 mg |
| | solid dispersion containing 80% Compound III, 19.5% hypromellose acetate succinate, and 0.5% sodium lauryl sulfate | 93-94 mg |
| | microcrystalline cellulose (e.g., PH101) | 86-87 mg |
| | croscarmellose sodium | 11-12 mg |
| | magnesium stearate | 3-4 mg |
| Extra-granular part | microcrystalline cellulose (e.g., PH102) | 43-44 mg |
| | croscarmellose sodium | 6-7 mg |

TABLE 17

| | Component | Amount (mg) per composition |
|---|---|---|
| Intra-granular part | potassium salt of Compound I (in some embodiments, potassium salt crystalline Form B) | 127.7 mg |
| | solid dispersion containing 80% Compound II, 20% hypromellose | 62.5 mg |
| | solid dispersion containing 80% Compound III, 19.5% hypromellose acetate succinate, and 0.5% sodium lauryl sulfate | 93.8 mg |
| | microcrystalline cellulose (e.g., PH101) | 86.9 mg |
| | croscarmellose sodium | 11.6 mg |
| | magnesium stearate | 3.9 mg |
| Extra-granular part | microcrystalline cellulose (e.g., PH102) | 43.7 mg |
| | croscarmellose sodium | 6.5 mg |
| | Uncoated Tablet | 436.6 mg |
| | Coating | 13.5 mg |

TABLE 18

| | Component | Amount (mg) per composition |
|---|---|---|
| Intra-granular part | potassium salt of Compound I (in some embodiments, potassium salt crystalline Form B) | 127-128 mg |
| | solid dispersion containing 80% Compound II, 20% hypromellose | 62-63 mg |
| | solid dispersion containing 80% Compound III, 19.5% hypromellose acetate succinate, and 0.5% sodium lauryl sulfate | 93-94 mg |
| | microcrystalline cellulose (e.g., PH101) | 86-87 mg |
| | croscarmellose sodium | 11-12 mg |
| | magnesium stearate | 1-2 mg |

TABLE 18-continued

| | Component | Amount (mg) per composition |
|---|---|---|
| Extra-granular part | microcrystalline cellulose (e.g., PH102) | 43-44 mg |
| | croscarmellose sodium | 6-7 mg |
| | magnesium stearate | 1-2 mg |

TABLE 19

| | Component | Amount (mg) per composition |
|---|---|---|
| Intra-granular part | potassium salt of Compound I (in some embodiments, potassium salt crystalline Form B) | 127.7 mg |
| | solid dispersion containing 80% Compound II, 20% hypromellose | 62.5 mg |
| | solid dispersion containing 80% Compound III, 19.5% hypromellose acetate succinate, and 0.5% sodium lauryl sulfate | 93.8 mg |
| | microcrystalline cellulose (e.g., PH101) | 86.3 mg |
| | croscarmellose sodium | 11.5 mg |
| | magnesium stearate | 1.9 mg |
| Extra-granular part | microcrystalline cellulose (e.g., PH102) | 43.6 mg |
| | croscarmellose sodium | 6.5 mg |
| | magnesium stearate. | 1.9 mg |
| | Uncoated tablet | 435.8 mg |
| | Coating | 13.5 mg |

TABLE 20

| Component | Amount (mg) per composition |
|---|---|
| potassium salt of Compound I (in some embodiments, potassium salt crystalline Form B) | 45-80 mg |
| solid dispersion containing 80% Compound II, 20% hypromellose | 20-50 mg |
| solid dispersion containing 80% Compound III, 19.5% hypromellose acetate succinate, and 0.5% sodium lauryl sulfate | 30-70 mg |
| microcrystalline cellulose | 60-150 mg |
| croscarmellose sodium | 5-25 mg |
| magnesium stearate | 1-7 mg |

TABLE 21

| Component | weight % based on the total weight of composition |
|---|---|
| potassium salt of Compound I (in some embodiments, potassium salt crystalline Form B) | 15-45 wt % |
| solid dispersion containing 80% Compound II, 20% hypromellose | 5-20 wt % |
| solid dispersion containing 80% Compound III or Compound III-d, 19.5% hypromellose acetate succinate, and 0.5% sodium lauryl sulfate | 10-40 wt % |

TABLE 22

| Component | weight % based on the total weight of composition |
|---|---|
| potassium salt of Compound I (in some embodiments, potassium salt crystalline Form B) | 15-45 wt % |
| solid dispersion containing 80% Compound II, 20% hypromellose | 5-20 wt % |
| solid dispersion containing 80% Compound III or Compound III-d, 19.5% hypromellose acetate succinate, and 0.5% sodium lauryl sulfate | 10-40 wt % |
| microcrystalline cellulose | 5-50 wt % |
| croscarmellose sodium (CCS) | 1-10 wt % |

Optionally magnesium stearate in an amount of 0.05 wt %-2 wt %

TABLE 23

| Component | weight % based on the total weight of composition |
|---|---|
| potassium salt of Compound I (in some embodiments, potassium salt crystalline Form B) | 15-45 wt % |
| solid dispersion containing 80% Compound II, 20% hypromellose | 5-20 wt % |
| solid dispersion containing 80% Compound III or Compound III-d, 19.5% hypromellose acetate succinate, and 0.5% sodium lauryl sulfate | 10-40 wt % |
| microcrystalline cellulose | 5-50 wt % |
| croscarmellose sodium (CCS) | 1-10 wt % |
| magnesium stearate | 0.05-2 wt % |

TABLE 24

| Component | weight % based on the total weight of composition |
|---|---|
| potassium salt of Compound I (in some embodiments, potassium salt crystalline Form B) | 15-35 wt % |
| solid dispersion containing 80% Compound II, 20% hypromellose | 5-20 wt % |
| solid dispersion containing 80% Compound III, 19.5% hypromellose acetate succinate, and 0.5% sodium lauryl sulfate | 20-40 wt % |
| microcrystalline cellulose | 20-40 wt % |
| croscarmellose sodium (CCS) | 1-10 wt % |
| magnesium stearate | 0.05-2 wt % |

TABLE 25

| Component | weight % based on the total weight of composition |
|---|---|
| potassium salt of Compound I (in some embodiments, potassium salt crystalline Form B) | 20-40 wt % |
| solid dispersion containing 80% Compound II, 20% hypromellose | 5-20 wt % |
| solid dispersion containing 80% Compound III, 19.5% hypromellose acetate succinate, and 0.5% sodium lauryl sulfate | 10-25 wt % |
| microcrystalline cellulose | 20-40 wt % |
| croscarmellose sodium (CCS) | 1-10 wt % |
| magnesium stearate | 0.05-2 wt % |

TABLE 26

| Component | weight % based on the total weight of composition |
|---|---|
| potassium salt of Compound I (in some embodiments, potassium salt crystalline Form B) | 30-40 wt % |
| solid dispersion containing 80% Compound II, 20% hypromellose | 5-15 wt % |
| solid dispersion containing 80% Compound III, 19.5% hypromellose acetate succinate, and 0.5% sodium lauryl sulfate | 10-20 wt % |
| microcrystalline cellulose | 25-35 wt % |
| croscarmellose sodium (CCS) | 2-7 wt % |
| magnesium stearate | 0.05-2 wt % |

TABLE 27

| Component | weight % based on the total weight of composition |
|---|---|
| potassium salt of Compound I (in some embodiments, potassium salt crystalline Form B) | 33-38 wt % |
| solid dispersion containing 80% Compound II, 20% hypromellose | 8-13 wt % |
| solid dispersion containing 80% Compound III, 19.5% hypromellose acetate succinate, and 0.5% sodium lauryl sulfate | 13-18 wt % |
| microcrystalline cellulose | 30-35 wt % |
| croscarmellose sodium (CCS) | 2-7 wt % |
| magnesium stearate | 0.05-2 wt % |

TABLE 28

| Component | weight % based on the total weight of composition |
|---|---|
| potassium salt of Compound I (in some embodiments, potassium salt crystalline Form B) | 25-35 wt % |
| solid dispersion containing 80% Compound II, 20% hypromellose | 10-20 wt % |
| solid dispersion containing 80% Compound III, 19.5% hypromellose acetate succinate, and 0.5% sodium lauryl sulfate | 15-25 wt % |
| microcrystalline cellulose | 25-35 wt % |
| croscarmellose sodium (CCS) | 2-7 wt % |
| magnesium stearate | 0.05-2 wt % |

TABLE 29

| Component | weight % based on the total weight of composition |
|---|---|
| potassium salt of Compound I (in some embodiments, potassium salt crystalline Form B) | 27-32 wt % |
| solid dispersion containing 80% Compound II, 20% hypromellose | 12-17 wt % |
| solid dispersion containing 80% Compound III, 19.5% hypromellose acetate succinate, and 0.5% sodium lauryl sulfate | 18-23 wt % |
| microcrystalline cellulose | 25-35 wt % |
| croscarmellose sodium (CCS) | 3-6 wt % |
| magnesium stearate | 0.05-1.5 wt % |

TABLE 30

| | Component | Amount (mg) per composition |
|---|---|---|
| Intra-granular part | potassium salt of Compound I (in some embodiments, potassium salt crystalline Form B) | 207-217 |
| | solid dispersion containing 80% Compound II, 20% hypromellose | 58-68 |
| | solid dispersion containing 80% Compound III, 19.5% hypromellose acetate succinate, and 0.5% sodium lauryl sulfate | 182-193 |
| | microcrystalline cellulose (e.g., PH101) | 125-145 |
| | croscarmellose sodium | 10-20 |
| | magnesium stearate | 3-9 |
| Extra-granular part | microcrystalline cellulose (e.g., PH102) | 50-70 |
| | croscarmellose sodium | 5-15 |

TABLE 31

| | Component | Amount (mg) per composition |
|---|---|---|
| Intra-granular part | potassium salt of Compound I (in some embodiments, potassium salt crystalline Form B) | 212-213 |
| | solid dispersion containing 80% Compound II, 20% hypromellose | 62-63 |
| | solid dispersion containing 80% Compound III, 19.5% hypromellose acetate succinate, and 0.5% sodium lauryl sulfate | 187-188 |
| | microcrystalline cellulose (e.g., PH101) | 136-138 |
| | croscarmellose sodium | 15-16 |
| | magnesium stearate | 5-6 |
| Extra-granular part | microcrystalline cellulose (e.g., PH102) | 59-60 |
| | croscarmellose sodium | 8-9 |

TABLE 32

| Component | weight % based on the total weight of composition |
|---|---|
| potassium salt of Compound I (in some embodiments, potassium salt crystalline Form B) | 28-33 wt % |
| solid dispersion containing 80% Compound II, 20% hypromellose | 7-12 wt % |
| solid dispersion containing 80% Compound III, 19.5% hypromellose acetate succinate, and 0.5% sodium lauryl sulfate | 25-30 wt % |
| microcrystalline cellulose | 25-35 wt % |
| croscarmellose sodium (CCS) | 2-5 wt % |
| magnesium stearate | 0.05-1.5 wt % |

TABLE 33

| Component | Amount (mg) per composition |
|---|---|
| potassium salt of Compound I (in some embodiments, potassium salt crystalline Form B) | 122-132 |
| solid dispersion containing 80% Compound II, 20% hypromellose | 58-68 |
| solid dispersion containing 80% Compound III, 19.5% hypromellose acetate succinate, and 0.5% sodium lauryl sulfate | 182-193 |

TABLE 33-continued

| Component | Amount (mg) per composition |
|---|---|
| microcrystalline cellulose | 110-145 |
| croscarmellose sodium | 13-25 |
| magnesium stearate | 1.5-8 |

TABLE 34

| | Component | Amount (mg) per composition |
|---|---|---|
| Intra-granular part | potassium salt of Compound I (in some embodiments, potassium salt crystalline Form B) | 127-128 |
| | solid dispersion containing 80% Compound II, 20% hypromellose | 62-63 |
| | solid dispersion containing 80% Compound III, 19.5% hypromellose acetate succinate, and 0.5% sodium lauryl sulfate | 187-188 |
| | microcrystalline cellulose (e.g., PH101) | 86-87 |
| | croscarmellose sodium | 11-12 |
| | magnesium stearate | 1-2.5 |
| Extra-granular part | microcrystalline cellulose (e.g., PH102) | 43-44 |
| | croscarmellose sodium | 6-7 |
| | magnesium stearate | 1-2.5 |

TABLE 35

| | Component | Amount (mg) per composition |
|---|---|---|
| Intra-granular part | potassium salt of Compound I (in some embodiments, potassium salt crystalline Form B) | 127-128 |
| | solid dispersion containing 80% Compound II, 20% hypromellose | 62-63 |
| | solid dispersion containing 80% Compound III, 19.5% hypromellose acetate succinate, and 0.5% sodium lauryl sulfate | 187-188 |
| | microcrystalline cellulose (e.g., PH101) | 86-88 |
| | croscarmellose sodium | 13-16 |
| | magnesium stearate | 1-1.5 |
| Extra-granular part | microcrystalline cellulose (e.g., PH102) | 48-50 |
| | croscarmellose sodium | 7-9 |
| | magnesium stearate | 4-5.5 |

TABLE 36

| | Component | Amount (mg) per composition |
|---|---|---|
| Intra-granular part | potassium salt of Compound I (in some embodiments, potassium salt crystalline Form B) | 62-65 |
| | solid dispersion containing 80% Compound II, 20% hypromellose | 30-33 |
| | solid dispersion containing 80% Compound III, 19.5% hypromellose acetate succinate, and 0.5% sodium lauryl sulfate | 90-95 |
| | microcrystalline cellulose (e.g., PH101) | 42-45 |
| | croscarmellose sodium | 7-8 |
| | magnesium stearate | 0.5-1 |
| Extra-granular part | microcrystalline cellulose (e.g., PH102) | 23-26 |
| | croscarmellose sodium | 3-5 |
| | magnesium stearate | 2-3.5 |

TABLE 37

| Component | Amount (mg) per composition |
|---|---|
| potassium salt of Compound I (in some embodiments, potassium salt crystalline Form B) | 58-68 |
| solid dispersion containing 80% Compound II, 20% hypromellose | 25-35 |
| solid dispersion containing 80% Compound III, 19.5% hypromellose acetate succinate, and 0.5% sodium lauryl sulfate | 87-97 |
| microcrystalline cellulose | 60-100 |
| croscarmellose sodium | 5-15 |
| magnesium stearate | 1.5-7 |

TABLE 38

| Component | Amount (mg) per composition |
|---|---|
| potassium salt of Compound I (in some embodiments, potassium salt crystalline Form B) | 50-80 |
| solid dispersion containing 80% Compound II, 20% hypromellose | 20-40 |
| solid dispersion containing 80% Compound III, 19.5% hypromellose acetate succinate, and 0.5% sodium lauryl sulfate | 70-120 |
| microcrystalline cellulose | 60-300 |
| croscarmellose sodium | 5-25 |
| magnesium stearate | 1-7 |

TABLE 39

| Component | weight % based on the total weight of composition |
|---|---|
| potassium salt of Compound I (in some embodiments, potassium salt crystalline Form B) | 20-30 wt % |
| solid dispersion containing 80% Compound II, 20% hypromellose | 7-15 wt % |
| solid dispersion containing 80% Compound III, 19.5% hypromellose acetate succinate, and 0.5% sodium lauryl sulfate | 30-40 wt % |
| microcrystalline cellulose | 15-40 wt % |
| croscarmellose sodium (CCS) | 2-7 wt % |
| magnesium stearate | 0.05-1.5 wt % |

TABLE 40

| Component | weight % based on the total weight of composition |
|---|---|
| potassium salt of Compound I (in some embodiments, potassium salt crystalline Form B) | 22-27 wt % |
| solid dispersion containing 80% Compound II, 20% hypromellose | 8-13 wt % |
| solid dispersion containing 80% Compound III, 19.5% hypromellose acetate succinate, and 0.5% sodium lauryl sulfate | 32-37 wt % |
| microcrystalline cellulose | 20-30 wt % |
| croscarmellose sodium (CCS) | 2-5 wt % |
| magnesium stearate | 0.05-1.5 wt % |

TABLE 41

| | Component | Amount (mg) per composition |
|---|---|---|
| Intra-granular part | potassium salt of Compound I (in some embodiments, potassium salt crystalline Form B) | 207-217 |
| | solid dispersion containing 80% Compound II, 20% hypromellose | 58-68 |
| | solid dispersion containing 80% Compound III-d, 19.5% hypromellose acetate succinate, and 0.5% sodium lauryl sulfate | 120-130 |
| | microcrystalline cellulose (e.g., PH101) | 125-150 |
| | croscarmellose sodium | 10-20 |
| | magnesium stearate | 3-8 |
| Extra-granular part | microcrystalline cellulose (e.g., PH102) | 50-70 |
| | croscarmellose sodium | 5-12 |

TABLE 42

| | Component | Amount (mg) per composition |
|---|---|---|
| Intra-granular part | potassium salt of Compound I (in some embodiments, potassium salt crystalline Form B) | 212-213 |
| | solid dispersion containing 80% Compound II, 20% hypromellose | 62-63 |
| | solid dispersion containing 80% Compound III-d, 19.5% hypromellose acetate succinate, and 0.5% sodium lauryl sulfate | 124-126 |
| | microcrystalline cellulose (e.g., PH101) | 137-138 |
| | croscarmellose sodium | 15-16 |
| | magnesium stearate | 5-6 |
| Extra-granular part | microcrystalline cellulose (e.g., PH102) | 59-60 |
| | croscarmellose sodium | 8-9 |

TABLE 43

| Component | weight % based on the total weight of composition |
|---|---|
| potassium salt of Compound I (in some embodiments, potassium salt crystalline Form B) | 25-40 wt % |
| solid dispersion containing 80% Compound II, 20% hypromellose | 7-15 wt % |
| solid dispersion containing 80% Compound III-d, 19.5% hypromellose acetate succinate, and 0.5% sodium lauryl sulfate | 15-35 wt % |
| microcrystalline cellulose | 25-35 wt % |
| croscarmellose sodium (CCS) | 2-5 wt % |
| magnesium stearate | 0.05-1.5 wt % |

TABLE 44

| Component | weight % based on the total weight of composition |
|---|---|
| potassium salt of Compound I (in some embodiments, potassium salt crystalline Form B) | 29-36 wt % |
| solid dispersion containing 80% Compound II, 20% hypromellose | 8-13 wt % |
| solid dispersion containing 80% Compound III-d, 19.5% hypromellose acetate succinate, and 0.5% sodium lauryl sulfate | 15-25 wt % |
| microcrystalline cellulose | 25-35 wt % |
| croscarmellose sodium (CCS) | 2-5 wt % |
| magnesium stearate | 0.05-1.5 wt % |

TABLE 45

| Component | Amount (mg) per composition |
|---|---|
| potassium salt of Compound I (in some embodiments, potassium salt crystalline Form B) | 122-132 |
| solid dispersion containing 80% Compound II, 20% hypromellose | 58-68 |
| solid dispersion containing 80% Compound III-d, 19.5% hypromellose acetate succinate, and 0.5% sodium lauryl sulfate | 124-126 |
| microcrystalline cellulose | 129-131 |
| croscarmellose sodium | 17-19 |
| magnesium stearate | 3-5 |

TABLE 46

| | Component | Amount (mg) per composition |
|---|---|---|
| Intra-granular part | potassium salt of Compound I (in some embodiments, potassium salt crystalline Form B) | 122-132 |
| | solid dispersion containing 80% Compound II, 20% hypromellose | 58-68 |
| | solid dispersion containing 80% Compound III-d, 19.5% hypromellose acetate succinate, and 0.5% sodium lauryl sulfate | 124-126 |
| | microcrystalline cellulose (e.g., PH101) | 86-87 |
| | croscarmellose sodium | 11-12 |
| | magnesium stearate | 3-4 |
| Extra-granular part | microcrystalline cellulose (e.g., PH102) | 43-44 |
| | croscarmellose sodium | 6-7 |

TABLE 47

| | Component | Amount (mg) per composition |
|---|---|---|
| Intra-granular part | potassium salt of Compound I (in some embodiments, potassium salt crystalline Form B) | 122-132 |
| | solid dispersion containing 80% Compound II, 20% hypromellose | 58-68 |
| | solid dispersion containing 80% Compound III-d, 19.5% hypromellose acetate succinate, and 0.5% sodium lauryl sulfate | 124-126 |
| | microcrystalline cellulose (e.g., PH101) | 86-87 |
| | croscarmellose sodium | 11-12 |
| | magnesium stearate | 1.5-2.5 |
| Extra-granular part | microcrystalline cellulose (e.g., PH102) | 43-44 |
| | croscarmellose sodium | 6-7 |
| | magnesium stearate | 1.5-2.5 |

TABLE 48

| | Component | Amount (mg) per composition |
|---|---|---|
| Intra-granular part | potassium salt of Compound I (in some embodiments, potassium salt crystalline Form B) | 122-132 |
| | solid dispersion containing 80% Compound II, 20% hypromellose | 58-68 |
| | solid dispersion containing 80% Compound III-d, 19.5% hypromellose acetate succinate, and 0.5% sodium lauryl sulfate | 120-130 |
| | Microcrystalline cellulose | 75-95 |
| | Croscarmellose sodium | 5-20 |
| | Magnesium Stearate | 1-6 |
| Extra-granular part | Microcrystalline cellulose | 35-50 |
| | Croscarmellose sodium | 3-10 |

TABLE 49

| | Component | Amount (mg) per composition |
|---|---|---|
| Intra-granular part | potassium salt of Compound I (in some embodiments, potassium salt crystalline Form B) | 127-128 |
| | solid dispersion containing 80% Compound II, 20% hypromellose | 62-63 |
| | solid dispersion containing 80% Compound III-d, 19.5% hypromellose acetate succinate, and 0.5% sodium lauryl sulfate | 124-126 |
| | Microcrystalline cellulose | 84-85 |
| | Croscarmellose sodium | 11-12 |
| | Magnesium Stearate | 3-4 |
| Extra-granular part | Microcrystalline cellulose | 43-44 |
| | Croscarmellose sodium | 6-7 |

TABLE 50

| Component | Amount (mg) per composition |
|---|---|
| potassium salt of Compound I (in some embodiments, potassium salt crystalline Form B) | 250-260 |
| solid dispersion containing 80% Compound II, 20% hypromellose | 120-130 |
| solid dispersion containing 80% Compound III-d, 19.5% hypromellose acetate succinate, and 0.5% sodium lauryl sulfate | 245-255 |
| Microcrystalline cellulose | 80-110 |
| Croscarmellose sodium | 15-30 |
| optionally magnesium stearate | 0.01-10 |

TABLE 51

| Component | Amount (mg) per composition |
|---|---|
| potassium salt of Compound I (in some embodiments, potassium salt crystalline Form B) | 255-256 |
| solid dispersion containing 80% Compound II, 20% hypromellose | 124-126 |
| solid dispersion containing 80% Compound III-d, 19.5% hypromellose acetate succinate, and 0.5% sodium lauryl sulfate | 249-251 |
| microcrystalline cellulose | 89-98 |
| mroscarmellose sodium | 22-23 | optionally magnesium stearate in an amount of 0.01-10 mg per composition

TABLE 52

| Component | Amount (mg) per composition |
|---|---|
| potassium salt of Compound I (in some embodiments, potassium salt crystalline Form B) | 122-132 |
| solid dispersion containing 80% Compound II, 20% hypromellose | 57-67 |
| solid dispersion containing 80% Compound III-d, 19.5% hypromellose acetate succinate, and 0.5% sodium lauryl sulfate | 120-130 |
| microcrystalline cellulose | 275-305 |
| croscarmellose sodium | 10-25 | optionally magnesium stearate in an amount of 0.05-10 mg per composition

TABLE 53

| Component | Amount (mg) per composition |
|---|---|
| potassium salt of Compound I (in some embodiments, potassium salt crystalline Form B) | 127-128 |
| solid dispersion containing 80% Compound II, 20% hypromellose | 62-63 |
| solid dispersion containing 80% Compound III-d, 19.5% hypromellose acetate succinate, and 0.5% sodium lauryl sulfate | 124-126 |
| Microcrystalline cellulose | 289-297 |
| Croscarmellose sodium | 18-19 | optionally magnesium stearate in an amount of 0.01-10 mg per composition

TABLE 54

| Component | Amount (mg) per composition |
|---|---|
| potassium salt of Compound I (in some embodiments, potassium salt crystalline Form B) | 122-132 |
| solid dispersion containing 80% Compound II, 20% hypromellose | 58-68 |
| solid dispersion containing 80% Compound III-d, 19.5% hypromellose acetate succinate, and 0.5% sodium lauryl sulfate | 120-130 |
| microcrystalline cellulose | 110-130 |
| croscarmellose sodium | 10-20 | optionally magnesium stearate in an amount of 0.01-10 mg per composition

TABLE 55

| Component | Amount (mg) per composition |
|---|---|
| potassium salt of Compound I (in some embodiments, potassium salt crystalline Form B) | 127-128 |
| solid dispersion containing 80% Compound II, 20% hypromellose | 62-63 |
| solid dispersion containing 80% Compound III-d, 19.5% hypromellose acetate succinate, and 0.5% sodium lauryl sulfate | 124-126 |
| Microcrystalline cellulose | 117-122 |
| Croscarmellose sodium | 13-14 | optionally magnesium stearate in an amount of 0.01-10 mg per composition

TABLE 56

| Component | weight % based on the total weight of composition |
|---|---|
| potassium salt of Compound I (in some embodiments, potassium salt crystalline Form B) | 15-40 wt % |
| solid dispersion containing 80% Compound II, 20% hypromellose | 5-20 wt % |
| solid dispersion containing 80% Compound III-d, 19.5% hypromellose acetate succinate, and 0.5% sodium lauryl sulfate | 20-40 wt % |
| microcrystalline cellulose | 10-50 wt % |
| croscarmellose sodium (CCS) | 2-7 wt % | optionally magnesium stearate in an amount of 0.01 wt %-2 wt % based on the total weight of composition

TABLE 57

| Component | weight % based on the total weight of composition |
|---|---|
| potassium salt of Compound I (in some embodiments, potassium salt crystalline Form B) | 20-30 wt % |
| solid dispersion containing 80% Compound II, 20% hypromellose | 8-18 wt % |
| solid dispersion containing 80% Compound III-d, 19.5% hypromellose acetate succinate, and 0.5% sodium lauryl sulfate | 20-30 wt % |
| microcrystalline cellulose | 20-30 wt % |
| croscarmellose sodium (CCS) | 2-5 wt % | optionally magnesium stearate in an amount of 0.01 wt %-1.5 wt % based on the total weight of composition

TABLE 58

| Component | weight % based on the total weight of composition |
|---|---|
| potassium salt of Compound I (in some embodiments, potassium salt crystalline Form B) | 28-38 wt % |
| solid dispersion containing 80% Compound II, 20% hypromellose | 10-20 wt % |
| solid dispersion containing 80% Compound III-d, 19.5% hypromellose acetate succinate, and 0.5% sodium lauryl sulfate | 27-37 wt % |
| microcrystalline cellulose | 5-20 wt % |
| croscarmellose sodium (CCS) | 2-5 wt % | optionally magnesium stearate in an amount of 0.01 wt %-1.5 wt % based on the total weight of composition

TABLE 59

| Component | weight % based on the total weight of composition |
|---|---|
| potassium salt of Compound I (in some embodiments, potassium salt crystalline Form B) | 15-25 wt % |
| solid dispersion containing 80% Compound II, 20% hypromellose | 5-15 wt % |
| solid dispersion containing 80% Compound III-d, 19.5% hypromellose acetate succinate, and 0.5% sodium lauryl sulfate | 15-25 wt % |
| microcrystalline cellulose | 40-50 wt % |
| croscarmellose sodium (CCS) | 2-5 wt % | optionally magnesium stearate in an amount of 0.01 wt %-1.5 wt % based on the total weight of composition

TABLE 60

| Component | weight % based on the total weight of composition |
|---|---|
| potassium salt of Compound I (in some embodiments, potassium salt crystalline Form B) | 22-32 wt % |
| solid dispersion containing 80% Compound II, 20% hypromellose | 10-20 wt % |
| solid dispersion containing 80% Compound III-d, 19.5% hypromellose acetate succinate, and 0.5% sodium lauryl sulfate | 20-30 wt % |
| microcrystalline cellulose | 20-30 wt % |
| croscarmellose sodium (CCS) | 2-5 wt % | optionally magnesium stearate in an amount of 0.01 wt %-1.5 wt % based on the total weight of composition

TABLE 61

| Component | Amount (mg) per composition |
|---|---|
| potassium salt of Compound I (in some embodiments, potassium salt crystalline Form B) | 50-80 |
| solid dispersion containing 80% Compound II, 20% hypromellose | 20-40 |
| solid dispersion containing 80% Compound III-d, 19.5% hypromellose acetate succinate, and 0.5% sodium lauryl sulfate | 45-80 |
| microcrystalline cellulose | 60-300 |
| croscarmellose sodium | 5-25 | optionally magnesium stearate in an amount of 0.01-10 mg per composition

TABLE 62

| Component | Amount (mg) per composition |
|---|---|
| potassium salt of Compound I (in some embodiments, potassium salt crystalline Form B) | 95-160 |
| solid dispersion containing 80% Compound II, 20% hypromellose | 45-80 |
| solid dispersion containing 80% Compound III-d, 19.5% hypromellose acetate succinate, and 0.5% sodium lauryl sulfate | 95-155 |
| Microcrystalline cellulose | 60-300 |
| Croscarmellose sodium | 5-25 | optionally magnesium stearate in an amount of 0.01-10 mg per composition

Processes of Making Tablets

The tablets of the disclosure can be produced by compacting or compressing an admixture or composition, for example, powder or granules, under pressure to form a stable three-dimensional shape (e.g., a tablet). As used herein, "tablet" includes compressed pharmaceutical dosage unit forms of all shapes and sizes, whether coated or uncoated. In some embodiments, the methods of preparing the tablets disclosed herein comprise (a) mixing a potassium salt of Compound I (in some embodiments, potassium salt crystalline Form B) and the first and second solid dispersions to form a first mixture; and (b) compressing a tablet mixture comprising the first mixture into a tablet. As used herein, the term "mixing" include mixing, blending and combining. In some embodiments, the tablet mixture further comprises one or more pharmaceutically acceptable excipients, and the methods further comprise mixing the first mixture with said one or more excipients to form the tablet mixture. Mixing the first mixture with one or more excipients can be performed in one or more steps. In one embodiment, the one or more excipients are mixed to form a second mixture; and the first and second mixtures are mixed together to form the tablet mixture prior to the compression step. In one embodiment, the one or more excipients can be mixed with the first mixture in more than one parts, for example, some excipients mixed with the first mixture first and the other excipients followed later. In some embodiments, the tablets disclosed herein an intra-granular part and an extra-granular part as described above, and one or more excipients included in the intra-granular part are mixed to form a second mixture, and one or more excipients included in the extra-granular part are mixed to form a third mixture, and the first mixture are combined with the second mixture, and the combined first and second mixtures are combined with the third mixture to form a tablet mixture.

In some embodiments, the methods of preparing the tablets disclosed herein comprise: (a) mixing a potassium salt of Compound I (in some embodiments, potassium salt crystalline Form B) and the first and second solid dispersions to form a first mixture; (b) mixing the first mixture with a microcrystalline cellulose, croscarmellose sodium and magnesium stearate to form a tablet mixture; and (c) compressing the tablet mixture into a tablet.

In some embodiments, the methods of preparing the tablets disclosed herein comprise:

(a) mixing a potassium salt of Compound I (in some embodiments, potassium salt crystalline Form B) and the first and second solid dispersions described above to form a first mixture;

(b) mixing a microcrystalline cellulose, croscarmellose sodium and magnesium stearate in an intra-granular part to form a second mixture;

(c) mixing a microcrystalline cellulose and croscarmellose sodium in an extra-granular part to form a third mixture;

(d) mixing the first, second, and third mixtures to form a tablet mixture; and (e) compressing the tablet mixture comprising the first, second and third mixtures into a tablet. It is noted that step (a) can occur prior to step (b) or step (b) can occur prior to step (a).

In some embodiments, the methods of preparing the tablets disclosed herein comprise:

(a) mixing a potassium salt of Compound I (in some embodiments, potassium salt crystalline Form B) and the first and second solid dispersions to form a first mixture;

(b) mixing a microcrystalline cellulose, croscarmellose sodium and magnesium stearate in an intra-granular part to form a second mixture;

(c) mixing a microcrystalline cellulose, croscarmellose sodium, and magnesium stearate comprised in an extra-granular part to form a third mixture;

(d) mixing the first, second, and third mixtures to form a tablet mixture;

(e) compressing the tablet mixture comprising the first, second and third mixtures into a tablet.

In some embodiments, the methods disclosed herein further comprise coating the tablet.

In some embodiments, the methods disclosed herein further comprise granulating the first, second, and/or third mixtures prior to the compression the tablet mixture. Any suitable methods known in the art for granulation and compression of pharmaceutical compositions can be used. It is noted that step (a) can occur prior to step (b) or step (b) can occur prior to step (a).

Granulation and Compression

In some embodiments, solid forms, including powders comprising one or more APIs (e.g., Compound I, Compound II, and/or Compound III or III-d) and the included pharmaceutically acceptable excipients (e.g. filler, diluent, disintegrant, surfactant, glidant, binder, lubricant, or any combination thereof) can be subjected to a dry granulation process. The dry granulation process causes the powder to agglomerate into larger particles having a size suitable for further processing. Dry granulation can improve the flowability of a mixture to produce tablets that comply with the demand of mass variation or content uniformity.

In some embodiments, formulations can be produced using one or more mixing and dry granulations steps. The order and the number of the mixing by granulation. At least one of the excipients and the API(s) can be subject to dry granulation or wet high shear granulation or twin screw wet granulation before compression into tablets. Dry granulation can be carried out by a mechanical process, which transfers energy to the mixture without any use of any liquid substances (neither in the form of aqueous solutions, solutions based on organic solutes, or mixtures thereof) in contrast to wet granulation processes, also contemplated herein. Generally, the mechanical process requires compaction such as the one provided by roller compaction. An example of an alternative method for dry granulation is slugging. In some embodiments, wet granulations instead of the dry granulation can be used.

In some embodiments, roller compaction is a granulation process comprising mechanical compacting of one or more substances. In some embodiments, a pharmaceutical composition comprising an admixture of powders is pressed, that is roller compacted, between two rotating rollers to make a solid sheet that is subsequently crushed in a sieve to form a particulate matter. In this particulate matter, a close mechanical contact between the ingredients can be obtained. An example of roller compaction equipment is Minipactor® a Gerteis 3W-Polygran from Gerteis Maschinen+Process engineering AG.

In some embodiments, tablet compression according to the disclosure can occur without any use of any liquid substances (neither in the form of aqueous solutions, solutions based on organic solutes, or mixtures thereof), i.e., a dry granulation process. In a typical embodiment the resulting core or tablet has a compressive strength in the range of from 1 kp to 15 kP; such as 1.5 to 12.5 kP, preferably in the range of 2 to 10 kP.

In some embodiments, the ingredients are weighed according to the formula set herein. Next, all of the intra-granular ingredients are sifted and mixed well. The ingredients can be lubricated with a suitable lubricant, for example, magnesium stearate. The next step can comprise compaction/slugging of the powder admixture and sized ingredients. Next, the compacted or slugged blends are milled into granules and sifted to obtain the desired size. Next, the granules can be further lubricated with, for example, magnesium stearate. Next, the granular composition of the disclosure can be compressed on suitable punches into various pharmaceutical formulations in accordance with the disclosure. Optionally the tablets can be coated with a film coat.

Another aspect of the disclosure provides a method for producing a pharmaceutical composition comprising an admixture of a composition comprising one or more APIs (e.g., Compound I, Compound II and/or Compound III); and one or more excipients selected from: one or more fillers, a diluent, a binder, a glidant, a surfactant, a lubricant, a disintegrant, and compressing the composition into a tablet.

Coating

In some embodiments, the tablets disclosed herein can be coated with a film coating and optionally labeled with a logo, other image and/or text using a suitable ink. In still other embodiments, the tablets disclosed herein can be coated with a film coating, waxed, and optionally labeled with a logo, other image and/or text using a suitable ink. Suitable film coatings and inks are compatible with the other ingredients of the tablets, e.g., they do not substantially reduce the solubility, the chemical stability, the physical stability, the hardness, or the biological activity of the tablets. The suitable colorants and inks can be any color and are water based or solvent based. In one embodiment, the tablets disclosed herein are coated with a colorant and then labeled with a logo, other image, and/or text using a suitable ink.

In some embodiments, the tablets disclosed herein are coated with a film that comprises 2-6 wt % by the weight of the uncoated tablet. In some embodiments, the film comprises one or more colorants and/or pigments. In some embodiments, the tablets disclosed herein are coated with a film that comprises one or more colorants and/or pigments and wherein the film comprises 2-5 wt % by the weight of the uncoated tablet. In some embodiments, the tablets disclosed herein are coated with a film that comprises one or more colorants and/or pigments and wherein the film comprises 2-4 wt % by the weight of the uncoated tablet. The colored tablets can be labeled with a logo and text indicating the strength of the active ingredient in the tablet using a suitable ink.

Methods of Treatment

One aspect of the invention provides methods of treating, lessening the severity of, or symptomatically treating cystic fibrosis in a patient comprising administering an effective amount of at least one crystalline form of Compound I or pharmaceutically acceptable salt thereof disclosed herein, alone or in combination with one or more additional CFTR modulating agents to the patient. In some embodiments, the method comprises administering at least one crystalline form of Compound I or pharmaceutically acceptable salt thereof disclosed herein, in combination with Compound II, and/or Compound III or Compound III-d. In some embodiments, the combination may include 3-(6-(1-(2,2-difluorobenzo[d][1,3]dioxol-5-yl)cyclopropanecarboxamido)-3-methylpyridin-2-yl)benzoic acid ("Compound IV"):

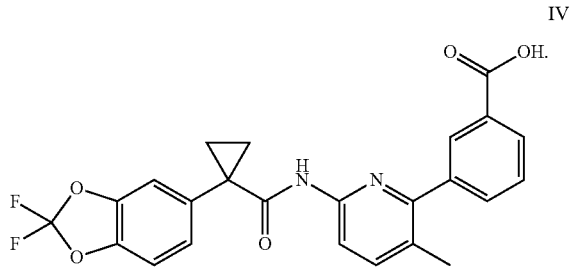 [SMILES: Cc1ccc(NC(=O)C2(c3ccc4c(c3)OC(F)(F)O4)CC2)nc1-c1cccc(C(=O)O)c1]

In some embodiments, the method comprises administering a potassium salt of Compound I (in some embodiments, potassium salt crystalline Form B), alone or in combination with one or more additional CFTR modulating agents, to the patient in need thereof. In some embodiments, the method comprises administering a potassium salt of Compound I (in some embodiments, potassium salt crystalline Form B) in combination Compound II, and, optionally, one or more additional CFTR modulating agents. In some embodiments, the method comprises administering a potassium salt of Compound I (in some embodiments, potassium salt crystalline Form B) in combination Compound III, and, optionally, one or more additional CFTR modulating agents. In some embodiments, the method comprises administering a potassium salt of Compound I (in some embodiments, potassium salt crystalline Form B), in combination with Compound II, and Compound III or III-d. In some embodiments, the combination may include Compound IV.

In one embodiment, the method of treating, lessening the severity of, or symptomatically treating cystic fibrosis in a patient comprises administering an effective amount of at least one crystalline form, including crystalline salt forms, of Compound I as disclosed herein, in combination with one or more additional CFTR modulating agents, wherein the at least one crystalline form of Compound I as disclosed herein and the additional modulating agent(s) are administered together in a single composition. In some embodiment, the at least one crystalline form of Compound I as disclosed herein and the additional modulating agent(s) are administered as two or more separate compositions.

In some embodiments, the method of treating, lessening the severity of, or symptomatically treating cystic fibrosis in a patient comprises administering an effective amount of at least one crystalline form, including crystalline salt forms, of Compound I as disclosed herein, in combination with Compound II and/or Compound III or III-d, wherein the at least one crystalline form of Compound I as disclosed herein and Compound II and/or Compound III or III-d are administered together in a single composition. In some embodiment, the at least one crystalline form of Compound I as disclosed herein and Compound II and/or Compound III or III-d are administered as two or more separate compositions.

In some embodiments, the method comprises administering an effective amount of a potassium salt of Compound I (in some embodiments, potassium salt crystalline Form B) in combination with one or more additional CFTR modulating agents, wherein the potassium salt of Compound I and the additional modulating agent(s) are administered together in a single composition. In some embodiments, the potassium salt of Compound I and the additional modulating agent(s) are administered as two or more separate compositions.

In some embodiments, the method of treating, lessening the severity of, or symptomatically treating cystic fibrosis in a patient comprises administering an effective amount of a potassium salt of Compound I (in some embodiments, potassium salt crystalline Form B) in combination with Compound II and/or Compound III or III-d, wherein the potassium salt of Compound I and Compound II and/or Compound III or III-d are administered together in a single composition. In some embodiments, the potassium salt of Compound I and Compound II and/or Compound III or III-d are administered in two or more separate compositions.

In some embodiments, the patient has a F508del heterozygous or homozygous genotype. In some embodiments, the patient is homozygous or heterozygous for the CFTR genetic mutation G551D. In some embodiments, the patient is heterozygous for the G551D genetic mutation on one allele and the other CF-causing genetic mutation on the other allele is any one of F508del, G542X, $N_{1303}K$, W1282X, R117H, R553X, 1717-1G->A, 621+1G->T, 2789+5G->A, 3849+10kbC->T, R1162X, G85E, 3120+1G->A, ΔI507, 1898+1G->A, 3659delC, R347P, R560T, R334W, A455E, 2184delA, or 711+1G->T. In some embodiments, the patient is heterozygous for the G551D genetic mutation, and the other CFTR genetic mutation is F508del. In some embodiments, the patient is heterozygous for the G551D genetic mutation, and the other CFTR genetic mutation is R117H.

In some embodiments, disclosed herein is a method of treating, lessening the severity of, or symptomatically treating cystic fibrosis in a patient comprising administering an effective amount of a pharmaceutical composition of this disclosure to the patient, such as a mammal, wherein the patient possesses a CFTR genetic mutation F508del. In some embodiments, the patient is homozygous for the F508del genetic mutation. In some embodiments, the patient is heterozygous for the F508del genetic mutation wherein the patient has the F508del genetic mutation on one allele and any CF-causing genetic mutation on the other allele. In some embodiments, the patient is heterozygous for F508del, and the other CFTR genetic mutation is any CF-causing mutation, including, but not limited to G551D, G542X, $N_{1303}K$, W1282X, R117H, R553X, 1717-1G->A, 621+1G->T, 2789+5G->A, 3849+10kbC->T, R1162X, G85E, 3120+1G->A, ΔI507, 1898+1G->A, 3659delC, R347P, R560T, R334W, A455E, 2184delA, or 711+1G->T. In some embodiments, the patient is heterozygous for F508del, and the other CFTR genetic mutation is G551D. In some embodiments, the patient is heterozygous for F508del, and the other CFTR genetic mutation is R117H.

In some embodiments, disclosed herein is a method of treating, lessening the severity of, or symptomatically treating cystic fibrosis in a patient comprising administering an effective amount of a pharmaceutical composition of this disclosure to the patient, such as a mammal, wherein the patient possesses a CFTR genetic mutation selected from G178R, G551S, G970R, G1244E, S1255P, G1349D, S549N, S549R, S1251N, E193K, F1052V, G1069R, R117C, D110H, R347H, R352Q, E56K, P67L, L206W, A455E, D579G, S1235R, S945L, R1070W, F1074L, D110E, D1270N, D1152H, 1717-1G->A, 621+1G->T, 3120+1G->A, 1898+1G->A, 711+1G->T, 2622+1G->A, 405+1G->A, 406-1G->A, 4005+1G->A, 1812-1G->A, 1525-1G->A, 712-1G->T, 1248+1G->A, 1341+1G->A, 3121-1G->A, 4374+1G->T, 3850-1G->A, 2789+5G->A, 3849+10kbC->T, 3272-26A->G, 711+5G->A, 3120G->A, 1811+1.6kbA->G, 711+3A->G, 1898+3A->G, 1717-8G->A, 1342-2A->C, 405+3A->C, 1716G/A, 1811+1G->C, 1898+5G->T, 3850-3T->G, IVS14b+5G->A, 1898+1G->T, 4005+2T->C, 621+3A->G, 1949del84, 3141del9, 3195del6, 3199del6, 3905InsT, 4209TGTT->A, A1006E, A120T, A234D, A349V, A613T, C524R, D192G, D443Y, D513G, D836Y, D924N, D979V, E116K, E403D, E474K, E588V, E60K, E822K, F1016S, F1099L, F191V, F311del, F311L, F508C, F575Y, G1061R, G1249R, G126D, G149R, G194R, G194V, G27R, G314E, G458V, G463V, G480C, G622D, G628R, G628R(G->A), G91R, G970D, H1054D, H1085P, H1085R, H1375P, H139R, H199R, H609R, H939R, 11005R, 11234V, 11269N, 11366N, 1175V, 1502T, 1506S, 1506T, 1601F, 1618T, 1807M, 1980K, L102R, L1324P, L1335P, L138ins, L1480P, L15P, L165S, L320V, L346P, L453S, L571S, L967S, M1101R, M152V, M1T, M1V, M265R, M952I, M952T, P574H, P5L, P750L, P99L, Q1100P, Q1291H, Q1291R, Q237E, Q237H, Q452P, Q98R, R1066C, R1066H, R117G, R117L, R117P, R1283M, R1283S, R170H, R258G, R31L, R334L, R334Q, R347L, R352W, R516G, R553Q, R751L, R792G, R933G, S1118F, S1159F, S1159P, S13F, S549R(A->C), S549R(T->G), S589N, S737F, S912L, T1036N, T1053I, T1246I, T604I, V1153E, V1240G, V1293G, V201M, V232D, V456A, V456F, V562I, W1098C, W1098R, W1282R, W361R, W57G, W57R, Y1014C, Y1032C, Y109N, Y161D, Y161S, Y563D, Y563N, Y569C, and Y913C. In some embodiments, the patient has at least one combination mutation chosen from: G178R, G551S, G970R, G1244E, S1255P, G1349D, S549N, S549R, S1251N, E193K, F1052V, G1069R, R117C, D110H, R347H, R352Q, E56K, P67L, L206W, A455E, D579G, S1235R, S945L, R1070W, F1074L, D110E, D1270N, D1152H, 1717-1G->A, 621+1G->T, 3120+1G->A, 1898+1G->A, 711+1G->T, 2622+1G->A, 405+1G->A, 406-1G->A, 4005+1G->A, 1812-1G->A, 1525-1G->A, 712-1G->T, 1248+1G->A, 1341+1G->A, 3121-1G->A, 4374+1G->T, 3850-1G->A, 2789+5G->A, 3849+10kbC->T, 3272-26A->G, 711+5G->A, 3120G->A, 1811+1.6kbA->G, 711+3A->G, 1898+3A->G, 1717-8G->A, 1342-2A->C, 405+3A->C, 1716G/A, 1811+1G->C, 1898+5G->T, 3850-3T->G, IVS14b+5G->A, 1898+1G->T, 4005+2T->C, and 621+3A->G.

In some embodiments, the patient has at least one combination mutation chosen from: 1949del84, 3141del9, 3195del6, 3199del6, 3905InsT, 4209TGTT->A, A1006E, A120T, A234D, A349V, A613T, C524R, D192G, D443Y, D513G, D836Y, D924N, D979V, E116K, E403D, E474K, E588V, E60K, E822K, F1016S, F1099L, F191V, F311del, F311L, F508C, F575Y, G1061R, G1249R, G126D, G149R, G194R, G194V, G27R, G314E, G458V, G463V, G480C, G622D, G628R, G628R(G->A), G91R, G970D, H1054D, H1085P, H1085R, H1375P, H139R, H199R, H609R, H939R, 11005R, 11234V, 11269N, 11366N, 1175V, 1502T, 1506S, 1506T, 1601F, 1618T, 1807M, 1980K, L102R, L1324P, L1335P, L138ins, L1480P, L15P, L165S, L320V, L346P, L453S, L571S, L967S, M1101R, M152V, M1T, M1V, M265R, M952I, M952T, P574H, P5L, P750L, P99L, Q1100P, Q1291H, Q1291R, Q237E, Q237H, Q452P, Q98R, R1066C, R1066H, R117G, R117L, R117P, R1283M, R1283S, R170H, R258G, R31L, R334L, R334Q, R347L, R352W, R516G, R553Q, R751L, R792G, R933G, S1118F, S1159F, S1159P, S13F, S549R(A->C), S549R(T->G), S589N, S737F, S912L, T1036N, T1053I, T1246I, T604I, V1153E, V1240G, V1293G, V201M, V232D, V456A, V456F, V562I, W1098C, W1098R, W1282R, W361R, W57G, W57R, Y1014C, Y1032C, Y109N, Y161D, Y161S, Y563D, Y563N, Y569C, and Y913C.

In some embodiments, the patient has at least one combination mutation chosen from:
D443Y; G576A; R668C,
F508C; S 1251N,
G576A; R668C,
G970R; M470V,
R74W; D1270N,
R74W; V201M, and
R74W; V201M; D1270N.

In some embodiments, disclosed herein is a method of treating, lessening the severity of, or symptomatically treating cystic fibrosis in a patient comprising administering an effective amount of a pharmaceutical composition of this disclosure to the patient, such as a mammal, wherein the patient possesses a CFTR genetic mutation selected from G178R, G551S, G970R, G1244E, S1255P, G1349D, S549N, S549R, S1251N, E193K, F1052V and G1069R. In some embodiments, this disclosure provides a method of treating CFTR comprising administering a compound of Formula (I), (II), (III), (IV), (V), or a pharmaceutically acceptable salt thereof to a patient possessing a human CFTR mutation selected from G178R, G551S, G970R, G1244E, S1255P, G1349D, S549N, S549R and S1251N. In some embodiments, disclosed herein is a method of treating, lessening the severity of, or symptomatically treating cystic fibrosis in a patient comprising administering an effective amount of a pharmaceutical composition of this disclosure to the patient, such as a mammal, wherein the patient possesses a CFTR genetic mutation selected from E193K, F1052V and G1069R. In some embodiments, the method produces an increase in chloride transport relative to baseline chloride transport of the patient.

In some embodiments, disclosed herein is a method of treating, lessening the severity of, or symptomatically treating cystic fibrosis in a patient comprising administering an effective amount of a pharmaceutical composition of this disclosure to the patient, such as a mammal, wherein the patient possesses a CFTR genetic mutation selected from R117C, D110H, R347H, R352Q, E56K, P67L, L206W, A455E, D579G, S1235R, S945L, R1070W, F1074L, D110E, D1270N and D1152H. In some embodiments, the method produces an increase in chloride transport above the baseline chloride transport of the patient.

In some embodiments, disclosed herein is a method of treating, lessening the severity of, or symptomatically treating cystic fibrosis in a patient comprising administering an effective amount of a pharmaceutical composition of this disclosure to the patient, such as a mammal, wherein the patient possesses a CFTR genetic mutation selected from 1717-1G->A, 621+1G->T, 3120+1G->A, 1898+1G->A, 711+1G->T, 2622+1G->A, 405+1G->A, 406-1G->A, 4005+1G->A, 1812-1G->A, 1525-1G->A, 712-1G->T, 1248+1G->A, 1341+1G->A, 3121-1G->A, 4374+1G->T, 3850-1G->A, 2789+5G->A, 3849+10kbC->T, 3272-26A->G, 711+5G->A, 3120G->A, 1811+1.6kbA->G, 711+3A->G, 1898+3A->G, 1717-8G->A, 1342-2A->C, 405+3A->C, 1716G/A, 1811+1G->C, 1898+5G->T, 3850-3T->G, IVS14b+5G->A, 1898+1G->T, 4005+2T->C and 621+3A->G. In some embodiments, disclosed herein is a method of treating, lessening the severity of, or symptomatically treating cystic fibrosis in a patient comprising administering an effective amount of a pharmaceutical composition of this disclosure to the patient, such as a mammal, wherein the patient possesses a CFTR genetic mutation selected from 1717-1G->A, 1811+1.6kbA->G, 2789+5G->A, 3272-26A->G and 3849+10kbC->T. In some embodiments, disclosed herein is a method of treating, lessening the severity of, or symptomatically treating cystic fibrosis in a patient comprising administering an effective amount of a pharmaceutical composition of this disclosure to the patient, such as a mammal, wherein the patient possesses a CFTR genetic mutation selected from 2789+5G->A and 3272-26A->G.

In some embodiments, disclosed herein is a method of treating, lessening the severity of, or symptomatically treating cystic fibrosis in a patient comprising administering an effective amount of a pharmaceutical composition of this disclosure to the patient, such as a mammal, wherein the patient possesses a CFTR genetic mutation selected from G178R, G551S, G970R, G1244E, S1255P, G1349D, S549N, S549R, S1251N, E193K, F1052V, G1069R, R117C, D110H, R347H, R352Q, E56K, P67L, L206W, A455E, D579G, S1235R, S945L, R1070W, F1074L, D110E, D1270N, D1152H, 1717-1G->A, 621+1G->T, 3120+1G->A, 1898+1G->A, 711+1G->T, 2622+1G->A, 405+1G->A, 406-1G->A, 4005+1G->A, 1812-1G->A, 1525-1G->A, 712-1G->T, 1248+1G->A, 1341+1G->A, 3121-1G->A, 4374+1G->T, 3850-1G->A, 2789+5G->A, 3849+10kbC->T, 3272-26A->G, 711+5G->A, 3120G->A, 1811+1.6kbA->G, 711+3A->G, 1898+3A->G, 1717-8G->A, 1342-2A->C, 405+3A->C, 1716G/A, 1811+1G->C, 1898+5G->T, 3850-3T->G, IVS14b+5G->A, 1898+1G->T, 4005+2T->C and 621+3A->G, and a human CFTR mutation selected from F508del, R117H, and G551D.

In some embodiments, disclosed herein is a method of treating, lessening the severity of, or symptomatically treating cystic fibrosis in a patient comprising administering an effective amount of a pharmaceutical composition of this disclosure to the patient, such as a mammal, wherein the patient possesses a CFTR genetic mutation selected from G178R, G551S, G970R, G1244E, S1255P, G1349D, S549N, S549R, S1251N, E193K, F1052V and G1069R, and a human CFTR mutation selected from F508del, R117H, and G551D. In some embodiments, disclosed herein is a method of treating, lessening the severity of, or symptomatically treating cystic fibrosis in a patient comprising administering an effective amount of a pharmaceutical composition of this disclosure to the patient, such as a mammal, wherein the patient possesses a CFTR genetic mutation selected from G178R, G551S, G970R, G1244E, S1255P, G1349D, S549N, S549R and S1251N, and a human CFTR mutation selected from F508del, R117H, and G551D. In some embodiments, disclosed herein is a method of treating, lessening the severity of, or symptomatically treating cystic fibrosis in a patient comprising administering an effective amount of a pharmaceutical composition of this disclosure to the patient, such as a mammal, wherein the patient possesses a CFTR genetic mutation selected from E193K, F1052V and G1069R, and a human CFTR mutation selected from F508del, R117H, and G551D. In some embodiments, the method produces an increase in chloride transport relative to baseline chloride transport of the patient.

In some embodiments, disclosed herein is a method of treating, lessening the severity of, or symptomatically treating cystic fibrosis in a patient comprising administering an effective amount of a pharmaceutical composition of this disclosure to the patient, such as a mammal, wherein the patient possesses a CFTR genetic mutation selected from R117C, D110H, R347H, R352Q, E56K, P67L, L206W, A455E, D579G, S1235R, S945L, R1070W, F1074L, D110E, D1270N and D1152H, and a human CFTR mutation selected from F508del, R117H, and G551D. In some embodiments, the method produces an increase in chloride transport which is above the baseline chloride transport of the patient.

In some embodiments, disclosed herein is a method of treating, lessening the severity of, or symptomatically treating cystic fibrosis in a patient comprising administering an effective amount of a pharmaceutical composition of this disclosure to the patient, such as a mammal, wherein the patient possesses a CFTR genetic mutation selected from 1717-1G->A, 621+1G->T, 3120+1G->A, 1898+1G->A, 711+1G->T, 2622+1G->A, 405+1G->A, 406-1G->A, 4005+1G->A, 1812-1G->A, 1525-1G->A, 712-1G->T, 1248+1G->A, 1341+1G->A, 3121-1G->A, 4374+1G->T, 3850-1G->A, 2789+5G->A, 3849+10kbC->T, 3272-26A->G, 711+5G->A, 3120G->A, 1811+1.6kbA->G, 711+3A->G, 1898+3A->G, 1717-8G->A, 1342-2A->C, 405+3A->C, 1716G/A, 1811+1G->C, 1898+5G->T, 3850-3T->G, IVS14b+5G->A, 1898+1G->T, 4005+2T->C and 621+3A->G, and a human CFTR mutation selected from F508del, R117H, and G551D. In some embodiments, disclosed herein is a method of treating, lessening the severity of, or symptomatically treating cystic fibrosis in a patient comprising administering an effective amount of a pharmaceutical composition of this disclosure to the patient, such as a mammal, wherein the patient possesses a CFTR genetic mutation selected from 1717-1G->A, 1811+1.6kbA->G, 2789+5G->A, 3272-26A->G and 3849+10kbC->T, and a human CFTR mutation selected from F508del, R117H, and G551D. In some embodiments, disclosed herein is a method of treating, lessening the severity of, or symptomatically treating cystic fibrosis in a patient comprising administering an effective amount of a pharmaceutical composition of this disclosure to the patient, such as a mammal, wherein the patient possesses a CFTR genetic mutation selected from 2789+5G->A and 3272-26A->G, and a human CFTR mutation selected from F508del, R117H.

In some embodiments, disclosed herein is a method of treating, lessening the severity of, or symptomatically treating cystic fibrosis in a patient comprising administering an effective amount of a pharmaceutical composition of this disclosure to the patient, such as a mammal, wherein the patient possesses a CFTR genetic mutation selected from G178R, G551S, G970R, G1244E, S1255P, G1349D, S549N, S549R, S1251N, E193K, F1052V, G1069R, R117C, D110H, R347H, R352Q, E56K, P67L, L206W, A455E, D579G, S1235R, S945L, R1070W, F1074L, D110E, D1270N, D1152H, 1717-1G->A, 621+1G->T, 3120+1G->A, 1898+1G->A, 711+1G->T, 2622+1G->A, 405+1G->A, 406-1G->A, 4005+1G->A, 1812-1G->A, 1525-1G->A, 712-1G->T, 1248+1G->A, 1341+1G->A, 3121-1G->A, 4374+1G->T, 3850-1G->A, 2789+5G->A, 3849+10kbC->T, 3272-26A->G, 711+5G->A, 3120G->A, 1811+1.6kbA->G, 711+3A->G, 1898+3A->G, 1717-8G->A, 1342-2A->C, 405+3A->C, 1716G/A, 1811+1G->C, 1898+5G->T, 3850-3T->G, IVS14b+5G->A, 1898+1G->T, 4005+2T->C and 621+3A->G, and a human CFTR mutation selected from F508del, R117H, and G551D.

In some embodiments, disclosed herein is a method of treating, lessening the severity of, or symptomatically treating cystic fibrosis in a patient comprising administering an effective amount of a pharmaceutical composition of this disclosure to the patient, such as a mammal, wherein the patient possesses a CFTR genetic mutation selected from G178R, G551S, G970R, G1244E, S1255P, G1349D, S549N, S549R, S1251N, E193K, F1052V and G1069R. In some embodiments, disclosed herein is a method of treating, lessening the severity of, or symptomatically treating cystic fibrosis in a patient comprising administering an effective amount of a pharmaceutical composition of this disclosure to the patient, such as a mammal, wherein the patient possesses a CFTR genetic mutation selected from G178R, G551S, G970R, G1244E, S1255P, G1349D, S549N, S549R and S1251N. In some embodiments, disclosed herein is a method of treating, lessening the severity of, or symptomatically treating cystic fibrosis in a patient comprising administering an effective amount of a pharmaceutical composition of this disclosure to the patient, such as a mammal, wherein the patient possesses a CFTR genetic mutation selected from E193K, F1052V and G1069R. In some embodiments, the method produces an increase in chloride transport relative to baseline chloride transport of the patient.

In some embodiments, disclosed herein is a method of treating, lessening the severity of, or symptomatically treating cystic fibrosis in a patient comprising administering an effective amount of a pharmaceutical composition of this disclosure to the patient, such as a mammal, wherein the patient possesses a CFTR genetic mutation selected from R117C, D110H, R347H, R352Q, E56K, P67L, L206W, A455E, D579G, S1235R, S945L, R1070W, F1074L, D110E, D1270N and D1152H. In some embodiments, the method produces an increase in chloride transport which is above the baseline chloride transport of the patient.

In some embodiments, disclosed herein is a method of treating, lessening the severity of, or symptomatically treating cystic fibrosis in a patient comprising administering an effective amount of a pharmaceutical composition of this disclosure to the patient, such as a mammal, wherein the patient possesses a CFTR genetic mutation selected from 1717-1G->A, 621+1G->T, 3120+1G->A, 1898+1G->A, 711+1G->T, 2622+1G->A, 405+1G->A, 406-1G->A, 4005+1G->A, 1812-1G->A, 1525-1G->A, 712-1G->T, 1248+1G->A, 1341+1G->A, 3121-1G->A, 4374+1G->T, 3850-1G->A, 2789+5G->A, 3849+10kbC->T, 3272-26A->G, 711+5G->A, 3120G->A, 1811+1.6kbA->G, 711+3A->G, 1898+3A->G, 1717-8G->A, 1342-2A->C, 405+3A->C, 1716G/A, 1811+1G->C, 1898+5G->T, 3850-3T->G, IVS14b+5G->A, 1898+1G->T, 4005+2T->C and 621+3A->G. In some embodiments, disclosed herein is a method of treating, lessening the severity of, or symptomatically treating cystic fibrosis in a patient comprising administering an effective amount of a pharmaceutical composition of this disclosure to the patient, such as a mammal, wherein the patient possesses a CFTR genetic mutation selected from 1717-1G->A, 1811+1.6kbA->G, 2789+5G->A, 3272-26A->G and 3849+10kbC->T. In some embodiments, disclosed herein is a method of treating, lessening the severity of, or symptomatically treating cystic fibrosis in a patient comprising administering an effective amount of a pharmaceutical composition of this disclosure to the patient, such as a mammal, wherein the patient possesses a CFTR genetic mutation selected from 2789+5G->A and 3272-26A->G.

In some embodiments, disclosed herein is a method of treating, lessening the severity of, or symptomatically treating cystic fibrosis in a patient comprising administering an effective amount of a pharmaceutical composition of this disclosure to the patient, such as a mammal, wherein the patient possesses a CFTR genetic mutation selected from G178R, G551S, G970R, G1244E, S1255P, G1349D, S549N, S549R, S1251N, E193K, F1052V, G1069R, R117C, D110H, R347H, R352Q, E56K, P67L, L206W, A455E, D579G, S1235R, S945L, R1070W, F1074L, D110E, D1270N, D1152H, 1717-1G->A, 621+1G->T, 3120+1G->A, 1898+1G->A, 711+1G->T, 2622+1G->A, 405+1G->A, 406-1G->A, 4005+1G->A, 1812-1G->A, 1525-1G->A, 712-1G->T, 1248+1G->A, 1341+1G->A, 3121-1G->A, 4374+1G->T, 3850-1G->A, 2789+5G->A, 3849+10kbC->T, 3272-26A->G, 711+5G->A, 3120G->A, 1811+1.6kbA->G, 711+3A->G, 1898+3A->G, 1717-8G->A, 1342-2A->C, 405+3A->C, 1716G/A, 1811+1G->C, 1898+5G->T, 3850-3T->G, IVS14b+5G->A, 1898+1G->T, 4005+2T->C and 621+3A->G, and a human CFTR mutation selected from F508del, R117H, and G551D, and one or more human CFTR mutations selected from F508del, R117H, and G551D.

In some embodiments, disclosed herein is a method of treating, lessening the severity of, or symptomatically treating cystic fibrosis in a patient comprising administering an effective amount of a pharmaceutical composition of this disclosure to the patient, such as a mammal, wherein the patient possesses a CFTR genetic mutation selected from G178R, G551S, G970R, G1244E, S1255P, G1349D, S549N, S549R, S1251N, E193K, F1052V and G1069R, and one or more human CFTR mutations selected from F508del, R117H, and G551D. In some embodiments, disclosed herein is a method of treating, lessening the severity of, or symptomatically treating cystic fibrosis in a patient comprising administering an effective amount of a pharmaceutical composition of this disclosure to the patient, such as a mammal, wherein the patient possesses a CFTR genetic mutation selected from G178R, G551S, G970R, G1244E, S1255P, G1349D, S549N, S549R and S1251N, and one or more human CFTR mutations selected from F508del, R117H, and G551D. In some embodiments, disclosed herein is a method of treating, lessening the severity of, or symptomatically treating cystic fibrosis in a patient comprising administering an effective amount of a pharmaceutical composition of this disclosure to the patient, such as a mammal, wherein the patient possesses a CFTR genetic mutation selected from E193K, F1052V and G1069R, and one or more human CFTR mutations selected from F508del, R117H, and G551D. In some embodiments, the method produces an increase in chloride transport relative to baseline chloride transport of the patient.

In some embodiments, disclosed herein is a method of treating, lessening the severity of, or symptomatically treating cystic fibrosis in a patient comprising administering an effective amount of a pharmaceutical composition of this disclosure to the patient, such as a mammal, wherein the patient possesses a CFTR genetic mutation selected from R117C, D110H, R347H, R352Q, E56K, P67L, L206W, A455E, D579G, S1235R, S945L, R1070W, F1074L, D110E, D1270N and D1152H, and one or more human CFTR mutations selected from F508del, R117H, and G551D. In some embodiments, the method produces an increase in chloride transport which is above the baseline chloride transport of the patient.

In some embodiments, disclosed herein is a method of treating, lessening the severity of, or symptomatically treating cystic fibrosis in a patient comprising administering an effective amount of a pharmaceutical composition of this disclosure to the patient, such as a mammal, wherein the patient possesses a CFTR genetic mutation selected from 1717-1G->A, 621+1G->T, 3120+1G->A, 1898+1G->A, 711+1G->T, 2622+1G->A, 405+1G->A, 406-1G->A, 4005+1G->A, 1812-1G->A, 1525-1G->A, 712-1G->T, 1248+1G->A, 1341+1G->A, 3121-1G->A, 4374+1G->T, 3850-1G->A, 2789+5G->A, 3849+10kbC->T, 3272-26A->G, 711+5G->A, 3120G->A, 1811+1.6kbA->G, 711+3A->G, 1898+3A->G, 1717-8G->A, 1342-2A->C, 405+3A->C, 1716G/A, 1811+1G->C, 1898+5G->T, 3850-3T->G, IVS14b+5G->A, 1898+1G->T, 4005+2T->C and 621+3A->G, and one or more human CFTR mutations selected from F508del, R117H, and G551D. In some embodiments, disclosed herein is a method of treating, lessening the severity of, or symptomatically treating cystic fibrosis in a patient comprising administering an effective amount of a pharmaceutical composition of this disclosure to the patient, such as a mammal, wherein the patient possesses a CFTR genetic mutation selected from 1717-1G->A, 1811+1.6kbA->G, 2789+5G->A, 3272-26A->G and 3849+10kbC->T, and one or more human CFTR mutations selected from F508del, R117H, and G551D. In some embodiments, disclosed herein is a method of treating, lessening the severity of, or symptomatically treating cystic fibrosis in a patient comprising administering an effective amount of a pharmaceutical composition of this disclosure to the patient, such as a mammal, wherein the patient possesses a CFTR genetic mutation selected from 2789+5G->A and 3272-26A->G, and one or more human CFTR mutations selected from F508del, R117H, and G551D.

In some embodiments, the patient is heterozygous having one CF-causing mutation on one allele and another CF-causing mutation on the other allele. In some embodiments, the patient is heterozygous for F508del, and the other CFTR genetic mutation is any CF-causing mutation, including, but not limited to F508del on one CFTR allele and a CFTR mutation on the second CFTR allele that is associated with minimal CFTR function, residual CFTR function, or a defect in CFTR channel gating activity.

In some embodiments, the CF-causing mutation is selected from Table 63. In some embodiments, the patient is heterozygous having one CF-causing mutation on one CFTR allele selected from the mutations listed in the table from FIG. 17 and another CF-causing mutation on the other CFTR allele is selected from the CFTR mutations listed in Table 63.

TABLE 63

| CFTR Mutations |
|---|

Criteria: Truncation mutations
% PI > 50% and/or SwCl$^-$ > 86 mmol/L
no full-length protein

| S4X | C276X | G542X | R792X | E1104X |
|---|---|---|---|---|
| G27X | Q290X | G550X | E822X | R1158X |
| Q39X | G330X | Q552X | W846X | R1162X |
| W57X | W401X | R553X | Y849X | S1196X |
| E60X | Q414X | E585X | R851X | W1204X |
| R75X | S434X | G673X | Q890X | L1254X |
| E92X | S466X | Q685X | S912X | S1255X |
| Q98X | S489X | R709X | Y913X | W1282X |
| Y122X | Q493X | K710X | W1089X | Q1313X |
| E193X | W496X | L732X | Y1092X | E1371X |
| L218X | C524X | R764X | W1098X | Q1382X |
| Q220X | Q525X | R785X | R1102X | Q1411X |

Criteria: Splice Mutations
% PI > 50% and/or SwCl$^-$ > 86 mmol/L
no or little mature mRNA

| 185 + 1G→T | 711 + 5G→A | 1717 − 8G→A | 2622 + 1G→A | 3121 − 1G→A |
|---|---|---|---|---|
| 296 + 1G→A | 712 − 1G→T | 1717 − 1G→A | 2790 − 1G→C | 3500 − 2A→G |
| 405 + 1G→A | 1248 + 1G→A | 1811 + 1G→C | 3040G→C | 3600 + 2insT |
| 405 + 3A→C | 1249 − 1G→A | 1811 + 1.6kbA→G | (G970R) | 3850 − 1G→A |
| 406 − 1G→A | 1341 + 1G→A | 1812 − 1G→A | 3120G→A | 4005 + 1G→A |
| 621 + 1G→T | 1525 − 2A→G | 1898 + 1G→A | 3120 + 1G→A | 4374 + 1G→T |
| 711 + 1G→T | 1525 − 1G→A | 1898 + 1G→C | 3121 − 2A→G | |

Criteria: Small (≤3 nucleotide) insertion/deletion (ins/del) frameshift mutations
% PI > 50% and/or SwCl$^-$ > 86 mmol/L
garbled and/or truncated protein TABLE 63-continued CFTR Mutations

| | | | | |
|---|---|---|---|---|
| 182delT | 1119delA | 1782delA | 2732insA | 3876delA |
| 306insA | 1138insG | 1824delA | 2869insG | 3878delG |
| 365 – 366insT | 1154insTC | 2043delG | 2896insAG | 3905insT |
| 394delTT | 1161delC | 2143delT | 2942insT | 4016insT |
| 442delA | 1213delT | 2183AA→G$^a$ | 2957delT | 4021dupT |
| 444delA | 1259insA | 2184delA | 3007delG | 4040delA |
| 457TAT→G | 1288insTA | 2184insA | 3028delA | 4279insA |
| 541delC | 1471delA | 2307insA | 3171delC | 4326delTC |
| 574delA | 1497delGG | 2347delG | 3659delC | |
| 663delT | 1548delG | 2585delT | 3737delA | |
| 935delA | 1609del CA | 2594delGT | 3791delC | |
| 1078delT | 1677delTA | 2711delT | 3821delT | |

Note:
$^a$= Also known as 2183delAA→G.
Criteria: Non-small (>3 nucleotide) insertion/deletion (ins/del) frameshift mutations
% PI > 50% and/or SwCl⁻ > 86 mmol/L
garbled and/or truncated protein

| | | |
|---|---|---|
| CFTRdele2,3 | 1461ins4 | 2991del32 |
| CFTRdele22,23 | 1924del7 | 3667ins4 |
| 124del23bp | 2055del9→A | 4010del4 |
| 852del22 | 2105 – 2117del13insAGAAA | 4209TGTT→AA |
| 991del5 | 2721del11 | |

Criteria: Class II, III, IV mutations not responsive to Compound III alone or in
combination with Compound II or Compound IV
% PI > 50% and/or SwCl >86 mmol/L and
Not responsive in vitro to Compound III alone or in combination with
Compound II or Compound IV

| | | | |
|---|---|---|---|
| A46D$^b$ | V520F | Y569D$^b$ | N1303K |
| G85E | A559T$^b$ | L1065P | |
| R347P | R560T | R1066C | |
| L467P$^b$ | R560S | L1077P$^b$ | |
| I507del | A561E | M1101K | |

Note:
% PI: percentage of F508del-CFTR heterozygous patients in the CFTR2
patient registry who are pancreatic insufficient; SwCl⁻: mean sweat chloride
of F508del-CFTR heterozygous patients in the CFTR2 patient registry
$^b$= Unpublished data.

Additional CFTR Mutations

| | | | |
|---|---|---|---|
| 4382delA | S341P | G178R | 2789 + 5G→A |
| 3600 + 2insT | R1066M | S549N | 3849 + 10kbC→T |
| T338I | H1085R | S549R | 3272 – 26A→G |
| L927P | F1052V | G551D | 711 + 3A→G |
| A455E | R1070W | G551S | E56K |
| D579G | F1074L | G1244E | P67L |
| E831X | D1152H | S1251N | R74W |
| S945L | D1270N | S1255P | D110E |
| S977F | R117H | G1349D | D110H |
| R117C | L206W | R347H | R352Q |
| G178R | G551D | G1244E | S1255P |
| S549N | G551S | S1251N | G1349D |
| S549R | | | |

Table 63 above includes certain exemplary CFTR minimal function mutations, which are detectable by an FDA-cleared genotyping assay, but does not include an exhaustive list.

In some embodiments, the patient has F508del/MF (F/MF) genotypes; with F508del/F508del (F/F) genotype (homozygous for F508del); and/or with F508del/gating (F/G) genotypes (heterozygous for F508del and a gating mutation known to be CFTR modulator-responsive (e.g., Compound III-responsive). In some embodiments, a patient with F508del/MF (F/MF) genotypes has any one of the MF mutations in Table 63.

In some embodiments, the patient is heterozygous for F508del, and the other CFTR genetic mutation is any CF-causing mutation, including truncation mutations, splice mutations, small (≤3 nucleotide) insertion or deletion (ins/del) frameshift mutations; non-small (>3 nucleotide) insertion or deletion (ins/del) frameshift mutations; and Class II, III, IV mutations not responsive to Compound III alone or in combination with Compound II or Compound IV.

In some embodiments, the patient is heterozygous for F508del, and the other CFTR genetic mutation is a truncation mutation. In some specific embodiments, the truncation mutation is a truncation mutation listed in Table 63.

In some embodiments, the patient is heterozygous for F508del, and the other CFTR genetic mutation is a splice mutation. In some specific embodiments, the splice mutation is a splice mutation listed in Table 63.

In some embodiments, the patient is heterozygous for F508del, and the other CFTR genetic mutation is a small (≤3 nucleotide) insertion or deletion (ins/del) frameshift mutation. In some specific embodiments, the small (≤3 nucleotide) insertion or deletion (ins/del) frameshift mutation is a small (≤3 nucleotide) insertion or deletion (ins/del) frameshift mutation listed in Table 63.

In some embodiments, the patient is heterozygous for F508del, and the other CFTR genetic mutation is any CF-causing mutation expected to be and/or is responsive to, based on in vitro and/or clinical data, the combination of a crystalline form of Compound I, or pharmaceutically acceptable salt thereof disclosed herein, Compound II (or a pharmaceutically acceptable salts thereof), and/or Compound III or Compound III-d (or a pharmaceutically acceptable salt thereof).

In some embodiments, the patient is heterozygous for F508del, and the other CFTR genetic mutation is any CF-causing mutation expected to be and/or is responsive, based on in vitro and/or clinical data, to the triple combination of a crystalline form of Compound I, or pharmaceutically acceptable salt thereof disclosed herein, Compound II (or pharmaceutically acceptable salt thereof) and/or Compound III or Compound III-d (or a pharmaceutically acceptable salts thereof).

In some embodiments, the patient is heterozygous for F508del, and the other CFTR genetic mutation is a non-small (>3 nucleotide) insertion or deletion (ins/del) frameshift mutation. In some specific embodiments, the non-small (>3 nucleotide) insertion or deletion (ins/del) frameshift mutation is a non-small (>3 nucleotide) insertion or deletion (ins/del) frameshift mutation listed in Table 63.

In some embodiments, the patient is heterozygous for F508del, and the other CFTR genetic mutation is a Class II, III, IV mutations not responsive to Compound III alone or in combination with Compound II. In some specific embodiments, the Class II, III, IV mutations not responsive to Compound III alone or in combination with Compound II is a Class II, III, IV mutations not responsive to Compound III alone or in combination with Compound II or Compound IV listed in Table 63.

In some embodiments, the patient is heterozygous for F508del, and the other CFTR genetic mutation is any mutation listed in Table 63.

In some embodiments, the patient is heterozygous for F508del, and the other CFTR genetic mutation is any mutation listed in FIG. 17.

In some embodiments, the patient is homozygous for F508del.

In some embodiments, the patient is heterozygous having one CF-causing mutation on one CFTR allele selected from the mutations listed in the table from FIG. 17 and another CF-causing mutation on the other CFTR allele is selected from the CFTR mutations listed in Table 63.

Patients with an F508del/gating mutation genotype are defined as patients that are heterozygous F508del-CFTR with a second CFTR allele that contains a mutation associated with a gating defect and clinically demonstrated to be responsive to Compound III. Examples of such mutations include: G178R, S549N, S549R, G551D, G551S, G1244E, S1251N, S1255P, and G1349D.

Patients with an F508del/residual function genotype are defined as patients that are heterozygous F508del-CFTR with a second CFTR allele that contains a mutation that results in reduced protein quantity or function at the cell surface which can produce partial CFTR activity. CFTR gene mutations known to result in a residual function phenotype include in some embodiments, a CFTR residual function mutation selected from 2789+5G→A, 3849+ 10kbC→T, 3272-26A→G, 711+3A→G, E56K, P67L, R74W, D110E, D110H, R117C, L206W, R347H, R352Q, A455E, D579G, E831X, S945L, S977F, F1052V, R1070W, F1074L, D1152H, D1270N, E193K, and K1060T. In some embodiments, the CFTR residual function mutation is selected from R117H, S1235R, I1027T, R668C, G576A, M470V, L997F, R75Q, R1070Q, R31C, D614G, G1069R, R1162L, E56K, A1067T, E193K, or K1060T. In some embodiments, the CFTR residual function mutation is selected from R117H, S1235R, I1027T, R668C, G576A, M470V, L997F, R75Q, R1070Q, R31C, D614G, G1069R, R1162L, E56K, or A1067T.

In some embodiments, disclosed herein is a method of treating, lessening the severity of, or symptomatically treating cystic fibrosis in a patient comprising administering an effective amount of a pharmaceutical composition of this disclosure to the patient, such as a mammal, wherein the patient possesses a CFTR genetic mutation selected from the mutations listed in FIG. 17.

In some embodiments, the composition disclosed herein is useful for treating, lessening the severity of, or symptomatically treating cystic fibrosis in patients who exhibit residual CFTR activity in the apical membrane of respiratory and non-respiratory epithelia. The presence of residual CFTR activity at the epithelial surface can be readily detected using methods known in the art, e.g., standard electrophysiological, biochemical, or histochemical techniques. Such methods identify CFTR activity using in vivo or ex vivo electrophysiological techniques, measurement of sweat or salivary Cl⁻ concentrations, or ex vivo biochemical or histochemical techniques to monitor cell surface density. Using such methods, residual CFTR activity can be readily detected for patients that are heterozygous or homozygous for a variety of different mutations, including patients heterozygous for the most common mutation, F508del, as well as other mutations such as the G551D mutation, or the R117H mutation. In some embodiments, compositions disclosed herein are useful for treating, lessening the severity of, or symptomatically treating cystic fibrosis in patients who exhibit little to no residual CFTR activity. In some embodiments, compositions disclosed herein are useful for treating, lessening the severity of, or symptomatically treating cystic fibrosis in patients who exhibit little to no residual CFTR activity in the apical membrane of respiratory epithelia.

In some embodiments, the compositions disclosed herein are useful for treating or lessening the severity of cystic fibrosis in patients who exhibit residual CFTR activity using pharmacological methods. Such methods increase the amount of CFTR present at the cell surface, thereby inducing a hitherto absent CFTR activity in a patient or augmenting the existing level of residual CFTR activity in a patient.

In some embodiments, the compositions disclosed herein are useful for treating or lessening the severity of cystic fibrosis in patients with certain genotypes exhibiting residual CFTR activity.

In some embodiments, compositions disclosed herein are useful for treating, lessening the severity of, or symptomatically treating cystic fibrosis in patients within certain clinical phenotypes, e.g., a mild to moderate clinical phenotype that typically correlates with the amount of residual CFTR activity in the apical membrane of epithelia. Such phenotypes include patients exhibiting pancreatic sufficiency.

In some embodiments, the compositions disclosed herein are useful for treating, lessening the severity of, or symptomatically treating patients diagnosed with pancreatic sufficiency, idiopathic pancreatitis and congenital bilateral absence of the vas deferens, or mild lung disease wherein the patient exhibits residual CFTR activity.

In some embodiments, this disclosure relates to a method of augmenting or inducing anion channel activity in vitro or in vivo, comprising contacting the channel with a composition disclosed herein. In some embodiments, the anion channel is a chloride channel or a bicarbonate channel. In some embodiments, the anion channel is a chloride channel.

The exact amount of a pharmaceutical composition required will vary from subject to subject, depending on the species, age, and general condition of the subject, the severity of the disease, the particular agent, its mode of administration, and the like. The compounds of this disclosure may be formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of this disclosure will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, such as a mammal, and even further such as a human.

In some embodiments, the disclosure also is directed to methods of treatment using isotope-labelled compounds of the afore-mentioned compounds, which have the same structures as disclosed herein except that one or more atoms therein have been replaced by an atom or atoms having an atomic mass or mass number which differs from the atomic mass or mass number of the atom which usually occurs naturally (isotope labelled). Examples of isotopes which are commercially available and suitable for the disclosure include isotopes of hydrogen, carbon, nitrogen, oxygen, phosphorus, fluorine and chlorine, for example $^{2}H$, $^{3}H$, $^{13}C$, $^{14}C$, $^{15}N$, $^{18}O$, $^{17}O$, $^{31}P$, $^{32}P$, $^{35}S$, $^{18}F$ and $^{36}Cl$, respectively. In some embodiments, the isotope-labelled compounds and salts are deuterium ($^{2}H$)-labelled ones. In some specific embodiments, the isotope-labelled compounds and salts are deuterium ($^{2}H$)-labelled, wherein one or more hydrogen atoms therein have been replaced by deuterium. In chemical structures, deuterium is represented as "$^{2}H$" or "D."

In some embodiments, the pharmaceutical compositions are a tablet. In some embodiments, the tablets are suitable for oral administration. In some embodiments, the tablets can be administered concurrently with, prior to, or subsequent to, at least one active pharmaceutical ingredients or medical procedures.

The compositions disclosed herein comprising a potassium salt of Compound I (in some embodiments, potassium salt crystalline Form B), alone or in combination with Compound II and/or Compound III or Compound III-d can be administered once a day, twice a day, or three times a day. In some embodiments, one or more of the tablets are administered per dosing. In some embodiments, two tablets per dosing are administered. In some embodiments, two tablets per dosing are administered twice a day. An effective amount of the APIs (e.g., Compound I) is administered to the patient with or using one or more tablets disclosed herein.

In some embodiments, methods of treating, lessening the severity of, or symptomatically treating patients diagnosed with cystic fibrosis or a CFTR mediated disease comprise administering a crystalline form of Compound I as disclosed herein, in a daily dosage amount of 100 mg to 260 mg. In some embodiments, a 100 mg to 260 mg daily dose of a crystalline form of Compound I, or pharmaceutically acceptable salt thereof disclosed herein, is administered with 50 mg to 150 mg/day of Compound II and/or 50 mg to 300 mg/day of Compound III or III-d.

In some embodiments, methods of treating, lessening the severity of, or symptomatically treating patients diagnosed with cystic fibrosis or a CFTR mediated disease comprise administering 100 mg to 260 mg of Compound I potassium salt (in some embodiments, potassium salt crystalline Form B) daily. In some embodiments, the 100 mg to 260 mg daily dose of Compound I potassium salt is administered with 50 mg to 150 mg/day of Compound II and/or 50 mg to 300 mg/day of Compound III or III-d either in a single composition or in separate compositions.

In some embodiments, methods of treating, lessening the severity of, or symptomatically treating patients diagnosed with cystic fibrosis or a CFTR mediated disease comprise administering about 128 mg or about 255-256 mg of a potassium salt of Compound I (in some embodiments, potassium salt crystalline Form B) daily. In some embodiments, the about 128 mg or about 255-256 mg daily dose of Compound I potassium salt is administered with 50 mg or 100 mg/day of Compound II and/or 75 mg, 150 mg, 200 mg, or 300 mg/day of Compound III or III-d either in a single composition or in separate compositions.

In some embodiments, about 255-256 mg of a potassium salt of Compound I (in some embodiments, potassium salt crystalline Form B) is administered daily with 100 mg of Compound II and either 300 mg of Compound III or 200 mg of Compound III-d. In some embodiments, the methods of treating, lessening the severity of, or symptomatically treating patients diagnosed with cystic fibrosis or a CFTR mediated disease comprise administering about 128 mg of a potassium salt of Compound I (in some embodiments, potassium salt crystalline Form B), 50 mg of Compound II, and 75 mg of Compound III and optionally administering an additional 150 mg of Compound III daily. For example, two compositions each comprising about 128 mg of a potassium salt of Compound I (in some embodiments, potassium salt crystalline Form B), 50 mg of Compound II, and 75 mg of Compound III may be administered in the morning and one composition comprising 150 mg of Compound III may be administered in the evening. In some embodiments, the methods comprise administering about 128 mg of a crystalline potassium salt of Compound I (in some embodiments, potassium salt crystalline Form B). In some embodiments, the methods comprise administering two compositions, each with about 128 mg of a crystalline potassium salt of Compound I in Form B.

In some embodiments, about 128 mg of a potassium salt of Compound I (in some embodiments, potassium salt crystalline Form B) is administered with 50 mg of Compound II and 150 mg of Compound III daily. In some embodiments, the methods of treating, lessening the severity of, or symptomatically treating patients diagnosed with cystic fibrosis or a CFTR mediated disease comprise administering daily two pharmaceutical compositions, each comprising about 64 mg of crystalline Form B of a potassium salt of Compound I (in some embodiments, potassium salt crystalline Form B), 25 mg of Compound II, and 35 mg to 40 mg of Compound III and optionally administering an additional 75 mg of Compound III daily. For example, two compositions each comprising about 64 mg of crystalline Form B of a potassium salt of Compound I (in some embodiments, potassium salt crystalline Form B), 25 mg of Compound II, and 35 mg to 40 mg of Compound III may be administered in the morning and 75 mg of Compound III may be administered in the evening.

Some embodiments of the invention provide a method of treating, lessening the severity of, or symptomatically treating patients diagnosed with cystic fibrosis or a CFTR mediated disease comprising administering a fixed dose composition comprising about 128 mg of a crystalline form of a potassium salt of Compound I (in some embodiments, potassium salt crystalline Form B), 50 mg of Compound II, and 150 mg of Compound III twice a day, e.g., morning and evening or every 12 hours. In an alternate embodiment, the methods comprise administering a fixed dose composition comprising about 128 mg of a crystalline form of a potassium salt of Compound I (in some embodiments, potassium salt crystalline Form B), 50 mg of Compound II, and 100 mg of Compound III-d twice a day. In an alternate embodiment, the methods comprise administering two fixed dose compositions, each comprising about 128 mg of a crystalline form of a potassium salt of Compound I (in some embodiments, potassium salt crystalline Form B), 50 mg of Compound II, and 100 mg of Compound III-d, once a day. In an alternate embodiment, the methods comprise administering a fixed dose composition comprising about 255-256 mg of a crystalline form of a potassium salt of Compound I (in some embodiments, potassium salt crystalline Form B), 100 mg of Compound II, and 200 mg of Compound III-d once a day.

EXEMPLARY EMBODIMENTS

Exemplary embodiments of the invention include:

1. A pharmaceutical composition comprising (a) 50 mg to 600 mg of a crystalline form selected from a potassium salt of Compound I (in some embodiments, potassium salt crystalline Form B), a sodium salt of Compound I (Form A, D, E, H, or M) and crystalline Form A of Compound I:

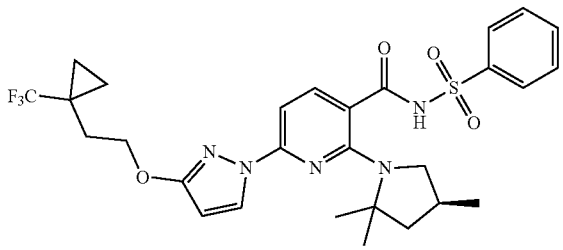

(b) a first solid dispersion comprising 25 mg to 125 mg of Compound II:

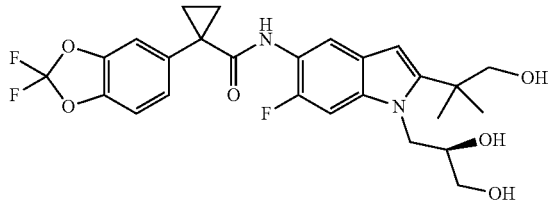 [SMILES: CC(C)(CO)c1cc2cc(NC(=O)C3(c4ccc5c(c4)OC(F)(F)O5)CC3)c(F)cc2n1C[C@@H](O)CO]

and 10 wt % to 30 wt % of a polymer relative to the total weight of the first solid dispersion; and (c) a second solid dispersion comprising 5 mg to 300 mg of Compound III or Compound III-d:

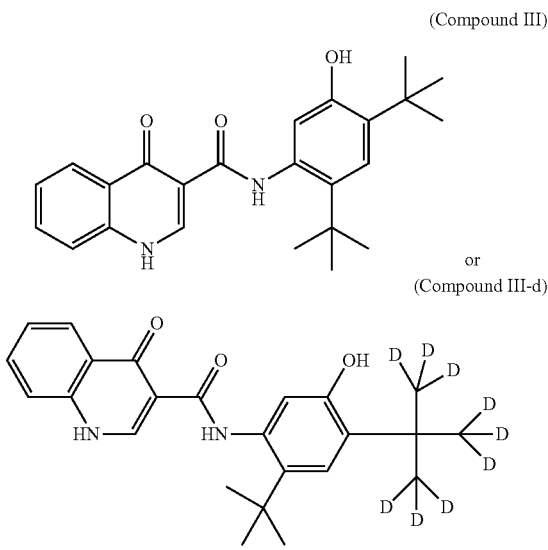

and 10 wt % to 30 wt % of a polymer relative to the total weight of the second solid dispersion.

2. The pharmaceutical composition of embodiment 1, wherein at least one of the first or second solid dispersions is a spray-dried dispersion.

3. The pharmaceutical composition of embodiment 1, wherein both of the first and second solid dispersions are spray-dried dispersions.

4. The pharmaceutical composition of embodiment 1, wherein said polymer for the first solid dispersion is hypromellose; and said polymer for the second solid dispersion is hypromellose acetate succinate.

5. The pharmaceutical composition of embodiment 1, wherein said polymer for the first solid dispersion is HPMC E15; and said polymer for the second solid dispersion is hypromellose acetate succinate H.

6. The pharmaceutical composition of embodiment 1, wherein said polymer for the first solid dispersion is HPMC E15; and said polymer for the second solid dispersion is hypromellose acetate succinate HG.

7. The pharmaceutical composition of any one of embodiments 1-6, comprising 50 mg to 500 mg of a potassium salt of Compound I (in some embodiments, potassium salt crystalline Form B).

8. The pharmaceutical composition of any one of embodiments 1-6, comprising 50 mg to 400 mg, 50 mg to 300 mg, 100 mg to 300 mg, 100 mg to 250 mg, 100 mg to 150 mg, or 200 mg to 250 mg of a potassium salt of Compound I (in some embodiments, potassium salt crystalline Form B).

9. The pharmaceutical composition of any one of embodiments 1-6, comprising 100 mg to 250 mg of a potassium salt of Compound I (in some embodiments, potassium salt crystalline Form B).

10. The pharmaceutical composition of any one of embodiments 1-6, comprising 100 mg to 150 mg or 150 mg to 250 mg of a potassium salt of Compound I (in some embodiments, potassium salt crystalline Form B).

11. The pharmaceutical composition of any one of embodiments 1-10, wherein the first solid dispersion comprises 25 mg to 75 mg of Compound II.

12. The pharmaceutical composition of any one of embodiments 1-10, wherein the first solid dispersion comprises 30 mg to 60 mg of Compound II.

13. The pharmaceutical composition of any one of embodiments 1-10, wherein the second solid dispersion comprises 25 mg to 50 mg, 25 mg to 75 mg, 50 mg to 100 mg, 75 mg to 125 mg, or 125 mg to 175 mg of Compound III or Compound III-d.

14. The pharmaceutical composition of any one of embodiments 1-10, wherein the second solid dispersion comprises 50 mg to 100 mg of Compound III or Compound III-d.

15. The pharmaceutical composition of any one of embodiments 1-6, comprising 100 mg to 250 mg of a potassium salt of Compound I (in some embodiments, potassium salt crystalline Form B); and wherein the first solid dispersion comprises 25 mg to 75 mg of Compound II; and the second solid dispersion comprises 50 mg to 100 mg of Compound III or Compound III-d.

16. The pharmaceutical composition of any one of embodiments 1-6, comprising 100 mg to 150 mg of a potassium salt of Compound I (in some embodiments, potassium salt crystalline Form B); and wherein the first solid dispersion comprises 50 mg of Compound II; and the second solid dispersion comprises 75 mg or 150 mg of Compound III or 100 mg of Compound III-d.

17. The pharmaceutical composition of any one of embodiments 1-6, comprising 170 mg to 250 mg of a potassium salt of Compound I (in some embodiments, potassium salt crystalline Form B); and wherein the first solid dispersion comprises 50 mg or 100 mg of Compound II; and the second solid dispersion comprises 75 mg or 150 mg of Compound III or 100 mg or 200 mg of Compound III-d.

18. The pharmaceutical composition of any one of embodiments 1-17, wherein the second solid dispersion further comprises 0.5% sodium lauryl sulfate relative to the total weight of the second solid dispersion.

19. The pharmaceutical composition of any one of embodiments 1-18, further comprising one or more pharmaceutically acceptable excipients selected from one or more fillers, a disintegrant, and a lubricant.

20. The pharmaceutical composition of embodiment 19, wherein one or more fillers are selected from microcrystalline cellulose, silicified microcrystalline cellulose, lactose, dicalcium phosphate, mannitol, copovidone, hydroxypropyl cellulose, hypromellose, methyl cellulose, ethyl cellulose, starch, Maltodextrin, agar, and guar gum.

21. The pharmaceutical composition of embodiment 19, wherein the disintegrant is selected from croscarmellose sodium, sodium starch glycolate, crospovidone, corn or pre-gelatinized starch, sodium carboxymethyl cellulose, calcium carboxymethyl cellulose, and microcrystalline cellulose.

22. The pharmaceutical composition of embodiment 19, wherein the lubricant is selected from magnesium stearate, sodium stearyl fumarate, calcium stearate, sodium stearate, stearic acid, and talc.

23. The pharmaceutical composition of any one of embodiments 1-22, wherein the potassium salt of Compound I is substantially crystalline, and wherein each of Compound II, Compound III and Compound III-d are independently substantially amorphous.

24. A pharmaceutical composition comprising:

(a) 15 wt % to 45 wt % of a potassium salt of Compound I (in some embodiments, potassium salt crystalline Form B):

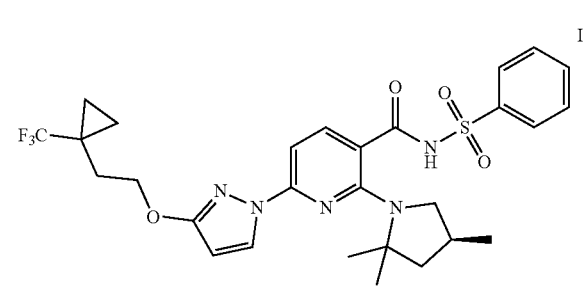 [SMILES: C[C@@H]1CN(c2nc(-n3ccc(OCCC4(C(F)(F)F)CC4)n3)ccc2C(=O)NS(=O)(=O)c2ccccc2)C(C)(C)C1]

relative to the total weight of the pharmaceutical composition;

(b) 5 wt % to 20 wt % of a first solid dispersion relative to the total weight of the pharmaceutical composition, wherein the first solid dispersion comprises 70 wt % to 90 wt % of Compound II relative to the total weight of the first solid dispersion:

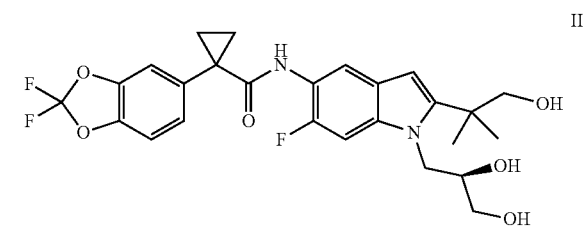 [SMILES: CC(C)(CO)c1cc2cc(NC(=O)C3(c4ccc5c(c4)OC(F)(F)O5)CC3)c(F)cc2n1C[C@@H](O)CO]

and 10 wt % to 30 wt % of a polymer relative to the total weight of the first solid dispersion; and (c) 10 wt % to 40 wt % of a second solid dispersion relative to the total weight of the pharmaceutical composition;

wherein the second solid dispersion comprises 70 wt % to 90 wt % of Compound III or Compound III-d relative to the total weight of the second solid dispersion:

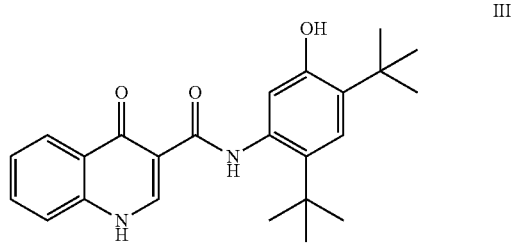

-continued

III-d

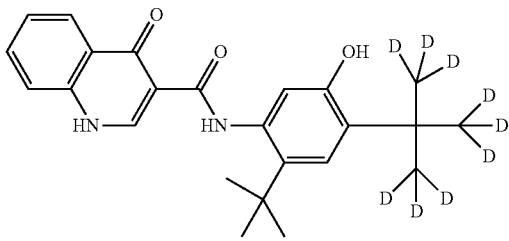

and 10 wt % to 30 wt % of a polymer relative to the total weight of the second solid dispersion.
25. The pharmaceutical composition of embodiment 24, wherein at least one of the first or second solid dispersions is a spray-dried dispersion.
26. The pharmaceutical composition of embodiment 24, wherein both of the first and second solid dispersions are spray-dried dispersions.
27. The pharmaceutical composition of embodiment 24, wherein said polymer for the first solid dispersion is hypromellose; and said polymer for the second solid dispersion is hypromellose acetate succinate.
28. The pharmaceutical composition of embodiment 24, wherein said polymer for the first solid dispersion is hypromellose (HPMC E15); and said polymer for the second solid dispersion is hypromellose acetate succinate H.
29. The pharmaceutical composition of embodiment 24, wherein:
the first solid dispersion comprises 70 wt % to 85 wt % of Compound II relative to the total weight of the first solid dispersion, and the polymer is a hydroxypropyl methylcellulose in an amount of 15 wt % to 30 wt % relative to the total weight of the first solid dispersion; and
the second solid dispersion comprises 70 wt % to 85 wt % of Compound III or Compound III-d relative to the total weight of the second solid dispersion, 0.5% sodium lauryl sulfate relative to the total weight of the second solid dispersion, and the polymer is hypromellose acetate succinate in an amount of 14.5 wt % to 29.5 wt % relative to the total weight of the second solid dispersion.
30. The pharmaceutical composition of any one of embodiments 24-29, wherein the first solid dispersion comprises 75 wt % to 85 wt % of Compound II relative to the total weight of the first solid dispersion.
31. The pharmaceutical composition of any one of embodiments 24-29, wherein the first solid dispersion comprises 80 wt % of Compound II relative to the total weight of the first solid dispersion; and 20 wt % of a hydroxypropyl methylcellulose relative to the total weight of the first solid dispersion.
32. The pharmaceutical composition of any one of embodiments 24-31, wherein the second solid dispersion comprises 75 wt % to 85 wt % of Compound III or Compound III-d relative to the total weight of the second solid dispersion.
33. The pharmaceutical composition of any one of embodiments 24-32, wherein the second solid dispersion comprises 80 wt % of Compound III or Compound III-d relative to the total weight of the second solid dispersion; 0.5% of sodium lauryl sulfate relative to the total weight of the second solid dispersion, and 19.5 wt % of hypromellose acetate succinate relative to the total weight of the second solid dispersion.
34. The pharmaceutical composition of any one of embodiments 24-33, further comprising one or more pharmaceutically acceptable excipients selected from fillers, disintegrants, and lubricants.

35. The pharmaceutical composition of embodiment 34, wherein the filler is selected from microcrystalline cellulose, silicified microcrystalline cellulose, lactose, dicalcium phosphate, mannitol, copovidone, hydroxypropyl cellulose, hypromellose, methyl cellulose, ethyl cellulose, starch, Maltodextrin, agar, and guar gum.
36. The pharmaceutical composition of embodiment 34, wherein the disintegrant is selected from croscarmellose sodium, sodium starch glycolate, crospovidone, corn or pre-gelatinized starch, sodium carboxymethyl cellulose, calcium carboxymethyl cellulose, and microcrystalline cellulose.
37. The pharmaceutical composition of embodiment 34, wherein the lubricant is selected from magnesium stearate, sodium stearyl fumarate, calcium stearate, sodium stearate, stearic acid, and talc.
38. The pharmaceutical composition of any one of embodiments 24-37, the potassium salt of Compound I is substantially crystalline, and wherein each of Compound II, Compound III and Compound III-d is independently substantially amorphous.
39. A single tablet comprising:
(a) 200 mg to 215 mg of a potassium salt of Compound I (in some embodiments, potassium salt crystalline Form B);
(b) 60 mg to 65 mg of a first solid dispersion comprising 80 wt % Compound II relative to the total weight of the first solid dispersion and 20 wt % of a hypromellose relative to the total weight of the first solid dispersion; and
(c) 90 mg to 95 mg of a second solid dispersion comprising 80 wt % of Compound III relative to the total weight of the second solid dispersion, 0.5 wt % of sodium lauryl sulfate relative to the total weight of the second solid dispersion; and 19.5 wt % of a hypromellose acetate succinate to the total weight of the second solid dispersion
(d) 175 mg to 215 mg of a microcrystalline cellulose;
(e) 20 mg to 30 mg of a croscarmellose sodium; and
(f) 3 mg to 7 mg of magnesium stearate.
40. The single tablet of embodiment 39, wherein the tablet comprises:
(a) 200 mg to 215 mg of said potassium salt of Compound I (in some embodiments, potassium salt crystalline Form B);
(b) 60 mg to 65 mg of said first solid dispersion;
(c) 90 mg to 95 mg of said second solid dispersion;
(d) 175 mg to 215 mg of said microcrystalline cellulose;
(e) 15 mg to 30 mg of said croscarmellose sodium; and
(f) 3 mg to 7 mg of magnesium stearate.
41. The single tablet of embodiment 39, wherein the tablet comprises an intra-granular part and extra-granular part, and
(a) wherein the intra-granular part comprises:
 (i) 200 mg to 215 mg of said potassium salt of Compound I (in some embodiments, potassium salt crystalline Form B);
 (ii) 60 mg to 65 mg of said first solid dispersion;
 (iii) 90 mg to 95 mg of said second solid dispersion;
 (iv) 120 mg to 150 mg of said microcrystalline cellulose;
 (v) 10 mg to 20 mg of said croscarmellose sodium; and
 (vi) 3 mg to 7 mg of magnesium stearate; and
(b) wherein the extra-granular part comprises:
 (i) 55 mg to 65 mg of said microcrystalline cellulose; and
 (ii) 5 mg to 10 mg of said croscarmellose sodium.
42. The single tablet of embodiment 39, wherein the tablet comprises:
(a) 210 mg to 215 mg of said potassium salt of Compound I (in some embodiments, potassium salt crystalline Form B);
(b) 60 mg to 65 mg of said first solid dispersion;
(c) 90 mg to 95 mg of said second solid dispersion;

(d) 193 mg to 203 mg of said microcrystalline cellulose;
(e) 21 mg to 27 mg of said croscarmellose sodium; and
(f) 4 mg to 7 mg of magnesium stearate.

43. The single tablet of embodiment 39, wherein the tablet comprises an intra-granular part and extra-granular part, and
(a) wherein the intra-granular part comprises:
  (i) 210 mg to 215 mg of said potassium salt of Compound I (in some embodiments, potassium salt crystalline Form B);
  (ii) 60 mg to 65 mg of said first solid dispersion;
  (iii) 90 mg to 95 mg of said second solid dispersion;
  (iv) 135 mg to 140 mg of said microcrystalline cellulose;
  (v) 14 mg to 17 mg of said croscarmellose sodium; and
  (vi) 4 mg to 7 mg of magnesium stearate; and
(b) wherein the extra-granular part comprises:
  (i) 58 mg to 63 mg of said microcrystalline cellulose; and
  (ii) 7 mg to 10 mg of said croscarmellose sodium.

44. A single tablet comprising:
(a) 115 mg to 140 mg of a potassium salt of Compound I (in some embodiments, potassium salt crystalline Form B);
(b) 60 mg to 65 mg of a first solid dispersion comprising 80 wt % Compound II relative to the total weight of the first solid dispersion and 20 wt % of a hypromellose relative to the total weight of the first solid dispersion; and
(c) 90 mg to 95 mg of a second solid dispersion comprising 80 wt % of Compound III relative to the total weight of the second solid dispersion, 0.5 wt % of sodium lauryl sulfate relative to the total weight of the second solid dispersion; and 19.5 wt % of a hypromellose acetate succinate to the total weight of the second solid dispersion;
(d) 120 mg to 135 mg of a microcrystalline cellulose;
(e) 15 mg to 25 mg of a croscarmellose sodium; and
(f) 2 mg to 6 mg of magnesium stearate.

45. The single tablet of embodiment 44, wherein the tablet comprises:
(a) 115 mg to 140 mg of said potassium salt of Compound I (in some embodiments, potassium salt crystalline Form B);
(b) 60 mg to 65 mg of said first solid dispersion;
(c) 90 mg to 95 mg of said second solid dispersion;
(d) 120 mg to 135 mg of said microcrystalline cellulose;
(e) 15 mg to 25 mg of said croscarmellose sodium; and
(f) 3 mg to 5 mg of magnesium stearate.

46. The single tablet of embodiment 44, wherein the tablet comprises an intra-granular part and extra-granular part, and
(a) wherein the intra-granular part comprises:
  (i) 115 mg to 140 mg of said potassium salt of Compound I (in some embodiments, potassium salt crystalline Form B);
  (ii) 60 mg to 65 mg of said first solid dispersion;
  (iii) 90 mg to 95 mg of said second solid dispersion;
  (iv) 80 mg to 90 mg of said microcrystalline cellulose;
  (v) 10 mg to 15 mg of said croscarmellose sodium; and
  (vi) 3 mg to 5 mg of magnesium stearate; and
(b) wherein the extra-granular part comprises:
  (i) 40 mg to 45 mg of said microcrystalline cellulose; and
  (i) 5 mg to 10 mg of said croscarmellose sodium.

47. The single tablet of embodiment 44, wherein the tablet comprises:
(a) 115 mg to 140 mg of said potassium salt of Compound I (in some embodiments, potassium salt crystalline Form B);
(b) 60 mg to 65 mg of said first solid dispersion;
(c) 90 mg to 95 mg of said second solid dispersion;
(d) 125 mg to 140 mg of said microcrystalline cellulose;
(e) 15 mg to 25 mg of said croscarmellose sodium; and
(f) 2 mg to 6 mg of magnesium stearate.

48. The single tablet of embodiment 44, wherein the tablet comprises an intra-granular part and extra-granular part, and
(a) wherein the intra-granular part comprises:
  (i) 115 mg to 140 mg of said potassium salt of Compound I (in some embodiments, potassium salt crystalline Form B);
  (ii) 60 mg to 65 mg of said first solid dispersion;
  (iii) 90 mg to 95 mg of said second solid dispersion;
  (iv) 85 mg to 95 mg of said microcrystalline cellulose;
  (v) 10 mg to 15 mg of said croscarmellose sodium; and
  (vi) 1 mg to 3 mg of magnesium stearate; and
(b) wherein the extra-granular part comprises:
  (i) 40 mg to 45 mg of said microcrystalline cellulose; and
  (ii) 5 mg to 10 mg of said croscarmellose sodium; and
  (iii) 1 mg to 3 mg of magnesium stearate.

49. The pharmaceutical composition of any one of embodiments 1-48, wherein the pharmaceutical composition is a single tablet.

50. The pharmaceutical composition of any one of embodiments 1-49, further comprising a microcrystalline cellulose in an amount 20 wt %-40 wt % relative to the total weight of the pharmaceutical composition.

51. The pharmaceutical composition of embodiment 50, further comprising a croscarmellose sodium in an amount 1 wt %-10 wt % relative to the total weight of the pharmaceutical composition.

52. The pharmaceutical composition of embodiment 51, further comprising a magnesium stearate in an amount 0.5 wt %-1.5 wt % relative to the total weight of the pharmaceutical composition.

53. A pharmaceutical composition comprising:
(a) 20 wt % to 35 wt % of a potassium salt of Compound I (in some embodiments, potassium salt crystalline Form B) relative to the total weight of the pharmaceutical composition;
(b) 5 wt % to 20 wt % of a first solid dispersion relative to the total weight of the pharmaceutical composition, wherein the first solid dispersion comprises 70 wt % to 90 wt % of Compound II relative to the total weight of the first solid dispersion and 10 wt % to 30 wt % of a polymer relative to the total weight of the first solid dispersion; and
(c) 20 wt % to 40 wt % of a second solid dispersion relative to the total weight of the pharmaceutical composition, wherein the second solid dispersion comprises 70 wt % to 90 wt % of Compound III relative to the total weight of the second solid dispersion, and 10 wt % to 30 wt % of a polymer relative to the total weight of the second solid dispersion.

54. The pharmaceutical composition of embodiment 53, wherein at least one of the first or second solid dispersions is a spray-dried dispersion.

55. The pharmaceutical composition of embodiment 53, wherein both of the first and second solid dispersions are spray-dried dispersions.

56. The pharmaceutical composition of embodiment 53, wherein said polymer for the first solid dispersion is hypromellose; and said polymer for the second solid dispersion is hypromellose acetate succinate.

57. The pharmaceutical composition of embodiment 53, wherein said polymer for the first solid dispersion is hypromellose (HPMC E15); and said polymer for the second solid dispersion is hypromellose acetate succinate H.

58. The pharmaceutical composition of embodiment 53, wherein:
the first solid dispersion comprises 70 wt % to 85 wt % of Compound II relative to the total weight of the first solid dispersion, and the polymer is a hydroxypropyl methylcellulose in an amount of 15 wt % to 30 wt % relative to the total weight of the first solid dispersion; and
the second solid dispersion comprises 70 wt % to 85 wt % of Compound III relative to the total weight of the second solid dispersion, 0.5% sodium lauryl sulfate relative to the total weight of the second solid dispersion, and the polymer is hypromellose acetate succinate in an amount of 14.5 wt % to 29.5 wt % relative to the total weight of the second solid dispersion.

59. The pharmaceutical composition of any one of embodiments 53-58, wherein the first solid dispersion comprises 75 wt % to 85 wt % of Compound II relative to the total weight of the first solid dispersion.

60. The pharmaceutical composition of embodiment 59, wherein the first solid dispersion comprises 80 wt % of Compound II relative to the total weight of the first solid dispersion; and 20 wt % of a hydroxypropyl methylcellulose relative to the total weight of the first solid dispersion.

61. The pharmaceutical composition of any one of embodiments 53-60, wherein the second solid dispersion comprises 75 wt % to 85 wt % of Compound III relative to the total weight of the second solid dispersion.

62. The pharmaceutical composition of embodiment 61, wherein the second solid dispersion comprises 80 wt % of Compound III relative to the total weight of the second solid dispersion; 0.5% of sodium lauryl sulfate relative to the total weight of the second solid dispersion, and 19.5 wt % of a hypromellose acetate succinate relative to the total weight of the second solid dispersion.

63. The pharmaceutical composition of any one of embodiments 53-62, further comprising one or more pharmaceutically acceptable excipients selected from fillers, disintegrants, and lubricants.

64. The pharmaceutical composition of embodiment 63, wherein the filler is selected from microcrystalline cellulose, silicified microcrystalline cellulose, lactose, dicalcium phosphate, mannitol, copovidone, hydroxypropyl cellulose, hypromellose, methyl cellulose, ethyl cellulose, starch, Maltodextrin, agar, and guar gum.

65. The pharmaceutical composition of embodiment 64, wherein the disintegrant is selected from croscarmellose sodium, sodium starch glycolate, crospovidone, corn or pre-gelatinized starch, sodium carboxymethyl cellulose, calcium carboxymethyl cellulose, and microcrystalline cellulose.

66. The pharmaceutical composition of embodiment 65, wherein the lubricant is selected from magnesium stearate, sodium stearyl fumarate, calcium stearate, sodium stearate, stearic acid, and talc.

67. The pharmaceutical composition of any one of embodiments 53-66, the potassium salt of Compound I is substantially crystalline, and wherein each of Compound II and Compound III is independently substantially amorphous.

68. The pharmaceutical composition of any one of embodiments 1-38 and 49-52, wherein said potassium salt of Compound I, said Compound II, and said Compound III are present in a ratio of 8:2:3 based on the respective weight of free base Compound I: Compound II: Compound III.

69. The pharmaceutical composition of any one of embodiments 1-38 and 49-52, wherein said potassium salt of Compound I, said Compound II, and said Compound III are present in a ratio of 24:10:15 based on the respective weight of free base Compound I: Compound II: Compound III.

70. The pharmaceutical composition of any one of embodiments 1-38 and 49-52, wherein said potassium salt of Compound I, said Compound II, and said Compound III-d are present in a ratio of 4:1:2 based on the respective weight of free base Compound I: Compound II: Compound III-d.

71. The pharmaceutical composition of any one of embodiments 1-38 and 49-52, wherein said potassium salt of Compound I, said Compound II, and said Compound III-d are present in a ratio of 12:5:10 based on the respective weight of free base Compound I: Compound II: Compound III-d.

72. The pharmaceutical composition of any one of embodiments 1-38 and 53-67, wherein said potassium salt of Compound I, said Compound II, and said Compound III are present in a ratio of 4:1:3 based on the respective weight of free base Compound I: Compound II: Compound III.

73. The pharmaceutical composition of any one of embodiments 1-38 and 53-67, wherein said potassium salt of Compound I, said Compound II, and said Compound III are present in a ratio of 12:5:15 based on the respective weight of free base Compound I: Compound II: Compound III.

74. The pharmaceutical composition of embodiment 24, wherein the pharmaceutical composition comprises:

| Component | weight % based on the total weight of composition |
|---|---|
| potassium salt of Compound I (in some embodiments, potassium salt crystalline Form B) | 20-45 wt % |
| solid dispersion containing 80% Compound II, 20% hypromellose | 5-20 wt % |
| solid dispersion containing 80% Compound III, 19.5% hypromellose acetate succinate, and 0.5% sodium lauryl sulfate | 10-30 wt % |

75. The pharmaceutical composition of embodiment 24, further comprising microcrystalline cellulose, croscarmellose sodium and magnesium stearate, wherein the pharmaceutical composition comprises:

| Component | weight % based on the total weight of composition |
|---|---|
| potassium salt of Compound I (in some embodiments, potassium salt crystalline Form B) | 15-45 wt % |
| solid dispersion containing 80% Compound II, 20% hypromellose | 5-20 wt % |
| solid dispersion containing 80% Compound III or Compound III-d, 19.5% hypromellose acetate succinate, and 0.5% sodium lauryl sulfate | 10-40 wt % |
| microcrystalline cellulose | 5-50 wt % |
| croscarmellose sodium (CCS) | 1-10 wt % | optionally magnesium stearate in an amount of 0.01 wt %-2 wt % based on the total weight of composition 76. The pharmaceutical composition of embodiment 24, further comprising microcrystalline cellulose, croscarmellose sodium and magnesium stearate, wherein the pharmaceutical composition comprises:

| Component | weight % based on the total weight of composition |
|---|---|
| potassium salt of Compound I (in some embodiments, potassium salt crystalline Form B) | 15-45 wt % |
| solid dispersion containing 80% Compound II, 20% hypromellose | 5-20 wt % |
| solid dispersion containing 80% Compound III or Compound III-d, 19.5% hypromellose acetate succinate, and 0.5% sodium lauryl sulfate | 10-40 wt % |

-continued

| Component | weight % based on the total weight of composition |
|---|---|
| microcrystalline cellulose | 5-50 wt % |
| croscarmellose sodium (CCS) | 1-10 wt % |
| magnesium stearate | 0.05-2 wt % |

77. The pharmaceutical composition of embodiment 24, further comprising microcrystalline cellulose, croscarmellose sodium and magnesium stearate, wherein the pharmaceutical composition comprises:

| Component | weight % based on the total weight of composition |
|---|---|
| potassium salt of Compound I (in some embodiments, potassium salt crystalline Form B) | 15-35 wt % |
| solid dispersion containing 80% Compound II, 20% hypromellose | 5-20 wt % |
| solid dispersion containing 80% Compound III, 19.5% hypromellose acetate succinate, and 0.5% sodium lauryl sulfate | 20-40 wt % |
| microcrystalline cellulose | 20-40 wt % |
| croscarmellose sodium (CCS) | 1-10 wt % |
| magnesium stearate | 0.05-2 wt % |

78. The pharmaceutical composition of embodiment 24, further comprising microcrystalline cellulose, croscarmellose sodium and magnesium stearate, wherein the pharmaceutical composition comprises:

| Component | weight % based on the total weight of composition |
|---|---|
| potassium salt of Compound I (in some embodiments, potassium salt crystalline Form B) | 20-40 wt % |
| solid dispersion containing 80% Compound II, 20% hypromellose | 5-20 wt % |
| solid dispersion containing 80% Compound III, 19.5% hypromellose acetate succinate, and 0.5% sodium lauryl sulfate | 10-25 wt % |
| microcrystalline cellulose | 20-40 wt % |
| croscarmellose sodium (CCS) | 1-10 wt % |
| magnesium stearate | 0.05-2 wt % |

79. The pharmaceutical composition of embodiment 24, further comprising microcrystalline cellulose, croscarmellose sodium and magnesium stearate, wherein the pharmaceutical composition comprises:

| Component | weight % based on the total weight of composition |
|---|---|
| potassium salt of Compound I (in some embodiments, potassium salt crystalline Form B) | 30-40 wt % |
| solid dispersion containing 80% Compound II, 20% hypromellose | 5-15 wt % |
| solid dispersion containing 80% Compound III, 19.5% hypromellose acetate succinate, and 0.5% sodium lauryl sulfate | 10-20 wt % |
| microcrystalline cellulose | 25-35 wt % |
| croscarmellose sodium (CCS) | 2-7 wt % |
| magnesium stearate | 0.05-2 wt % |

80. The pharmaceutical composition of embodiment 24, further comprising microcrystalline cellulose, croscarmellose sodium and magnesium stearate, wherein the pharmaceutical composition comprises:

| Component | weight % based on the total weight of composition |
|---|---|
| potassium salt of Compound I (in some embodiments, potassium salt crystalline Form B) | 33-38 wt % |
| solid dispersion containing 80% Compound II, 20% hypromellose | 8-13 wt % |
| solid dispersion containing 80% Compound III, 19.5% hypromellose acetate succinate, and 0.5% sodium lauryl sulfate | 13-18 wt % |
| microcrystalline cellulose | 30-35 wt % |
| croscarmellose sodium (CCS) | 2-7 wt % |
| magnesium stearate | 0.05-2 wt % |

81. The pharmaceutical composition of embodiment 24, further comprising microcrystalline cellulose, croscarmellose sodium and magnesium stearate, wherein the pharmaceutical composition comprises:

| Component | weight % based on the total weight of composition |
|---|---|
| potassium salt of Compound I (in some embodiments, potassium salt crystalline Form B) | 28-33 wt % |
| solid dispersion containing 80% Compound II, 20% hypromellose | 7-12 wt % |
| solid dispersion containing 80% Compound III, 19.5% hypromellose acetate succinate, and 0.5% sodium lauryl sulfate | 25-30 wt % |
| microcrystalline cellulose | 25-35 wt % |
| croscarmellose sodium (CCS) | 2-5 wt % |
| magnesium stearate | 0.05-1.5 wt % |

82. The pharmaceutical composition of embodiment 24, further comprising microcrystalline cellulose, croscarmellose sodium and magnesium stearate, wherein the pharmaceutical composition comprises:

| Component | weight % based on the total weight of composition |
|---|---|
| potassium salt of Compound I (in some embodiments, potassium salt crystalline Form B) | 25-35 wt % |
| solid dispersion containing 80% Compound II, 20% hypromellose | 10-20 wt % |
| solid dispersion containing 80% Compound III, 19.5% hypromellose acetate succinate, and 0.5% sodium lauryl sulfate | 15-25 wt % |
| microcrystalline cellulose | 25-35 wt % |
| croscarmellose sodium (CCS) | 2-7 wt % |
| magnesium stearate | 0.05-2 wt % |

83. The pharmaceutical composition of embodiment 24, further comprising microcrystalline cellulose, croscarmellose sodium and magnesium stearate, wherein the pharmaceutical composition comprises:

| Component | weight % based on the total weight of composition |
|---|---|
| potassium salt of Compound I (in some embodiments, potassium salt crystalline Form B) | 27-32 wt % |

| Component | weight % based on the total weight of composition |
|---|---|
| solid dispersion containing 80% Compound II, 20% hypromellose | 12-17 wt % |
| solid dispersion containing 80% Compound III, 19.5% hypromellose acetate succinate, and 0.5% sodium lauryl sulfate | 18-23 wt % |
| microcrystalline cellulose | 25-35 wt % |
| croscarmellose sodium (CCS) | 3-6 wt % |
| magnesium stearate | 0.05-1.5 wt % |

84. The pharmaceutical composition of embodiment 24, further comprising microcrystalline cellulose, croscarmellose sodium and magnesium stearate, wherein the pharmaceutical composition comprises:

| Component | weight % based on the total weight of composition |
|---|---|
| potassium salt of Compound I (in some embodiments, potassium salt crystalline Form B) | 20-30 wt % |
| solid dispersion containing 80% Compound II, 20% hypromellose | 7-15 wt % |
| solid dispersion containing 80% Compound III, 19.5% hypromellose acetate succinate, and 0.5% sodium lauryl sulfate | 30-40 wt % |
| microcrystalline cellulose | 15-40 wt % |
| croscarmellose sodium (CCS) | 2-7 wt % |
| magnesium stearate | 0.05-1.5 wt % |

85. The pharmaceutical composition of embodiment 24, further comprising microcrystalline cellulose, croscarmellose sodium and magnesium stearate, wherein the pharmaceutical composition comprises:

| Component | weight % based on the total weight of composition |
|---|---|
| potassium salt of Compound I (in some embodiments, potassium salt crystalline Form B) | 22-27 wt % |
| solid dispersion containing 80% Compound II, 20% hypromellose | 8-13 wt % |
| solid dispersion containing 80% Compound III, 19.5% hypromellose acetate succinate, and 0.5% sodium lauryl sulfate | 32-37 wt % |
| microcrystalline cellulose | 20-30 wt % |
| croscarmellose sodium (CCS) | 2-5 wt % |
| magnesium stearate | 0.05-1.5 wt % |

86. The pharmaceutical composition of embodiment 24, further comprising microcrystalline cellulose, croscarmellose sodium and magnesium stearate, wherein the pharmaceutical composition comprises:

| Component | weight % based on the total weight of composition |
|---|---|
| potassium salt of Compound I (in some embodiments, potassium salt crystalline Form B) | 25-40 wt % |
| solid dispersion containing 80% Compound II, 20% hypromellose | 7-15 wt % |
| solid dispersion containing 80% Compound III-d, 19.5% hypromellose acetate succinate, and 0.5% sodium lauryl sulfate | 15-35 wt % |
| microcrystalline cellulose | 25-35 wt % |
| croscarmellose sodium (CCS) | 2-5 wt % |
| magnesium stearate | 0.05-1.5 wt % |

87. The pharmaceutical composition of embodiment 24, further comprising microcrystalline cellulose, croscarmellose sodium and magnesium stearate, wherein the pharmaceutical composition comprises:

| Component | weight % based on the total weight of composition |
|---|---|
| potassium salt of Compound I (in some embodiments, potassium salt crystalline Form B) | 29-36 wt % |
| solid dispersion containing 80% Compound II, 20% hypromellose | 8-13 wt % |
| solid dispersion containing 80% Compound III-d, 19.5% hypromellose acetate succinate, and 0.5% sodium lauryl sulfate | 15-25 wt % |
| microcrystalline cellulose | 25-35 wt % |
| croscarmellose sodium (CCS) | 2-5 wt % |
| magnesium stearate | 0.05-1.5 wt % |

88. The pharmaceutical composition of embodiment 24, further comprising microcrystalline cellulose, croscarmellose sodium and optionally magnesium stearate, wherein the pharmaceutical composition comprises:

| Component | weight % based on the total weight of composition |
|---|---|
| potassium salt of Compound I (in some embodiments, potassium salt crystalline Form B) | 15-40 wt % |
| solid dispersion containing 80% Compound II, 20% hypromellose | 5-20 wt % |
| solid dispersion containing 80% Compound III-d, 19.5% hypromellose acetate succinate, and 0.5% sodium lauryl sulfate | 20-40 wt % |
| microcrystalline cellulose | 10-50 wt % |
| croscarmellose sodium (CCS) | 2-7 wt % | optionally magnesium stearate in an amount of 0.01 wt %-2 wt % based on the total weight of composition 89. The pharmaceutical composition of embodiment 24, further comprising microcrystalline cellulose, croscarmellose sodium and optionally magnesium stearate, wherein the pharmaceutical composition comprises:

| Component | weight % based on the total weight of composition |
|---|---|
| potassium salt of Compound I (in some embodiments, potassium salt crystalline Form B) | 20-30 wt % |
| solid dispersion containing 80% Compound II, 20% hypromellose | 8-18 wt % |

| Component | weight % based on the total weight of composition |
|---|---|
| solid dispersion containing 80% Compound III-d, 19.5% hypromellose acetate succinate, and 0.5% sodium lauryl sulfate | 20-30 wt % |
| microcrystalline cellulose | 20-30 wt % |
| croscarmellose sodium (CCS) | 2-5 wt % | optionally magnesium stearate in an amount of 0.01 wt %-1.5 wt % based on the total weight of composition 90. The pharmaceutical composition of embodiment 24, further comprising microcrystalline cellulose, croscarmellose sodium and optionally magnesium stearate, wherein the pharmaceutical composition comprises:

| Component | weight % based on the total weight of composition |
|---|---|
| potassium salt of Compound I (in some embodiments, potassium salt crystalline Form B) | 28-38 wt % |
| solid dispersion containing 80% Compound II, 20% hypromellose | 10-20 wt % |
| solid dispersion containing 80% Compound III-d, 19.5% hypromellose acetate succinate, and 0.5% sodium lauryl sulfate | 27-37 wt % |
| microcrystalline cellulose | 5-20 wt % |
| croscarmellose sodium (CCS) | 2-5 wt % | optionally magnesium stearate in an amount of 0.01 wt %-1.5 wt % based on the total weight of composition 91. The pharmaceutical composition of embodiment 24, further comprising microcrystalline cellulose, croscarmellose sodium and optionally magnesium stearate, wherein the pharmaceutical composition comprises:

| Component | weight % based on the total weight of composition |
|---|---|
| potassium salt of Compound I (in some embodiments, potassium salt crystalline Form B) | 15-25 wt % |
| solid dispersion containing 80% Compound II, 20% hypromellose | 5-15 wt % |
| solid dispersion containing 80% Compound III-d, 19.5% hypromellose acetate succinate, and 0.5% sodium lauryl sulfate | 15-25 wt % |
| microcrystalline cellulose | 40-50 wt % |
| croscarmellose sodium (CCS) | 2-5 wt % | optionally magnesium stearate in an amount of 0.01 wt %-1.5 wt % based on the total weight of composition 92. The pharmaceutical composition of embodiment 24, wherein the pharmaceutical composition comprises:

| Component | weight % based on the total weight of composition |
|---|---|
| potassium salt of Compound I (in some embodiments, potassium salt crystalline Form B) | 22-32 wt % |
| solid dispersion containing 80% Compound II, 20% hypromellose | 10-20 wt % |
| solid dispersion containing 80% Compound III-d, 19.5% hypromellose acetate succinate, and 0.5% sodium lauryl sulfate | 20-30 wt % |
| microcrystalline cellulose | 20-30 wt % |
| croscarmellose sodium (CCS) | 2-5 wt % | optionally magnesium stearate in an amount of 0.01 wt %-1.5 wt % based on the total weight of composition 93. The pharmaceutical composition of embodiment 1, further comprising microcrystalline cellulose, croscarmellose sodium and magnesium stearate, wherein the pharmaceutical composition comprises:

| Component | Amount (mg) per composition |
|---|---|
| potassium salt of Compound I (in some embodiments, potassium salt crystalline Form B) | 207-217 |
| solid dispersion containing 80% Compound II, 20% hypromellose | 58-68 |
| solid dispersion containing 80% Compound III, 19.5% hypromellose acetate succinate, and 0.5% sodium lauryl sulfate | 182-193 |
| microcrystalline cellulose (e.g., PH101) | 175-215 |
| croscarmellose sodium | 15-35 |
| magnesium stearate | 3-9 |

94. The pharmaceutical composition of embodiment 1, further comprising microcrystalline cellulose, croscarmellose sodium and magnesium stearate, wherein the pharmaceutical composition comprises:

| Component | Amount (mg) per composition |
|---|---|
| potassium salt of Compound I (in some embodiments, potassium salt crystalline Form B) | 122-132 |
| solid dispersion containing 80% Compound II, 20% hypromellose | 58-68 |
| solid dispersion containing 80% Compound III, 19.5% hypromellose acetate succinate, and 0.5% sodium lauryl sulfate | 182-193 |
| microcrystalline cellulose | 110-145 |
| croscarmellose sodium | 13-25 |
| magnesium stearate | 1.5-8 |

95. The pharmaceutical composition of embodiment 1, further comprising microcrystalline cellulose, croscarmellose sodium and magnesium stearate, wherein the pharmaceutical composition comprises:

| Component | Amount (mg) per composition |
|---|---|
| potassium salt of Compound I (in some embodiments, potassium salt crystalline Form B) | 62-65 |
| solid dispersion containing 80% Compound II, 20% hypromellose | 30-33 |
| solid dispersion containing 80% Compound III, 19.5% hypromellose acetate succinate, and 0.5% sodium lauryl sulfate | 90-95 |
| microcrystalline cellulose | 65-71 |
| croscarmellose sodium | 10-13 |
| magnesium stearate | 2.5-4.5 |

96. The pharmaceutical composition of embodiment 1, further comprising microcrystalline cellulose, croscarmellose sodium and magnesium stearate, wherein the pharmaceutical composition comprises:

| Component | Amount (mg) per composition |
|---|---|
| potassium salt of Compound I (in some embodiments, potassium salt crystalline Form B) | 58-68 |
| solid dispersion containing 80% Compound II, 20% hypromellose | 25-35 |
| solid dispersion containing 80% Compound III, 19.5% hypromellose acetate succinate, and 0.5% sodium lauryl sulfate | 87-97 |
| microcrystalline cellulose | 60-100 |
| croscarmellose sodium | 5-15 |
| magnesium stearate | 1.5-7 |

97. The pharmaceutical composition of embodiment 1, further comprising microcrystalline cellulose, croscarmellose sodium and magnesium stearate, wherein the pharmaceutical composition comprises:

| Component | Amount (mg) per composition |
|---|---|
| potassium salt of Compound I (in some embodiments, potassium salt crystalline Form B) | 207-217 |
| solid dispersion containing 80% Compound II, 20% hypromellose | 58-68 |
| solid dispersion containing 80% Compound III-d, 19.5% hypromellose acetate succinate, and 0.5% sodium lauryl sulfate | 120-130 |
| microcrystalline cellulose | 175-220 |
| croscarmellose sodium | 15-32 |
| magnesium stearate | 3-8 |

98. The pharmaceutical composition of embodiment 1, further comprising microcrystalline cellulose, croscarmellose sodium and magnesium stearate, wherein the pharmaceutical composition comprises:

| Component | Amount (mg) per composition |
|---|---|
| potassium salt of Compound I (in some embodiments, potassium salt crystalline Form B) | 122-132 |
| solid dispersion containing 80% Compound II, 20% hypromellose | 58-68 |
| solid dispersion containing 80% Compound III-d, 19.5% hypromellose acetate succinate, and 0.5% sodium lauryl sulfate | 124-126 |
| microcrystalline cellulose (e.g., PH101) | 129-131 |
| croscarmellose sodium | 17-19 |
| magnesium stearate | 3-5 |

99. The pharmaceutical composition of embodiment 1, further comprising microcrystalline cellulose, croscarmellose sodium and magnesium stearate, wherein the pharmaceutical composition comprises:

| Component | Amount (mg) per composition |
|---|---|
| potassium salt of Compound I (in some embodiments, potassium salt crystalline Form B) | 122-132 |
| solid dispersion containing 80% Compound II, 20% hypromellose | 58-68 |
| solid dispersion containing 80% Compound III-d, 19.5% hypromellose acetate succinate, and 0.5% sodium lauryl sulfate | 120-130 |
| Microcrystalline cellulose | 110-145 |
| Croscarmellose sodium | 8-30 |
| Magnesium Stearate | 1-7 |

100. The pharmaceutical composition of embodiment 1, further comprising microcrystalline cellulose, croscarmellose sodium and optionally magnesium stearate, wherein the pharmaceutical composition comprises:

| Component | Amount (mg) per composition |
|---|---|
| potassium salt of Compound I (in some embodiments, potassium salt crystalline Form B) | 250-260 |
| solid dispersion containing 80% Compound II, 20% hypromellose | 120-130 |
| solid dispersion containing 80% Compound III-d, 19.5% hypromellose acetate succinate, and 0.5% sodium lauryl sulfate | 245-255 |
| Microcrystalline cellulose | 80-110 |
| Croscarmellose sodium | 15-30 | and optionally further comprises magnesium stearate, in an amount of 0.01 mg-10 mg per composition.

101. The pharmaceutical composition of embodiment 1, further comprising microcrystalline cellulose, croscarmellose sodium and optionally magnesium stearate, wherein the pharmaceutical composition comprises:

| Component | Amount (mg) per composition |
|---|---|
| potassium salt of Compound I (in some embodiments, potassium salt crystalline Form B) | 122-132 |
| solid dispersion containing 80% Compound II, 20% hypromellose | 57-67 |
| solid dispersion containing 80% Compound III-d, 19.5% hypromellose acetate succinate, and 0.5% sodium lauryl sulfate | 120-130 |
| Microcrystalline cellulose | 275-305 |
| Croscarmellose sodium | 10-25 | and optionally further comprises magnesium stearate, in an amount of 0.01 mg-10 mg per composition.

102. The pharmaceutical composition of embodiment 1, further comprising microcrystalline cellulose, croscarmellose sodium and optionally magnesium stearate, wherein the pharmaceutical composition comprises:

| Component | Amount (mg) per composition |
|---|---|
| potassium salt of Compound I (in some embodiments, potassium salt crystalline Form B) | 122-132 |
| solid dispersion containing 80% Compound II, 20% hypromellose | 58-68 |
| solid dispersion containing 80% Compound III-d, 19.5% hypromellose acetate succinate, and 0.5% sodium lauryl sulfate | 120-130 |
| Microcrystalline cellulose | 100-135 |
| Croscarmellose sodium | 10-20 | and optionally further comprises magnesium stearate, in an amount of 0.01 mg-10 mg per composition.

103. The pharmaceutical composition of embodiment 1, further comprising microcrystalline cellulose, croscarmellose sodium and magnesium stearate, wherein the pharmaceutical composition comprises:

| Component | Amount (mg) per composition |
| --- | --- |
| potassium salt of Compound I (in some embodiments, potassium salt crystalline Form B) | 45-80 mg |
| solid dispersion containing 80% Compound II, 20% hypromellose | 20-50 mg |
| solid dispersion containing 80% Compound III, 19.5% hypromellose acetate succinate, and 0.5% sodium lauryl sulfate | 30-70 mg |
| microcrystalline cellulose | 60-300 mg |
| croscarmellose sodium | 5-25 mg |
| magnesium stearate | 1-7 mg |

104. The pharmaceutical composition of embodiment 1, further comprising microcrystalline cellulose, croscarmellose sodium and optionally magnesium stearate, wherein the pharmaceutical composition comprises:

| Component | Amount (mg) per composition |
| --- | --- |
| potassium salt of Compound I (in some embodiments, potassium salt crystalline Form B) | 50-80 |
| solid dispersion containing 80% Compound II, 20% hypromellose | 20-40 |
| solid dispersion containing 80% Compound III, 19.5% hypromellose acetate succinate, and 0.5% sodium lauryl sulfate | 70-120 |
| microcrystalline cellulose | 60-300 |
| croscarmellose sodium | 5-25 |
| magnesium stearate | 1-7 |

105. The pharmaceutical composition of embodiment 1, further comprising microcrystalline cellulose, croscarmellose sodium and magnesium stearate, wherein the pharmaceutical composition comprises:
(a)

| Component | Amount (mg) per composition |
| --- | --- |
| potassium salt of Compound I (in some embodiments, potassium salt crystalline Form B) | 50-80 |
| solid dispersion containing 80% Compound II, 20% hypromellose | 20-40 |
| solid dispersion containing 80% Compound III-d, 19.5% hypromellose acetate succinate, and 0.5% sodium lauryl sulfate | 45-80 |
| microcrystalline cellulose | 60-300 |
| croscarmellose sodium | 5-25 | and optionally further comprises magnesium stearate, in an amount of 0.01 mg-10 mg per composition; or
(b)

| Component | Amount (mg) per composition |
| --- | --- |
| potassium salt of Compound I (in some embodiments, potassium salt crystalline Form B) | 95-160 |
| solid dispersion containing 80% Compound II, 20% hypromellose | 45-80 |
| solid dispersion containing 80% Compound III-d, 19.5% hypromellose acetate succinate, and 0.5% sodium lauryl sulfate | 95-155 |
| Microcrystalline cellulose | 60-300 |
| Croscarmellose sodium | 5-25 | and optionally further comprises magnesium stearate, in an amount of 0.01 mg-10 mg per composition.

106. A single tablet comprising:
(a) 50 mg to 140 mg of a potassium salt of Compound I (in some embodiments, potassium salt crystalline Form B);
(b) 25 mg to 65 mg of a first solid dispersion comprising 80 wt % Compound II relative to the total weight of the first solid dispersion and 20 wt % of a hypromellose relative to the total weight of the first solid dispersion; and
(c) 75 mg to 200 mg of a second solid dispersion comprising 80 wt % of Compound III relative to the total weight of the second solid dispersion, 0.5 wt % of sodium lauryl sulfate relative to the total weight of the second solid dispersion, and 19.5 wt % of a hypromellose acetate succinate to the total weight of the second solid dispersion
(d) 60 mg to 150 mg of a microcrystalline cellulose;
(e) 5 mg to 25 mg of a croscarmellose sodium; and
(f) 1 mg to 6 mg of magnesium stearate.

107. The single tablet of embodiment 106, wherein the single tablet comprises:
(a) 115 mg to 140 mg of said potassium salt of Compound I (in some embodiments, potassium salt crystalline Form B);
(b) 60 mg to 65 mg of said first solid dispersion;
(c) 170 mg to 200 mg of said second solid dispersion;
(d) 60 mg to 140 mg of said microcrystalline cellulose;
(e) 10 mg to 30 mg of said croscarmellose sodium; and
(f) 3 mg to 8 mg of said magnesium stearate.

108. The single tablet of embodiment 106, wherein the tablet comprises:
(a) 115 mg to 140 mg of said potassium salt of Compound I (in some embodiments, potassium salt crystalline Form B);
(b) 60 mg to 65 mg of said first solid dispersion;
(c) 180 mg to 190 mg of said second solid dispersion;
(d) 120 mg to 135 mg of said microcrystalline cellulose;
(e) 15 mg to 25 mg of said croscarmellose sodium; and
(f) 3 mg to 5 mg of magnesium stearate.

109. The single tablet of embodiment 106, wherein the tablet comprises:
(a) 115 mg to 140 mg of said potassium salt of Compound I (in some embodiments, potassium salt crystalline Form B);
(b) 60 mg to 65 mg of said first solid dispersion;
(c) 180 mg to 190 mg of said second solid dispersion;
(d) 130 mg to 140 mg of said microcrystalline cellulose;
(e) 20 mg to 30 mg of said croscarmellose sodium; and
(f) 5 mg to 8 mg of magnesium stearate.

110. The single tablet of embodiment 106, wherein the single tablet comprises:
(a) 60 mg to 65 mg of said potassium salt of Compound I (in some embodiments, potassium salt crystalline Form B);
(b) 28 mg to 33 mg of said first solid dispersion;
(c) 90 mg to 95 mg of said second solid dispersion;
(d) 50 mg to 100 mg of said microcrystalline cellulose;
(e) 5 mg to 15 mg of said croscarmellose sodium; and
(f) 1 mg to 5 mg of said magnesium stearate.

111. A single tablet comprising:
(a) 100 mg to 250 mg of a potassium salt of Compound I (in some embodiments, potassium salt crystalline Form B);
(b) 30 mg to 65 mg of a first solid dispersion comprising 80 wt % Compound II relative to the total weight of the first solid dispersion and 20 wt % of a hypromellose relative to the total weight of the first solid dispersion; and
(c) 75 mg to 200 mg of a second solid dispersion comprising 80 wt % of Compound III relative to the total weight of the second solid dispersion 0.5 wt % of sodium lauryl sulfate relative to the total weight of the second solid dispersion, and 19.5 wt % of a hypromellose acetate succinate to the total weight of the second solid dispersion.

(d) 85 mg to 215 mg of a microcrystalline cellulose;
(e) 10 mg to 30 mg of a croscarmellose sodium; and
(f) 1 mg to 7 mg of magnesium stearate.
112. The single tablet of embodiment 111, wherein the tablet comprises:
(a) 103 mg to 108 mg of said potassium salt of Compound I (in some embodiments, potassium salt crystalline Form B);
(b) 30 mg to 35 mg of said first solid dispersion;
(c) 90 mg to 95 mg of said second solid dispersion;
(d) 85 mg to 215 mg of said microcrystalline cellulose;
(e) 10 mg to 30 mg of said croscarmellose sodium; and
(f) 1 mg to 7 mg of magnesium stearate.
113. A single tablet comprising:
(a) 100 mg to 215 mg of a potassium salt of Compound I (in some embodiments, potassium salt crystalline Form B);
(b) 30 mg to 65 mg of a first solid dispersion comprising 80 wt % Compound II relative to the total weight of the first solid dispersion and 20 wt % of a hypromellose relative to the total weight of the first solid dispersion; and
(c) 50 mg to 300 mg of a second solid dispersion comprising 80 wt % of Compound III-d relative to the total weight of the second solid dispersion, 0.5 wt % of sodium lauryl sulfate relative to the total weight of the second solid dispersion, and 19.5 wt % of a hypromellose acetate succinate to the total weight of the second solid dispersion;
(d) 85 mg to 215 mg of a microcrystalline cellulose;
(e) 10 mg to 30 mg of a croscarmellose sodium; and
(f) 1 mg to 7 mg of magnesium stearate.
114. The single tablet of embodiment 113, wherein the tablet comprises:
(a) 200 mg to 215 mg of said potassium salt of Compound I (in some embodiments, potassium salt crystalline Form B);
(b) 60 mg to 65 mg of said first solid dispersion;
(c) 100 mg to 150 mg of said second solid dispersion;
(d) 85 mg to 215 mg of said microcrystalline cellulose;
(e) 10 mg to 30 mg of said croscarmellose sodium; and
(f) 1 mg to 7 mg of magnesium stearate.
115. The single tablet of embodiment 113, wherein the tablet comprises:
(a) 100 mg to 110 mg of said potassium salt of Compound I (in some embodiments, potassium salt crystalline Form B);
(b) 30 mg to 35 mg of said first solid dispersion;
(c) 50 mg to 75 mg of said second solid dispersion;
(d) 85 mg to 215 mg of said microcrystalline cellulose;
(e) 10 mg to 30 mg of said croscarmellose sodium; and
(f) 1 mg to 7 mg of magnesium stearate.
116. A single tablet comprising:
(a) 55 mg to 300 mg of a potassium salt of Compound I (in some embodiments, potassium salt crystalline Form B);
(b) 30 mg to 130 mg of a first solid dispersion comprising 80 wt % Compound II relative to the total weight of the first solid dispersion, and 20 wt % of a hypromellose relative to the total weight of the first solid dispersion; and
(c) 50 mg to 300 mg of a second solid dispersion comprising 80 wt % of Compound III-d relative to the total weight of the second solid dispersion, 0.5 wt % of sodium lauryl sulfate relative to the total weight of the second solid dispersion; and 19.5 wt % of a hypromellose acetate succinate to the total weight of the second solid dispersion
(d) 60 mg to 300 mg of a microcrystalline cellulose;
(e) 7 mg to 25 mg of a croscarmellose sodium; and
(f) optionally 0.05 mg to 6 mg of magnesium stearate.
117. The single tablet of embodiment 116, wherein the tablet comprises:
(a) 245 mg to 260 mg of said potassium salt of Compound I (in some embodiments, potassium salt crystalline Form B);
(b) 120 mg to 130 mg of said first solid dispersion;
(c) 230 mg to 275 mg of said second solid dispersion;
(d) 60 mg to 135 mg of said microcrystalline cellulose;
(e) 7 mg to 25 mg of said croscarmellose sodium; and
(f) optionally 0.05 mg to 6 mg of magnesium stearate.
118. The single tablet of embodiment 116, wherein the tablet comprises:
(a) 115 mg to 140 mg of said potassium salt of Compound I (in some embodiments, potassium salt crystalline Form B);
(b) 60 mg to 65 mg of said first solid dispersion;
(c) 100 mg to 150 mg of said second solid dispersion;
(d) 60 mg to 135 mg of said microcrystalline cellulose;
(e) 7 mg to 25 mg of said croscarmellose sodium; and
(f) optionally 0.05 mg to 6 mg of magnesium stearate.
119. The single tablet of embodiment 116, wherein the tablet comprises:
(a) 60 mg to 70 mg of said potassium salt of Compound I (in some embodiments, potassium salt crystalline Form B);
(b) 25 mg to 35 mg of said first solid dispersion;
(c) 55 mg to 65 mg of said second solid dispersion;
(d) 60 mg to 135 mg of said microcrystalline cellulose;
(e) 7 mg to 25 mg of said croscarmellose sodium; and
(f) optionally 0.05 mg to 6 mg of magnesium stearate.
120. The single tablet of embodiment 116, wherein the tablet comprises:
(a) 125 mg to 130 mg of said potassium salt of Compound I (in some embodiments, potassium salt crystalline Form B);
(b) 60 mg to 65 mg of said first solid dispersion;
(c) 122 mg to 127 mg of said second solid dispersion;
(d) 275 mg to 325 mg of said microcrystalline cellulose;
(e) 10 mg to 25 mg of said croscarmellose sodium; and
(f) optionally 0.05 mg to 6 mg of magnesium stearate.
121. The single tablet of embodiment 116, wherein the tablet comprises:
(a) 125 mg to 130 mg of said potassium salt of Compound I (in some embodiments, potassium salt crystalline Form B);
(b) 60 mg to 65 mg of said first solid dispersion;
(c) 122 mg to 127 mg of said second solid dispersion;
(d) 110 mg to 125 mg of said microcrystalline cellulose;
(e) 10 mg to 25 mg of said croscarmellose sodium; and
(f) optionally 0.05 mg to 6 mg of magnesium stearate.
122. A method of treating cystic fibrosis in a patient comprising orally administering to the patient one or more of the pharmaceutical composition of any one of embodiments 1-38 and 49-105 or the single tablet of any one of embodiments 39-48 and 106-121.
123. The method of embodiment 122, wherein one or more of the pharmaceutical compositions or single tablets are administered once daily.
124. The method of embodiment 122, wherein one or more of the pharmaceutical compositions or single tablets are administered twice daily.
125. The method of embodiment 122, wherein two pharmaceutical compositions or tablets are administered concurrently per dosing.
126. The method according to any one of embodiments 122-125, wherein said patient has cystic fibrosis is chosen from patients with F508del/minimal function genotypes, patients with F508del/F508del genotypes, patients with F508del/gating genotypes, and patients with F508del/residual function genotypes.
127. The method of embodiment 126, wherein the patient with a F508del/minimal function genotype has a minimal function mutation selected from:

| Mutation | | | | |
|---|---|---|---|---|
| S4X | C276X | G542X | R792X | E1104X |
| G27X | Q290X | G550X | E822X | R1158X |
| Q39X | G330X | Q552X | W846X | R1162X |
| W57X | W401X | R553X | Y849X | S1196X |
| E60X | Q414X | E585X | R851X | W1204X |
| R75X | S434X | G673X | Q890X | L1254X |
| E92X | S466X | Q685X | S912X | S1255X |
| Q98X | S489X | R709X | Y913X | W1282X |
| Y122X | Q493X | K710X | W1089X | Q1313X |
| E193X | W496X | L732X | Y1092X | E1371X |
| L218X | C524X | R764X | W1098X | Q1382X |
| Q220X | Q525X | R785X | R1102X | Q1411X |
| 185 + 1G→T | 711 + 5G→A | 1717 − 8G→A | 2622 + 1G→A | 3121 − 1G→A |
| 296 + 1G→A | 712 − 1G→T | 1717 − 1G→A | 2790 − 1G→C | 3500 − 2A→G |
| 405 + 1G→A | 1248 + 1G→A | 1811 + 1G→C | 3040G→C | 3600 + 2insT |
| 405 + 3A→C | 1249 − 1G→A | 1811 + 1.6kbA→G | (G970R) | 3850 − 1G→A |
| 406 − 1G→A | 1341 + 1G→A | 1812 − 1G→A | 3120G→A | 4005 + 1G→A |
| 621 + 1G→T | 1525 − 2A→G | 1898 + 1G→A | 3120 + 1G→A | 4374 + 1G→T |
| 711 + 1G→T | 1525 − 1G→A | 1898 + 1G→C | 3121 − 2A→G | |
| 182delT | 1119delA | 1782delA | 2732insA | 3876delA |
| 306insA | 1138insG | 1824delA | 2869insG | 3878delG |
| 365-366insT | 1154insTC | 2043delG | 2896insAG | 3905insT |
| 394delTT | 1161delC | 2143delT | 2942insT | 4016insT |
| 442delA | 1213delT | 2183AA→G | 2957delT | 4021dupT |
| 444delA | 1259insA | 2184delA | 3007delG | 4040delA |
| 457TAT→G | 1288insTA | 2184insA | 3028delA | 4279insA |
| 541delC | 1471delA | 2307insA | 3171delC | 4326delTC |
| 574delA | 1497delGG | 2347delG | 3659delC | |
| 663delT | 1548delG | 2585delT | 3737delA | |
| 935delA | 1609del CA | 2594delGT | 3791delC | |
| 1078delT | 1677delTA | 2711delT | 3821delT | |

| | | | |
|---|---|---|---|
| CFTRdele2,3 | 1461ins4 | 2991del32 | |
| CFTRdele22,23 | 1924del7 | 3667ins4 | |
| 124del23bp | 2055del9→A | 4010del4 | |
| 852del22 | 2105-2117del13insAGAAA | 4209TGTT→AA | |
| 991del5 | 2721del11 | | |

| | | | |
|---|---|---|---|
| A46D | V520F | Y569D | N1303K |
| G85E | A559T | L1065P | |
| R347P | R560T | R1066C | |
| L467P | R560S | L1077P | |
| I507del | A561E | M1101K | |

128. The method of embodiment 127, wherein the patient with a F508del/gating genotype has a gating mutation selected from G178R, S549N, S549R, G551D, G551S, G1244E, S1251N, S1255P, and G1349D. 129. The method of embodiment 127, wherein the patient with a F508del/residual function genotype has a residual function mutation selected from 2789+5G→A, 3849+10kbC→T, 3272-26A→G, 711+3A→G, E56K, P67L, R74W, D110E, D110H, R117C, L206W, R347H, R352Q, A455E, D579G, E831X, S945L, S977F, F1052V, R1070W, F1074L, D1152H, D1270N, E193K, K1060T, R117H, S1235R, 11027T, R668C, G576A, M470V, L997F, R75Q, R1070Q, R31C, D614G, G1069R, R1162L, E56K, A1067T, E193K, and K1060T.

130. A method of preparing a pharmaceutical composition of embodiment 1, 24 or 49, wherein the pharmaceutical composition is a tablet and the method comprises:

(a) mixing the potassium salt of Compound I (in some embodiments, potassium salt crystalline Form B) and the first and second solid dispersions to form a first mixture; and (b) compressing a tablet mixture comprising the first mixture into a tablet.

131. The method of embodiment 130, wherein the tablet mixture further comprises one or more pharmaceutically acceptable excipients, and the method further comprising mixing the first mixture with said one or more excipients to form the tablet mixture.

132. The method of embodiment 130 or 131, further comprising coating the tablet.

133. A method of preparing a single tablet of any one of embodiments 39-48 and 106-121, comprising (a) mixing the potassium salt of Compound I (in some embodiments, potassium salt crystalline Form B) and the first and second solid dispersions to form a first mixture;

(b) mixing the first mixture with said microcrystalline cellulose, croscarmellose sodium and magnesium stearate to form a tablet mixture; and (c) compressing the tablet mixture into a tablet.

134. The method of embodiment 133, further comprising coating the tablet.

135. A method of preparing a single tablet of embodiment 39, 42, 74, 77, or 80, comprising (a) mixing the potassium salt of Compound I (in some embodiments, potassium salt crystalline Form B) and the first and second solid dispersions to form a first mixture;

(b) mixing a first portion of said microcrystalline cellulose, a first portion of said croscarmellose sodium and a first portion of said magnesium stearate comprised in the intragranular part to form a second mixture;

(c) mixing a second portion of said microcrystalline cellulose and a second portion of said croscarmellose sodium to form a third mixture;

(d) mixing the first, second, and third mixtures to form a tablet mixture; and (e) compressing the tablet mixture comprising the first, second and third mixtures into a tablet.

136. The method of embodiment 135, further comprising coating the tablet.

137. A method of preparing a single tablet of any one of embodiments 1, 39-48 and 106-123, comprising (a) mixing the potassium salt of Compound I (in some embodiments, potassium salt crystalline Form B) and the first and second solid dispersions to form a first mixture;

(b) mixing a first portion of said microcrystalline cellulose, a first portion of said croscarmellose sodium and magnesium stearate to form a second mixture;

(c) mixing a second portion of said microcrystalline cellulose and a second portion of said croscarmellose sodium comprised to form a third mixture;

(d) mixing the first, second, and third mixtures to form a tablet mixture; and (e) compressing the tablet mixture comprising the first, second and third mixtures into a tablet.

138. The method of embodiment 137, further comprising coating the tablet.

139. A method of preparing a single tablet of any one of embodiments 39-48 and 106-123, comprising (a) mixing the potassium salt of Compound I (in some embodiments, potassium salt crystalline Form B) and the first and second solid dispersions to form a first mixture;

(b) mixing a first portion of said microcrystalline cellulose, a first portion of said croscarmellose sodium and a first portion of said magnesium stearate to form a second mixture;

(c) mixing said a second portion of said microcrystalline cellulose, a second portion of said croscarmellose sodium, and a second portion of said magnesium stearate to form a third mixture;

(d) mixing the first, second, and third mixtures to form a tablet mixture; and (e) compressing the tablet mixture comprising the first, second and third mixtures into a tablet.

140. The method of embodiment 139, further comprising coating the tablet.

141. A pharmaceutical composition comprising (a) 50 mg to 600 mg of a crystalline form selected from a potassium salt of Compound I (in some embodiments, potassium salt crystalline Form B), a sodium salt of Compound I (Form A, D, E, H, or M) and crystalline Form A of Compound I:

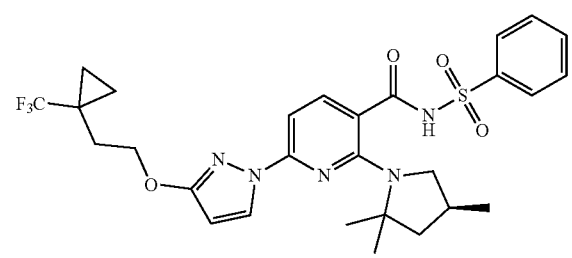

(b) a first solid dispersion comprising 15 mg to 75 mg of Compound II:

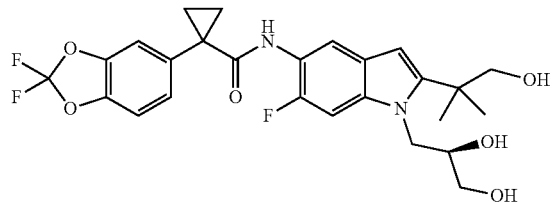 [SMILES: CC(C)(CO)c1cc2cc(NC(=O)C3(c4ccc5c(c4)OC(F)(F)O5)CC3)c(F)cc2n1C[C@@H](O)CO]

and 10 wt % to 30 wt % of a polymer relative to the total weight of the first solid dispersion; and (c) a second solid dispersion comprising 5 mg to 300 mg of Compound III or Compound III-d:

(Compound III)

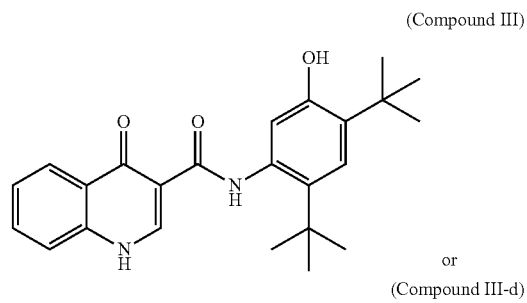

or (Compound III-d)

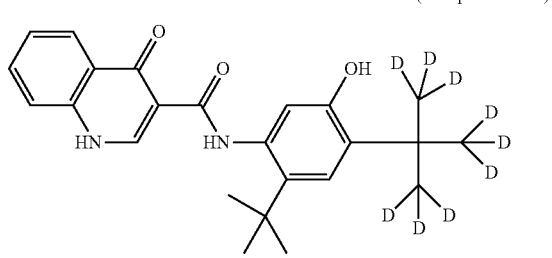

and 10 wt % to 30 wt % of a polymer relative to the total weight of the second solid dispersion.

142. The pharmaceutical composition of embodiment 141, wherein at least one of the first or second solid dispersions is a spray-dried dispersion.

143. The pharmaceutical composition of embodiment 141, wherein both of the first and second solid dispersions are spray-dried dispersions.

144. The pharmaceutical composition of embodiment 141, wherein said polymer for the first solid dispersion is hypromellose; and said polymer for the second solid dispersion is hypromellose acetate succinate.

145. The pharmaceutical composition of embodiment 141, wherein said polymer for the first solid dispersion is HPMC E15; and said polymer for the second solid dispersion is hypromellose acetate succinate H.

146. The pharmaceutical composition of embodiment 141, wherein said polymer for the first solid dispersion is HPMC E15; and said polymer for the second solid dispersion is hypromellose acetate succinate HG.

147. The pharmaceutical composition of any one of embodiments 141-146, comprising 50 mg to 500 mg of a potassium salt of Compound I (in some embodiments, potassium salt crystalline Form B).

148. The pharmaceutical composition of any one of embodiments 141-146, comprising 50 mg to 400 mg, 50 mg to 300 mg, 100 mg to 300 mg, 100 mg to 250 mg, 100 mg to 150 mg, or 200 mg to 250 mg of a potassium salt of Compound I (in some embodiments, potassium salt crystalline Form B).

149. The pharmaceutical composition of any one of embodiments 141-146, comprising 100 mg to 250 mg of a potassium salt of Compound I (in some embodiments, potassium salt crystalline Form B).

150. The pharmaceutical composition of any one of embodiments 141-146, comprising 100 mg to 150 mg or 150 mg to 250 mg of a potassium salt of Compound I (in some embodiments, potassium salt crystalline Form B).

151. The pharmaceutical composition of any one of embodiments 141-150, wherein the first solid dispersion comprises 20 mg to 60 mg of Compound II.

152. The pharmaceutical composition of any one of embodiments 141-150, wherein the second solid dispersion comprises 25 mg to 75 mg of Compound III or Compound III-d.

153. The pharmaceutical composition of any one of embodiments 1-10, wherein the second solid dispersion comprises 150 mg to 250 mg of Compound III or Compound III-d.

154. The pharmaceutical composition of any one of embodiments 1-6, comprising 50 mg to 400 mg, 50 mg to 300 mg, 100 mg to 300 mg, 100 mg to 250 mg, 100 mg to 150 mg, or 200 mg to 250 mg of a sodium salt of Compound I (in some embodiments, sodium salt crystalline Form H).

155. The pharmaceutical composition of any one of embodiments 1-6, comprising
100 mg to 250 mg of a sodium salt of Compound I (in some embodiments, sodium salt crystalline Form H); and wherein
the first solid dispersion comprises 25 mg to 75 mg of Compound II; and
the second solid dispersion comprises 50 mg to 100 mg of Compound III or Compound III-d.

156. The pharmaceutical composition of any one of embodiments 1-6, comprising about 125 mg of a sodium salt of Compound I (in some embodiments, sodium salt crystalline Form H); and wherein
the first solid dispersion comprises about 50 mg of Compound II; and
the second solid dispersion comprises about 75 mg of Compound III or Compound III-d.

157. The pharmaceutical composition of embodiment 141, comprising
50 mg to 125 mg of a sodium salt of Compound I (in some embodiments, sodium salt crystalline Form H); and wherein
the first solid dispersion comprises 15 mg to 40 mg of Compound II; and
the second solid dispersion comprises 25 mg to 50 mg of Compound III or Compound III-d.

158. The pharmaceutical composition of embodiment 141, comprising
about 62 mg of a sodium salt of Compound I (in some embodiments, sodium salt crystalline Form H); and wherein
the first solid dispersion comprises about 25 mg of Compound II; and
the second solid dispersion comprises about 37-38 mg of Compound III or Compound III-d.

159. A pharmaceutical composition comprising:
(a) 20 wt % to 35 wt % of a sodium salt of Compound I (in some embodiments, sodium salt crystalline Form H) relative to the total weight of the pharmaceutical composition;
(b) 5 wt % to 20 wt % of a first solid dispersion relative to the total weight of the pharmaceutical composition, wherein the first solid dispersion comprises 70 wt % to 90 wt % of Compound II relative to the total weight of the first solid dispersion and 10 wt % to 30 wt % of a polymer relative to the total weight of the first solid dispersion; and
(c) 20 wt % to 40 wt % of a second solid dispersion relative to the total weight of the pharmaceutical composition, wherein the second solid dispersion comprises 70 wt % to 90 wt % of Compound III or Compound III-d relative to the total weight of the second solid dispersion and 10 wt % to 30 wt % of a polymer relative to the total weight of the second solid dispersion.

160. A pharmaceutical composition comprising:
(a) 10 wt % to 18 wt % of a sodium salt of Compound I (in some embodiments, sodium salt crystalline Form H) relative to the total weight of the pharmaceutical composition;
(b) 2 wt % to 10 wt % of a first solid dispersion relative to the total weight of the pharmaceutical composition, wherein the first solid dispersion comprises 70 wt % to 90 wt % of Compound II relative to the total weight of the first solid dispersion and 10 wt % to 30 wt % of a polymer relative to the total weight of the first solid dispersion; and
(c) 10 wt % to 20 wt % of a second solid dispersion relative to the total weight of the pharmaceutical composition, wherein the second solid dispersion comprises 70 wt % to 90 wt % of Compound III or Compound III-d relative to the total weight of the second solid dispersion and 10 wt % to 30 wt % of a polymer relative to the total weight of the second solid dispersion.

161. A method of treating cystic fibrosis in a patient comprising orally administering to the patient one or more of the pharmaceutical compositions of any one of embodiments 154-160.

162. The method of embodiment 161, wherein one or more of the pharmaceutical compositions are administered once daily.

163. The method of embodiment 161, wherein one or more of the pharmaceutical compositions are administered twice daily.

164. The method of embodiment 161, wherein two pharmaceutical compositions are administered concurrently per dosing.

General Experimental Procedures

Reagents and starting materials were obtained by commercial sources unless otherwise stated and were used without purification. Proton and carbon NMR spectra were acquired on either of a Bruker Biospin DRX 400 MHz FTNMR spectrometer operating at a $^1$H and $^{13}$C resonant frequency of 400 and 100 MHz respectively, or on a 300 MHz NMR spectrometer. One dimensional proton and carbon spectra were acquired using a broadband observe (BBFO) probe with 20 Hz sample rotation at 0.1834 and 0.9083 Hz/Pt digital resolution respectively. All proton and carbon spectra were acquired with temperature control at 30° C. using standard, previously published pulse sequences and routine processing parameters.

Solid state $^{13}$C and $^{19}$F NMR data was obtained using Bruker-Biospin 400 MHz wide-bore spectrometer equipped with Bruker-Biospin 4 mm HFX probe was used. Samples were packed into 4 mm rotors and spun under Magic Angle Spinning (MAS) condition with typical spinning speed of 12.5 kHz. The proton relaxation time was estimated from $^1$H MAS Ti saturation recovery relaxation experiment and used to set up proper recycle delay of the $^{13}$C cross-polarization (CP) MAS experiment. The fluorine relaxation time was estimated from $^{19}$F MAS Ti saturation recovery relaxation experiment and used to set up proper recycle delay of the $^{19}$F MAS experiment. The CP contact time of CPMAS experiments was set to 2 ms. A CP proton pulse with linear ramp (from 50% to 100%) was employed. All spectra were externally referenced by adjusting the magnetic field to set carbon resonance of adamantane to 29.5 ppm. TPPM15 proton decoupling sequence was used with the field strength of approximately 100 kHz for both $^{13}$C and $^{19}$F acquisitions.

Final purity of compounds was determined by reversed phase UPLC using an Acquity UPLC BEH C18 column (50×2.1 mm, 1.7 m particle) made by Waters (pn: 186002350), and a dual gradient run from 1-99% mobile phase B over 3.0 minutes. Mobile phase A=H$_2$O (0.05% CF$_3$CO$_2$H). Mobile phase B=CH$_3$CN (0.035% CF$_3$CO$_2$H). Flow rate=1.2 mL/min, injection volume=1.5 μL, and column temperature=60° C. Final purity was calculated by averaging the area under the curve (AUC) of two UV traces (220 nm, 254 nm). Low-resolution mass spectra were reported as [M+H]$^+$ species obtained using a single quadrupole mass spectrometer equipped with an electrospray ionization (ESI) source capable of achieving a mass accuracy of 0.1 Da and a minimum resolution of 1000 (no units on resolution) across the detection range. Optical purity of methyl (2S)-2,4-dimethyl-4-nitro-pentanoate was determined using chiral gas chromatography (GC) analysis on an Agilent 7890A/MSD 5975C instrument, using a Restek Rt-βDEXcst (30 m×0.25 mm×0.25 um_df) column, with a 2.0 mL/min flow rate (H2 carrier gas), at an injection temperature of 220° C. and an oven temperature of 120° C., 15 minutes.

Powder X-Ray Diffraction

The powder x-ray diffraction measurements were performed using PANalytical's X-pert Pro diffractometer at room temperature with copper radiation (1.54060 Å). The incident beam optic was comprised of a variable divergence slit to ensure a constant illuminated length on the sample and on the diffracted beam side; a fast linear solid state detector was used with an active length of 2.12 degrees 2 theta measured in a scanning mode. The powder sample was packed on the indented area of a zero background silicon holder and spinning was performed to achieve better statistics. A symmetrical scan was measured from 4-40 degrees 2 theta with a step size of 0.017 degrees and a scan step time of 15.5 s.

Modulated Differential Scanning Calorimetry (MDSC)

MDSC was used to determine the glass transition temperature of the amorphous material. MDSC was performed using TA Discovery DSC differential scanning calorimeter (TA Instruments, New Castle, Del.). The instrument was calibrated with indium. Samples of approximately 1-3 mg were weighed into hermetic pans that were crimped using lids with one hole. The MDSC sample was scanned from −20° C. to 200° C. at a heating rate of 2° C./min with +/−1° C. of modulation within 1 minute. Data was collected and analyzed by TA Instruments Trios Software (TA Instruments, New Castle, Del.).

Single-Crystal Analysis

X-ray diffraction data were acquired at 100K or 298K on a Bruker diffractometer equipped with Mo K$_\alpha$ radiation (λ=0.71073 Å) or Cu K$_\alpha$ radiation (X=1.5478) and an CCD detector. The structure was solved and refined using SHELX program (Sheldrick, G. M., Acta Cryst., (2008) A64, 112-122).

Thermogravimetric Analysis (TGA)

TGA was used to investigate the presence of residual solvents in the lots characterized, and identify the temperature at which decomposition of the sample occurs. TGA data were collected on a TA Discovery Thermogravimetric Analyzer or equivalent instrumentation. A sample with weight of approximately 1-5 mg was scanned from 25° C. to 350° C. at a heating rate of 10° C./min. Data were collected and analyzed by Trios software (TA Instruments, New Castle, Del.) or collected by Thermal Advantage Q Series™ software and analyzed by Universal Analysis software (TA Instruments, New Castle, Del.). Differential Scanning Calorimetry (DSC).

DSC data were acquired using a TA Instruments Q2000 or equivalent instrumentation. A sample with a weight between 1 and 10 mg was weighed into an aluminum pan. This pan was placed in the sample position in the calorimeter cell. An empty pan was placed in the reference position. The calorimeter cell was closed and a flow of nitrogen was passed through the cell. The heating program was set to heat the sample at a heating rate of 10° C./min to a temperature of 200-350° C. When the run was completed, the data were analyzed using the DSC analysis program in the system software. The observed endo- and exotherms were integrated between baseline temperature points that were above and below the temperature range over which the endotherm was observed. The data reported were the onset of decomposition temperature, peak temperature and enthalpy, Example 1: Synthesis of N-(benzenesulfonyl)-6-[3-[2-[1-(trifluoromethyl)cyclopropyl]ethoxy]pyrazol-1-yl]-2-[(4S)-2,2,4-trimethylpyrrolidin-1-yl]pyridine-3-carboxamide (Compound I)

Part A: Synthesis of (4S)-2,2,4-trimethylpyrrolidine hydrochloride

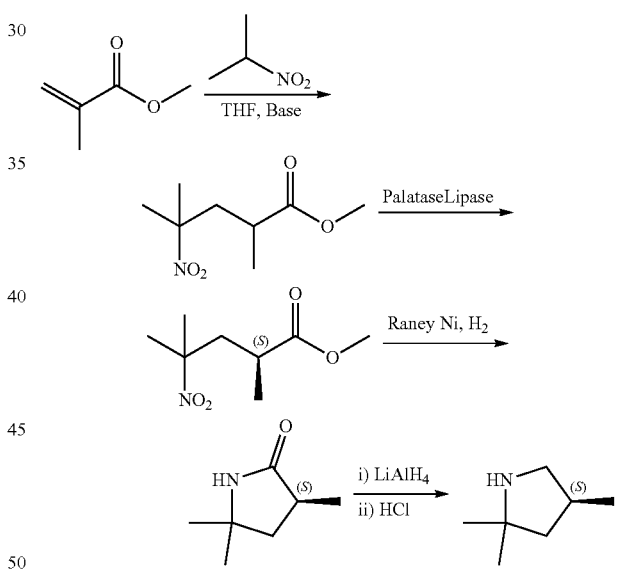

Step 1: Synthesis of methyl-2,4-dimethyl-4-nitro-pentanoate

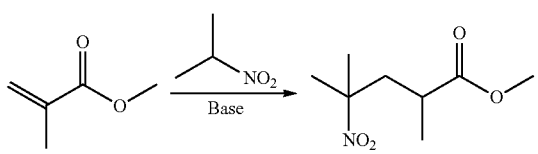

Tetrahydrofuran (THF, 4.5 L) was added to a 20 L glass reactor and stirred under N$_2$ at room temperature. 2-Nitropropane (1.5 kg, 16.83 mol) and 1,8-diazabicyclo[5.4.0]

undec-7-ene (DBU) (1.282 kg, 8.42 mol) were then charged to the reactor, and the jacket temperature was increased to 50° C. Once the reactor contents were close to 50° C., methyl methacrylate (1.854 kg, 18.52 mol) was added slowly over 100 minutes. The reaction temperature was maintained at or close to 50° C. for 21 hours. The reaction mixture was concentrated in vacuo then transferred back to the reactor and diluted with methyl tert-butyl ether (MTBE) (14 L). 2 M HCl (7.5 L) was added, and this mixture was stirred for 5 minutes then allowed to settle. Two clear layers were visible—a lower yellow aqueous phase and an upper green organic phase. The aqueous layer was removed, and the organic layer was stirred again with 2 M HCl (3 L). After separation, the HCl washes were recombined and stirred with MTBE (3 L) for 5 minutes. The aqueous layer was removed, and all of the organic layers were combined in the reactor and stirred with water (3 L) for 5 minutes. After separation, the organic layers were concentrated in vacuo to afford a cloudy green oil. This was dried with MgSO$_4$ and filtered to afford methyl-2,4-dimethyl-4-nitro-pentanoate as a clear green oil (3.16 kg, 99% yield). $^1$H NMR (400 MHz, Chloroform-d) δ 3.68 (s, 3H), 2.56-2.35 (m, 2H), 2.11-2.00 (m, 1H), 1.57 (s, 3H), 1.55 (s, 3H), 1.19 (d, J=6.8 Hz, 3H).

Step 2: Synthesis of methyl
(2S)-2,4-dimethyl-4-nitro-pentanoate

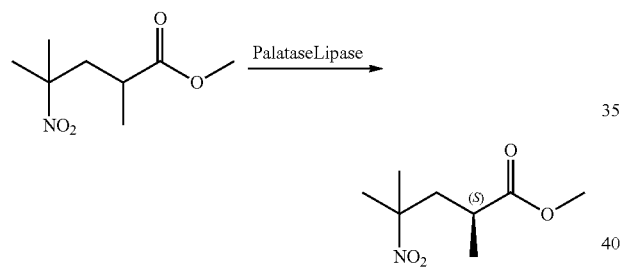

A reactor was charged with purified water (2090 L; 10 vol) and then potassium phosphate monobasic (27 kg, 198.4 moles; 13 g/L for water charge). The pH of the reactor contents was adjusted to pH 6.5 (+0.2) with 20% (w/v) potassium carbonate solution. The reactor was charged with racemic methyl-2,4-dimethyl-4-nitro-pentanoate (209 kg; 1104.6 moles), and Palatase 20000 L lipase (13 L, 15.8 kg; 0.06 vol).

The reaction mixture was adjusted to 32+2° C. and stirred for 15-21 hours, and pH 6.5 was maintained using a pH stat with the automatic addition of 20% potassium carbonate solution. When the racemic starting material was converted to >98% ee of the S-enantiomer, as determined by chiral GC, external heating was switched off. The reactor was then charged with MTBE (35 L; 5 vol), and the aqueous layer was extracted with MTBE (3 times, 400-1000 L). The combined organic extracts were washed with aqueous Na$_2$CO$_3$ (4 times, 522 L, 18% w/w 2.5 vol), water (523 L; 2.5 vol), and 10% aqueous NaCl (314 L, 1.5 vol). The organic layer was concentrated in vacuo to afford methyl (2S)-2,4-dimethyl-4-nitro-pentanoate as a mobile yellow oil (>98% ee, 94.4 kg; 45% yield).

Step 3: Synthesis of
(3S)-3,5,5-trimethylpyrrolidin-2-one

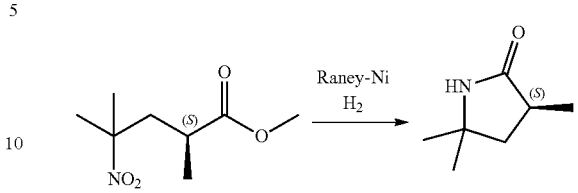

A 20 L reactor was purged with N$_2$. The vessel was charged sequentially with DI water-rinsed, damp Raney® Ni (2800 grade, 250 g), methyl (2S)-2,4-dimethyl-4-nitro-pentanoate (1741 g, 9.2 mol), and ethanol (13.9 L, 8 vol). The reaction was stirred at 900 rpm, and the reactor was flushed with H2 and maintained at ~2.5 bar. The reaction mixture was then warmed to 60° C. for 5 hours. The reaction mixture was cooled and filtered to remove Raney nickel, and the solid cake was rinsed with ethanol (3.5 L, 2 vol). The ethanolic solution of the product was combined with a second equal sized batch and concentrated in vacuo to reduce to a minimum volume of ethanol (~1.5 volumes). Heptane (2.5 L) was added, and the suspension was concentrated again to ~1.5 volumes. This was repeated 3 times; the resulting suspension was cooled to 0-5° C., filtered under suction, and washed with heptane (2.5 L). The product was dried under vacuum for 20 minutes then transferred to drying trays and dried in a vacuum oven at 40° C. overnight to afford (3S)-3,5,5-trimethylpyrrolidin-2-one as a white crystalline solid (2.042 kg, 16.1 mol, 87%). $^1$H NMR (400 MHz, Chloroform-d) δ 6.39 (s, 1H), 2.62 (ddq, J=9.9, 8.6, 7.1 Hz, 1H), 2.17 (dd, J=12.4, 8.6 Hz, 1H), 1.56 (dd, J=12.5, 9.9 Hz, 1H), 1.31 (s, 3H), 1.25 (s, 3H), 1.20 (d, J=7.1 Hz, 3H).

Step 4: Synthesis of (4S)-2,2,4-trimethylpyrrolidine
hydrochloride

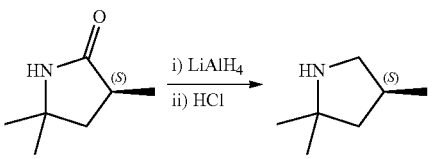

A glass lined 120 L reactor was charged with lithium aluminium hydride pellets (2.5 kg, 66 mol) and dry THF (60 L) and warmed to 30° C. The resulting suspension was charged with (S)-3,5,5-trimethylpyrrolidin-2-one (7.0 kg, 54 mol) in THF (25 L) over 2 hours while maintaining the reaction temperature at 30 to 40° C. After complete addition, the reaction temperature was increased to 60-63° C. and maintained overnight. The reaction mixture was cooled to 22° C., then cautiously quenched with the addition of ethyl acetate (EtOAc) (1.0 L, 10 moles), followed by a mixture of THF (3.4 L) and water (2.5 kg, 2.0 eq), and then a mixture of water (1.75 kg) with 50% aqueous sodium hydroxide (750 g, 2 equiv water with 1.4 equiv sodium hydroxide relative to aluminum), followed by 7.5 L water. After the addition was complete, the reaction mixture was cooled to room temperature, and the solid was removed by filtration and washed with THF (3×25 L). The filtrate and washings were combined and treated with 5.0 L (58 moles) of aqueous 37% HCl (1.05 equiv.) while maintaining the temperature below 30° C. The resultant solution was concentrated by vacuum distillation to a slurry. Isopropanol (8 L) was added and the solution was concentrated to near dryness by vacuum distillation. Isopropanol (4 L) was added, and the product was slurried by warming to about 50° C. MTBE (6 L) was added, and the slurry was cooled to 2-5° C. The product was collected by filtration and rinsed with 12 L MTBE and dried in a vacuum oven (55° C./300 torr/$N_2$ bleed) to afford (4S)-2,2,4-trimethylpyrrolidine*HCl as a white, crystalline solid (6.21 kg, 75% yield). $^1$H NMR (400 MHz, DMSO-d6) δ 9.34 (br d, 2H), 3.33 (dd, J=11.4, 8.4 Hz, 1H), 2.75 (dd, J=11.4, 8.6 Hz, 1H), 2.50-2.39 (m, 1H), 1.97 (dd, J=12.7, 7.7 Hz, 1H), 1.42 (s, 3H), 1.38 (dd, J=12.8, 10.1 Hz, 1H), 1.31 (s, 3H), 1.05 (d, J=6.6 Hz, 3H).

Part B: Synthesis of N-(benzenesulfonyl)-6-[3-[2-[1-(trifluoromethyl)cyclopropyl]ethoxy]pyrazol-1-yl]-2-[(4S)-2,2,4-trimethylpyrrolidin-1-yl]pyridine-3-carboxamide

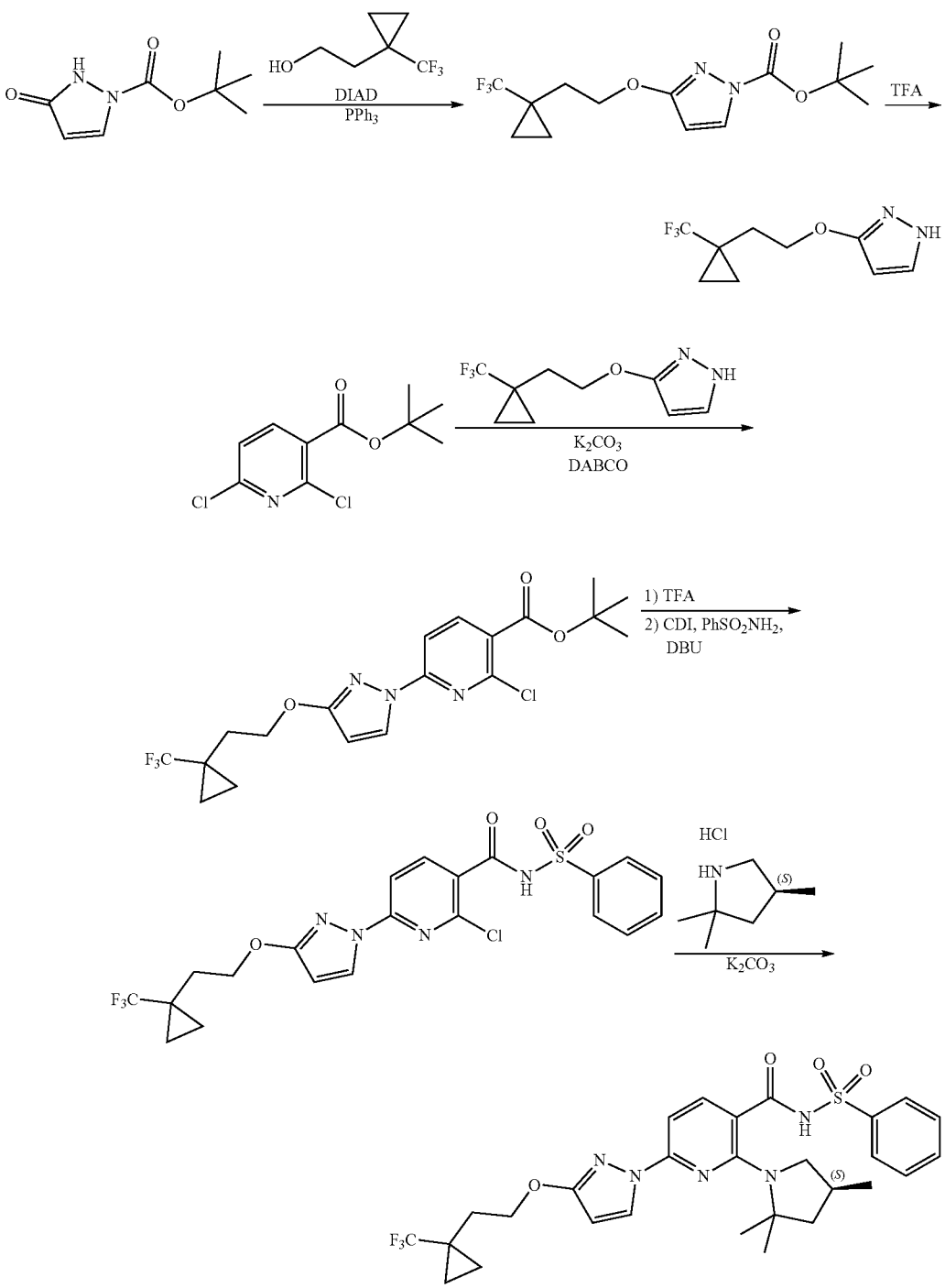

Synthesis of Starting Materials:

Synthesis of tert-Butyl 2,6-dichloropyridine-3-carboxylate

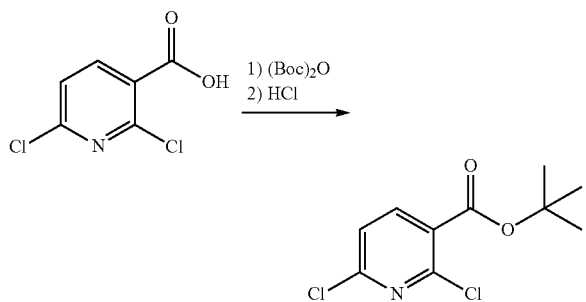

A solution of 2,6-dichloropyridine-3-carboxylic acid (10 g, 52.08 mmol) in THF (210 mL) was treated successively with di-tert-butyl dicarbonate (17 g, 77.89 mmol) and 4-(dimethylamino)pyridine (3.2 g, 26.19 mmol) and stirred overnight at room temperature. At this point, HCl 1N (400 mL) was added, and the mixture was stirred vigorously for about 10 minutes. The product was extracted with ethyl acetate (2×300 mL), and the combined organic layers were washed with water (300 mL) and brine (150 mL) and dried over sodium sulfate and concentrated under reduced pressure to give 12.94 g (96% yield) of tert-butyl 2,6-dichloropyridine-3-carboxylate as a colorless oil. ESI-MS m/z calc. 247.02, found 248.1 (M+1)+; Retention time: 2.27 minutes. $^1$H NMR (300 MHz, CDCl$_3$) ppm 1.60 (s, 9H), 7.30 (d, J=7.9 Hz, 1H), 8.05 (d, J=8.2 Hz, 1H).

Synthesis of tert-Butyl 3-oxo-2,3-dihydro-1H-pyrazole-1-carboxylate

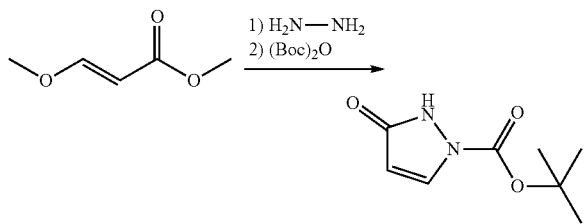

A 50 L reactor was started, and the jacket was set to 20° C., with stirring at 150 rpm, reflux condenser (10° C.) and nitrogen purge. MeOH (2.860 L) and methyl (E)-3-methoxyprop-2-enoate (2.643 kg, 22.76 mol) were added, and the reactor was capped. The reaction was heated to an internal temperature of 40° C., and the system was set to hold jacket temperature at 40° C. Hydrazine hydrate (1300 g of 55% w/w, 22.31 mol) was added portion wise via addition funnel over 30 min. The reaction was heated to 60° C. for 1 h. The reaction mixture was cooled to 20° C. and triethyamine (2.483 kg, 3.420 L, 24.54 mol) was added portion-wise, maintaining reaction temperature<30° C. A solution of Boc anhydride (di-tert-butyl dicarbonate) (4.967 kg, 5.228 L, 22.76 mol) in MeOH (2.860 L) was added portion-wise maintaining temperature<45° C. The reaction mixture was stirred at 20° C. for 16 h. The reaction solution was partially concentrated to remove MeOH, resulting in a clear, light amber oil. The resulting oil was transferred to the 50 L reactor, stirred and water (7.150 L) and heptane (7.150 L) were added. The additions caused a small amount of the product to precipitate. The aqueous layer was drained into a clean container, and the interface and heptane layer were filtered to separate the solid (product). The aqueous layer was transferred back to the reactor, and the collected solid was placed back into the reactor and mixed with the aqueous layer. A dropping funnel was added to the reactor and loaded with acetic acid (1.474 kg, 1.396 L, 24.54 mol) and added dropwise. The jacket was set to 0° C. to absorb the quench exotherm. After the addition was complete (pH=5), the reaction mixture was stirred for 1 h. The solid was collected by filtration and washed with water (7.150 L) and washed a second time with water (3.575 L). The crystalline solid was transferred into a 20 L rotovap bulb, and heptane (7.150 L) was added. The mixture was slurried at 45° C. for 30 mins, and 1-2 volumes of solvent were distilled off. The slurry in the rotovap flask was filtered, and the solids were washed with heptane (3.575 L). The solid was further dried in vacuo (50° C., 15 mbar) to give tert-butyl 5-oxo-1H-pyrazole-2-carboxylate (2921 g, 71%) as a coarse, crystalline solid. $^1$H NMR (400 MHz, DMSO-d6) δ 10.95 (s, 1H), 7.98 (d, J=2.9 Hz, 1H), 5.90 (d, J=2.9 Hz, 1H), 1.54 (s, 9H).

Synthesis of 2-[1-(trifluoromethyl)cyclopropyl]ethanol

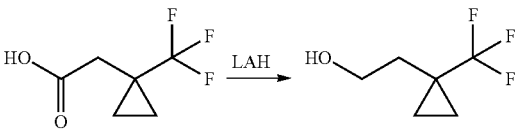 [SMILES: O=C(O)CC1(C(F)(F)F)CC1 ; OCCC1(C(F)(F)F)CC1]

To a solution of lithium aluminum hydride (293 mg, 7.732 mmol) in THF (10.00 mL) in an ice-bath, 2-[1-(trifluoromethyl)cyclopropyl]acetic acid (1.002 g, 5.948 mmol) in THF (3.0 mL) was added dropwise over a period of 30 minutes keeping the reaction temperature below 20° C. The mixture was allowed to gradually warm to ambient temperature and was stirred for 18 h. The mixture was cooled with an ice-bath and sequentially quenched with water (294 mg, 295 µL, 16.36 mmol), NaOH (297 µL of 6 M, 1.784 mmol), and then water (884.0 µL, 49.07 mmol) to afford a granular solid in the mixture. The solid was filtered off using celite, and the precipitate was washed with ether. The filtrate was further dried with MgSO$_4$ and filtered and concentrated in vacuo to afford the product with residual THF and ether. The mixture was taken directly into the next step without further purification.

Step 1: tert-Butyl 3-[2-[1-(trifluoromethyl)cyclopropyl]ethoxy]pyrazole-1-carboxylate

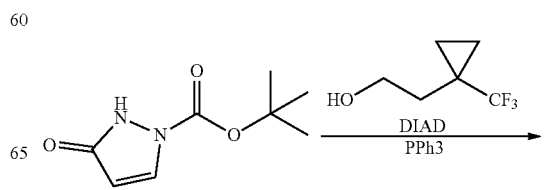

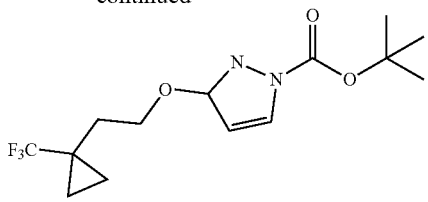

tert-Butyl 5-oxo-1H-pyrazole-2-carboxylate (1.043 g, 5.660 mmol), 2-[1-(trifluoromethyl)cyclopropyl]ethanol (916 mg, 5.943 mmol), and triphenyl phosphine (1.637 g, 6.243 mmol) were combined in THF (10.48 mL) and the reaction was cooled in an ice-bath. Diisopropyl azodicarboxylate (1.288 g, 1.254 mL, 6.368 mmol) was added dropwise to the reaction mixture, and the reaction was allowed to warm to room temperature for 16 hours. The mixture was evaporated, and the resulting material was partitioned between ethyl acetate (30 mL) and 1N sodium hydroxide (30 mL). The organic layer was separated, washed with brine (30 mL), dried over sodium sulfate, and concentrated. The crude material was purified by silica gel chromatography eluting with a gradient of ethyl acetate in hexanes (0-30%) to give tert-butyl 3-[2-[1-(trifluoromethyl)cyclopropyl]ethoxy]pyrazole-1-carboxylate (1.03 g, 57%). ESI-MS m/z calc. 320.13, found 321.1 (M+1)+; Retention time: 0.72 minutes.

Step 2: 3-[2-[1-(Trifluoromethyl)cyclopropyl]ethoxy]-1H-pyrazole

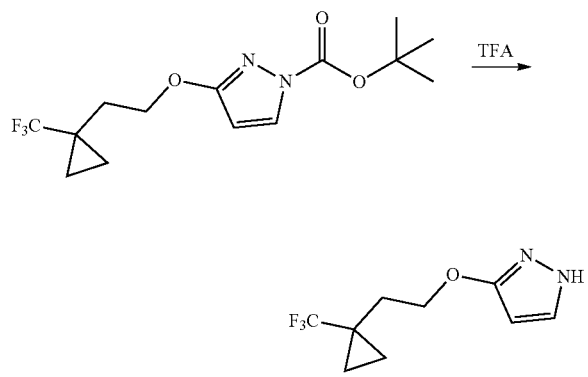

tert-Butyl-3-[2-[1-(trifluoromethyl)cyclopropyl]ethoxy]pyrazole-1-carboxylate (1.03 g, 3.216 mmol) was dissolved in dichloromethane (10.30 mL) with trifluoroacetic acid (2.478 mL, 32.16 mmol), and the reaction was stirred at room temperature for 2 hours. The reaction was evaporated, and the resulting oil was partitioned between ethyl acetate (10 mL) and a saturated sodium bicarbonate solution. The organic layer was separated, washed with brine, dried over sodium sulfate, and evaporated to give 3-[2-[1-(trifluoromethyl)ethyl)ethoxy]-1H-pyrazole (612 mg, 86%). ESI-MS m/z calc. 220.08, found 221.0 (M+1)+; Retention time: 0.5 minutes. $^1$H NMR (400 MHz, DMSO-d6) δ 11.86 (s, 1H), 7.50 (t, J=2.1 Hz, 1H), 5.63 (t, J=2.3 Hz, 1H), 4.14 (t, J=7.1 Hz, 2H), 2.01 (t, J=7.1 Hz, 2H), 0.96-0.88 (m, 2H), 0.88-0.81 (m, 2H).

Step 3: tert-Butyl 2-chloro-6-[3-[2-[1-(trifluoromethyl)cyclopropyl]ethoxy]pyrazol-1-yl]pyridine-3-carboxylate

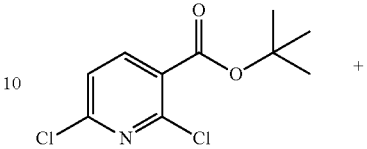

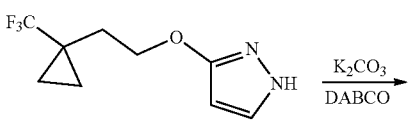

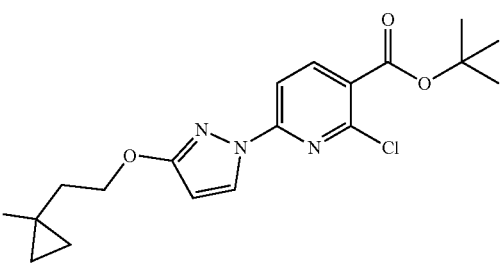

tert-Butyl 2,6-dichloropyridine-3-carboxylate (687 mg, 2.770 mmol), 3-[2-[1-(trifluoromethyl)cyclopropyl]ethoxy]-1H-pyrazole (610 mg, 2.770 mmol), and freshly ground potassium carbonate (459 mg, 3.324 mmol) were combined in anhydrous DMSO (13.75 mL). 1,4-diazabicyclo[2.2.2]octane (DABCO (1,4-diazabicyclo[2.2.2]octane), 62 mg, 0.5540 mmol) was added, and the mixture was stirred at room temperature under nitrogen for 16 hours. The reaction mixture was diluted with water (20 mL) and stirred for 15 minutes. The resulting solid was collected and washed with water. The solid was dissolved in dichloromethane and dried over magnesium sulfate. The mixture was filtered and concentrated to give tert-butyl 2-chloro-6-[3-[2-[1-(trifluoromethyl)cyclopropyl]ethoxy]pyrazol-1-yl]pyridine-3-carboxylate (1.01 g, 84%). ESI-MS m/z calc. 431.12, found 432.1 (M+1)+; Retention time: 0.88 minutes.

Step 4: 2-Chloro-6-[3-[2-[1-(trifluoromethyl)cyclopropyl]ethoxy]pyrazol-1-yl]pyridine-3-carboxylic acid

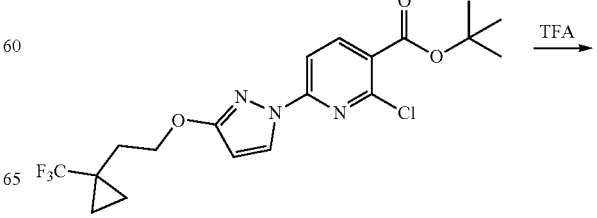

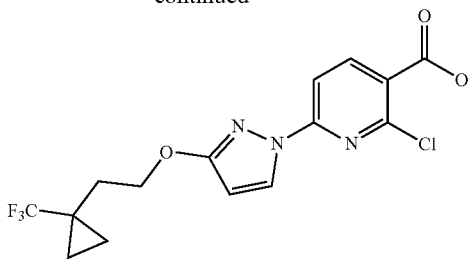

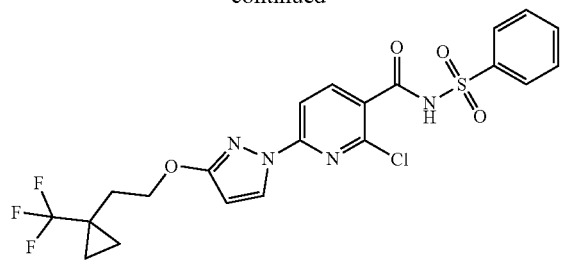

tert-Butyl 2-chloro-6-[3-[2-[1-(trifluoromethyl)cyclopropyl]ethoxy]pyrazol-1-yl]pyridine-3-carboxylate (1.01 g, 2.339 mmol) and trifluoroacetic acid (1.8 mL, 23.39 mmol) were combined in dichloromethane (10 mL) and heated at 40° C. for 3 h. The reaction was concentrated. Hexanes were added, and the mixture was concentrated again to give 2-chloro-6-[3-[2-[1-(trifluoromethyl)cyclopropyl]ethoxy]pyrazol-1-yl]pyridine-3-carboxylic acid (873 mg, 99%) ESI-MS m/z calc. 375.06, found 376.1 (M+1)+; Retention time: 0.69 minutes.

Step 5: N-(Benzenesulfonyl)-2-chloro-6-[3-[2-[1-(trifluoromethyl)cyclopropyl]ethoxy]pyrazol-1-yl]pyridine-3-carboxamide

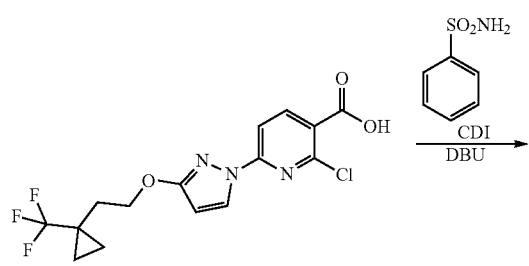

A solution of 2-chloro-6-[3-[2-[1-(trifluoromethyl)cyclopropyl]ethoxy]pyrazol-1-yl]pyridine-3-carboxylic acid (0.15 g, 0.3992 mmol) and carbonyl diimidazole (77 mg, 0.4790 mmol) in THF (2.0 mL) was stirred for one hour, and benzenesulfonamide (81 mg, 0.5190 mmol) and DBU (72 µL, 0.4790 mmol) were added. The reaction was stirred for 16 hours, acidified with 1 M aqueous citric acid, and extracted with ethyl acetate. The combined extracts were dried over sodium sulfate and evaporated. The residue was purified by silica gel chromatography eluting with a gradient of methanol in dichloromethane (0-5%) to give N-(benzenesulfonyl)-2-chloro-6-[3-[2-[1-(trifluoromethyl)cyclopropyl]ethoxy]pyrazol-1-yl]pyridine-3-carboxamide (160 mg, 78%). ESI-MS m/z calc. 514.07, found 515.1 (M+1)+; Retention time: 0.74 minutes.

Step 6: N-(Benzenesulfonyl)-6-[3-[2-[1-(trifluoromethyl)cyclopropyl]ethoxy]pyrazol-1-yl]-2-[(4S)-2,2,4-trimethylpyrrolidin-1-yl]pyridine-3-carboxamide

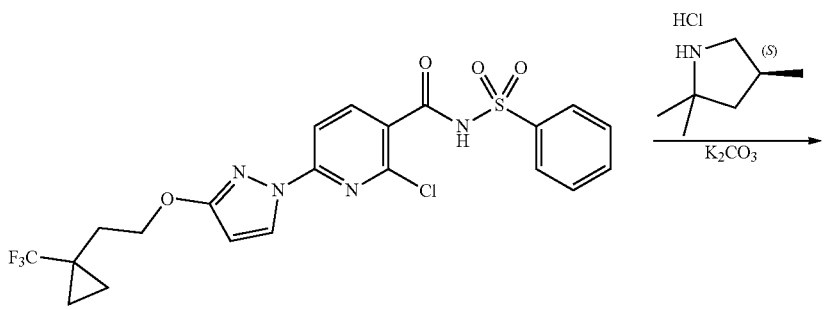

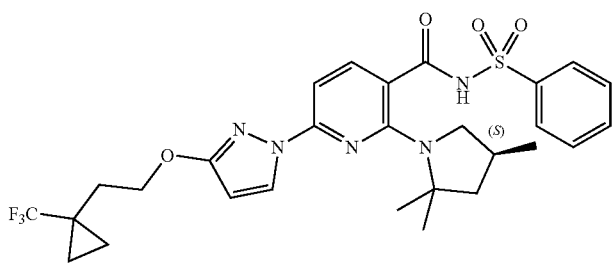

A mixture of N-(benzenesulfonyl)-2-chloro-6-[3-[2-[1-(trifluoromethyl)cyclopropyl]ethoxy]pyrazol-1-yl]pyridine-3-carboxamide (160 mg, 0.3107 mmol), (4S)-2,2,4-trimethylpyrrolidine hydrochloride salt (139 mg, 0.9321 mmol), and potassium carbonate (258 mg, 1.864 mmol) in DMSO (1.5 mL) was stirred at 130° C. for 17 hours. The reaction mixture was acidified with 1 M aqueous citric acid and extracted with ethyl acetate. The combined extracts were dried over sodium sulfate and evaporated to yield a crude product that was purified by reverse-phase HPLC utilizing a gradient of 10-99% acetonitrile in 5 mM aqueous HCl to yield N-(benzenesulfonyl)-6-[3-[2-[1-(trifluoromethyl)cyclopropyl]ethoxy]pyrazol-1-yl]-2-[(4S)-2,2,4-trimethylpyrrolidin-1-yl]pyridine-3-carboxamide (87 mg, 47%). ESI-MS m/z calc. 591.21, found 592.3 (M+1)+; Retention time: 2.21 minutes. $^1$H NMR (400 MHz, DMSO-d6) δ 12.48 (s, 1H), 8.19 (d, J=2.8 Hz, 1H), 8.04-7.96 (m, 2H), 7.81 (d, J=8.2 Hz, 1H), 7.77-7.70 (m, 1H), 7.70-7.62 (m, 2H), 6.92 (d, J=8.2 Hz, 1H), 6.10 (d, J=2.8 Hz, 1H), 4.31 (t, J=7.0 Hz, 2H), 2.42 (t, J=10.5 Hz, 1H), 2.28 (dd, J=10.2, 7.0 Hz, 1H), 2.17-2.01 (m, 3H), 1.82 (dd, J=11.9, 5.5 Hz, 1H), 1.52 (d, J=9.4 Hz, 6H), 1.36 (t, J=12.1 Hz, 1H), 1.01-0.92 (m, 2H), 0.92-0.85 (m, 2H), 0.65 (d, J=6.3 Hz, 3H). pKa: 4.95±0.06.

Synthesis of sodium salt of N-(benzenesulfonyl)-6-[3-[2-[1-(trifluoromethyl) cyclopropyl]ethoxy]pyrazol-1-yl]-2-[(4S)-2,2,4-trimethylpyrrolidin-1-yl]pyridine-3-carboxamide (sodium salt of Compound I)

Figure 16:
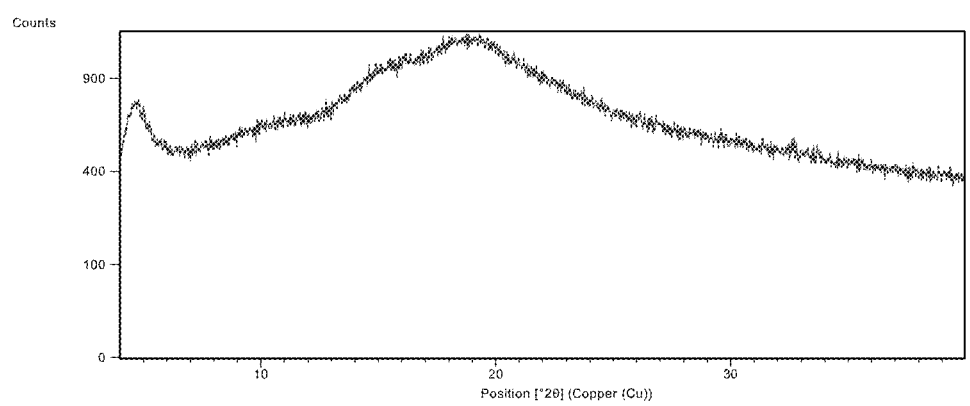
FIG. 16 shows the X-ray powder diffractogram spectrum of an amorphous sodium salt of Compound I.

N-(benzenesulfonyl)-6-[3-[2-[1-(trifluoromethyl)cyclopropyl]ethoxy]pyrazol-1-yl]-2-[(4S)-2,2,4-trimethylpyrrolidin-1-yl]pyridine-3-carboxamide (1000 mg, 1.679 mmol) was dissolved in ethanol (19.87 ml) under warming, filtered clear through a syringe filter (0.2 μm), washed with warm ethanol (10 ml) and the warm solution was treated with 1M NaOH (1.679 ml, 1.679 mmol). The solution was evaporated at 30-35° C., co-evaporated 3 times with ethanol (~20 ml), to give a solid, which was dried overnight under vacuum in a drying cabinet at 45° C. with a nitrogen bleed to give 951 mg of a cream colored solid. The solid was further dried under vacuum in a drying cabinet at 45° C. with a nitrogen bleed over the weekend. 930 mg (89%) of the sodium salt of N-(benzenesulfonyl)-6-[3-[2-[1-(trifluoromethyl)cyclopropyl]ethoxy]pyrazol-1-yl]-2-[(4S)-2,2,4-trimethylpyrrolidin-1-yl]pyridine-3-carboxamide was obtained as an off-white amorphous solid. $^1$H NMR (400 MHz, DMSO-d6) δ 8.15 (d, J=2.7 Hz, 1H), 7.81 (dd, J=6.7, 3.1 Hz, 2H), 7.61 (d, J=7.9 Hz, 1H), 7.39 (dd, J=4.9, 2.0 Hz, 3H), 6.74 (d, J=7.9 Hz, 1H), 6.01 (d, J=2.6 Hz, 1H), 4.29 (t, J=7.0 Hz, 2H), 2.93-2.78 (m, 2H), 2.07 (t, J=7.1 Hz, 3H), 1.78 (dd, J=11.8, 5.6 Hz, 1H), 1.52 (d, J=13.6 Hz, 6H), 1.33 (t, J=12.0 Hz, 1H), 1.00-0.92 (m, 2H), 0.89 (q, J=5.3, 4.6 Hz, 2H), 0.71 (d, J=6.3 Hz, 3H). ESI-MS m/z calc. 591.2127, found 592.0 (M+1)+; Retention time: 3.28 minutes. XRPD (see FIG. 16).

Alternate Synthesis of 2-Chloro-6-[3-[2-[1-(trifluoromethyl)cyclopropyl]ethoxy]pyrazol-1-yl]pyridine-3-carboxylic acid Step 1: ethyl 3-hydroxy-1H-pyrazole-4-carboxylate

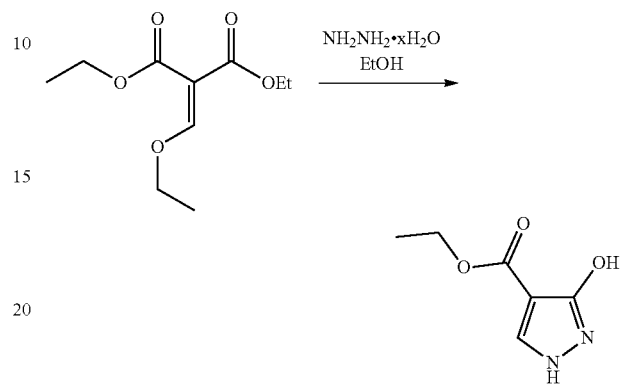

A mixture of EtOH (20.00 L, 10 vol) and diethyl 2-(ethoxymethylene) propanedioate (2000 g, 9.249 mol, 1.0 equiv) was added under nitrogen purge a to a 50 L reactor equipped with a reflux condenser (10° C.) and the jacket set to 40° C. The mixture was stirred, and then hydrazine hydrate (538.9 g of 55% w/w, 523.7 mL of 55% w/w, 9.249 mol, 1.00 equiv) was added in portions via an addition funnel. Once the addition was complete, the reaction was heated to 75° C. for 22 h to afford a solution of ethyl 3-hydroxy-1H-pyrazole-4-carboxylate that was used directly in the next step.

Step 2: 1-(tert-butyl) 4-ethyl 3-hydroxy-1H-pyrazole-1,4-dicarboxylate

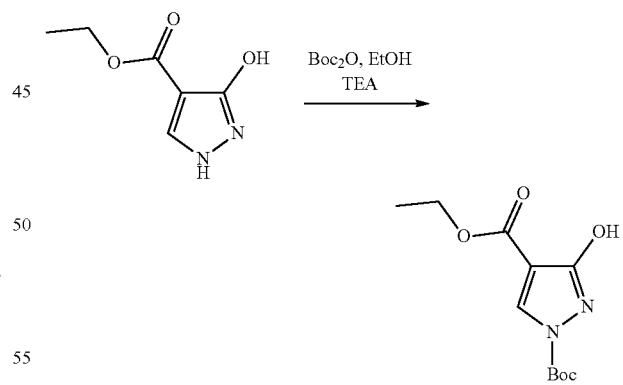

The solution of ethyl 3-hydroxy-1H-pyrazole-4-carboxylate was cooled from 75° C. to 40° C., then triethylamine (TEA) (46.80 g, 64.46 mL, 462.5 mmol, 0.05 eq.) was added. A solution of Boc anhydride (2.119 kg, 9.711 mol 1.05 equiv) in EtOH (2.000 L, 1 equiv) was added to the reactor over 35 min. The mixture was stirred for 4 hours to complete the reaction; then water (10.00 L, 5.0 vol) was added over 15 mins. The resulting mixture was cooled to 20° C. to complete crystallization of the product. The crystals were allowed to age for 1 hour, then the mixture was filtered.

The solid was washed with a mixture of EtOH (4.000 L, 2.0 vol) and water (2.000 L, 1.0 vol). The solid was then dried in vacuo to afford 1-(tert-butyl)-4-ethyl-3-hydroxy-1H-pyrazole-1,4-dicarboxylate (1530 g, 65%) as colorless, fine needle, crystalline solid. ¹H NMR (400 MHz, DMSO-d6) δ 11.61 (s, 1H), 8.40 (s, 1H), 4.20 (q, J=7.1 Hz, 2H), 1.56 (s, 9H), 1.25 (t, J=7.1 Hz, 3H).

Step 3: 1-(tert-butyl) 4-ethyl 3-(2-(1-(trifluoromethyl)cyclopropyl)ethoxy)-1H-pyrazole-1,4-dicarboxylate

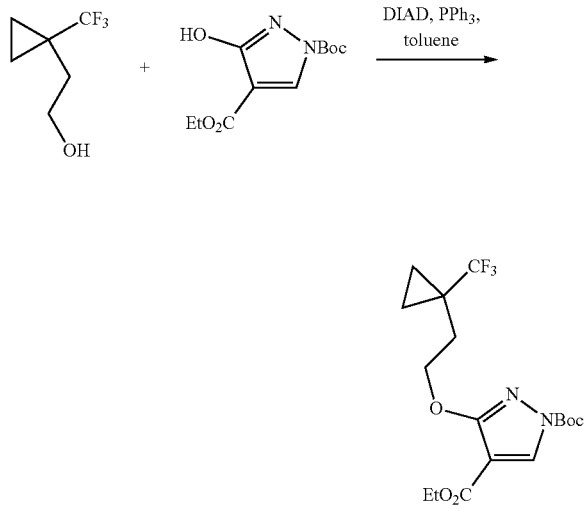

A 5 L reactor was started with the jacket set to 40° C., stirring at 450 rpm, reflux condenser at room temperature and nitrogen purge. The vessel was charged with toluene (1.0 L, 10.0 vol), 2-[1-(trifluoromethyl)cyclopropyl]ethanol (100.0 g, 648.8 mmol, 1.0 equiv), and 1-(tert-butyl) 4-ethyl 3-hydroxy-1H-pyrazole-1,4-dicarboxylate (166.3 g, 648.8 mmol), and the mixture was stirred. The reaction mixture was charged with triphenyl phosphine (195.7 g, 746.1 mmol, 1.15 equiv), then the reactor was set to maintain an internal temperature of 40° C. Diisopropyl azoldicarboxylate (150.9 g, 746.1 mmol, 1.15 equiv) was added into an addition funnel and was added to the reaction while maintaining the reaction temperature between 40 and 50° C. (addition was exothermic, exotherm addition controlled), and stirred for a total of 2.5 hours. Once the reaction was deemed complete by HPLC, heptane was added (400 mL, 4 vol), the solution was cooled to 20° C. over 60 minutes, and the bulk of triphenylphosphine oxide-DIAD complex (TPPO-DIAD) crystallized out. Once at room temp, the mixture was filtered, and the solid was washed with heptane (400 mL, 4.0 vol) and pulled dry. The filtrate was used in the next step as a solution in toluene-heptane without further purification.

Step 4: ethyl 3-(2-(1-(trifluoromethyl)cyclopropyl)ethoxy)-1H-pyrazole-4-carboxylate

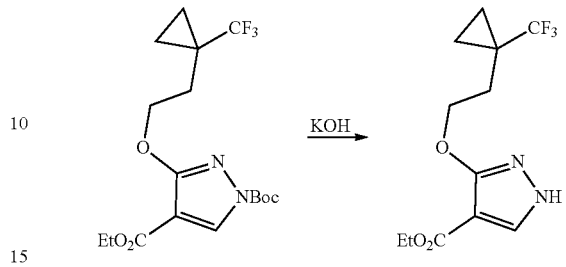

A 500 mL reactor was started with the jacket set to 40° C., stirring at 450 rpm, reflux condenser at room temp, and nitrogen purge. The vessel was charged with a toluene solution consisting of approximately 160 mmol, 65.0 g of 1-(tert-butyl) 4-ethyl 3-(2-(1-(trifluoromethyl)cyclopropyl)ethoxy)-1H-pyrazole-1,4-dicarboxylate in 3 vol of toluene (prepared by concentrating a 25% portion of filtrate from previous reaction down to 4 volumes in a rotovap). The reaction was set to maintain an internal temperature at 40° C. and KOH (33.1 g, 1.5 eq. of aqueous 45% KOH solution) was added in one portion, resulting in a mild exothermic addition, while C02 was generated upon removal of the protecting group. The reaction proceeded for 1.5 hr, monitored by HPLC, with the product partially crystallizing during the reaction. Heptane (160 mL, 2.5 vol) was added to the reaction mixture and the reaction was cooled to room temperature over 30 minutes. The resulting mixture was filtered, and the solid was washed with heptane (80.00 mL, 1.25 vol), pulled dry, then dried in vacuo (55° C., vacuum). 52.3 g of ethyl 3-(2-(1-(trifluoromethyl)cyclopropyl)ethoxy)-1H-pyrazole-4-carboxylate was obtained as a crude, colorless solid that was used without further purification.

Step 5: 3-(2-(1-(trifluoromethyl)cyclopropyl)ethoxy)-1H-pyrazole-4-carboxylic acid

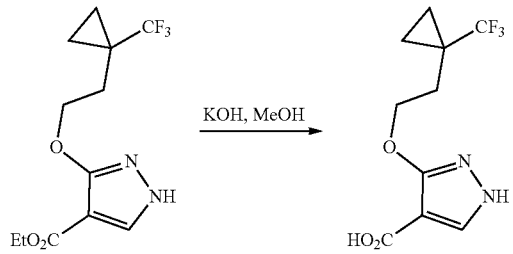 [SMILES: CCOC(=O)c1c[nH]nc1OCCC1(C(F)(F)F)CC1 ; O=C(O)c1c[nH]nc1OCCC1(C(F)(F)F)CC1]

A 500 mL reactor was started with the jacket set to 40° C., stirring at 450 rpm, reflux condenser at room temp, and nitrogen purge. The vessel was charged with methanol (150.0 mL, 3.0 vol), a solution of ethyl 3-(2-(1-(trifluoromethyl)cyclopropyl) ethoxy)-1H-pyrazole-4-carboxylate (50.0 g, 171.1 mmol, 1.0 equiv), and the reaction was stirred to suspend the solids. The reactor was set to maintain internal temperature at 40° C. To the mixture was added KOH (96 g of aqueous 45% KOH, 1.71 mol, 10.0 equiv) in portions maintaining the internal temperature<50° C. Once addition was complete, the reaction was set to maintain temperature at 50° C., and the reaction proceeded for 23 hours, monitored by HPLC. Once complete the reaction was cooled to 10° C. then partially concentrated on a rotary evaporator to remove most of the MeOH. The resulting solution was diluted with water (250 mL, 5.0 vol) and 2-Me-THF (150 mL, 3.0 vol), and transferred to the reactor, stirred at room temp, then stopped, and layers were allowed to separate. The layers were tested, with remaining TPPO-DIAD complex in the organic layer and product in the aqueous layer. The aqueous layer was washed again with 2-Me-THF (100 mL, 2.0 vol), the layers separated, and the aqueous layer returned to the reactor vessel. The stirrer was started and set to 450 rpm, and the reactor jacket was set to 0° C. The pH was adjusted to pH acidic by addition of 6M aqueous HCl (427 mL, 15 equiv) portion wise, maintaining the internal temperature between 10 and 30° C. The product began to crystallize close to pH neutral and was accompanied with strong off-gassing, and so the acid was added slowly, and then further added to reach pH 1 once the off-gassing had ended. To the resulting suspension was added 2-Me-THF (400 mL, 8.0 vol), and the product was allowed to dissolve into the organic layer. Stirring was stopped, the layers were separated, and the aqueous layer was returned to the reactor, stirred and re-extracted with 2-Me-THF (100 mL, 2.0 vol). The organic layers were combined in the reactor and stirred at room temperature, washed with brine (100 mL, 2 vols), dried over Na$_2$SO$_4$, filtered through celite, and the solid was washed with 2-Me-THF (50 mL, 1.0 vol). The filtrate was transferred to a clean rotovap flask, stirred, warmed to 50° C. and heptane (200 mL, 4.0 vol) added, and then partially concentrated with the addition of heptane (300 mL, 6.0 vol) and then seeded with 50 mg of 3-(2-(1-(trifluoromethyl)cyclopropyl)ethoxy)-1H-pyrazole-4-carboxylic acid), and the product crystallized during solvent removal. The distillation was stopped when the bulk of the 2-Me-THF had distilled off. The bath heater was turned off, the vacuum removed, and the mixture was allowed to stir and cool to room temperature. The mixture was filtered (slow speed) and the solid was washed with heptane (100 mL, 2.0 vol), and the solid was collected and dried in vacuo (50° C., rotovap). 22.47 g of 3-(2-(1-(trifluoromethyl)cyclopropyl)ethoxy)-1H-pyrazole-4-carboxylic acid was obtained as an off-white solid. $^1$H NMR (400 MHz, DMSO-d6) δ 12.45 (s, 2H), 8.01 (s, 1H), 4.26 (t, J=7.0 Hz, 2H), 2.05 (t, J=7.0 Hz, 2H), 0.92 (m, 4H).

Step 6: 3-(2-(1-(trifluoromethyl)cyclopropyl)ethoxy)-1H-pyrazole

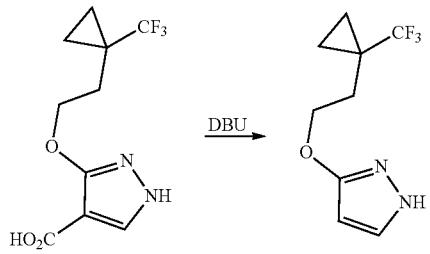 [SMILES: O=C(O)c1c[nH]nc1OCCC1(C(F)(F)F)CC1 ; "DBU" ; FC(F)(F)C1(CCOc2cc[nH]n2)CC1]

A mixture of toluene (490.0 mL), 3-(2-(1-(trifluoromethyl)cyclopropyl) ethoxy)-1H-pyrazole-4-carboxylic acid (70.0 g, 264.9 mmol), and DMSO (70.00 mL) was placed in a reactor and heated to 100° C. with stirring. DBU (approximately 20.16 g, 19.80 mL, 132.4 mmol) was added to the reactor over 15 min. The mixture was stirred for 20 h to complete the reaction and then cooled to 20° C. The mixture was washed with water (350.0 mL), then 0.5N aq HCl (280.0 mL), then water (2×140.0 mL), and lastly with brine (210.0 mL). The organic layer was dried with Na$_2$SO$_4$, and then activated charcoal (5 g, Darco 100 mesh) was added to the stirred slurry. The dried mixture was filtered through celite, and the solid was washed with toluene (140.0 mL) and then pulled dry. The filtrate was concentrated in a rotovap (50° C., vac) to afford 3-[2-[1-(trifluoromethyl)cyclopropyl]ethoxy]-1H-pyrazole (30.89 g, 53%) as an amber oil. $^1$H NMR (400 MHz, DMSO-d6) δ 11.87 (s, 1H), 7.50 (d, J=2.4 Hz, 1H), 5.63 (d, J=2.4 Hz, 1H), 4.23-4.06 (m, 2H), 2.01 (t, J=7.1 Hz, 2H), 1.00-0.77 (m, 4H).

Step 7: ethyl 2-chloro-6-[3-[2-[1-(trifluoromethyl)cyclopropyl]ethoxy]pyrazol-1-yl]pyridine-3-carboxylate

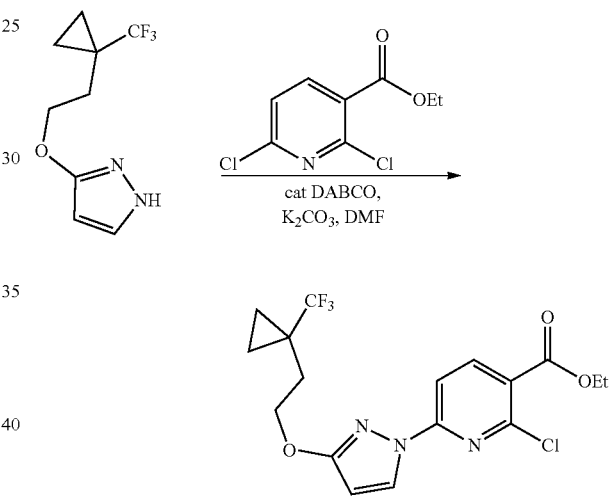

A mixture of DMF (180.0 mL), ethyl 2,6-dichloropyridine-3-carboxylate (approximately 29.97 g, 136.2 mmol), 3-[2-[1-(trifluoromethyl)cyclopropyl]ethoxy]-1H-pyrazole (30.0 g, 136.2 mmol), and K$_2$CO$_3$, (325 mesh, approximately 24.48 g, 177.1 mmol) was added to a stirred reactor at 20° C. DABCO (approximately 2.292 g, 20.43 mmol) was then added to the reactor, and the mixture was stirred at 20° C. for 1 hour, and then the temperature was increased to 30° C., and the mixture stirred for 24 hours to complete the reaction. The mixture was cooled to 20° C.; then water (360 mL) was added slowly. The mixture was then drained from the reactor and the solid was isolated by filtration. The solid was then washed with water (2×150 mL), and then the solid was dried under vacuum at 55° C. to afford ethyl 2-chloro-6-[3-[2-[1-(trifluoromethyl)cyclopropyl]ethoxy]pyrazol-1-yl]pyridine-3-carboxylate (51.37 g, 93%) as a fine, beige colored solid. $^1$H NMR (400 MHz, DMSO-d6) δ 8.44 (d, J=2.9 Hz, 1H), 8.41 (d, J=8.5 Hz, 1H), 7.75 (d, J=8.5 Hz, 1H), 6.21 (d, J=2.9 Hz, 1H), 4.34 (m, 4H), 2.09 (t, J=7.1 Hz, 2H), 1.34 (t, J=7.1 Hz, 3H), 1.00-0.84 (m, 4H).

Step 8: 2-Chloro-6-[3-[2-[1-(trifluoromethyl)cyclopropyl]ethoxy]pyrazol-1-yl]pyridine-3-carboxylic acid

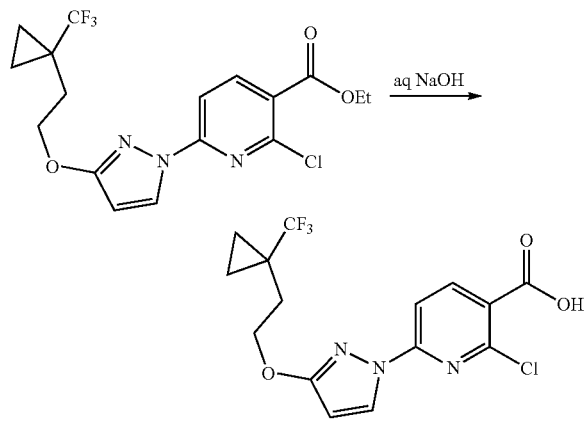

A solution of ethyl 2-chloro-6-[3-[2-[1-(trifluoromethyl)cyclopropyl]ethoxy]pyrazol-1-yl]pyridine-3-carboxylate (50.0 g, 123.8 mmol) in THF (300.0 mL) was prepared in a reactor at 20° C. EtOH (150.0 mL) was added, followed by aqueous NaOH (approximately 59.44 g of 10% w/w, 148.6 mmol). The mixture was stirred for 1 hour to complete the reaction; then aq 1N HCl (750.0 mL) was slowly added. The resulting suspension was stirred for 30 min at 10° C., and then the solid was isolated by filtration. The solid was washed with water (150 mL then 2×100 mL) and then pulled dry by vacuum. The solid was then further dried under vacuum with heating to afford 2-chloro-6-[3-[2-[1-(trifluoromethyl)cyclopropyl]ethoxy]pyrazol-1-yl]pyridine-3-carboxylic acid (42.29 g, 91%). $^1$H NMR (400 MHz, DMSO-d6) δ 13.63 (s, 1H), 8.48-8.35 (m, 2H), 7.73 (d, J=8.4 Hz, 1H), 6.20 (d, J=2.9 Hz, 1H), 4.35 (t, J=7.1 Hz, 2H), 2.09 (t, J=7.1 Hz, 2H), 1.01-0.82 (m, 4H).

Example 2: Preparation of a Spray Dried Dispersion (SDD) of Compound I

Figure 14:
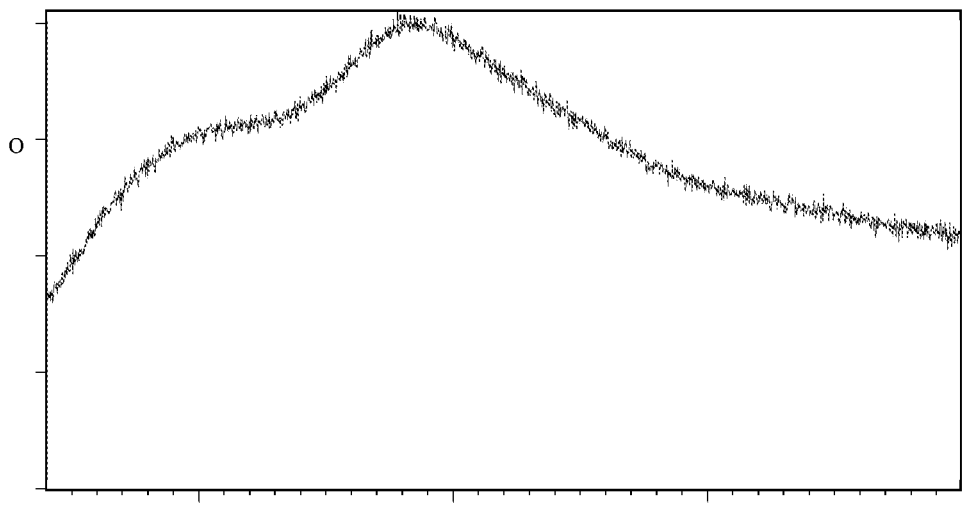
FIG. 14 shows the X-ray powder diffractogram of a spray-dried dispersion (SDD) of 50 wt % Compound I in HPMCAS-HG.
Figure 15:
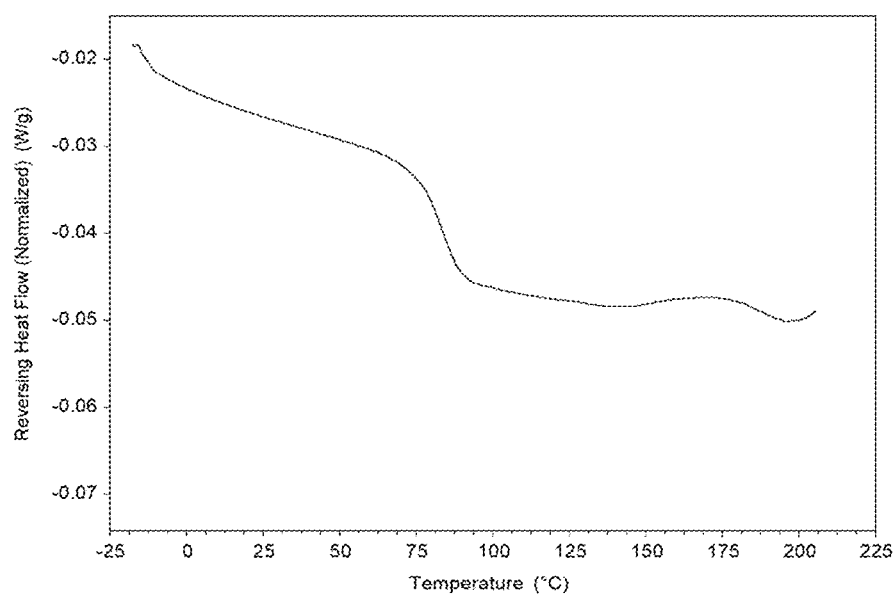
FIG. 15 is spectrum showing modulated differential scanning calorimetry (MDSC) plot of a SDD of 50 wt % Compound I in HPMCAS-HG.

A spray dried dispersion of Compound I (free form) was prepared using Buchi Mini Spray Dryer B290. HPMCAS-HG (6.0 grams) was dissolved in 200 mL of MeOH/DCM (1/1), and Compound I (6.0 grams) was added and stirred for 30 minutes forming a clear solution. The resulting solution was spray dried under the following conditions resulting in a 50 wt % Compound I/50 wt % HPMCAS-HG spray dried dispersion (Yield: 80%, Solid load: 6%). FIG. 14 shows the XRPD spectrum of a SDD of 50% Compound I in HPMCAS-HG. FIG. 15 is spectrum showing modulated differential scanning calorimetry (MDSC) spectrum of a spray dried dispersion (SDD) of 50% Compound I in HPMCAS-HG.

TABLE 64

| SDD of Compound I | |
|---|---|
| | Conditions |
| Inlet Temperature (° C.) | 77 |
| Outlet Temperature (° C.) | 39 |
| Nitrogen Pressure (PSI) | 95 |

TABLE 64-continued

| SDD of Compound I | |
|---|---|
| | Conditions |
| Aspirator (%) | 100 |
| Pump (%) | 30 |
| Rotameter (mm) | 60 |
| Filter Pressure (mBar) | −50 |
| Condenser Temperature (° C.) | −10 |

Example 3: Synthesis of Compound II: (R)-1-(2,2-Difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide

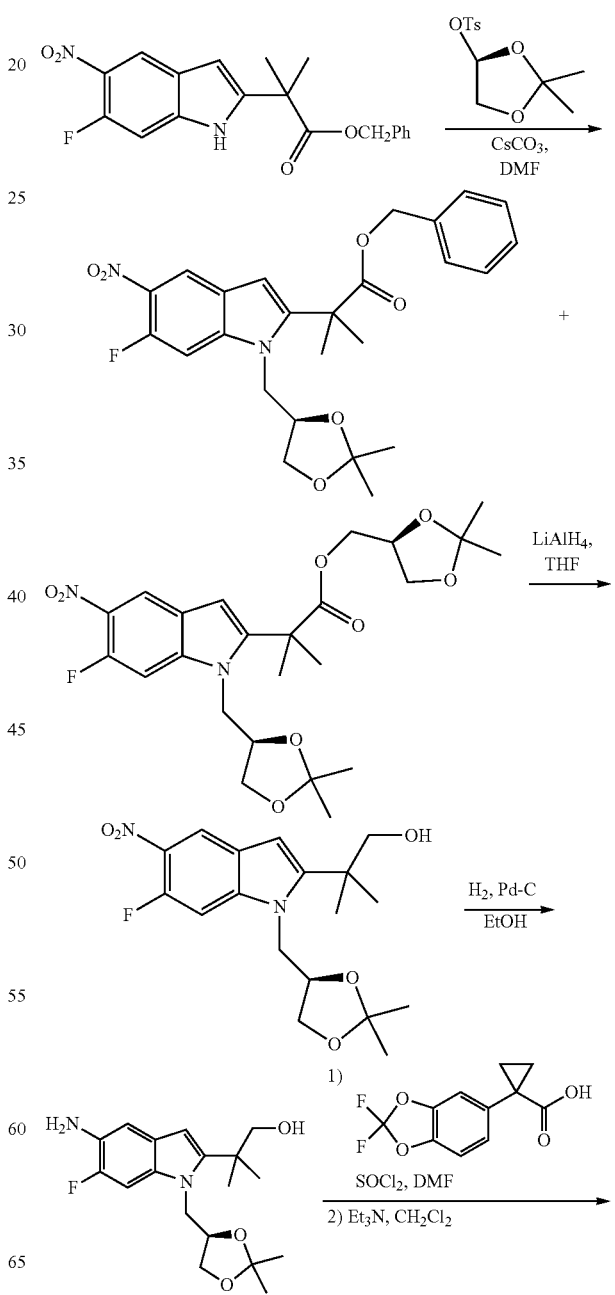

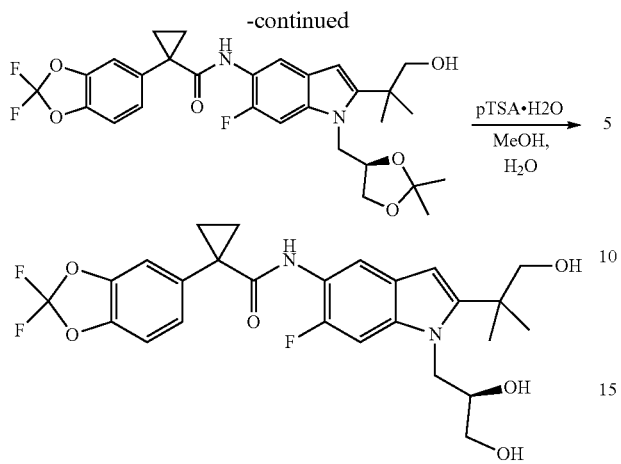

Step 1: (R)-Benzyl 2-(1-((2,2-dimethyl-1,3-dioxolan-4-yl)methyl)-6-fluoro-5-nitro-1H-indol-2-yl)-2-methylpropanoate and ((S)-2,2-Dimethyl-1,3-dioxolan-4-yl)methyl 2-(1-(((R)-2,2-dimethyl-1,3-dioxolan-4-yl)methyl)-6-fluoro-5-nitro-1H-indol-2-yl)-2-methylpropanoate Cesium carbonate (8.23 g, 25.3 mmol) was added to a mixture of benzyl 2-(6-fluoro-5-nitro-1H-indol-2-yl)-2-methylpropanoate (3.0 g, 8.4 mmol) and (S)-(2,2-dimethyl-1,3-dioxolan-4-yl)methyl 4-methylbenzenesulfonate (7.23 g, 25.3 mmol) in DMF (N,N-dimethylformamide) (17 mL). The reaction was stirred at 80° C. for 46 hours under a nitrogen atmosphere. The mixture was then partitioned between ethyl acetate and water. The aqueous layer was extracted with ethyl acetate. The combined ethyl acetate layers were washed with brine, dried over MgSO₄, filtered and concentrated. The crude product, a viscous brown oil which contains both of the products shown above, was taken directly to the next step without further purification. (R)-Benzyl 2-(1-((2,2-dimethyl-1,3-dioxolan-4-yl)methyl)-6-fluoro-5-nitro-1H-indol-2-yl)-2-methylpropanoate, ESI-MS m/z calc. 470.2, found 471.5 (M+1)⁺. Retention time 2.20 minutes. ((S)-2,2-Dimethyl-1,3-dioxolan-4-yl)methyl 2-(1-(((R)-2,2-dimethyl-1,3-dioxolan-4-yl)methyl)-6-fluoro-5-nitro-1H-indol-2-yl)-2-methylpropanoate, ESI-MS m/z calc. 494.5, found 495.7 (M+1)⁺. Retention time 2.01 minutes.

Step 2: (R)-2-(1-((2,2-dimethyl-1,3-dioxolan-4-yl)methyl)-6-fluoro-5-nitro-1H-indol-2-yl)-2-methylpropan-1-ol The crude reaction mixture obtained in step (A) was dissolved in THF (tetrahydrofuran) (42 mL) and cooled in an ice-water bath. LiAlH₄ (16.8 mL of 1 M solution, 16.8 mmol) was added drop-wise. After the addition was complete, the mixture was stirred for an additional 5 minutes. The reaction was quenched by adding water (1 mL), 15% NaOH solution (1 mL) and then water (3 mL). The mixture was filtered over Celite, and the solids were washed with THF and ethyl acetate. The filtrate was concentrated and purified by column chromatography (30-60% ethyl acetate-hexanes) to obtain (R)-2-(1-((2,2-dimethyl-1,3-dioxolan-4-yl)methyl)-6-fluoro-5-nitro-1H-indol-2-yl)-2-methylpropan-1-ol as a brown oil (2.68 g, 87% over 2 steps). ESI-MS m/z calc. 366.4, found 367.3 (M+1)⁺. Retention time 1.68 minutes. ¹H NMR (400 MHz, DMSO-d6) δ 8.34 (d, J=7.6 Hz, 1H), 7.65 (d, J=13.4 Hz, 1H), 6.57 (s, 1H), 4.94 (t, J=5.4 Hz, 1H), 4.64-4.60 (m, 1H), 4.52-4.42 (m, 2H), 4.16-4.14 (m, 1H), 3.76-3.74 (m, 1H), 3.63-3.53 (m, 2H), 1.42 (s, 3H), 1.38-1.36 (m, 6H) and 1.19 (s, 3H) ppm. (DMSO is dimethylsulfoxide).

Step 3: (R)-2-(5-amino-1-((2,2-dimethyl-1,3-dioxolan-4-yl)methyl)-6-fluoro-1H-indol-2-yl)-2-methylpropan-1-ol (R)-2-(1-((2,2-dimethyl-1,3-dioxolan-4-yl)methyl)-6-fluoro-5-nitro-1H-indol-2-yl)-2-methylpropan-1-ol (2.5 g, 6.82 mmol) was dissolved in ethanol (70 mL) and the reaction was flushed with N₂. Then Pd—C (250 mg, 5% wt) was added. The reaction was flushed with nitrogen again and then stirred under H2 (atm). After 2.5 hours only partial conversion to the product was observed by LCMS. The reaction was filtered through Celite and concentrated. The residue was re-subjected to the conditions above. After 2 hours LCMS indicated complete conversion to product. The reaction mixture was filtered through Celite. The filtrate was concentrated to yield the product (1.82 g, 79%). ESI-MS m/z calc. 336.2, found 337.5 (M+1)⁺. Retention time 0.86 minutes. ¹H NMR (400 MHz, DMSO-d6) δ 7.17 (d, J=12.6 Hz, 1H), 6.76 (d, J=9.0 Hz, 1H), 6.03 (s, 1H), 4.79-4.76 (m, 1H), 4.46 (s, 2H), 4.37-4.31 (m, 3H), 4.06 (dd, J=6.1, 8.3 Hz, 1H), 3.70-3.67 (m, 1H), 3.55-3.52 (m, 2H), 1.41 (s, 3H), 1.32 (s, 6H) and 1.21 (s, 3H) ppm.

Step 4: (R)-1-(2,2-difluorobenzo[d][1,3]dioxol-5-yl)-N-(1-((2,2-dimethyl-1,3-dioxolan-4-yl)methyl)-6-fluoro-2-(1-hydroxy-2-methylpropan-2-yl)-1H-indol-5-yl)cyclopropanecarboxamide DMF (3 drops) was added to a stirring mixture of 1-(2,2-difluorobenzo[d][1,3]dioxol-5-yl)cyclopropanecarboxylic acid (1.87 g, 7.7 mmol) and thionyl chloride (1.30 mL, 17.9 mmol). After 1 hour a clear solution had formed. The solution was concentrated under vacuum and then toluene (3 mL) was added and the mixture was concentrated again. The toluene step was repeated once more and the residue was placed on high vacuum for 10 minutes. The acid chloride was then dissolved in dichloromethane (10 mL) and added to a mixture of (R)-2-(5-amino-1-((2,2-dimethyl-1,3-dioxolan-4-yl)methyl)-6-fluoro-1H-indol-2-yl)-2-methylpropan-1-ol (1.8 g, 5.4 mmol) and triethylamine (2.24 mL, 16.1 mmol) in dichloromethane (45 mL). The reaction was stirred at room temperature for 1 hour. The reaction was washed with 1N HCl solution, saturated NaHCO₃ solution and brine, dried over MgSO₄ and concentrated to yield the product (3 g, 100%). ESI-MS m/z calc. 560.6, found 561.7 (M+1)⁺. Retention time 2.05 minutes. ¹H NMR (400 MHz, DMSO-d6) δ 8.31 (s, 1H), 7.53 (s, 1H), 7.42-7.40 (m, 2H), 7.34-7.30 (m, 3H), 6.24 (s, 1H), 4.51-4.48 (m, 1H), 4.39-4.34 (m, 2H), 4.08 (dd, J=6.0, 8.3 Hz, 1H), 3.69 (t, J=7.6 Hz, 1H), 3.58-3.51 (m, 2H), 1.48-1.45 (m, 2H), 1.39 (s, 3H), 1.34-1.33 (m, 6H), 1.18 (s, 3H) and 1.14-1.12 (m, 2H) ppm Step 5: (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide (R)-1-(2,2-difluorobenzo[d][1,3]dioxol-5-yl)-N-(1-((2,2-dimethyl-1,3-dioxolan-4-yl)methyl)-6-fluoro-2-(1-hydroxy-2-methylpropan-2-yl)-1H-indol-5-yl)cyclopropanecarboxamide (3.0 g, 5.4 mmol) was dissolved in methanol (52 mL).

Water (5.2 mL) was added followed by p-TsOH.H₂O (p-toluenesulfonic acid hydrate) (204 mg, 1.1 mmol). The reaction was heated at 80° C. for 45 minutes. The solution was concentrated and then partitioned between ethyl acetate and saturated NaHCO₃ solution. The ethyl acetate layer was dried over MgSO₄ and concentrated. The residue was purified by column chromatography (50-100% ethyl acetate—hexanes) to yield the product. (1.3 g, 47%, ee>98% by SFC). ESI-MS m/z calc. 520.5, found 521.7 (M+1)⁺. Retention time 1.69 minutes. ¹H NMR (400 MHz, DMSO-d6) δ 8.31 (s, 1H), 7.53 (s, 1H), 7.42-7.38 (m, 2H), 7.33-7.30 (m, 2H), 6.22 (s, 1H), 5.01 (d, J=5.2 Hz, 1H), 4.90 (t, J=5.5 Hz, 1H), 4.75 (t, J=5.8 Hz, 1H), 4.40 (dd, J=2.6, 15.1 Hz, 1H), 4.10 (dd, J=8.7, 15.1 Hz, 1H), 3.90 (s, 1H), 3.65-3.54 (m, 2H), 3.48-3.33 (m, 2H), 1.48-1.45 (m, 2H), 1.35 (s, 3H), 1.32 (s, 3H) and 1.14-1.11 (m, 2H) ppm.

Example 4: Synthesis of Compound III: N-(2,4-di-tert-butyl-5-hydroxyphenyl)-4-oxo-1,4-dihydroquinoline-3-carboxamide Part A: Synthesis of 4-oxo-1,4-dihydroquinoline-3-carboxylic acid

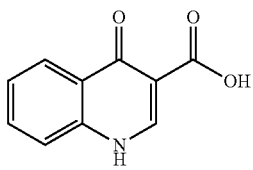 [SMILES: O=C(O)c1c[nH]c2ccccc2c1=O]

Step 1: 2-Phenylaminomethylene-malonic acid diethyl ester

A mixture of aniline (25.6 g, 0.275 mol) and diethyl 2-(ethoxymethylene)malonate (62.4 g, 0.288 mol) was heated at 140-150° C. for 2 h. The mixture was cooled to room temperature and dried under reduced pressure to afford 2-phenylaminomethylene-malonic acid diethyl ester as a solid, which was used in the next step without further purification. ¹H NMR (DMSO-d6) δ 11.00 (d, 1H), 8.54 (d, J=13.6 Hz, 1H), 7.36-7.39 (m, 2H), 7.13-7.17 (m, 3H), 4.17-4.33 (m, 4H), 1.18-1.40 (m, 6H).

Step 2: 4-Hydroxyquinoline-3-carboxylic acid ethyl ester

A 1 L three-necked flask fitted with a mechanical stirrer was charged with 2-phenylaminomethylene-malonic acid diethyl ester (26.3 g, 0.100 mol), polyphosphoric acid (270 g) and phosphoryl chloride (750 g). The mixture was heated to 70° C. and stirred for 4 h. The mixture was cooled to room temperature and filtered. The residue was treated with aqueous Na₂CO₃ solution, filtered, washed with water and dried. 4-Hydroxyquinoline-3-carboxylic acid ethyl ester was obtained as a pale brown solid (15.2 g, 70%). The crude product was used in next step without further purification.

Step 3: 4-Oxo-1,4-dihydroquinoline-3-carboxylic acid

4-Hydroxyquinoline-3-carboxylic acid ethyl ester (15 g, 69 mmol) was suspended in sodium hydroxide solution (2N, 150 mL) and stirred for 2 h at reflux. After cooling, the mixture was filtered, and the filtrate was acidified to pH 4 with 2N HCl. The resulting precipitate was collected via filtration, washed with water and dried under vacuum to give 4-oxo-1,4-dihydroquinoline-3-carboxylic acid as a pale white solid (10.5 g, 92%). ¹H NMR (DMSO-d6) δ 15.34 (s, 1H), 13.42 (s, 1H), 8.89 (s, 1H), 8.28 (d, J=8.0 Hz, 1H), 7.88 (m, 1H), 7.81 (d, J=8.4 Hz, 1H), 7.60 (m, 1H).

Part B: Synthesis of N-(2,4-di-tert-butyl-5-hydroxyphenyl)-4-oxo-1,4-dihydroquinoline-3-carboxamide

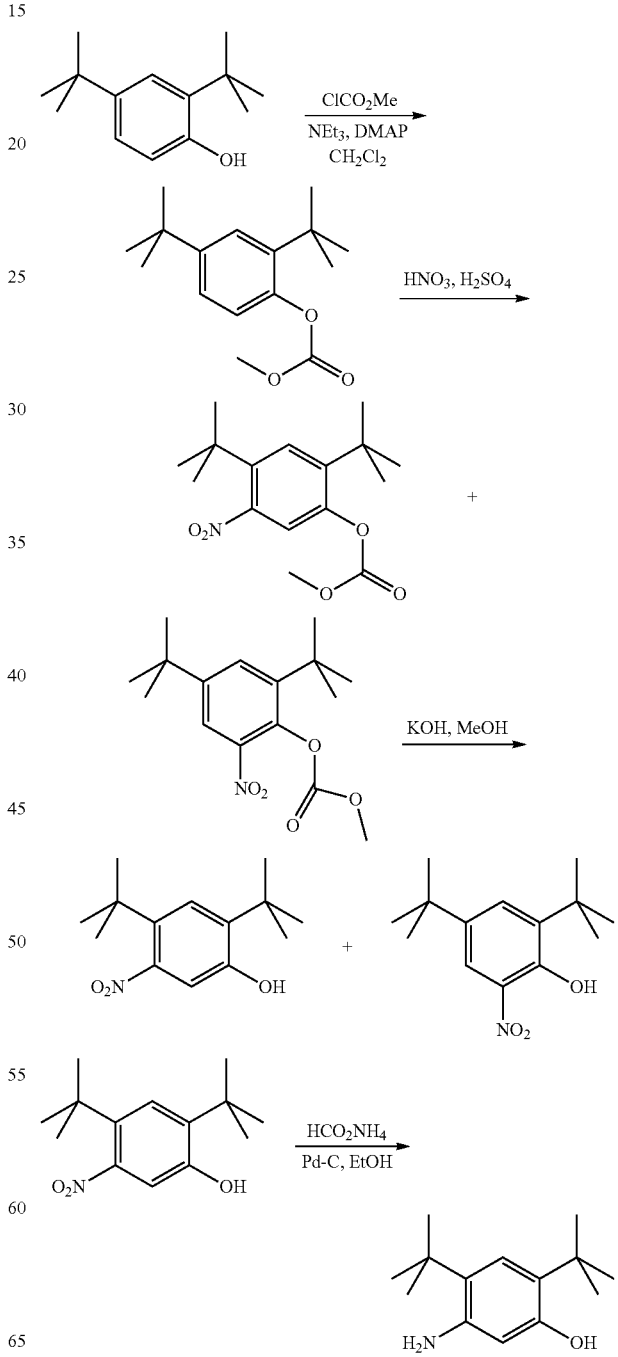

Step 1: Carbonic acid 2,4-di-tert-butyl-phenyl ester methyl ester

Methyl chloroformate (58 mL, 750 mmol) was added dropwise to a solution of 2,4-di-tert-butyl-phenol (103.2 g, 500 mmol), Et$_3$N (139 mL, 1000 mmol) and DMAP (3.05 g, 25 mmol) in dichloromethane (400 mL) cooled in an ice-water bath to 0° C. The mixture was allowed to warm to room temperature while stirring overnight, then filtered through silica gel (approx. 1 L) using 10% ethyl acetate—hexanes (~4 L) as the eluent. The combined filtrates were concentrated to yield carbonic acid 2,4-di-tert-butyl-phenyl ester methyl ester as a yellow oil (132 g, quant.). $^1$H NMR (400 MHz, DMSO-d6) δ 7.35 (d, J=2.4 Hz, 1H), 7.29 (dd, J=8.5, 2.4 Hz, 1H), 7.06 (d, J=8.4 Hz, 1H), 3.85 (s, 3H), 1.30 (s, 9H), 1.29 (s, 9H).

Step 2: Carbonic acid 2,4-di-tert-butyl-5-nitro-phenyl ester methyl ester and Carbonic acid 2,4-di-tert-butyl-6-nitro-phenyl ester methyl ester To a stirring mixture of carbonic acid 2,4-di-tert-butyl-phenyl ester methyl ester (4.76 g, 180 mmol) in conc. sulfuric acid (2 mL), cooled in an ice-water bath, was added a cooled mixture of sulfuric acid (2 mL) and nitric acid (2 mL). The addition was done slowly so that the reaction temperature did not exceed 50° C. The reaction was allowed to stir for 2 h while warming to room temperature. The reaction mixture was then added to ice-water and extracted into diethyl ether. The ether layer was dried (MgSO$_4$), concentrated and purified by column chromatography (0-10% ethyl acetate—hexanes) to yield a mixture of carbonic acid 2,4-di-tert-butyl-5-nitro-phenyl ester methyl ester and carbonic acid 2,4-di-tert-butyl-6-nitro-phenyl ester methyl ester as a pale yellow solid (4.28 g), which was used directly in the next step.

Step 3: 2,4-Di-tert-butyl-5-nitro-phenol and 2,4-Di-tert-butyl-6-nitro-phenol The mixture of carbonic acid 2,4-di-tert-butyl-5-nitrophenyl ester methyl ester and carbonic acid 2,4-di-tert-butyl-6-nitro-phenyl ester methyl ester (4.2 g, 14.0 mmol) was dissolved in MeOH (65 mL) before KOH (2.0 g, 36 mmol) was added. The mixture was stirred at room temperature for 2 h. The reaction mixture was then made acidic (pH 2-3) by adding conc. HCl and partitioned between water and diethyl ether. The ether layer was dried (MgSO$_4$), concentrated and purified by column chromatography (0-5% ethyl acetate—hexanes) to provide 2,4-di-tert-butyl-5-nitro-phenol (1.31 g, 29% over 2 steps) and 2,4-di-tert-butyl-6-nitro-phenol. 2,4-Di-tert-butyl-5-nitro-phenol: $^1$H NMR (400 MHz, DMSO-d6) δ 10.14 (s, 1H, OH), 7.34 (s, 1H), 6.83 (s, 1H), 1.36 (s, 9H), 1.30 (s, 9H). 2,4-Di-tert-butyl-6-nitro-phenol: $^1$H NMR (400 MHz, CDCl$_3$) δ 11.48 (s, 1H), 7.98 (d, J=2.5 Hz, 1H), 7.66 (d, J=2.4 Hz, 1H), 1.47 (s, 9H), 1.34 (s, 9H).

Step 4: 5-Amino-2,4-di-tert-butyl-phenol

To a refluxing solution of 2,4-di-tert-butyl-5-nitro-phenol (1.86 g, 7.40 mmol) and ammonium formate (1.86 g) in ethanol (75 mL) was added Pd-5% wt. on activated carbon (900 mg). The reaction mixture was stirred at reflux for 2 h, cooled to room temperature and filtered through Celite. The Celite was washed with methanol and the combined filtrates were concentrated to yield 5-amino-2,4-di-tert-butyl-phenol as a grey solid (1.66 g, quant.). $^1$H NMR (400 MHz, DMSO-d6) δ 8.64 (s, 1H, OH), 6.84 (s, 1H), 6.08 (s, 1H), 4.39 (s, 2H, NH$_2$), 1.27 (m, 18H); HPLC ret. time 2.72 min, 10-99% CH$_3$CN, 5 min run; ESI-MS 222.4 m/z [M+H]$^+$.

Step 5: N-(5-hydroxy-2,4-di-tert-butyl-phenyl)-4-oxo-1H-quinoline-3-carboxamide

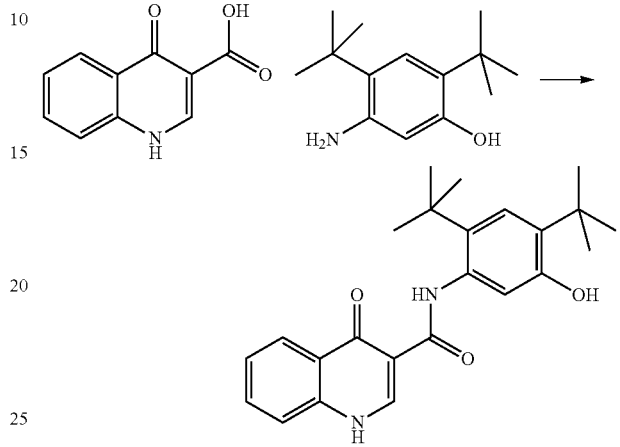

To a suspension of 4-oxo-1,4-dihydroquinolin-3-carboxylic acid (35.5 g, 188 mmol) and HBTU (85.7 g, 226 mmol) in DMF (280 mL) was added Et$_3$N (63.0 mL, 451 mmol) at ambient temperature. The mixture became homogeneous and was allowed to stir for 10 min before 5-amino-2,4-di-tert-butyl-phenol (50.0 g, 226 mmol) was added in small portions. The mixture was allowed to stir overnight at ambient temperature. The mixture became heterogeneous over the course of the reaction. After all of the acid was consumed (LC-MS analysis, MH+190, 1.71 min), the solvent was removed in vacuo. EtOH (ethyl alcohol) was added to the orange solid material to produce a slurry. The mixture was stirred on a rotovap (bath temperature 65° C.) for 15 min without placing the system under vacuum. The mixture was filtered and the captured solid was washed with hexanes to provide a white solid that was the EtOH crystalate. Et$_2$O (diethyl ether) was added to the solid obtained above until a slurry was formed. The mixture was stirred on a rotovapor (bath temperature 25° C.) for 15 min without placing the system under vacuum. The mixture was filtered and the solid captured. This procedure was performed a total of five times. The solid obtained after the fifth precipitation was placed under vacuum overnight to provide N-(5-hydroxy-2,4-di-tert-butyl-phenyl)-4-oxo-1H-quinoline-3-carboxamide (38 g, 52%). HPLC ret. time 3.45 min, 10-99% CH$_3$CN, 5 min run; $^1$H NMR (400 MHz, DMSO-d6) δ 12.88 (s, 1H), 11.83 (s, 1H), 9.20 (s, 1H), 8.87 (s, 1H), 8.33 (dd, J=8.2, 1.0 Hz, 1H), 7.83-7.79 (m, 1H), 7.76 (d, J=7.7 Hz, 1H), 7.54-7.50 (m, 1H), 7.17 (s, 1H), 7.10 (s, 1H), 1.38 (s, 9H), 1.37 (s, 9H); ESI-MS m/z calc'd 392.21; found 393.3 [M+H]$^+$.

Example 5: Preparation of Solid Forms of Sodium Salt of Compound I

A. Preparation of Crystalline Form a of a Sodium Salt of Compound I

Crystalline Form A of Compound I (free form) (1184 mg, 2 mmole) was dissolved in acetonitrile (ACN) at 100 mg/mL and reacted with 320 μL of 25% aqueous sodium hydroxide (2 mmol) in water at room temperature. After 5 minutes, the mixture was seeded with crystalline Form A of a sodium salt of Compound I and slurried at room temperature overnight. The resulting suspension was filtered under vacuum. The resulting solid has purity of 99.92% as determined by HPLC.

A seed for the preparation of crystalline Form A of a sodium salt of Compound I could be obtained by stirring approximately 60 mg of amorphous sodium salt of Compound (I) in 1 mL of acetonitrile at room temperature for 2 weeks.

The XRPD data of crystalline Form A of a sodium salt of Compound I are summarized below in Table 65. X-ray powder diffractogram of crystalline Form A of a sodium salt of Compound I is shown in FIG. 8A.

TABLE 65

XRPD signals for crystalline Form A of a sodium salt of Compound I

| Pos. [°2Th.] | D spacings |
|---|---|
| 4.65 | 18.97 |
| 4.88 | 18.11 |
| 6.30 | 14.03 |
| 7.95 | 11.11 |
| 8.32 | 10.62 |
| 11.08 | 7.98 |
| 12.19 | 7.26 |
| 12.61 | 7.02 |
| 13.96 | 6.34 |

The $C^{13}$ and $F^{19}$ solid state nmr data of crystalline Form A of a sodium salt of Compound I are summarized below in Tables 66 and 67 below.

TABLE 66

$C^{13}$ soild state nmr data of crystalline Form A of a sodium salt of Compound I

| Peak # | Chem Shift [ppm] | Intensity [rel] |
|---|---|---|
| 1 | 177.2 | 12.8 |
| 2 | 176.1 | 23.4 |
| 3 | 163.8 | 59.0 |
| 4 | 153.2 | 28.5 |
| 5 | 148.4 | 41.7 |
| 6 | 145.0 | 25.5 |
| 7 | 144.0 | 45.4 |
| 8 | 141.1 | 30.2 |
| 9 | 132.3 | 43.8 |
| 10 | 130.8 | 21.8 |
| 11 | 128.9 | 100.0 |
| 12 | 128.0 | 74.8 |
| 13 | 127.3 | 50.7 |
| 14 | 115.8 | 21.3 |
| 15 | 97.8 | 14.7 |
| 16 | 95.9 | 43.6 |
| 17 | 94.1 | 24.8 |
| 18 | 93.0 | 23.6 |
| 19 | 65.5 | 44.4 |
| 20 | 63.5 | 51.9 |
| 21 | 63.1 | 55.1 |
| 22 | 59.9 | 30.2 |
| 23 | 58.4 | 40.4 |
| 24 | 52.8 | 51.9 |
| 25 | 32.7 | 28.2 |
| 26 | 30.6 | 53.8 |
| 27 | 30.0 | 65.9 |
| 28 | 26.7 | 59.9 |
| 29 | 26.1 | 66.1 |
| 30 | 25.5 | 51.0 |
| 31 | 24.4 | 20.2 |
| 32 | 19.9 | 47.6 |

TABLE 66-continued $C^{13}$ soild state nmr data of crystalline Form A of a sodium salt of Compound I

| Peak # | Chem Shift [ppm] | Intensity [rel] |
|---|---|---|
| 33 | 17.0 | 40.7 |
| 34 | 16.5 | 60.1 |
| 35 | 11.7 | 13.4 |
| 36 | 9.8 | 24.1 |
| 37 | 8.1 | 38.6 |
| 38 | 7.3 | 27.9 |

TABLE 67

$F^{19}$ soild state nmr data of crystalline Form A of a sodium salt of Compound I Form A of a sodium salt of Compound I $^{19}F$ Chem. Shifts

| Peak # | Chem. Shift [ppm] | Intensity [rel] |
|---|---|---|
| 1 | −68.6 | 10.9 |
| 2 | −70.3 | 12.5 |

B. Preparation of Crystalline Form M of a Sodium Salt of Compound I (Variable Methanol-Hydrate Solvates of a Sodium Salt of Compound I)

Crystalline Form A of Compound I (free acid neutral form) (592.05 mg, 1 mmole) was dissolved in either MeOH at 33 mg/mL and reacted with 233 μL of 25% NaOMe in MeOH (1 mmole). The resulting solution was stirred at RT and become suspension. The suspension was stirred at RT for overnight. The resulting solid was collected by filtration under vacuum. The purity was 99.57% as determined by HPLC.

According to GC (gas chromatography) and KF (Karl Fisher) data, the resulting product contained 2.0 wt % of MeOH (theoreatical monomethanol would be 4.94 wt % of methanol) and 1.7 wt % of water, based on the weight of the product, were detected, indicating that the final form was solvates of a mixture of methanol and water. It was observed that the methanol in the product was labile and could leave the crystalline Form M and replaced with water without changes to the form according to the XRPD data. It is noted that Form M is isostructural to Form H by their X-ray powder diffractograms.

The XRPD data of crystalline Form M of a sodium salt of Compound I are summarized below in Table 68. X-ray powder diffractogram of crystalline Form M of a sodium salt of Compound I is shown in FIG. 10A.

TABLE 68

XRPD signals of crystalline Form M of a sodium salt of Compound I

| Pos. [°2Th.] | D spacings |
|---|---|
| 9.26 | 9.55 |
| 9.94 | 8.89 |
| 10.46 | 8.45 |
| 11.26 | 7.85 |
| 13.94 | 6.35 |
| 15.13 | 5.85 |
| 18.83 | 4.71 |
| 19.51 | 4.55 |
| 19.93 | 4.45 |

A single crystal structure of crystalline Form M of a sodium salt of Compound I that includes 1:1:1 in molar ratio of Na:Compound I:MeOH was obtained and the result is shown in Table 69. The single crystal was obtained by dissolving crystalline Form M of a sodium salt of Compound I in methanol followed by slow evaporation at room temperature overnight.

TABLE 69

Single crystal structure of Form M of Na salt of Compound I (1:1:1 Na: Compound I: MeOH in molar ratio)

| | |
|---|---|
| Empirical formula | C29H35F3N5NaO5S |
| Molecular formula | C29H35F3N5NaO5S |
| Formula weight | 645.67 |
| Temperature | 100.0 K |
| Wavelength | 1.54178 Å |
| Crystal system | Monoclinic |
| Space group | P 1 21 1 |
| Unit cell dimensions | a = 9.7434(2) Å    α = 90°. |
| | b = 10.7467(2) Å    β = 95.5790(10)°. |
| | c = 15.2452(3) Å    γ = 90°. |
| Volume | 1588.75(5) Å$^3$ |
| Z | 2 |
| Density (calculated) | 1.350 Mg/m$^3$ |

C. Preparation of Crystalline Form E of a Sodium Salt of Compound I (Variable Ethanol-Hydrate Solvates of a Sodium Salt of Compound I)

592.20 mg of Crystalline Form A of Compound I (free form) (1 mmole) was suspended in ethanol at 100 mg/mL and reacted 1:1 stoichiometry with NaOH in water. The resulting solution was stirred at room temperature and became suspension. The suspension was stirred overnight. The resulting solid was collected by filtration under vacuum.

It was observed that the ethanol in the product was labile and could leave the crystalline Form E and replaced with water without changes to the crystalline Form E according to the XRPD data. Desolvating Form E at 60° C. or 70° C. under vacuum resulted in Form H with variable amounts of water that is isostructural to Form M by their X-ray powder diffractograms.

The XRPD data of crystalline Form E of a sodium salt of Compound I are summarized below in Table 70. X-ray powder diffractogram of crystalline Form M of a sodium salt of Compound I is shown in FIG. 12A.

TABLE 70

XRPD signals for crystalline Form E of a sodium salt of Compound I

| Pos. [°2Th.] | D spacings |
|---|---|
| 11.36 | 7.79 |
| 15.23 | 5.81 |
| 18.96 | 4.68 |
| 5.67 | 15.56 |
| 17.30 | 5.12 |
| 9.94 | 8.90 |
| 9.05 | 9.77 |
| 14.01 | 6.32 |
| 16.33 | 5.42 |

A single crystal structure of Form E of Na salt of Compound I that includes 1:1:1 in molar ratio of Na:Compound I:EtOH was obtained and the result is shown in Table 71. The single crystal was obtained by dissolving crystalline Form E of a sodium salt of Compound I in ethanol and allowed for slow evaporation at room temperature overtime.

TABLE 71

Single crystal structure of Form E of Na salt of Compound I (1:1:1 in morlar ration of Na:Compound I:EtOH)

| | |
|---|---|
| Empirical formula | C30H37F3N5NaO5S |
| Molecular formula | C30H37F3N5NaO5S |
| Formula weight | 659.69 |
| Temperature | 100.0 K |
| Wavelength | 0.71073 Å |
| Crystal system | Monoclinic |
| Space group | P 1 21 1 |
| Unit cell dimensions | a = 9.8500(6) Å    α = 90°. |
| | b = 10.6432(7) Å    β = 96.671(2)°. |
| | c = 15.3937(9) Å    γ = 90°. |
| Volume | 1602.88(17) Å$^3$ |
| Z | 2 |
| Density (calculated) | 1.367 Mg/m$^3$ |

D. Preparation of Crystalline Form D of a Sodium Salt of Compound I

Crystalline Form D of a sodium salt of Compound I was obtained by heating either Form M of a sodium salt of Compound I or Form E of a sodium salt of Compound I at 290° C. under dry N$_2$. In one example, 8 mg of crystalline Form E of a sodium salt of Compound I was heated in a TGA pan at a 10° C./minute rate from room temperature to 290° C. and was then maintained at 290° C. for 2 minutes under dry N$_2$ (50 mL per minute).

The XRPD data of crystalline Form D of a sodium salt of Compound I are summarized below in Table 72. X-ray powder diffractogram of crystalline Form M of a sodium salt of Compound I is shown in FIG. 9A.

TABLE 72

XRPD signals for crystalline Form D of a sodium salt of Compound I

| Pos. [°2Th.] | D spacings |
|---|---|
| 4.89 | 18.04 |
| 5.68 | 15.54 |
| 6.95 | 12.71 |
| 8.03 | 11.00 |
| 9.76 | 9.05 |
| 11.32 | 7.81 |
| 12.23 | 7.23 |
| 14.01 | 6.32 |
| 16.01 | 5.53 |

E. Preparation of crystalline Form H of a sodium salt of Compound I

Crystalline Form H of a sodium salt of Compound I was obtained by desolvating (e.g., heating at ~70° C. to ~92° C. under vacuum) either Form M of a sodium salt of Compound I or Form E of a sodium salt of Compound I.

In one example, 7 mg of crystalline Form M of a sodium salt of Compound I was heated in a TGA pan at a 10° C./minute rate from room temperature to 92° C. and was then maintained at 92° C. for 2 minutes.

In another example, crystalline Form E of a sodium salt of Compound I was heated in a vacuum oven at 70° C. for 2 days to obtain crystalline Form H of a sodium salt of Compound I. Crystalline Form H of a sodium salt of Compound I was obtained and determined to contain 0.2 wt % EtOH by GC, 2.9 wt % water, based on the weight of the product, by Karl Fisher.

Crystalline Form H was iso-structural to crystalline Form M by their X-ray powder diffractograms. X-ray powder diffractogram of crystalline Form H of a sodium salt of Compound I, is shown in FIG. 11A.

Example 6: Preparation of Solid Forms of Potassium Salt of Compound I

A. Preparation of Crystalline Form B of a Potassium Salt of Compound I

Crystalline Form B of a potassium salt of Compound I, is a crystalline channel hydrate/variable-hydrate that has been found to be thermodynamically stable during development. Crystalline Form B of a potassium salt of Compound I demonstrated superior stability compared to neat amorphous or crystalline Form A Compound I. The potassium salt Form B of Compound I is stable across a wide humidity range. In addition, it was found to be particularly amenable to scale up manufacturing processes, providing substantially higher yields than seen with scale up of certain other crystalline forms, e.g., the sodium salt of Compound I.

Method 6A:

100 mg of Compound I (free form) was dissolved in 1 mL of acetonitrile. 10.0 mL of 0.1N KOH solution in water was stirred at room temperature, to which the Compound I acetonitrile solution was added slowly. Precipitate was observed during addition of acetonitrile solution, and solids formed on the stir bar. The mixture was stirred for several hours, during which time the clump broke up into smaller agglomerates. After stirring overnight (approximately 18 hours), solids were isolated by filtration, analyzed by XRPD, and determined to be crystalline Form B of a potassium salt of Compound I.

Method 6B:

25 g of Compound I (free form) was charged with 100 mL ethanol and 100 mL of water. The slurry was stirred to assure free flowing solids. Into the mixture was charged 1.6 eq of KOH. Water (40 mL) was added to the resulting solution to make a 60 vol % water solution. The resulting solution was heated to 40° C. then cooled to 20° C. and stirred for 1 hour. The solution cooled to 20° C. was seeded with 40 mg of crystalline Form B of a potassium salt of Compound I seed. Water (160 mL) was then charged over a 5-hour period of time. The resulting slurry was allowed to stir 12 hours. The resulting solids were collected by vacuum filtration and allowed to air dry for 2 hrs. The air-dried wet cake was transferred to a vacuum at 45° C. with a slight $N_2$ bleed for 18 hrs to yield 25.89 g of crystalline Form B of a potassium salt of Compound I (97% isolated yield).

An X-ray powder diffractogram, DVS, and DSC plots of crystalline Form B of a potassium salt of Compound I are shown in FIG. 1A, FIG. 3, and FIG. 4, respectively. The XRPD data of crystalline Form B of a potassium salt of Compound I are summarized below in Table 73.

TABLE 73

XRPD signals for crystalline Form B of a potassium salt of Compound I

| Pos. [°2Th.] | D spacings |
|---|---|
| 5.76 | 15.32 |
| 8.20 | 10.77 |
| 9.58 | 9.22 |
| 10.25 | 8.62 |
| 13.80 | 6.41 |
| 15.11 | 5.86 |
| 16.27 | 5.44 |
| 17.18 | 5.16 |
| 19.1 | 4.64 |

A single crystal structure of Form B of a potassium salt of Compound I was obtained and the result is shown in Table 74.

TABLE 74

Single crystal structure of Form B of a potassium salt of Compound I (1:1 in molar ratio of potassium:Compound I)

| | |
|---|---|
| Empirical Formula: | C28H31.76N5O4.38F3SK |
| Formula Weight: | 636.63 |
| Temperature (K): | 298(2) |
| Wavelength (Å): | 1.54178 |
| Crystal System: | Orthorhombic |
| Space Group: | P212121 |
| a (Å): | 9.0058(3) |
| b (Å): | 11.5389(4) |
| c (Å): | 30.9399(10) |
| α (°): | 90 |
| β (°): | 90 |
| γ (°): | 90 |
| V (Å3): | 3215.18(19) |
| Z/Z': | 4/1 |

$C^{13}$ and $F^{19}$ solid state nmr data of crystalline Form B of a potassium salt of Compound I are summarized in Tables 75 and 76.

TABLE 75

$C^{13}$ nmr peaks of crystalline Form B of a potassium salt of Compound I

| Peak # | Chem Shift [ppm] | Intensity [rel] |
|---|---|---|
| 1 | 178.0 | 32.8 |
| 2 | 165.0 | 50.7 |
| 3 | 151.9 | 20.7 |
| 4 | 147.7 | 35.1 |
| 5 | 143.2 | 39.7 |
| 6 | 141.5 | 27.8 |
| 7 | 132.7 | 31.5 |
| 8 | 129.9 | 7.8 |
| 9 | 127.8 | 49.2 |
| 10 | 127.1 | 9.6 |
| 11 | 121.3 | 37.6 |
| 12 | 96.1 | 44.9 |
| 13 | 89.0 | 47.0 |
| 14 | 68.5 | 47.0 |
| 15 | 63.6 | 66.0 |
| 16 | 56.8 | 41.5 |
| 17 | 51.3 | 48.8 |
| 18 | 30.3 | 100.0 |
| 19 | 26.4 | 81.7 |
| 20 | 24.7 | 72.4 |
| 21 | 20.5 | 31.2 |
| 22 | 15.9 | 79.8 |
| 23 | 10.3 | 31.5 |
| 24 | 8.1 | 27.8 |

TABLE 76

$F^{19}$ nmr peaks of crystalline Form B of a potassium salt of Compound I

| Peak # | Chem. Shift [ppm] | Intensity [rel] |
|---|---|---|
| 1 | −69.1 | 12.5 |

B. Hydration of Form B of a Potassium Salt of Compound I

As shown in FIG. 2 and FIG. 5, crystalline Form B of a potassium salt of Compound I can be hydrated with water without substantial changes to its crystalline form Form B.

FIG. 2 shows XRPD patterns of crystalline Form B of a potassium salt of Compound I at 3% relative humidity (RH) (red) initial and 100% RH (blue). FIG. 5 shows a TGA plot of crystalline Form B of a potassium salt of Compound I.

C. Preparation of Crystalline Form C of a Potassium Salt of Compound I

A solution of Form B of Compound I potassium salt in 1:10(v/v) acetonitrile (MeCN):water was kept at 75° C., and then the solvents were evaporated slowly at 75° C. Crystals were formed over approximately 24 h.

The XRPD data of crystalline Form C of a potassium salt of Compound I are summarized below in Table 77. An X-ray powder diffractogram of crystalline Form C of a potassium salt of Compound I is shown in FIG. 7A.

TABLE 77

XRPD signals for crystalline Form C of a potassium salt of Compound I

| Pos. [°2Th.] | D spacings |
| --- | --- |
| 3.66 | 24.14 |
| 6.96 | 12.68 |
| 7.41 | 11.92 |
| 8.70 | 10.16 |
| 9.49 | 9.31 |
| 11.40 | 7.75 |
| 11.52 | 7.68 |
| 12.43 | 7.11 |
| 16.04 | 5.52 |

Example 7: Preparation of Crystalline Form A of Compound I

Crystalline Form A of Compound I was generally prepared by de-solvating the ethanol solvates of Compound I under vacuum. In one particular example, it was prepared as described below:

N-(benzenesulfonyl)-2-chloro-6-[3-[2-[1-(trifluoromethyl)cyclopropyl]ethoxy]pyrazol-1-yl]pyridine-3-carboxamide (15.5 g, 30.10 mmol) and $K_2CO_3$ (20.80 g, 150.5 mmol) were stirred in NMP (77.50 mL) and 1,2-diethoxyethane (15.50 mL) and carefully treated with (4S)-2,2,4-trimethylpyrrolidine (Hydrochloric Acid (1)) (9.911 g, 66.22 mmol). The cream suspension was cycled 3 times under vacuum/nitrogen and heated at an external temperature of 135° C. (oil bath) for 20 hours. The suspension was carefully added to a stirred solution of acetic acid (27.11 g, 25.67 mL, 451.5 mmol) in water (465.0 mL) keeping the temperature at 15-20° C. by ice cooling. The resulting suspension was stirred at room temperature for 1 h, filtered and washed with water. The filtered solid was crystalized from ethanol (hot solution was filtered clear) and the formed needles were filtered, washed with a little dry ice cold ethanol and dried under vacuum in a drying cabinet at 45° C. with a nitrogen bleed over the weekend to give Form A of Compound I as colorless needles. $^1H$ and $^{19}F$ nmr (in DMSO): no EtOH was detected.

In the XRPD data of crystalline Form A of Compound I, there were some peak shifts from batch to batch due to inherent disorder during the desolvation process. The XRPD data were asummarized below in Table 78. An exemplary X-ray powder diffractogram of crystalline Form A of Compound I is shown in FIG. 13A.

TABLE 78

Ranges of XRPD signals for crystalline Form A of Compound I Pos. [°2Th.]

| |
| --- |
| 5.37-5.45 |
| 7.24-7.49 |
| 11.87-12.19 |
| 14.76-15.03 |
| 16.71-17.08 |
| 17.48-17.68 |
| 18.56-18.80 |
| 19.51-19.82 |
| 22.02-22.47 |

$C^{13}$ and $F^{19}$ solid state nmr data of Form A of Compound I are summarized below in Tables 79 and 80.

TABLE 79

$C^{13}$ nmr peaks of crystalline Form A of Compound I

| Peak # | Form A of Compound I $^{13}$C Chem Shift [ppm] | Intensity [rel] |
| --- | --- | --- |
| 1 | 165.4 | 26.1 |
| 2 | 164.9 | 40.2 |
| 3 | 154.1 | 22.0 |
| 4 | 151.8 | 30.3 |
| 5 | 141.3 | 23.2 |
| 6 | 138.8 | 12.6 |
| 7 | 136.8 | 36.2 |
| 8 | 130.8 | 100.0 |
| 9 | 128.6 | 46.0 |
| 10 | 127.3 | 59.0 |
| 11 | 109.4 | 26.4 |
| 12 | 98.1 | 50.2 |
| 13 | 97.4 | 42.2 |
| 14 | 65.5 | 88.3 |
| 15 | 60.4 | 28.6 |
| 16 | 51.0 | 38.1 |
| 17 | 29.9 | 58.2 |
| 18 | 28.2 | 17.2 |
| 19 | 26.1 | 51.7 |
| 20 | 25.5 | 46.0 |
| 21 | 20.1 | 26.5 |
| 22 | 16.4 | 53.1 |
| 23 | 6.8 | 43.3 |

TABLE 80

$F^{19}$ nmr peaks of crystalline Form A of Compound I

| Peak # | Chem Shift [ppm] | Intensity |
| --- | --- | --- |
| 1 | −72.3 | 12.5 |

Example 8: Preparation of Solvates of Compound I

A. Methanol Solvate of Compound I 1 mL of methanol (MeOH) was added to 60 mg of Compound I (free acid neutral form), and the resulting mixture was stirred at room temperature for 2 weeks. The resulting crystalline solids were methanol solvates of Compound I.

The XRPD data of methanol solvate of Compound I are summarized below in Table 81.

TABLE 81

XRPD signals for methanol solvate of Compound I

| Pos. [°2Th.] | D spacings |
|---|---|
| 5.23 | 16.88 |
| 8.31 | 10.63 |
| 10.27 | 8.61 |
| 11.54 | 7.66 |
| 11.78 | 7.51 |
| 14.36 | 6.16 |
| 15.66 | 5.65 |
| 19.11 | 4.64 |
| 22.20 | 4.00 |

A single crystal structure of methanol solvate of Compound I was obtained and the result is shown in Table 82.

TABLE 82

| Empirical formula | C30H40F3N5O6S | |
|---|---|---|
| Molecular formula | C28H32F3N5O4S, 2(CH4O) | |
| Formula weight | 655.73 | |
| Temperature | 100.0 K | |
| Wavelength | 0.71073 Å | |
| Crystal system | Monoclinic | |
| Space group | P 1 21 1 | |
| Unit cell dimensions | a = 11.7199(18) Å | α = 90°. |
| | b = 8.3852(12) Å | β = 102.973(5)°. |
| | c = 17.332(3) Å | γ = 90°. |
| Volume | 1659.8(4) Å³ | |
| Z | 2 | |
| Density (calculated) | 1.312 Mg/m³ | |

B. Ethanol Solvate of Compound I 1 mL ethanol (EtOH) was added to 100 mg of Compound I (neat free acid neutral form). The mixture was stirred at 60° C. for 30 minutes, and a solution was formed. The solution was cooled to room temperature, and crystalline solids of ethanol solvate of Compound I were precipitated.

The XRPD data of ethanol solvate of Compound I are summarized below in Table 83.

TABLE 83

XRPD signals for ethanol solvate of Compound I

| Pos. [°2Th.] | D spacings |
|---|---|
| 4.61 | 19.16 |
| 7.75 | 11.40 |
| 9.18 | 9.63 |
| 10.16 | 8.70 |
| 13.58 | 6.52 |
| 13.77 | 6.43 |
| 17.81 | 4.98 |
| 18.41 | 4.82 |
| 23.1 | 3.85 |

A single crystal structure of ethanol solvate of Compound I was obtained and the result is shown in Table 84.

TABLE 84

Single crystal structure of ethanol solvate of Compound I

| Empirical formula | C30H38F3N5O5S | |
|---|---|---|
| Molecular formula | C28H32F3N5O4S, C2H6O | |
| Formula weight | 637.71 | |
| Temperature | 100.0 K | |
| Wavelength | 0.71073 Å | |
| Crystal system | Monoclinic | |
| Space group | P 1 21 1 | |
| Unit cell dimensions | a = 11.9559(16) Å | α = 90°. |

TABLE 84-continued

Single crystal structure of ethanol solvate of Compound I

| | b = 7.5294(9) Å | β = 107.124(4)°. |
|---|---|---|
| | c = 19.662(2) Å | γ = 90°. |
| Volume | 1691.5(4) Å³ | |
| Z | 2 | |
| Density (calculated) | 1.25 Mg/m³ | |

C. IPA (Iso-Propyl Alcohol) Solvate of Compound I 1 mL isopropanol (2-PrOH) was added to 100 mg of Compound I (neat free acid neutral form). The mixture was stirred at 60° C. for 30 minutes, and a solution was formed. The solution was cooled to room temperature, and crystalline solids precipitated.

The XRPD data of isopropanol solvate of Compound I are summarized below in Table 85.

TABLE 85

XRPD signals for isopropanol solvate of Compound I

| Pos. [°2Th.] | D spacings |
|---|---|
| 4.64 | 19.03 |
| 7.82 | 11.30 |
| 9.30 | 9.50 |
| 10.12 | 8.73 |
| 10.27 | 8.61 |
| 12.62 | 7.01 |
| 13.72 | 6.45 |
| 15.62 | 5.67 |
| 18.08 | 4.90 |

A single crystal structure of isopropanol solvate of Compound I was obtained and the result is shown in Table 86.

TABLE 86

Single crystal structure of isopropanol solvate of Compound I

| Empirical formula | C31H40F3N5O5S | |
|---|---|---|
| Molecular formula | C28H32F3N5O4S, C3H8O | |
| Formula weight | 651.74 | |
| Temperature | 100.0 K | |
| Wavelength | 0.71073 Å | |
| Crystal system | Monoclinic | |
| Space group | P 1 21 1 | |
| Unit cell dimensions | a = 11.894(2) Å | α = 90°. |
| | b = 7.5356(16) Å | β = 106.569(6)°. |
| | c = 19.837(4) Å | γ = 90°. |
| Volume | 1704.2(6) Å³ | |
| Z | 2 | |
| Density (calculated) | 1.270 Mg/m³ | |

D. n-Butanol Solvate of Compound I 1 mL of n-butanol added to 199 mg of Compound I (neat free acid neutral form). The resulting slurry was stirred at room temperature for 10 days. Solids isolated were crystalline and shown to be a n-butanol solvate of Compound I.

The XRPD data of n-butanol solvate of Compound I are summarized below in Table 87.

TABLE 87

XRPD signals for n-butanol solvate of Compound I

| Pos. [°2Th.] | D spacings |
|---|---|
| 4.59 | 19.20 |
| 7.68 | 11.50 |
| 9.16 | 9.65 |
| 10.01 | 8.83 |

TABLE 87-continued

XRPD signals for n-butanol solvate of Compound I

| Pos. [°2Th.] | D spacings |
|---|---|
| 13.55 | 6.53 |
| 14.64 | 6.04 |
| 15.34 | 5.77 |
| 18.34 | 4.83 |
| 19.23 | 4.61 |

E. EtOAc (Ethyl Acetate) Solvate of Compound I 1 mL of ethyl acetate added to 60 mg of Compound I (neat free acid neutral form). A solution was formed. 5 mL of heptane added in 0.5 mL increments to the resulting solution. The resulting solution was then evaporated slowly. ethyl acetate solvates of Compound I were isolated.

The XRPD data of ethyl acetate solvate of Compound I are summarized below in Table 88.

TABLE 88

XRPD signals for ethyl acetate solvate of Compound I

| Pos. [°2Th.] | D spacings |
|---|---|
| 4.82 | 18.33 |
| 7.89 | 11.20 |
| 9.60 | 9.20 |
| 9.82 | 9.00 |
| 13.55 | 6.53 |
| 14.45 | 6.13 |
| 15.84 | 5.59 |
| 19.02 | 4.66 |
| 24.22 | 3.67 |

A single crystal structure of EtOAc solvate of Compound I was obtained and the result is shown in Table 89.

TABLE 89

Single crystal structure of EtOAc solvate of Compound I

| | |
|---|---|
| Empirical formula | C32H40F3N5O6S |
| Molecular formula | C28H32F3N5O4S, C4H8O2 |
| Formula weight | 679.75 |
| Temperature | 100.0 K |
| Wavelength | 1.54178 Å |
| Crystal system | Monoclinic |
| Space group | P 1 21 1 |
| Unit cell dimensions | a = 11.9825(4) Å  α = 90°. |
| | b = 8.0104(2) Å  β = 102.7770(10)°. |
| | c = 18.4808(6) Å  γ = 90°. |
| Volume | 1729.95(9) Å$^3$ |
| Z | 2 |
| Density (calculated) | 1.305 Mg/m$^3$ |

Example 9. Preparation of a Potassium Salt of Compound I Tablet Formulations Single tablets of fixed dose combination (FDC) of a potassium salt of Compound I in combination with a SDD of Compound II and a SDD of Compound III as shown in the Tables 90, 91, and 92 below were prepared.

A. Preparation of a Potassium Salt of Compound I FDC Tablet Formulations A1 and A2

TABLE 90

FDC Tablet A1

| | Component | mg/tablet | g/batch |
|---|---|---|---|
| Intra-granular part | potassium salt of Compound I | 212.9 mg | 550.0 g |
| | solid dispersion containing 80% Compound II, 20% hypromellose | 62.5 mg | 161.5 g |
| | solid dispersion containing 80% Compound III, 19.5% hypromellose acetate succinate, and 0.5% sodium lauryl sulfate | 93.8 mg | 242.2 g |
| | microcrystalline cellulose (e.g., PH101) | 137.1 mg | 354.2 g |
| | croscarmellose sodium | 15.8 mg | 40.8 g |
| | magnesium stearate | 5.3 mg | 13.7 g |
| Extra-granular part | microcrystalline cellulose (e.g., PH102) | 59.6 mg | 153.9 g[1] |
| | croscarmellose sodium | 8.9 mg | 23.1 g[1] |
| | Uncoated Tablet | 595.9 mg | n/a |
| | Coating (20A100017) | 18.4 mg | 47.6[2] |

[1]Weights adjusted based on granulation yield.
[2]Coating weight adjusted based on weight of tablet charged to coater. Actual coating was 2.75% of coated tablet.

TABLE 91

FDC Tablet A2

| | Component | mg/tablet | g/batch |
|---|---|---|---|
| Intra-granular part | potassium salt of Compound I | 212.9 mg | 550.0 g |
| | solid dispersion containing 80% Compound II, 20% hypromellose | 62.5 mg | 161.5 g |
| | solid dispersion containing 80% Compound III, 19.5% hypromellose acetate succinate, and 0.5% sodium lauryl sulfate | 93.8 mg | 242.2 g |
| | microcrystalline cellulose (e.g., PH101) | 137.1 mg | 354.2 g |
| | croscarmellose sodium | 15.8 mg | 40.8 g |
| | magnesium stearate | 5.3 mg | 13.7 g |
| Extra-granular part | microcrystalline cellulose (e.g., PH102) | 59.6 mg | 153.9 g[1] |
| | croscarmellose sodium | 8.9 mg | 23.1 g[1] |
| | Uncoated Tablet | 595.9 mg | n/a |

[1]Weights adjusted based on granulation yield.

Dry Granulation

Prior to granulation, the potassium salt of Compound I, the solid dispersion comprising 80 wt % substantially amorphous Compound II and 20 wt % HPMC (see PCT Publication No. WO 2015/160787, the entire contents are incorporated herein by reference), the solid dispersion comprising 80 wt % substantially amorphous Compound III, 19.5 wt % HPMCAS and 0.5 wt % sodium lauryl sulfate (see WO 2015/160787), and intragranular excipients were screened prior to or after weighing and then blended in a bin blender. The blend was granulated using a Gerteis roller compactor using combined smooth/smooth rolls and an integrated 1.0 mm mesh milling screen with pocketed rotor and paddle agitator. The roller compactor was operated with a roll gap of 2 mm, roll pressure of 4.7 kNcm, roll speed of 2 rpm, granulation speed of 80/80 (CW/CCW) rpm, and oscillation of 360/330 (CW/CCW) degrees.

Compression

For the FDC tablet A1 of Table 90, prior to compression, extragranular excipients were screened prior to or after weighing and then blended in a bin blender with the roller compacted granules. The blend was compressed into a tablet using a non-instrumented Riva Piccola rotary tablet press. The press was assembled with tooling of a desired shape and size. The tablet target weight was 595.9 mg. The hardness was 15.7 kp.

For the FDC tablet A2 of Table 91, the final uncoated tablet was compressed on the MTS. Using tooling of a desired shape and size, tablets were compressed to a target weight 301 mg and hardness of 10.2 kp.

Coating

For the FDC tablet A2 of Table 91, no coating was done. For the FDC tablet A1, the core tablets were film coated using a Thomas tablet film coater. The film coat suspension was prepared according to manufacturer instructions by adding the coating material to purified water and mixing with overhead mixer. The required amount of film coating suspension was sprayed onto the tablets to achieve the weight gain of 2.6% of the core tablet weight.

B. Preparation of a Potassium Salt of Compound I FDC Tablet Formulations B1

TABLE 92

| | FDC Tablet B1 | | |
|---|---|---|---|
| | Component | mg/tablet | g/batch |
| Intra-granular part | potassium salt of Compound I | 127.7 mg | 151.8 g |
| | solid dispersion containing 80% Compound II, 20% hypromellose | 62.5 mg | 75.3 g |
| | solid dispersion containing 80% Compound III, 19.5% hypromellose acetate succinate, and 0.5% sodium lauryl sulfate | 93.8 mg | 111.4 g |
| | microcrystalline cellulose (e.g., PH101) | 86.3 mg | 102.6 g |
| | croscarmellose sodium | 11.5 mg | 13.7 g |
| | magnesium stearate | 1.9 mg | 2.3 g |
| Extra-granular part | microcrystalline cellulose (e.g., PH102) | 43.6 mg | 51.8 g[1] |
| | croscarmellose sodium | 6.5 mg | 7.8 g[1] |
| | magnesium stearate | 1.9 mg | |
| | Uncoated Tablet | 435.8 mg | n/a |
| | Coating (20A100017) | 13.5 mg | 15.5[2] |

[1]Weights adjusted based on granulation yield.
[2]Coating weight adjusted based on weight of tablet charged to coater.

Dry Granulation:

Prior to granulation, the potassium salt of Compound I, the solid dispersion comprising 80 wt % substantially amorphous Compound II and 20 wt % HPMC (see PCT Publication No. WO 2015/160787, the entire contents are incorporated herein by reference), the solid dispersion comprising 80 wt % substantially amorphous Compound III, 19.5 wt % HPMCAS and 0.5 wt % sodium lauryl sulfate (see WO 2015/160787), and intragranular excipients were screened prior to or after weighing and then blended in a bin blender. The blend was granulated using a Gerteis roller compactor using combined smooth/smooth rolls and an integrated 1.0 mm mesh milling screen with pocketed rotor and paddle agitator. The roller compactor was operated with a roll gap of 2 mm, roll pressure of 4.7 kNcm, roll speed of 2 rpm, granulation speed of 80/80 (CW/CCW) rpm, and oscillation of 360/330 (CW/CCW) degrees.

Compression:

Prior to compression, extragranular excipients were screened prior to or after weighing and then blended in a bin blender with the roller compacted granules. The blend was compressed into a tablet using a non-instrumented Riva Piccola rotary tablet press. The press was assembled with tooling of a desired shape and size. The tablet target weight was 435.8 mg. The hardness was 12 kp.

Coating:

Some of the core tables during this manufacture were retained as uncoated tablets. The remainder of these core tablets were film coated using a Thomas tablet film coater. The film coat suspension was prepared according to manufacturer instructions by adding the coating material to purified water and mixing with overhead mixer. The required amount of film coating suspension was sprayed onto the tablets to achieve the weight gain of 3% of the core tablet weight.

Example 10: Dissolution Properties

For the purposes of the dissolution (Example 10) and bioavailability (Example 11) studies, FDC tablets A2 ("Compound I K salt FDC Tablet") that comprise a potassium salt of Compound I (crystalline Form B); a SDD comprising 80 wt % substantially amorphous Compound II and 20 wt % HPMC; and a SDD comprising 80 wt % substantially amorphous Compound III, 19.5 wt % HPMCAS and 0.5 wt % sodium lauryl sulfate (see Example 9A above) were used.

As control tablets in Examples 10 and 11, Control tablets 1 comprising a SDD of 50 wt % Compound I and 50 wt % HPMCAS-HG (see, for example, Example 2 above); and Control tablet 2 comprising a SDD of 80 wt % substantially amorphous Compound II and 20 wt % HPMC; and a SDD comprising 80 wt % substantially amorphous Compound III, 19.5 wt % HPMCAS and 0.5 wt % sodium lauryl sulfate were used.

A. Preparation of Control Tablets 1

Control tablets 1 were prepared as specified below in Table 93.

TABLE 93

| | Control Tablet 1 | | |
|---|---|---|---|
| | Component | mg/tablet | g/batch |
| Intra-granular part | Solid dispersion containing 50 wt % Compound I, 50 wt % hypromellose acetate succinate | 200.0 mg | 250 g |
| | microcrystalline cellulose (e.g., PH101) | 540.0 mg | 675 g |
| | croscarmellose sodium | 24.0 mg | 30 g |
| | sodium stearyl fumarate | 16.0 mg | 20 g |
| Extra-granular part | croscarmellose sodium | 12.0 mg | 15 g[1] |
| | sodium stearyl fumarate | 8.0 mg | 10 g[1] |
| | Uncoated Tablet | 800.0 mg | n/a |

[1]Weights adjusted based on granulation yield.

Dry Granulation:

Prior to granulation, solid dispersion containing 50 wt % Compound I, 50 wt % hypromellose acetate succinate (see Example 6) and intragranular excipients were screened prior to or after weighing and then blended in a bin blender. The blend was granulated with a Gerteis roller compactor using combined smooth/knurled rolls and an integrated 1.0 mm mesh milling screen with pocketed rotor and paddle agitator. The roller compactor was operated with a roll gap of 2 mm, roll pressure of 5.2 kNcm, roll speed of 2 rpm, granulation speed of 80/80 (CW/CCW) rpm, and oscillation of 360/330 (CW/CCW) degrees.

Compression:

Prior to compression, extragranular excipients were screened prior to or after weighing and then blended in a bin blender with the roller compacted granules. The blend was compressed into a tablet using the MTS. Using tooling of a desired shape and size, tablets were compressed to a target weight 800.0 mg and hardness of 14.8 kp.

B. Preparation of Control Tablets 2

Control tablets 2 were prepared as specified below in Table 94.

TABLE 94

| | Control Tablet 2 | | |
|---|---|---|---|
| | Components | mg/tablet | g/batch |
| Intra-granular part | solid dispersion containing 80% Compound II, 20% hypromellose | 31.3 mg | 1.25 g |
| | solid dispersion containing 80% Compound III, 19.5% hypromellose acetate succinate, and 0.5% sodium lauryl sulfate | 46.9 mg | 1.88 g |
| | microcrystalline cellulose (e.g., PH101) | 32.8 mg | 1.31 g |
| | croscarmellose sodium | 7.4 mg | 0.3 g |
| Extra-granular part | microcrystalline cellulose (e.g., PH102) | 28.1 mg | 1.1 g |
| | magnesium stearate | 1.5 mg | 0.06 g |
| | Uncoated Tablet | 148.0 mg | n/a |

Granules prepared at large scale. Batch size scaled down to match amount of granules used in the extragranular blend.

Dry Granulation:

Prior to granulation, the solid dispersion comprising 80 wt % substantially amorphous Compound II and 20 wt % HPMC (see PCT Publication No. WO 2015/160787, the entire contents are incorporated herein by reference), the solid dispersion comprising 80 wt % substantially amorphous Compound III, 19.5 wt % HPMCAS and 0.5 wt % sodium lauryl sulfate (see WO 2015/160787) and intragranular excipients were screened prior to or after weighing and then blended in a bin blender. The blend was granulated using a Gerteis roller compactor using combined smooth/knurled rolls and an integrated 1.0 mm mesh milling screen with pocketed rotor and paddle agitator. The roller compactor was operated with a roll gap of 2 mm, roll pressure of 5.2 kNcm, roll speed of 2 rpm, granulation speed of 80/80 (CW/CCW) rpm, and oscillation of 360/330 (CW/CCW) degrees.

Compression:

Prior to compression, extragranular excipients were screened prior to or after weighing and then blended in a turbula blender with the roller compacted granules. The blend was compressed into a tablet using the MTS. Using tooling of a desired shape and size, tablets were compressed to a target weight of 148.0 mg and hardness of 9.3 kp.

Dissolution Results

Figure 18:
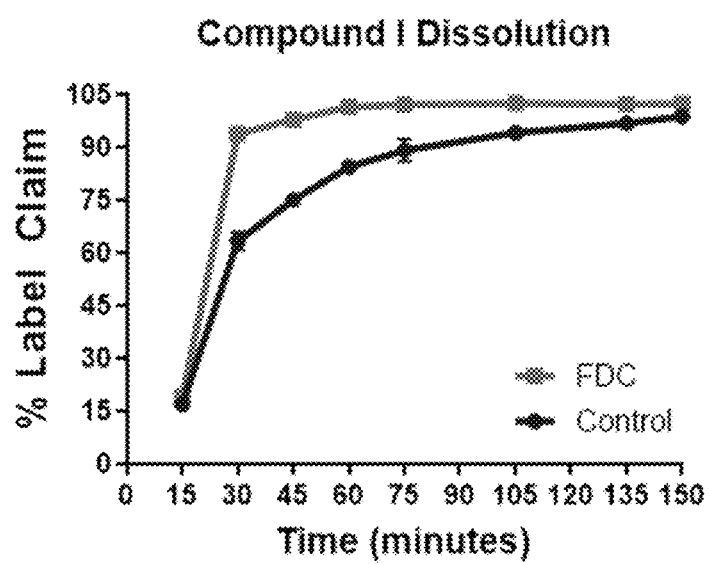
FIG. 18 shows tablet dissolution of Compound I of a Control tablet comprising a spray dried dispersion of Compound I, and a fixed dose combination (FDC) tablet comprising a potassium salt of Compound I, a spray dried dispersion of Compound II and a spray dried dispersion of Compound III.
Figure 19:
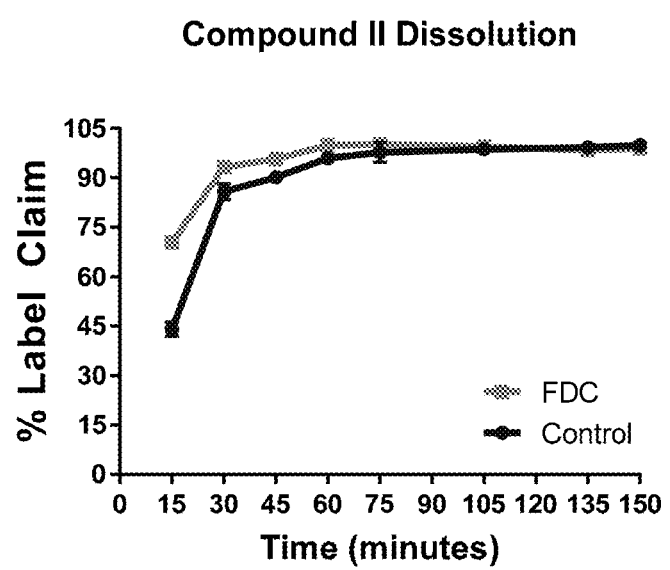
FIG. 19 shows tablet dissolution of Compound II of a Control tablet comprising a spray dried dispersion of Compound II and a spray dried dispersion of Compound III, and of an FDC tablet comprising a potassium salt of Compound I, a spray dried dispersion of Compound II and a spray dried dispersion of Compound III.
Figure 20:
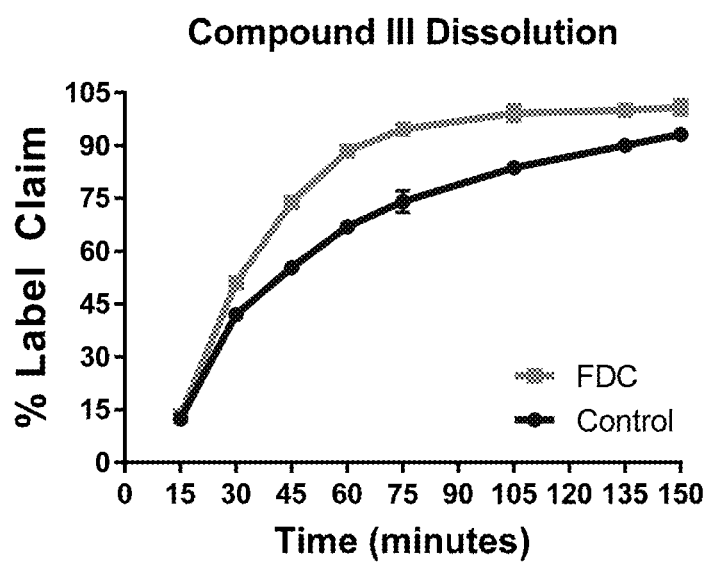
FIG. 20 shows tablet dissolution of Compound III of a Control tablet comprising a spray dried dispersion of Compound II and a spray dried dispersion of Compound III, and of an FDC tablet comprising a potassium salt of Compound I, a spray dried dispersion of Compound II and a spray dried dispersion of Compound III.

FIG. 18 shows comparison of tablet dissolution of Compound I of Control tablet 1 and FDC tablets A2. FIG. 19 shows comparison of tablet dissolution of Compound II of Control tablet 2 and FDC tablets A2. FIG. 20 shows comparison of tablet dissolution of Compound III of Control tablet 2 and FDC tablets A2.

For the data shown in FIGS. 18, 19, and 20, dissolution method was two stage; first stage media was 250 ml PH 5.5 simulated fed gastric fluid, second stage, 30 minutes after start, first stage media was diluted with 650 mls of PH 7.2 simulated fed intestinal fluid with a mixture final PH of 6.7. As shown in FIGS. 18, 19, and 20, the FDC tablets demonstrated higher concentrations of Compound I, Compound II and Compound III at earlier timepoints than the respective Control tablets.

C. Preparation of Stability Control Tablets 1

Stability Control Tablets 1 were prepared as specified below in Table 95.

TABLE 95

| | Stability Control Tablet 1 | | |
|---|---|---|---|
| | Component | mg/tablet | g/batch |
| Intra-granular part | Solid dispersion containing 50 wt % Compound I, 50 wt % hypromellose acetate succinate | 50.0 mg | 10 g |
| | microcrystalline cellulose (e.g., PH101) | 135.0 mg | 27 g |
| | croscarmellose sodium | 6.0 mg | 1.2 g |
| | sodium stearyl fumarate | 4.0 mg | 0.8 g |
| Extra-granular part | croscarmellose sodium | 3.0 mg | 0.58 g[1] |
| | sodium stearyl fumarate | 2.0 mg | 0.38 g[1] |
| | Uncoated Tablet | 200.0 mg | n/a |

1Weights adjusted based on granulation yield.

Dry Granulation:

Prior to granulation, solid dispersion containing 50 wt % Compound I, 50 wt % hypromellose acetate succinate (see Example 6) and intragranular excipients were screened prior to or after weighing and then blended in a turbula blender. The blend was granulated by slugging and then milling slugs through 1.0 mm screen.

Compression:

Prior to compression, extragranular excipients were screened prior to or after weighing and then blended in a Turbula blender with the roller compacted granules. The blend was compressed into a tablet using the Huxley Bertram compaction simulator. Using tooling of a desired shape and size, tablets were compressed to a target weight 200.0 mg.

Example 11: In Vivo Bioavailability

In this bioavailability study, FDC tablets A2 that comprise a potassium salt of Compound I (crystalline Form B); an SDD comprising 80 wt % substantially amorphous Compound II and 20 wt % HPMC; and an SDD comprising 80 wt % substantially amorphous Compound III, 19.5 wt % HPMCAS and 0.5 wt % sodium lauryl sulfate (see Example 9A above) were used. As control tablets, Control tablets 1 comprising a SDD of 50 wt % Compound I and 50 wt % HPMCAS-HG (see Example 10 above) and Control tablet 2 comprising a SDD of 80 wt % substantially amorphous Compound II and 20 wt % HPMC; and a SDD comprising 80 wt % substantially amorphous Compound III, 19.5 wt % HPMCAS and 0.5 wt % sodium lauryl sulfate (see Example 10 above) were used.

Figure 21:
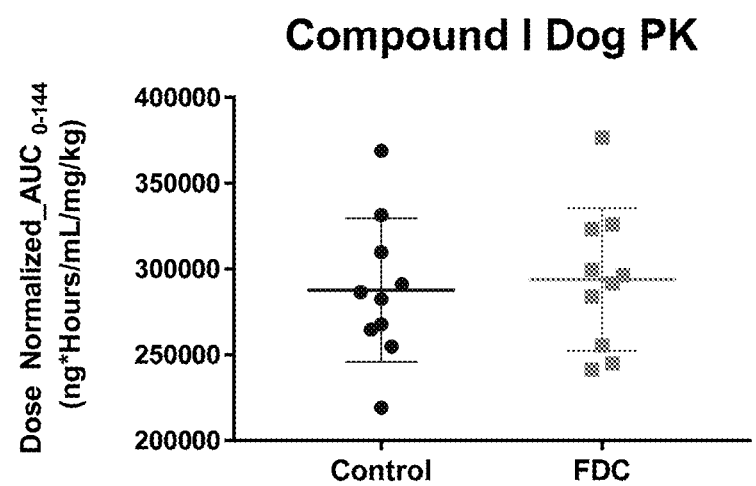
FIG. 21 shows bioavailability of Compound I of a Control tablet comprising a spray dried dispersion of Compound I, and an FDC tablet comprising a potassium salt of Compound I, a spray dried dispersion of Compound II and a spray dried dispersion of Compound III in a dog.
Figure 22:
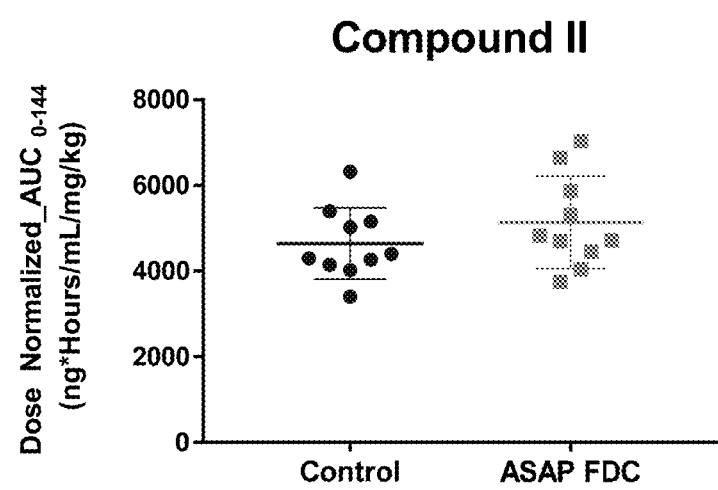
FIG. 22 shows bioavailability of Compound II of a Control tablet comprising a spray dried dispersion of Compound II and a spray dried dispersion of Compound III, and of an FDC tablet comprising a potassium salt of Compound I, a spray dried dispersion of Compound II and a spray dried dispersion of Compound III in a dog.
Figure 23:
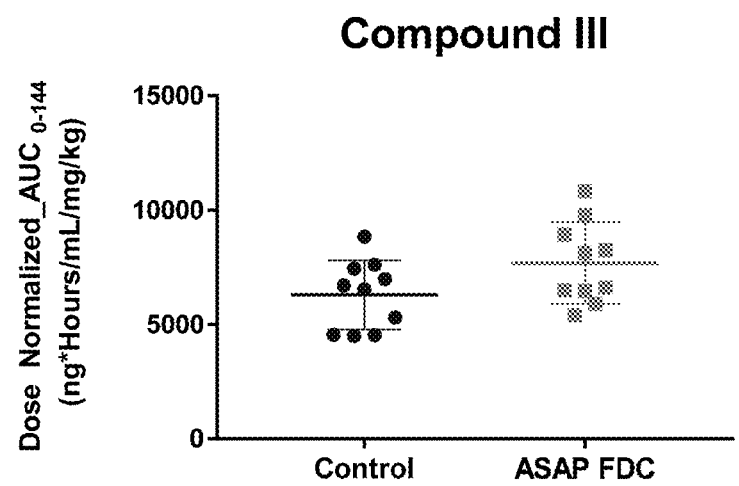
FIG. 23 shows bioavailability of Compound III of a Control tablet comprising a spray dried dispersion of Compound II and a spray dried dispersion of Compound III, and of an FDC tablet comprising a potassium salt of Compound I, a spray dried dispersion of Compound II and a spray dried dispersion of Compound III in a dog.

FIG. 21 shows bioavailability of Compound I of Control tablet 1 and FDC tablet A2. FIG. 22 shows bioavailability of Compound II of Control tablet 2 and FDC tablet A2. FIG. 23 shows comparison of tablet dissolution of Compound III of Control tablet 2 and FDC tablet A2.

For the data shown in FIG. 21, FIG. 22 and FIG. 23, the PK study design was a full crossover, two dose period with 5 dogs per dose group per period. Both the Control and FDC tablets demonstrated statistically equivalent Compound I bioavailability in dogs. The FDC tablets demonstrated statistically superior bioavailability in dog when compared to the Control tablets, for both Compound II and Compound III.

Example 12: Stability of Compound I SDD and Compound I K Salt Drug Substance

Crystalline Form B of a potassium salt of Compound I ("Compound I Potassium Salt") drug substance (DS) was shown to have greater chemical stability than the spray dried dispersion (SDD) of Compound I [Compound I SDD with HPMCAS, 500 mg/g drug load] ("Compound I SDD") (see Example 2) after 6 months at 25° C./60% RH (relative humidity) and 40° C./75% RH in open dish conditions. The degradation products (impurity 1 and impurity 2) in the Compound I Potassium Salt DS were below the ICH Q3A Reporting Threshold (<0.05% area), whereas the degradation products for the Compound I SDD were >1.0% area (total impurities). High Performance Liquid Chromatography (HPLC) was used to analyze the purity profile of the samples.

TABLE 96

Summary of Organic Impurity Results for Compound I SDD (see Example 1 above) and Compound I Potassium Salt Drug Substance (DS) in Open Dish Conditions.

| | | Total Impurities (% area) | Impurity 1 (% area) | Impurity 2 (% area) |
|---|---|---|---|---|
| Initial | Compound I SDD | 1.15 | 0.22 | 0.63 |
| | Compound I Potassium Salt DS | <RT | <RT | <RT |
| 25° C./60% RH, 6 Months | Compound I SDD | 1.49 | 0.33 | 0.75 |
| | Compound I Potassium Salt DS | <RT | <RT | <RT |
| 40° C./75% RH, 6 Months | Compound I SDD | 3.49 | 1.30 | 1.74 |
| | Compound I Potassium Salt DS | <RT | <RT | <RT |

RT = ICH Q3A Reporting Threshold (<0.05% area)

Impurities 1 and 2 are degradation products of Compound I:

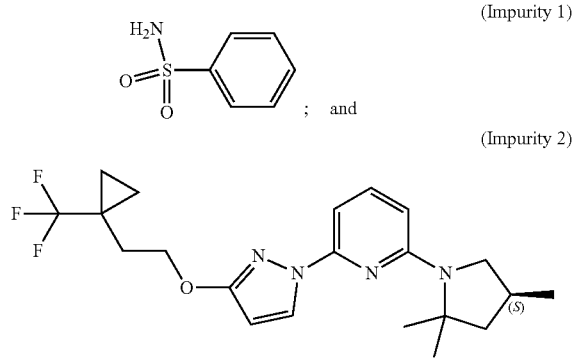

(Impurity 1); and (Impurity 2)

The FDC tablets A2 containing a potassium salt of Compound I (crystalline Form B) in combination with the Compound II SDD and Compound III SDD (see Table 91 and Example 9 above) ("Compound I K salt FDC Tablet" in Table 97 below) showed to have greater chemical stability than Stability Control Tablet 1 ("Compound I Mono Tablet" in Table 97 below) (see Example 9 above), comprised of Compound I SDD [Compound I SDD with HPMCAS, 500 mg/g drug load] at accelerated conditions in open dish. High Performance Liquid Chromatography (HPLC) was used to analyze the purity profile of the samples.

TABLE 97

Summary of Degradation Product Results for Compound I Mono Tablets[1] and Compound I K Salt Fixed Dose Combination (FDC)[2] Tablets (Open Dish Conditions)

| | | Total Impurities (% area) | Impurity 1 (% area) | Impurity 2 (% area) |
|---|---|---|---|---|
| 50° C./75% RH, 14 days | Compound I Mono Tablet | 1.13 | 0.20 | 0.47 |
| | Compound I K salt FDC Tablet | 0.04 | <RT | 0.01 |
| 60° C./40% RH, 14 days | Compound I Mono Tablet | 3.14 | 0.58 | 1.42 |
| | Compound I K salt FDC Tablet | 0.06 | <RT | 0.01 |
| 70° C./5% RH, 14 days | Compound I Mono Tablet | 11.06 | 2.06 | 5.50 |
| | Compound I K salt FDC Tablet | 0.08 | <RT | 0.01 |
| 70° C./75% RH, 3 days | Compound I Mono Tablet | 4.82 | 0.87 | 2.26 |
| | Compound I K salt FDC Tablet | 0.35 | <RT | 0.02 |

RT = ICH Q3A Reporting Threshold (<0.05% area)
[1]Compound I Mono Tablets are comprised of 50 mg/g Spray Dried Dispersion of Compound I
[2]Compound I K salt FDC Tablets contain Compound I Potassium Salt, Compound II SDD (80% Compound II, 20% HPMC-E15), and Compound III SDD (80% Compound III, 19.5% HPMCAS-H, 0.5% SLS).

Example 13: Stability Study of Compounds in Formulations

A. Preparation of Stability Control Tablets 1

Stability Control Tablets 1 were prepared as specified below in Table 98.

TABLE 98

Stability Control Tablet 1

| | Component | mg/tablet | g/batch |
|---|---|---|---|
| Intra-granular part | Solid dispersion containing 50 wt % Compound I, 50 wt % hypromellose acetate succinate | 50.0 mg | 10 g |
| | microcrystalline cellulose (e.g., PH101) | 135.0 mg | 27 g |
| | croscarmellose sodium | 6.0 mg | 1.2 g |
| | sodium stearyl fumarate | 4.0 mg | 0.8 g |
| Extra-granular part | croscarmellose sodium | 3.0 mg | 0.58 g[1] |
| | sodium stearyl fumarate | 2.0 mg | 0.38 g[1] |
| | Uncoated Tablet | 200.0 mg | n/a |

[1]Weights adjusted based on granulation yield.

Dry Granulation:

Prior to granulation, solid dispersion containing 50 wt % Compound I, 50 wt % hypromellose acetate succinate (see Example 2) and intragranular excipients were screened prior to or after weighing and then blended in a turbula blender. The blend was granulated by slugging and then milling slugs through 1.0 mm screen.

Compression:

Prior to compression, extragranular excipients were screened prior to or after weighing and then blended in a Turbula blender with the roller compacted granules. The blend was compressed into a tablet using the Huxley Bertram compaction simulator. Using tooling of a desired shape and size, tablets were compressed to a target weight 200.0 mg.

B. Stability Results

The FDC tablets A2 containing a potassium salt of Compound I (crystalline Form B) in combination with the Compound II SDD and Compound III SDD (see Example 9A above) ("Compound I K salt FDC Tablet" in Table 99 below) showed to have greater chemical stability than the Stability Control Tablet 1 ("Compound I Mono Tablet" in Table 99 below) (see above Stability Control Tablet 1) comprised of Compound I SDD [Compound I SDD with HPMCAS, 500 mg/g drug load] at accelerated conditions in open dish. High Performance Liquid Chromatography (HPLC) was used to analyze the purity profile of the samples.

TABLE 99

Summary of Degradation Product Results for Compound I Mono Tablets[1] and Compound I K Salt Fixed Dose Combination (FDC)[2] Tablets (Open Dish Conditions)

|  |  | Total Impurities (% area) | Impurity 1 (% area) | Impurity 2 (% area) |
|---|---|---|---|---|
| 50° C./75% RH, 14 days | Compound I Mono Tablet | 1.13 | 0.20 | 0.47 |
|  | Compound I K salt FDC Tablet | 0.04 | <RT | 0.01 |
| 60° C./40% RH, 14 days | Compound I Mono Tablet | 3.14 | 0.58 | 1.42 |
|  | Compound I K salt FDC Tablet | 0.06 | <RT | 0.01 |
| 70° C./5% RH, 14 days | Compound I Mono Tablet | 11.06 | 2.06 | 5.50 |
|  | Compound I K salt FDC Tablet | 0.08 | <RT | 0.01 |
| 70° C./75% | Compound I | 4.82 | 0.87 | 2.26 |

TABLE 99-continued

Summary of Degradation Product Results for Compound I Mono Tablets[1] and Compound I K Salt Fixed Dose Combination (FDC)[2] Tablets (Open Dish Conditions)

|  |  | Total Impurities (% area) | Impurity 1 (% area) | Impurity 2 (% area) |
|---|---|---|---|---|
| RH, 3 days | Mono Tablet Compound I K salt FDC Tablet | 0.35 | <RT | 0.02 |

RT = ICH Q3A Reporting Threshold (<0.05% area)
[1]Compound I Mono Tablets are comprised of 50 mg/g Spray Dried Dispersion of Compound I
[2]Compound I K salt FDC Tablets contain Compound I Potassium Salt, Compound II SDD (80% Compound II, 20% HPMC-E15), and Compound III SDD (80% Compound III, 19.5% HPMCAS-H, 0.5% SLS).

Figure 24:
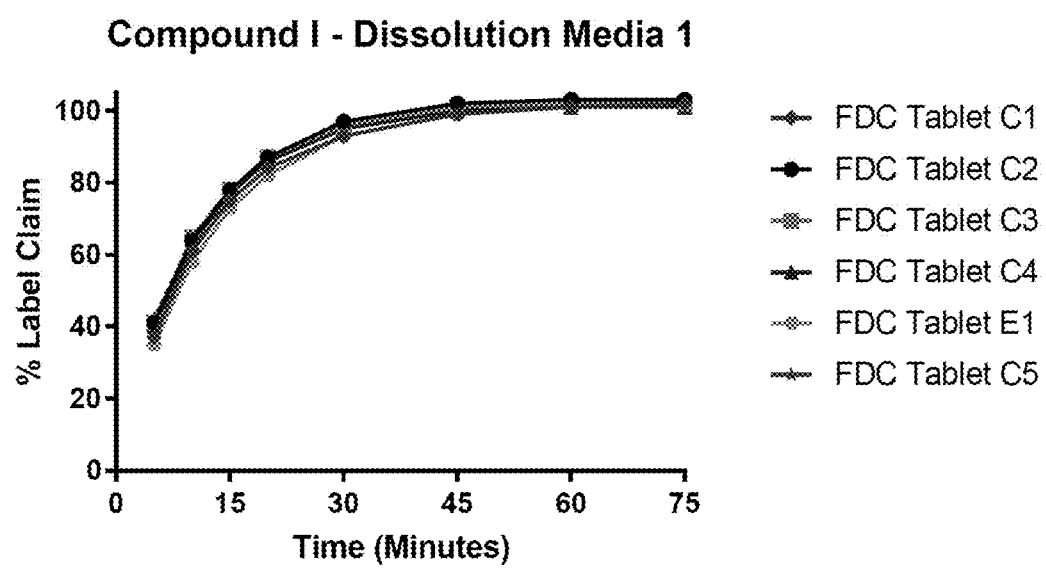
FIG. 24 shows tablet dissolution data of K salt of Compound I of FDC Tablets C1, C2, C3, C4, and C5. The tablet dissolution data were obtained using dissolution media 1, which included 0.8 wt % SDS in pH 6.8 sodium phosphate buffer.
Figure 25:
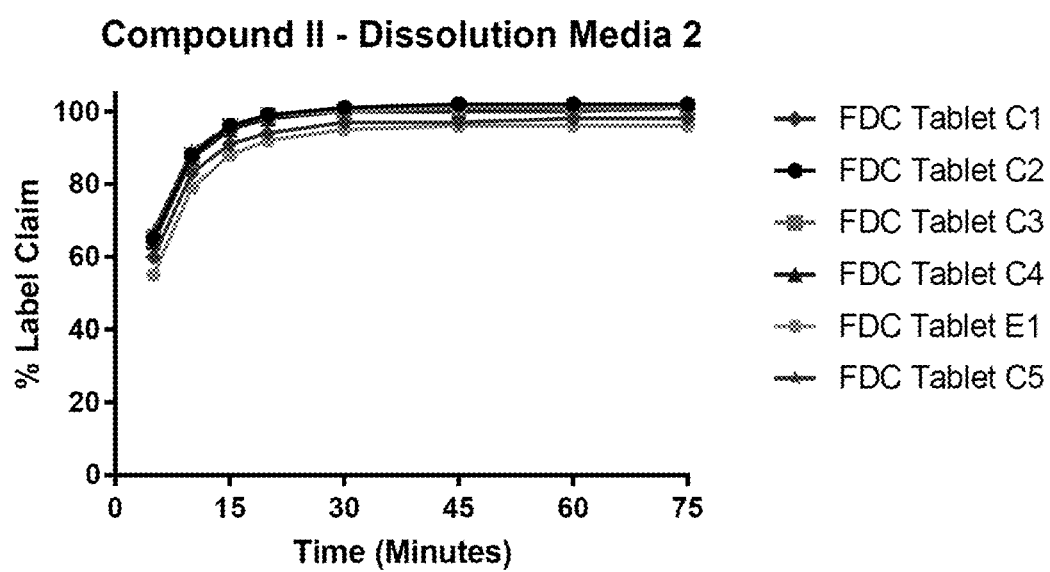
FIG. 25 shows tablet dissolution data for Compound II of FDC Tablets C1, C2, C3, C4, and C5. The tablet dissolution data were obtained using dissolution media 2, which included 0.1 wt % SDS in 0.1 N HCl.
Figure 26:
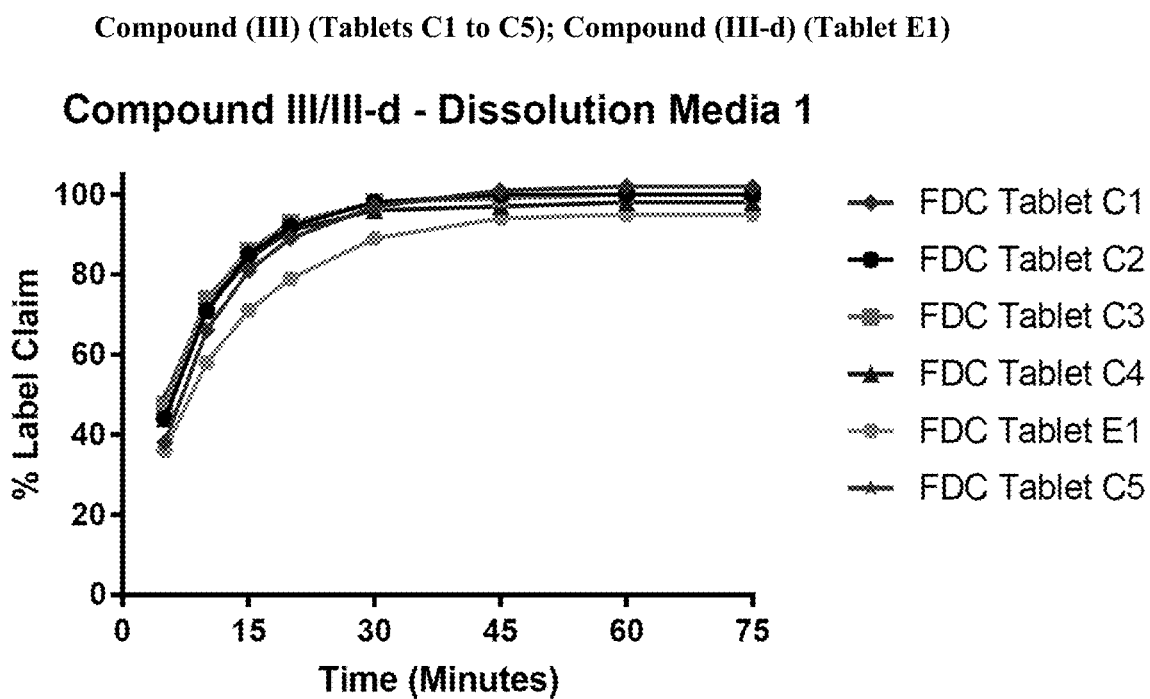
FIG. 26 shows tablet dissolution data for Compound III of FDC Tablets C1, C2, C3, C4, and C5. The tablet dissolution data were obtained using dissolution media 1, which included 0.8 wt % SDS in pH 6.8 sodium phosphate buffer.

Example 14. Preparation of Additional Fixed Dose Combination Tablet Formulations of a Potassium Salt of Compound I The FDC Tablets C1–C5 were made in a similar manner as described in Example 9 above. FIGS. 24, 25 and 26 show tablet dissolution data of K salt of Compound I, Compound II, and Compound III, respectively, of FDC Tablets C1, C2, C3, C4, and C5. The tablet dissolution data were obtained using dissolution media 1 for the K salt of Compound I and Compound III, and dissolution media 2 for Compound II. The dissolution media 1 included 0.8 wt % SDS in pH 6.8 sodium phosphate buffer. The dissolution media 2 included 0.1 wt % SDS in 0.1 N HCl. The dissolution testing of the tablets was performed using USP Apparatus II at 65 rpm for both media. Samples were collected and analyzed using reverse phase HPLC.

TABLE 100

| FDC Tablet C1 | | | | | |
|---|---|---|---|---|---|
|  | Component | Amount per Tablet (mg) | % IG | % EG | % Tablet (% w/w) |
|  | Core Tablet |  |  |  |  |
| Intra-granular (IG) | Compound I Potassium Salt | 127.73 | 33.28 | 29.46 | 28.6 |
|  | solid dispersion containing 80 wt % Compound II, 20 wt % hypromellose | 62.5 | 16.29 | 14.41 | 13.99 |
|  | solid dispersion containing 80 wt % Compound III, 19.5 wt % hypromellose acetate succinate, and 0.5 wt % sodium lauryl sulfate | 93.75 | 24.43 | 21.62 | 20.99 |
|  | Croscarmellose sodium | 11.51 | 3.00 | 2.65 | 2.58 |
|  | Microcrystalline cellulose | 84.43 | 22.00 | 19.47 | 18.9 |
|  | Magnesium Stearate | 3.84 | 1.00 | 0.89 | 0.86 |
| Extra-granular (EG) | Microcrystalline cellulose | 43.36 | — | 10.00 | 9.71 |
|  | Croscarmellose sodium | 6.5 | — | 1.50 | 1.46 |
|  | Total (core tablet) | 433.62 | 100.00 | 100.00 | 97.09 |
| Film Coat | film coat | 13.01 | — | — | 2.91 |
|  | Total (final tablet) | 446.63 |  |  | 100 |

TABLE 101

FDC Tablet C2

|  | Component | Amount per Tablet (mg) | % IG | % EG | Tablet Content (% w/w) |
|---|---|---|---|---|---|
|  | Core Tablet |  |  |  |  |
| Intra-granular | Compound I Potassium Salt | 127.73 | 33.28 | 29.46 | 28.6 |
|  | solid dispersion containing 80 wt % Compound II, 20 wt % hypromellose | 62.5 | 16.29 | 14.41 | 13.99 |
|  | solid dispersion containing 80 wt % Compound III, 19.5 wt % hypromellose acetate succinate, and 0.5 wt % sodium lauryl sulfate | 93.75 | 24.43 | 21.62 | 20.99 |
|  | Croscarmellose sodium | 11.51 | 3.00 | 2.65 | 2.58 |
|  | Microcrystalline cellulose | 88.27 | 23.00 | 20.36 | 19.76 |
|  | Magnesium Stearate | 0 | 0.00 | 0.00 | 0 |
| Extra-granular | Microcrystalline cellulose | 39.52 | — | 9.11 | 8.85 |
|  | Croscarmellose sodium | 6.5 | — | 1.50 | 1.46 |
|  | Magnesium Stearate | 3.84 | — | 0.89 | 0.86 |
|  | Total (core tablet) | 433.62 | 100 | 100.00 | 97.09 |
| Film Coat | film coat | 13.01 | — | — | 2.91 |
|  | Total (final tablet) | 446.63 |  |  | 100 |

TABLE 102

FDC Tablet C3

|  | Component | Amount per Tablet (mg) | % IG | % EG | Tablet Content (% w/w) |
|---|---|---|---|---|---|
|  | Core Tablet |  |  |  |  |
| Intra-granular | Compound I Potassium Salt | 127.73 | 33.28 | 29.46 | 28.6 |
|  | solid dispersion containing 80 wt % Compound II, 20 wt % hypromellose | 62.5 | 16.29 | 14.41 | 13.99 |
|  | solid dispersion containing 80 wt % Compound III, 19.5 wt % hypromellose acetate succinate, and 0.5 wt % sodium lauryl sulfate | 93.75 | 24.43 | 21.62 | 20.99 |
|  | Croscarmellose sodium | 11.51 | 3.00 | 2.65 | 2.58 |
|  | Microcrystalline cellulose | 87.31 | 22.75 | 20.14 | 19.55 |
|  | Magnesium Stearate | 0.96 | 0.25 | 0.22 | 0.21 |
| Extra-granular | Microcrystalline cellulose | 40.48 | — | 9.34 | 9.06 |
|  | Croscarmellose sodium | 6.5 | — | 1.50 | 1.46 |
|  | Magnesium Stearate | 2.88 | — | 0.66 | 0.64 |
|  | Total (core tablet) | 433.62 | 100 | 100.00 | 97.09 |
| Film Coat | film coat | 13.01 | — |  | 2.91 |
|  | Total (final tablet) | 446.63 |  |  | 100 |

TABLE 103

FDC Tablet C4

| | Component | Amount per Tablet (mg) | % IG | % EG | Tablet Content (% w/w) |
|---|---|---|---|---|---|
| | Core Tablet | | | | |
| Intra-granular | Compound I Potassium Salt | 127.73 | 33.28 | 29.46 | 28.60 |
| | solid dispersion containing 80 wt % Compound II, 20 wt % hypromellose | 62.5 | 16.29 | 14.41 | 13.99 |
| | solid dispersion containing 80 wt % Compound III, 19.5 wt % hypromellose acetate succinate, and 0.5 wt % sodium lauryl sulfate | 93.75 | 24.43 | 21.62 | 20.99 |
| | Croscarmellose sodium | 11.51 | 3.00 | 2.65 | 2.58 |
| | Microcrystalline cellulose | 87.31 | 22.75 | 20.14 | 19.55 |
| | Magnesium Stearate | 0.96 | 0.25 | 0.22 | 0.21 |
| Extra-granular | Microcrystalline cellulose | 39.03 | — | 9.00 | 8.74 |
| | Croscarmellose sodium | 6.5 | — | 1.50 | 1.46 |
| | Magnesium Stearate | 4.33 | — | 1.00 | 0.97 |
| | Total (core tablet) | 433.62 | 100 | 100.00 | 97.09 |
| Film Coat | film coat | 13.01 | — | — | 2.91 |
| | Total (final tablet) | 446.63 | | | 100 |

TABLE 104

FDC Tablet C5

| | Component | Amount per Tablet (mg) | % IG | % EG | Tablet Content (% w/w) |
|---|---|---|---|---|---|
| | Core Tablet | | | | |
| Intra-granular | Compound I Potassium Salt | 127.73 | 33.28 | 29.46 | 28.60 |
| | solid dispersion containing 80 wt % Compound II, 20 wt % hypromellose | 62.5 | 16.29 | 14.41 | 13.99 |
| | solid dispersion containing 80 wt % Compound III, 19.5 wt % hypromellose acetate succinate, and 0.5 wt % sodium lauryl sulfate | 93.75 | 24.43 | 21.62 | 20.99 |
| | Croscarmellose sodium | 11.51 | 3.00 | 2.65 | 2.58 |
| | Microcrystalline cellulose | 87.31 | 22.75 | 20.14 | 19.55 |
| | Magnesium Stearate | 0.96 | 0.25 | 0.22 | 0.21 |
| Extra-granular | Microcrystalline cellulose | 39.41 | — | 9.09 | 8.82 |
| | Croscarmellose sodium | 6.5 | — | 1.50 | 1.46 |
| | Magnesium Stearate | 3.95 | — | 0.91 | 0.89 |
| | Total (core tablet) | 433.62 | 100 | 100.00 | 97.09 |
| Film Coat | film coat | 13.01 | — | — | 2.91 |
| | Total (final tablet) | 446.63 | | | 100 |

FDC Tablet C5-1 can be made in a similar manner as described in Example 9 above. In some embodiments, "Compound I Potassium Salt" in Table 105 below refers to Compound I potassium salt crystalline Form B.

TABLE 105

FDC Tablet C5-1

| | Component | Amount per Tablet (mg) | % IG | % EG | Tablet Content (% w/w) |
|---|---|---|---|---|---|
| | Core Tablet | | | | |
| Intra-granular | Compound I Potassium Salt | 63.87 | 33.28 | 29.46 | 28.60 |
| | solid dispersion containing 80 wt % Compound II, 20 wt % hypromellose | 31.25 | 16.29 | 14.41 | 13.99 |
| | solid dispersion containing 80 wt % Compound III, 19.5 wt % hypromellose acetate succinate, and 0.5 wt % sodium lauryl sulfate | 46.88 | 24.43 | 21.62 | 20.99 |
| | Croscarmellose sodium | 5.76 | 3.00 | 2.65 | 2.58 |
| | Microcrystalline cellulose | 43.66 | 22.75 | 20.14 | 19.55 |
| | Magnesium Stearate | 0.48 | 0.25 | 0.22 | 0.21 |
| Extra-granular | Microcrystalline cellulose | 19.70 | — | 9.09 | 8.82 |
| | Croscarmellose sodium | 3.25 | — | 1.50 | 1.46 |
| | Magnesium Stearate | 1.98 | — | 0.91 | 0.89 |
| | Total (core tablet) | 216.81 | 100.00 | 100.00 | 97.09 |
| Film Coat | film coat | 6.51 | — | — | 2.91 |
| | Total (final tablet) | 223.32 | | | 100 |

Example 15. Preparation of Additional Fixed Dose Combination Tablet Formulations of a Potassium Salt of Compound I The tablets D1-D2 can be made in a similar manner as described in Example 9 above. In some embodiments, "Compound I Potassium Salt" in Tables 106 and 107 below refers to Compound I potassium salt crystalline Form B.

TABLE 106

FDC Tablet D1

| | Component | Amount per Tab (mg) | % IG | % EG | Tablet Content (% w/w) |
|---|---|---|---|---|---|
| | Core Tablet | | | | |
| Intra-granular | Compound I Potassium Salt | 127.73 | 26.57 | 23.51 | 22.83 |
| | solid dispersion containing 80 wt % Compound II, 20 wt % hypromellose | 62.5 | 13.00 | 11.51 | 11.17 |
| | solid dispersion containing 80 wt % Compound III, 19.5 wt % hypromellose acetate succinate, and 0.5 wt % sodium lauryl sulfate | 187.5 | 39.00 | 34.52 | 33.51 |

TABLE 106-continued

FDC Tablet D1

| | Component | Amount per Tab (mg) | % IG | % EG | Tablet Content (% w/w) |
|---|---|---|---|---|---|
| | Croscarmellose sodium | 14.5 | 3.02 | 2.67 | 2.59 |
| | Microcrystalline cellulose | 87.31 | 18.16 | 16.07 | 15.60 |
| | Magnesium Stearate | 1.2 | 0.25 | 0.22 | 0.21 |
| Extra-granular | Microcrystalline cellulose | 49.38 | — | 9.09 | 8.83 |
| | Croscarmellose sodium | 8.15 | — | 1.50 | 1.46 |
| | Magnesium Stearate | 4.94 | — | 0.91 | 0.88 |
| | Total (core tablet) | 543.21 | 100 | 100.00 | 97.09 |
| Film Coat | film coat | 16.3 | — | — | 2.91 |
| | Total (final tablet) | 559.51 | | | 100 |

TABLE 107

FDC Tablet D2

| | Component | Amount per Tab (mg) | % IG | % EG | Tablet Content (% w/w) |
|---|---|---|---|---|---|
| | Core Tablet | | | | |
| Intra-granular | Compound I Potassium Salt | 63.865 | 26.57 | 23.51 | 22.83 |
| | solid dispersion containing 80 wt % Compound II, 20 wt % hypromellose | 31.25 | 13.00 | 11.51 | 11.17 |
| | solid dispersion containing 80 wt % Compound III, 19.5 wt % hypromellose acetate succinate, and 0.5 wt % sodium lauryl sulfate | 93.75 | 39.00 | 34.52 | 33.51 |
| | Croscarmellose sodium | 7.25 | 3.02 | 2.67 | 2.59 |
| | Microcrystalline cellulose | 43.655 | 18.16 | 16.07 | 15.60 |
| | Magnesium Stearate | 0.6 | 0.25 | 0.22 | 0.21 |
| Extra-granular | Microcrystalline cellulose | 24.69 | — | 9.09 | 8.83 |
| | Croscarmellose sodium | 4.075 | — | 1.50 | 1.46 |
| | Magnesium Stearate | 2.47 | — | 0.91 | 0.88 |
| | Total (core ablet) | 271.605 | 100 | 100.00 | 97.09 |
| Film Coat | film coat | 8.15 | — | — | 2.91 |
| | Total (final tablet) | 279.755 | | | 100 |

FDC Tablets D3, D4, and D5, shown in Tables 108-111 below, were prepared in a similar manner as described in Example 9 above. Tablet D6, shown in Table 108 below, was prepared in a similar manner as described in Example 9, but using direct compression and not including an intermediate granulation of ingredients.

Figure 27:
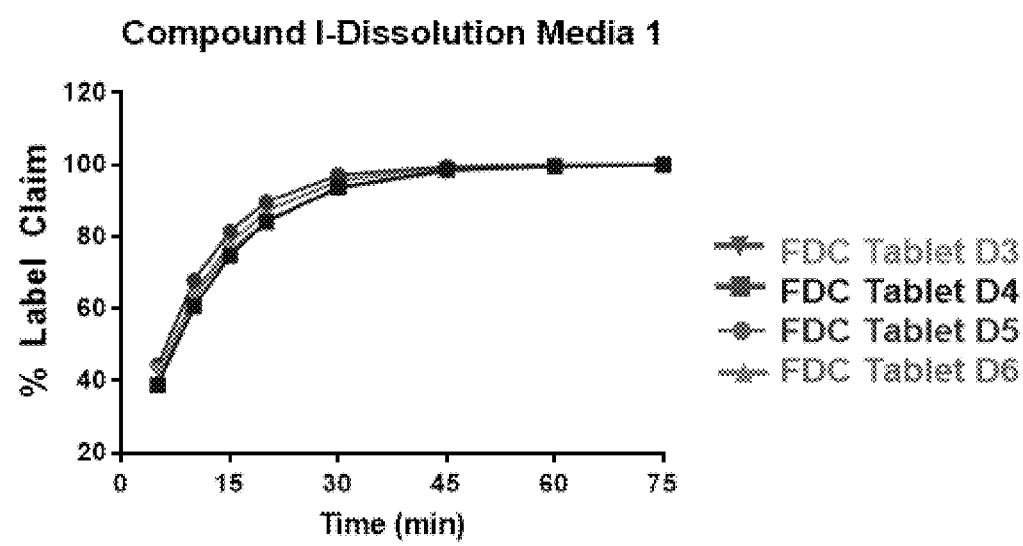
FIG. 27 shows tablet dissolution data of the potassium salt of Compound I of FDC Tablets D3, D4, D5, and D6. The tablet dissolution data were obtained using dissolution media 1, which included 1.0% SDS in 50 mM sodium phosphate monobasic buffer at pH 6.8.
Figure 28:
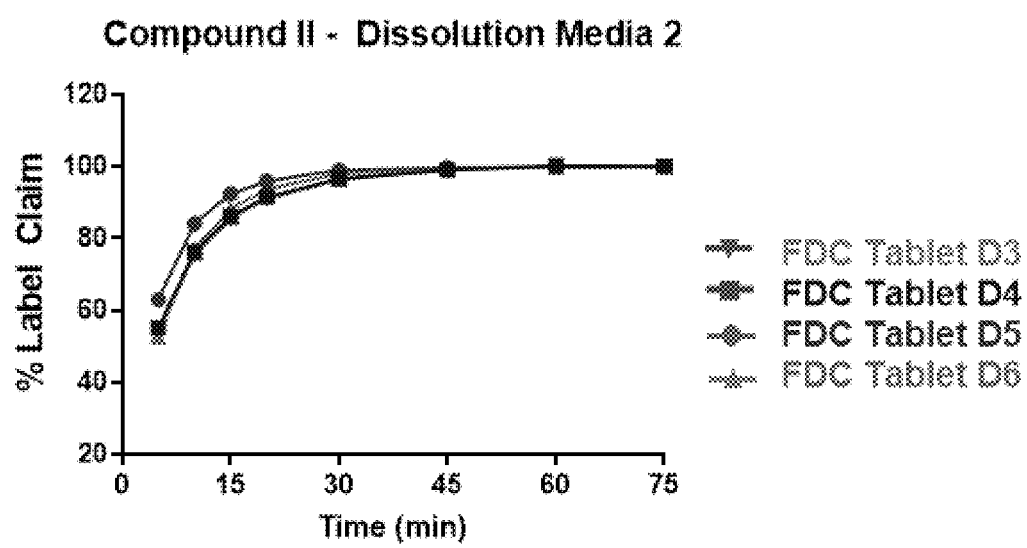
FIG. 28 shows tablet dissolution data for Compound II of FDC Tablets D3, D4, D5, and D6. The tablet dissolution data were obtained using dissolution media 2, which included 0.07% SDS in 0.1 N HCl.
Figure 29:
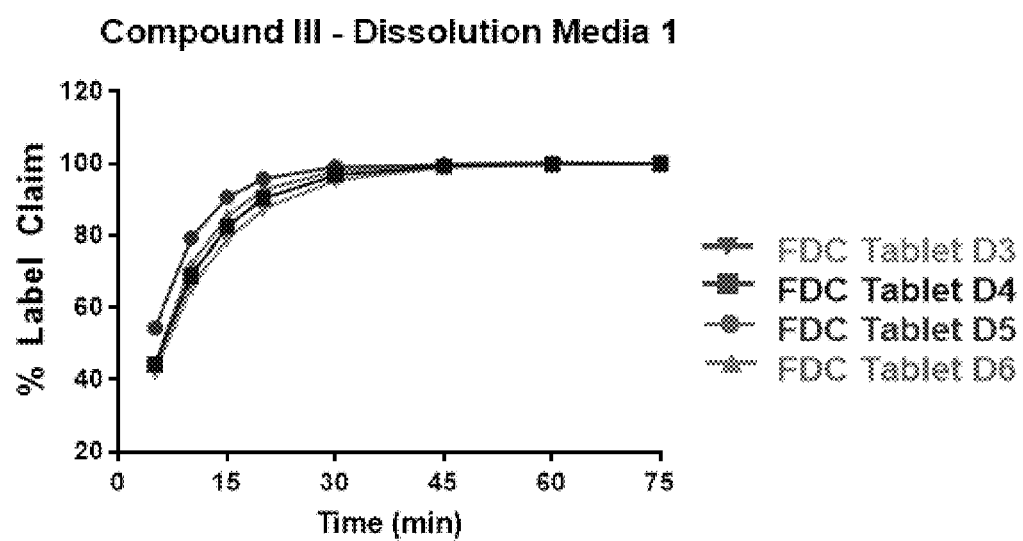
FIG. 29 shows tablet dissolution data for Compound III of FDC Tablets D3, D4, D5, and D6. The tablet dissolution data were obtained using dissolution media 1, which included 1.0% SDS in 50 mM sodium phosphate monobasic buffer at pH 6.8.

Dissolution data for FDC Tablets D3, D4, D5, and D6 are shown in FIGS. 27, 28 and 29. The dissolution media 1 included 1.0% SDS in 50 mM sodium phosphate monobasic buffer, pH 6.8. The dissolution media 2 included 0.07% SDS in 0.1 N HCl. The dissolution testing of the tablets was performed using USP Apparatus II (paddle apparatus) at 65 rpm for both media. Samples were collected and analyzed using reverse phase HPLC. USP Apparatus II (paddle apparatus) is described in the United States Pharmacopeia (USP) in General Chapter Dissolution <711>.

TABLE 108

FDC Tablet D3

| | Component | Amount per Tablet (mg) | % IG | % EG |
|---|---|---|---|---|
| | Core Tablet | | | |
| Intra-granular (IG) | Compound I Potassium Salt | 127.73 | 26.75 | 23.40 |
| | solid dispersion containing 80 wt % Compound II, 20 wt % hypromellose | 62.50 | 13.09 | 11.45 |
| | solid dispersion containing 80 wt % Compound III, 19.5 wt % hypromellose acetate succinate, and 0.5 wt % sodium lauryl sulfate | 187.50 | 39.26 | 34.36 |
| | Croscarmellose sodium | 11.52 | 2.41 | 2.11 |
| | Microcrystalline cellulose | 87.33 | 18.29 | 16.00 |
| | Magnesium Stearate | 0.96 | 0.20 | 0.18 |
| Extra-granular (EG) | Microcrystalline cellulose | 54.58 | — | 10.00 |
| | Croscarmellose sodium | 8.19 | — | 1.50 |
| | Magnesium Stearate | 5.46 | — | 1.00 |
| | Total (core tablet) | 545.75 | 100 | 100 |

TABLE 109

FDC Tablet D4

| | Component | Amount per Tablet (mg) | % IG | % EG |
|---|---|---|---|---|
| | Core Tablet | | | |
| Intra-granular (IG) | Compound I Potassium Salt | 127.73 | 25.03 | 22.14 |
| | solid dispersion containing 80 wt % Compound II, 20 wt % hypromellose | 62.5 | 12.25 | 10.84 |
| | solid dispersion containing 80 wt % Compound III, 19.5 wt % hypromellose acetate succinate, and 0.5 wt % sodium lauryl sulfate | 187.5 | 36.74 | 32.51 |
| | Croscarmellose sodium | 15.30 | 3.00 | 2.65 |
| | Microcrystalline cellulose | 116.10 | 22.75 | 20.13 |
| | Magnesium Stearate | 1.26 | 0.25 | 0.22 |
| Extra-granular (EG) | Microcrystalline cellulose | 52.50 | — | 9.10 |
| | Croscarmellose sodium | 8.65 | — | 1.50 |
| | Magnesium Stearate | 5.25 | — | 0.91 |
| | Total (core tablet) | 576.79 | 100 | 100.00 |

TABLE 110

FDC Tablet D5

| | Component | Amount per Tablet (mg) | % IG | % EG |
|---|---|---|---|---|
| | Core Tablet | | | |
| Intra-granular (IG) | Compound I Potassium Salt | 127.73 | 24.26 | 21.23 |
| | solid dispersion containing 80 wt % Compound II, 20 wt % hypromellose | 62.50 | 11.87 | 10.39 |
| | solid dispersion containing 80 wt % Compound III, 19.5 wt % hypromellose acetate succinate, and 0.5 wt % sodium lauryl sulfate | 187.50 | 35.62 | 31.16 |
| | Croscarmellose sodium | 17.16 | 3.26 | 2.85 |
| | Microcrystalline cellulose | 130.13 | 24.72 | 21.63 |
| | Magnesium Stearate | 1.43 | 0.27 | 0.24 |
| Extra-granular (EG) | Microcrystalline cellulose | 60.17 | — | 10.00 |
| | Croscarmellose sodium | 9.02 | — | 1.50 |
| | Magnesium Stearate | 6.02 | — | 1.00 |
| | Total (core tablet) | 601.66 | 100 | 100 |

TABLE 111

FDC Tablet D6

| Component | Amount per Tablet (mg) | Tablet Content (% w/w) |
|---|---|---|
| Core Tablet | | |
| Compound I Potassium Salt | 127.73 | 21.98 |
| solid dispersion containing 80 wt % Compound II, 20 wt % hypromellose | 62.50 | 10.76 |
| solid dispersion containing 80 wt % Compound III, 19.5 wt % hypromellose acetate succinate, and 0.5 wt % sodium lauryl sulfate | 187.50 | 32.27 |
| Croscarmellose sodium | 17.43 | 3.00 |
| Microcrystalline cellulose | 180.15 | 31.00 |
| Magnesium Stearate | 5.81 | 1.00 |
| Total (core tablet) | 581.12 | 581.12 |

FDC Tablets D3, D4, D5, and D6 can be film coated between about 2-4% w/w of the final tablet content, as shown in Tables 112-115 below. In some embodiments, "Compound I Potassium Salt" in Tables 112-115 below refers to Compound I potassium salt crystalline Form B.

TABLE 112

FDC Tablet D3, film coated

| | Component | Amount per Tablet (mg) | % IG | % EG | Tablet Content (% w/w) |
|---|---|---|---|---|---|
| | Core Tablet | | | | |
| Intra-granular (IG) | Compound I Potassium Salt | 127.73 | 26.75 | 23.40 | 22.72 |
| | solid dispersion containing 80 wt % Compound II, 20 wt % hypromellose | 62.50 | 13.09 | 11.45 | 11.12 |
| | solid dispersion containing 80 wt % Compound III, 19.5 wt % hypromellose acetate succinate, and 0.5 wt % sodium lauryl sulfate | 187.50 | 39.26 | 34.36 | 33.36 |
| | Croscarmellose sodium | 11.52 | 2.41 | 2.11 | 2.05 |
| | Microcrystalline cellulose | 87.33 | 18.29 | 16.00 | 15.54 |
| | Magnesium Stearate | 0.96 | 0.20 | 0.18 | 0.17 |
| Extra-granular (EG) | Microcrystalline cellulose | 54.58 | — | 10.00 | 9.71 |
| | Croscarmellose sodium | 8.19 | — | 1.50 | 1.46 |
| | Magnesium Stearate | 5.46 | — | 1.00 | 0.97 |
| | Total (core tablet) | 545.75 | 100 | 100 | 97.09 |
| Film Coat | film coat | 16.37 | — | — | 2.91 |
| | Total (final tablet) | 562.12 | | | 100 |

TABLE 113

FDC Tablet D4, film coated

| | Component | Amount per Tablet (mg) | % IG | % EG | Tablet Content (% w/w) |
|---|---|---|---|---|---|
| | Core Tablet | | | | |
| Intra-granular (IG) | Compound I Potassium Salt | 127.73 | 25.03 | 22.14 | 21.50 |
| | solid dispersion containing 80 wt % Compound II, 20 wt % hypromellose | 62.5 | 12.25 | 10.84 | 10.52 |
| | solid dispersion containing 80 wt % Compound III, 19.5 wt % hypromellose acetate succinate, and 0.5 wt % sodium lauryl sulfate | 187.5 | 36.74 | 32.51 | 31.56 |
| | Croscarmellose sodium | 15.30 | 3.00 | 2.65 | 2.58 |
| | Microcrystalline cellulose | 116.10 | 22.75 | 20.13 | 19.54 |
| | Magnesium Stearate | 1.26 | 0.25 | 0.22 | 0.21 |
| Extra-granular (EG) | Microcrystalline cellulose | 52.50 | — | 9.10 | 8.84 |
| | Croscarmellose sodium | 8.65 | — | 1.50 | 1.46 |
| | Magnesium Stearate | 5.25 | — | 0.91 | 0.88 |
| | Total (core tablet) | 576.79 | 100 | 100.00 | 97.09 |
| Film Coat | film coat | 17.30 | — | — | 2.91 |
| | Total (final tablet) | 594.09 | | | 100 |

TABLE 114

FDC Tablet D5, film coated

| | Component | Amount per Tablet (mg) | % IG | % EG | Tablet Content (% w/w) |
|---|---|---|---|---|---|
| | Core Tablet | | | | |
| Intra-granular (IG) | Compound I Potassium Salt | 127.73 | 24.26 | 21.23 | 20.61 |
| | solid dispersion containing 80 wt % Compound II, 20 wt % hypromellose | 62.50 | 11.87 | 10.39 | 10.09 |
| | solid dispersion containing 80 wt % Compound III, 19.5 wt % hypromellose acetate succinate, and 0.5 wt % sodium lauryl sulfate | 187.50 | 35.62 | 31.16 | 30.26 |
| | Croscarmellose sodium | 17.16 | 3.26 | 2.85 | 2.77 |
| | Microcrystalline cellulose | 130.13 | 24.72 | 21.63 | 21.00 |
| | Magnesium Stearate | 1.43 | 0.27 | 0.24 | 0.23 |
| Extra-granular (EG) | Microcrystalline cellulose | 60.17 | — | 10.00 | 9.71 |
| | Croscarmellose sodium | 9.02 | — | 1.50 | 1.46 |
| | Magnesium Stearate | 6.02 | — | 1.00 | 0.97 |
| | Total (core tablet) | 601.66 | 100 | 100 | 97.09 |
| Film Coat | film coat | 18.05 | — | — | 2.91 |
| | Total (final tablet) | 619.71 | | | 100 |

TABLE 115

FDC Tablet D6, film coated

| | Component | Amount per Tablet (mg) | % Core Tablet | Tablet Content (% w/w) |
|---|---|---|---|---|
| | Core Tablet | | | |
| Intra-granular (IG) | Compound I Potassium Salt | 127.73 | 21.98 | 21.34 |
| | solid dispersion containing 80 wt % Compound II, 20 wt % hypromellose | 62.50 | 10.76 | 10.44 |
| | solid dispersion containing 80 wt % Compound III, 19.5 wt % hypromellose acetate succinate, and 0.5 wt % sodium lauryl sulfate | 187.50 | 32.27 | 31.33 |
| | Croscarmellose sodium | 17.43 | 3.00 | 2.91 |
| | Microcrystalline cellulose | 180.15 | 31.00 | 30.10 |
| | Magnesium Stearate | 5.81 | 1.00 | 0.97 |
| | Total (core tablet) | 581.12 | 100.00 | 97.09 |
| Film Coat | film coat | 17.42 | | 2.91 |
| | Total (final tablet) | 598.54 | | 100 |

Example 16. Preparation of Additional Fixed Dose Combination Tablet Formulations of a Potassium Salt of Compound I in Combination with Compound II and Compound III-d The FDC Tablet E1 was prepared in a similar manner as described in Example 9 above. FIGS. 24, 25, and 26 show tablet dissolution data of K salt of Compound I, Compound II, and Compound III-d, respectively, of FDC Tablet E1. The tablet dissolution data were obtained using dissolution media 1 for the K salt of Compound I and Compound III-d, and dissolution media 2 for Compound II. The dissolution media 1 included 0.8 wt % SDS in pH 6.8 sodium phosphate buffer. The dissolution media 2 included 0.1 wt % SDS in 0.1 N HCl. The dissolution testing of the tablets was performed using USP Apparatus II at 65 rpm for both media. Samples were collected and analyzed using reverse phase HPLC.

The tablets E2-E4 can be prepared in a similar manner as described in Example 9 above, but using direct compression and may not include intermediate granulation of ingredients. The solid dispersion containing 80 wt % Compound III-d, 19.5 wt % hypromellose acetate succinate, and 0.5% sodium lauryl sulfate can be made in the same manner as that for the solid dispersion containing 80 wt % Compound III, 19.5 wt % hypromellose acetate succinate, and 0.5% sodium lauryl sulfate.

TABLE 116

FDC Tablet E1

| IG/EG | Component | Tablet Qty (mg) | % IG | % EG | % Coated tablet |
|---|---|---|---|---|---|
| IG | Compound I Potassium Salt | 127.73 | 30.78 | 27.48% | 26.68% |
| | solid dispersion containing 80 wt % Compound II, 20 wt % hypromellose | 62.5 | 15.06 | 13.44% | 13.05% |
| | solid dispersion containing 80 wt % Compound III-d, 19.5 wt % hypromellose acetate succinate, and 0.5 wt % sodium lauryl sulfate | 125 | 30.12 | 26.89% | 26.11% |
| | Microcrystalline cellulose | 84.43 | 20.34 | 18.16% | 17.63% |
| | Croscarmellose sodium | 11.51 | 2.77 | 2.48% | 2.40% |
| | Magnesium Stearate | 3.84 | 0.93 | 0.83% | 0.80% |
| EG | Microcrystalline cellulose | 43.36 | | 9.33% | 9.06% |
| | Croscarmellose sodium | 6.5 | | 1.40% | 1.36% |
| | Magnesium Stearate | | | | 0.00% |
| Coating | film coat | 13.95 | | | 2.91% |
| Total | | 478.82 | 100.00 | 100.00% | 100.00% |

TABLE 117

FDC Tablet E2

| Component | Tablet Qty (mg) | % Core tablet | % Coated tablet |
|---|---|---|---|
| Compound I K salt | 255.46 | 34.06% | 33.07% |
| solid dispersion containing 80 wt % Compound II, 20 wt % hypromellose | 125 | 16.67% | 16.18% |
| solid dispersion containing 80 wt % Compound III-d, 19.5 wt % hypromellose acetate succinate, and 0.5 wt % sodium lauryl sulfate | 250 | 33.33% | 32.36% |
| Microcrystalline cellulose | 89.54-97.04 | 11.94-12.94% | 11.59-12.56% |
| Croscarmellose sodium | 22.5 | 3.00% | 2.91% |
| Magnesium Stearate | 0-7.5 | 0-1% | 0-0.97% |
| Total Core | 750 | 100.00% | 97.09% |
| film coating | 22.5 | | 2.91% |
| Total coated | 772.5 | | 100.00% |

TABLE 118

FDC Tablet E3

| Component | Tablet Qty (mg) | % Core tablet | % Coated tablet |
|---|---|---|---|
| Compound I K salt | 127.73 | 20.26% | 19.67% |
| solid dispersion containing 80 wt % Compound II, 20 wt % hypromellose | 62.5 | 9.91% | 9.62% |
| solid dispersion containing 80 wt % Compound III-d, 19.5 wt % hypromellose acetate succinate, and 0.5 wt % sodium lauryl sulfate | 125 | 19.83% | 19.25% |

TABLE 118-continued

FDC Tablet E3

| Component | Tablet Qty (mg) | % Core tablet | % Coated tablet |
|---|---|---|---|
| Microcrystalline cellulose | 290.01-296.32 | 46-47% | 44.66-45.63% |
| Croscarmellose sodium | 18.91 | 3.00% | 2.91% |
| Magnesium Stearate | 0-6.31 | 0-1% | 0-0.97% |
| Total Core | 630.46 | 100.00% | 97.09% |
| film coating | 18.91 | | 2.91% |
| Total coated | 649.37 | | 100.00% |

TABLE 119

FDC Tablet E4

| Component | Tablet Qty (mg) | % Core tablet | % Coated tablet |
|---|---|---|---|
| Compound I K salt | 127.73 | 28.36% | 27.54% |
| solid dispersion containing 80 wt % Compound II, 20 wt % hypromellose | 62.5 | 13.88% | 13.47% |
| solid dispersion containing 80 wt % Compound III-d, 19.5 wt % hypromellose acetate succinate, and 0.5 wt % sodium lauryl sulfate | 125 | 27.76% | 26.95% |
| Microcrystalline cellulose | 117.09-121.59 | 26-27% | 25.24-26.21% |
| Croscarmellose sodium | 13.51 | 3.00% | 2.91% |
| Magnesium Stearate | 0-4.5 | 0-1% | 0-0.97% |
| Total Core | 450.33 | 100.00% | 97.09% |
| film coating | 13.51 | | 2.91% |
| Total coated | 463.84 | | 100.00% |

Example 17: Assays & Data

17A. Assays for Detecting and Measuring F508del-CFTR Modulator Properties of Compounds Membrane Potential Optical Methods for Assaying Properties of F508del-CFTR Modulators The assay utilizes fluorescent voltage sensing dyes to measure changes in membrane potential using a fluorescent plate reader (e.g., FLIPR III, Molecular Devices, Inc.) as a readout for increase in functional F508del in NIH 3T3 cells. The driving force for the response is the creation of a chloride ion gradient in conjunction with channel activation and concurrent with compound treatment by a single liquid addition step after the cells have previously been loaded with a voltage sensing dye.

17A-A1. Identification of F508del-CFTR Modulators

To identify modulators of F508del, a fluorescence based HTS assay format was developed. This HTS assay utilizes fluorescent voltage sensing dyes to measure changes in membrane potential on the FLIPR III as a measurement for increase in gating (conductance) of F508del NIH 3T3 cells. The driving force for the response is the creation of a chloride ion gradient in conjunction with channel activation and concurrent with compound treatment by a single liquid addition step after the cells have previously been loaded with a voltage sensing dye. Data for Compounds I that were obtained using the assay described here are summarized in Table 120 below. For example, using this method, Compound I had an $EC_{50}$ of less than 3 µM and a % Efficacy of ≥100% relative to Compound II.

Solutions

Bath Solution #1:

(in mM) NaCl 160, KCl 4.5, $CaCl_2$ 2, $MgCl_2$ 1, HEPES 10, pH 7.4 with NaOH, Glucose 10.

Chloride-Free Bath Solution:

Chloride salts in Bath Solution #1 (above) are substituted with gluconate salts.

Cell Culture

NIH3T3 mouse fibroblasts stably expressing F508del are used for optical measurements of membrane potential. The cells are maintained at 37° C. in 5% $CO_2$ and 90% humidity in Dulbecco's modified Eagle's medium supplemented with 2 mM glutamine, 10% fetal bovine serum, 1×NEAA, β-ME, 1× pen/strep, and 25 mM HEPES in 175 $cm^2$ culture flasks. For all optical assays, the cells were seeded at 12,000 cells/well in 384-well matrigel-coated plates and cultured for 18-24 hrs at 37° C. for the potentiator assay. For the correction assays, the cells are cultured at 37° C. with and without compounds for 18-24 hours.

Electrophysiological Assays for Assaying F508del Modulation Properties of Compounds.

Using Chamber Assay

Using chamber experiments were performed on polarized airway epithelial cells expressing F508del to further characterize the F508del modulators identified in the optical assays. Non-CF and CF airway epithelia were isolated from bronchial tissue, cultured as previously described (Galietta, L. J. V., Lantero, S., Gazzolo, A., Sacco, O., Romano, L., Rossi, G. A., & Zegarra-Moran, O. (1998) *In Vitro Cell. Dev. Biol.* 34, 478-481), and plated onto Costar® Snapwell™ filters that were precoated with NIH3T3-conditioned media. After four days the apical media was removed and the cells were grown at an air liquid interface for >14 days prior to use. This resulted in a monolayer of fully differentiated columnar cells that were ciliated, features that are characteristic of airway epithelia. Non-CF HBE were isolated from non-smokers that did not have any known lung disease. CF-HBE were isolated from patients homozygous for F508del or compound heterozygous for F508del with a different disease causing mutation on the other allele.

HBE grown on Costar® Snapwell™ cell culture inserts were mounted in an Using chamber (Physiologic Instruments, Inc., San Diego, Calif.), and the transepithelial resistance and short-circuit current in the presence of a basolateral to apical Cl⁻ gradient ($I_{SC}$) were measured using a voltage-clamp system (Department of Bioengineering, University of Iowa, IA). Briefly, HBE were examined under voltage-clamp recording conditions ($V_{hold}$=0 mV) at 37° C. The basolateral solution contained (in mM) 145 NaCl, 0.83 $K_2HPO_4$, 3.3 $KH_2PO_4$, 1.2 $MgCl_2$, 1.2 $CaCl_2$, 10 Glucose, 10 HEPES (pH adjusted to 7.35 with NaOH) and the apical solution contained (in mM) 145 NaGluconate, 1.2 $MgCl_2$, 1.2 $CaCl_2$), 10 glucose, 10 HEPES (pH adjusted to 7.35 with NaOH).

17A-A2. Identification of F508del-CFTR Modulators

Typical protocol utilized a basolateral to apical membrane Cl⁻ concentration gradient. To set up this gradient, normal ringers was used on the basolateral membrane, whereas apical NaCl was replaced by equimolar sodium gluconate (titrated to pH 7.4 with NaOH) to give a large Cl⁻ concentration gradient across the epithelium. Modulators were added either to the basolateral side 18-24 prior to assay or to the apical side during the assay. Forskolin (10 µM) was added to the apical side during the assay to stimulate CFTR-mediated Cl⁻ transport.

Patch-Clamp Recordings

Total Cl⁻ current in F508del-NIH3T3 cells was monitored using the perforated-patch recording configuration as previously described (Rae, J., Cooper, K., Gates, P., & Watsky, M. (1991) *J. Neurosci. Methods* 37, 15-26). Voltage-clamp recordings were performed at 22° C. using an Axopatch 200B patch-clamp amplifier (Axon Instruments Inc., Foster City, Calif.). The pipette solution contained (in mM) 150 N-methyl-D-glucamine (NMDG)-Cl, 2 $MgCl_2$, 2 $CaCl_2$), 10 EGTA, 10 HEPES, and 240 µg/mL amphotericin-B (pH adjusted to 7.35 with HCl). The extracellular medium contained (in mM) 150 NMDG-Cl, 2 $MgCl_2$, 2 $CaCl_2$), 10 HEPES (pH adjusted to 7.35 with HCl). Pulse generation, data acquisition, and analysis were performed using a PC equipped with a Digidata 1320 A/D interface in conjunction with Clampex 8 (Axon Instruments Inc.). To activate F508del, 10 µM forskolin and 20 µM genistein were added to the bath and the current-voltage relation was monitored every 30 sec.

17A-A3. Identification of F508del-CFTR modulators

The ability of F508del-CFTR modulators to increase the macroscopic F508del Cl⁻ current ($I_{F508del}$) in NIH3T3 cells stably expressing F508del was also investigated using perforated-patch-recording techniques. Modulators identified from the optical assays evoked a dose-dependent increase in $I\Delta_{F508}$ with similar potency and efficacy observed in the optical assays.

Cell Culture

NIH3T3 mouse fibroblasts stably expressing F508del are used for whole-cell recordings. The cells are maintained at 37° C. in 5% C02 and 90% humidity in Dulbecco's modified Eagle's medium supplemented with 2 mM glutamine, 10% fetal bovine serum, 1×NEAA, β-ME, 1× pen/strep, and 25 mM HEPES in 175 $cm^2$ culture flasks. For whole-cell recordings, 2,500-5,000 cells were seeded on poly-L-lysine-coated glass coverslips and cultured for 18-24 hrs in the presence or absence of modulators 37° C.

Single-Channel Recordings

Gating activity of F508del-CFTR expressed in NIH3T3 cells following modulator treatment was observed using excised inside-out membrane patch recordings as previously described (Dalemans, W., Barbry, P., Champigny, G., Jallat, S., Dott, K., Dreyer, D., Crystal, R. G., Pavirani, A., Lecocq, J-P., Lazdunski, M. (1991) *Nature* 354, 526-528) using an Axopatch 200B patch-clamp amplifier (Axon Instruments Inc.). The pipette contained (in mM): 150 NMDG, 150 aspartic acid, 5 $CaCl_2$), 2 $MgCl_2$, and 10 HEPES (pH adjusted to 7.35 with Tris base). The bath contained (in mM): 150 NMDG-Cl, 2 $MgCl_2$, 5 EGTA, 10 TES, and 14 Tris base (pH adjusted to 7.35 with HCl). After excision, both wt- and F508del were activated by adding 1 mM Mg-ATP, 75 nM of the catalytic subunit of cAMP-dependent protein kinase (PKA; Promega Corp. Madison, Wis.), and 10 mM NaF to inhibit protein phosphatases, which prevented current rundown. The pipette potential was maintained at 80 mV. Channel activity was analyzed from membrane patches containing ≤2 active channels. The maximum number of simultaneous openings determined the number of active channels during the course of an experiment. To determine the single-channel current amplitude, the data recorded from 120 sec of F508del activity was filtered "off-line" at 100 Hz and then used to construct all-point amplitude histograms that were fitted with multigaussian functions using Bio-Patch Analysis software (Bio-Logic Comp. France). The total microscopic current and open probability ($P_o$) were determined from 120 sec of channel activity. The $P_o$ was determined using the Bio-Patch software or from the relationship $P_o=I/i(N)$, where I=mean current, i=single-channel current amplitude, and N=number of active channels in patch.

Cell Culture

NIH3T3 mouse fibroblasts stably expressing F508del are used for excised-membrane patch-clamp recordings. The cells are maintained at 37° C. in 5% C02 and 90% humidity in Dulbecco's modified Eagle's medium supplemented with 2 mM glutamine, 10% fetal bovine serum, 1×NEAA, β-ME, 1× pen/strep, and 25 mM HEPES in 175 $cm^2$ culture flasks. For single channel recordings, 2,500-5,000 cells were seeded on poly-L-lysine-coated glass coverslips and cultured for 18-24 hrs in the presence or absence of modulators at 37° C.

17B. Chromatographic Determination of Human Serum Albumin (HSA) Assay

Chromatographic determination of Human Serum Albumin (HSA) values was performed on a UPLC-MS system using a ChiralPak® HSA column (p/n: 58469AST) from Sigma Aldrich. Mobile phase A consisted of 50 mM ammonium acetate buffer in water adjusted to pH=7.4, and mobile phase B was 2-propanol. The column compartment was kept at constant temperature of 30° C. Determination of retention time on the HSA column was performed by injecting 3 mL of 0.5 mM of compound (in DMSO) using a linear gradient from 0%-30% B in 2.5 minutes, followed by a hold at 30% B for 2 minutes, and the final equilibration step from 30%-0% B in 1.5 minutes, for a total run time of 6 minutes. Flow rate was kept constant throughout the gradient and set to 1.8 mL/min. Compound retention time on the HSA column was converted to % HSA values according to a previously published protocol (Valko, et. al, 2003) correlating column retention times to standard plasma protein binding (PPB) values obtained from dialysis experiments.

Valko, K., Nunhuck, S., Bevan, C., Abraham, M. H., Reynolds, D. P. Fast Gradient HPLC Method to Determine Compounds Binding to Human Serum Albumin. Relationships with Octanol/Water and Immobilized Artificial Membrane Lipophilicity. *J. of Pharm. Sci.* 2003, 92, 2236-2248.

17C. Experimental Protocol for Rat IV and PO PK Studies

The tested compound was administered to male Sprague-Dawley rats as a single nominal intravenous dose of 3.0 mg/kg as a solution in 10% NMP, 10% solutol, 15% EtOH, 35% PEG400 and 30% D5W. The tested compound was also administered to male Sprague-Dawley rats at single nominal oral dose of 3 mg/kg as a solution in 5% NMP, 30% PEG400, 10% TPGS, 5% PVP-$K_{30}$ at 5 mL/kg dose volume. Analyses of plasma and dose preparations were performed using LC/MS/MS.

Plasma concentration-time profiles of the tested compound in Sprague-Dawley rats at scheduled (nominal) sampling times were analyzed by noncompartmental pharmacokinetic methods using PK function within Watson LIMS software, Version 7.4.2 (Thermo Scientific Inc, Waltham, Mass.). AUC values were calculated using the linear trapezoidal rule.

17D. Experimental Protocol for PXR Assay

The propensity for PXR mediated CYP3A4 induction is assessed using the DPX-2 cell line in vitro. This cell line, which has been licensed from Puracyp Inc. was derived from HepG2 cells and has been stably transfected with genes encoding human PXR as well as a modified luciferase reporter linked to the CYP3A4 promoter region and related distal and proximal enhancers.

The assay is run in 384 well format and each test article is administered in 11 doses ranging from 0.1 to 60 µM. On day 1, DPX-2 cells which have previously been expanded in-house and cryopreserved are thawed and seeded in tissue culture plates. The following day, media is changed and cells are cultured in media containing test article, vehicle control or the positive control compound, the clinically validated CYP3A4 inducer rifampicin. Cells are cultured in the presence of test article for 48 hours and then cell viability is assessed using fluorescence based assay (Cell Titer-Fluor, Promega) with an EnVision Plate Reader (PerkinElmer). Subsequently, CYP3A4 transactivation, which is proportional to luciferase activity, is measured by reading luminescence using the Promega One-Glo reagent system using the same plate reader.

Data processing within the Genedata software package allows reporting of max fold induction compared to vehicle control, an $EC_{50}$ value for CYP3A4 inducers and an 11 point-dose response curve. Wells with cell viability less than 70% are not used for the analysis and plates where the rifampicin positive control response falls outside of the expected range, either in potency or max fold induction, are not reported.

17E. CFTR Data of Compound I

Compound I is useful as a modulator of CFTR activity. The Table 120 below illustrates the EC50 of Compound I using procedures described above (assay described above in Example 11A-A1). In Table 120 below, the following meanings apply. EC50: "+++" means <0.1 µM; "++" means between 0.1 µM and 1 µM; "+" means greater than 1 µM.

TABLE 120

| CFTR Activity | |
|---|---|
| Comp. No. | CFTRdF508 EC50 (µM) |
| I | +++ |

Example 18: Chloride Transport Experiments

In one Using Chamber experiment with F508del/F508del-HBE cells, Compound I enhanced chloride transport. The effect of Compound I on chloride transport was additive to the effect of Compound II. In addition, F508del-CFTR delivered to the cell surface by either Compound I alone or in combination with Compound II was potentiated by Compound III. The triple combination of Compound I/Compound II/Compound III provided a superior (approximately 3-fold) increase in chloride transport compared to the 3 dual regimens under most conditions tested.

Example 19: F508del-CFTR Processing and Trafficking In Vitro Experiments

In vitro, Compound I improved the processing and trafficking of F508del-CFTR, thereby increasing the quantity of functional F508del-CFTR protein at the cell surface. The CFTR protein delivered to the cell surface by Compound I alone or in combination with Compound II (Compound I/Compound II) was potentiated by Compound III. In human bronchial epithelial (HBE) cells studied in vitro, the triple combination of Compound I, Compound II, and Compound III (Compound I/Compound II/Compound III) increased CFTR chloride transport more than any of the dual combinations (Compound I/Compound II, Compound I/Compound III, and Compound II/Compound III) or individual components (Compound I, Compound II, and Compound III) under most conditions studied.

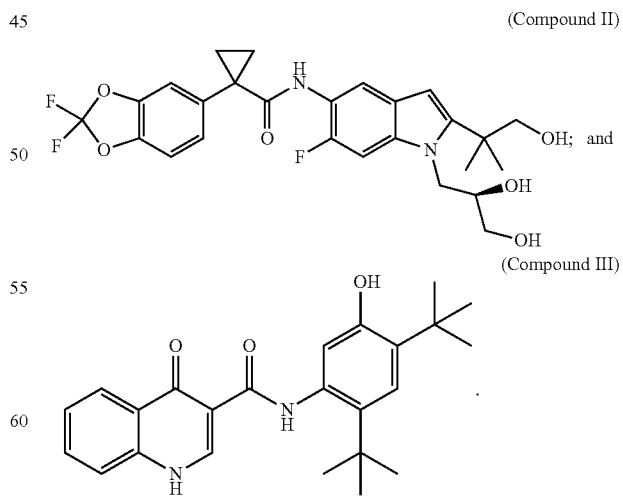

Processing and trafficking of F508del-CFTR was directly monitored by the appearance of a 170 to 180 kDa band. Such monitoring established that Compound I is a CFTR correc-

The invention claimed is:

1. Crystalline Form B of a potassium salt of Compound I:

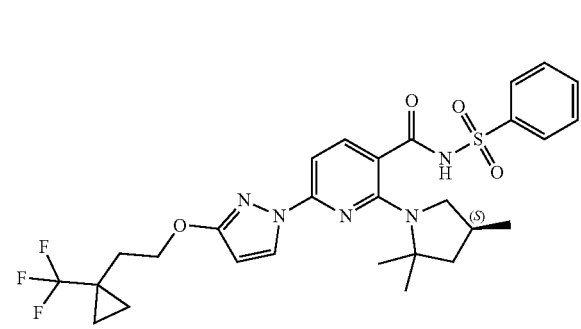

characterized by an X-ray powder diffractogram having a signal at least three two-theta values chosen from 5.8±0.2, 8.2±0.2, 9.6±0.2, 10.2±0.2, 13.8±0.2, 15.1±0.2, 16.3±0.2, 17.2±0.2, and 19.1±0.2.

2. Crystalline Form B of a potassium salt of Compound I:

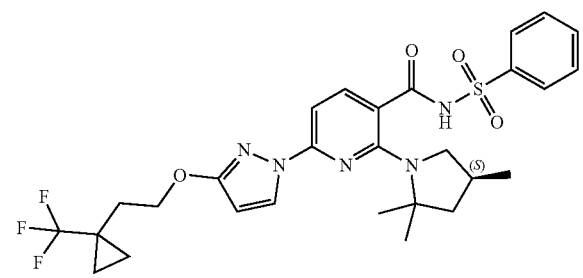

having a unit cell characterized by three edges of 9.0±0.2A, 11.5±0.2A, and 31.0±0.2A.

3. A method of preparing crystalline Form B of a potassium salt of Compound I of claim 1 or claim 2, comprising reacting Compound I with a potassium base.

4. A pharmaceutical composition comprising:
(a) 50 mg to 600 mg of crystalline Form B of a potassium salt of Compound I of claim 1 or claim 2:

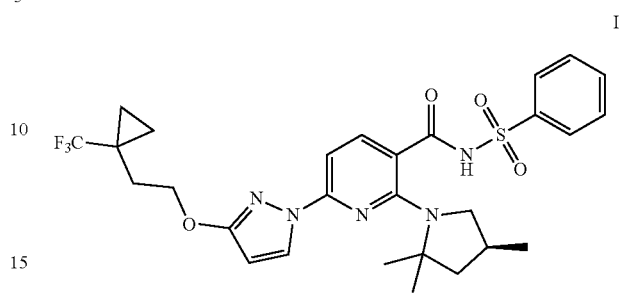

(b) a first solid dispersion comprising 25 mg to 125 mg of Compound II:

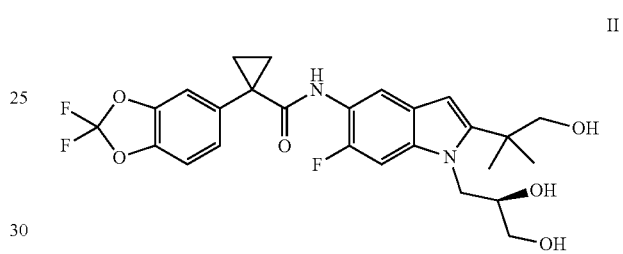

and 10 wt % to 30 wt % of a polymer relative to the total weight of the first solid dispersion; and
(c) a second solid dispersion comprising 5 mg to 300 mg of Compound III or Compound III-d:

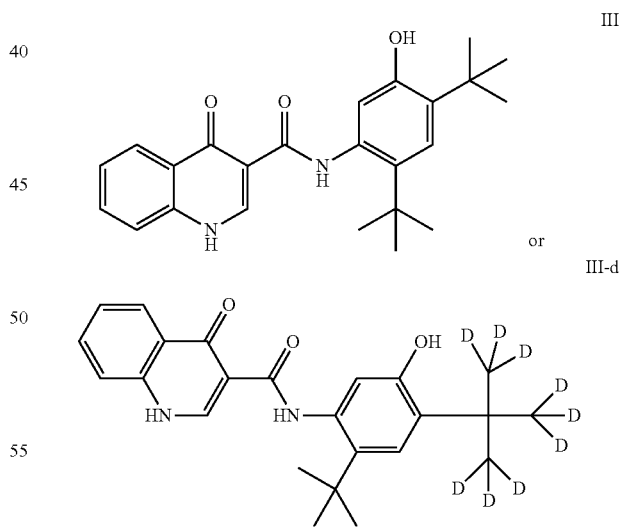

and 10 wt % to 30 wt % of a polymer relative to the total weight of the second solid dispersion.

5. The pharmaceutical composition of claim 4, wherein the composition comprises:
(a) 15 wt % to 45 wt % of crystalline Form B of a potassium salt of Compound I of claim 1 or claim 2 relative to the total weight of the pharmaceutical composition;

(b) 5 wt % to 20 wt % of a first solid dispersion relative to the total weight of the pharmaceutical composition, wherein the first solid dispersion comprises 70 wt % to 90 wt % of Compound II relative to the total weight of the first solid dispersion and 10 wt % to 30 wt % of a polymer relative to the total weight of the first solid dispersion; and (c) 10 wt % to 40 wt % of a second solid dispersion relative to the total weight of the pharmaceutical composition, wherein the second solid dispersion comprises 70 wt % to 90 wt % of Compound III or Compound III-d relative to the total weight of the second solid dispersion, and 10 wt % to 30 wt % of a polymer relative to the total weight of the second solid dispersion.

6. The pharmaceutical composition of claim 4, wherein the composition comprises:
(a) 20 wt % to 35 wt % of crystalline Form B of a potassium salt of Compound I of claim 1 or claim 2 relative to the total weight of the pharmaceutical composition;
(b) 5 wt % to 20 wt % of a first solid dispersion relative to the total weight of the pharmaceutical composition, wherein the first solid dispersion comprises 70 wt % to 90 wt % of Compound II relative to the total weight of the first solid dispersion, and 10 wt % to 30 wt % of a polymer relative to the total weight of the first solid dispersion; and
(c) 20 wt % to 40 wt % of a second solid dispersion relative to the total weight of the pharmaceutical composition, wherein the second solid dispersion comprises 70 wt % to 90 wt % of Compound III relative to the total weight of the second solid dispersion, and 10 wt % to 30 wt % of a polymer relative to the total weight of the second solid dispersion.

7. The pharmaceutical composition of claim 4, wherein at least one of the first or second solid dispersions is a spray-dried dispersion.

8. The pharmaceutical composition of claim 4, comprising 100 mg to 250 mg of crystalline Form B of a potassium salt of Compound I of claim 1 or claim 2.

9. The pharmaceutical composition of claim 4, wherein the first solid dispersion comprises 25 mg to 100 mg of Compound II.

10. The pharmaceutical composition of claim 4, wherein the second solid dispersion comprises 25 mg to 175 mg of Compound III or Compound III-d.

11. The pharmaceutical composition of claim 4, comprising 100 mg to 250 mg of crystalline Form B of a potassium salt of Compound I of claim 1 or claim 3; and wherein the first solid dispersion comprises 25 mg to 75 mg of Compound II and the second solid dispersion comprises 50 mg to 100 mg of Compound III or Compound III-d.

12. The pharmaceutical composition of claim 11, comprising 100 mg to 150 mg of crystalline Form B of a potassium salt of Compound I of claim 1 or claim 2, and wherein the first solid dispersion comprises 50 mg of Compound II and the second solid dispersion comprises 75 mg or 150 mg of Compound II or 100 mg of Compound III-d.

13. The pharmaceutical composition of claim 4, wherein the composition comprises:
(a) 115 mg to 140 mg of crystalline Form B of a potassium salt of Compound I of claim 1 or claim 2;
(b) 60 mg to 65 mg of a first solid dispersion comprising 80 wt % Compound II relative to the total weight of the first solid dispersion, and 20 wt % of a hypromellose relative to the total weight of the first solid dispersion; and
(c) 90 mg to 95 mg of a second solid dispersion comprising 80 wt % of Compound III relative to the total weight of the second solid dispersion, 0.5 wt % of sodium lauryl sulfate relative to the total weight of the second solid dispersion, and 19.5 wt % of a hypromellose acetate succinate to the total weight of the second solid dispersion;
(d) 120 mg to 135 mg of a microcrystalline cellulose;
(e) 15 mg to 25 mg of a croscarmellose sodium; and
(f) 2 mg to 6 mg of magnesium stearate.

14. The pharmaceutical composition of claim 4 selected from:

(a)

| Component | weight % based on the total weight of composition |
|---|---|
| crystalline Form B of a potassium salt of Compound I of claim 1 or claim 3 | 20-45 wt % |
| solid dispersion containing 80% Compound II, 20% hypromellose | 5-20 wt % |
| solid dispersion containing 80% Compound III, 19.5% hypromellose acetate succinate, and 0.5% sodium lauryl sulfate | 10-30 wt % |

(b)

| Component | weight % based on the total weight of composition |
|---|---|
| crystalline Form B of a potassium salt of Compound I of claim 1 or claim 2 | 15-45 wt % |
| solid dispersion containing 80% Compound II, 20% hypromellose | 5-20 wt % |
| solid dispersion containing 80% Compound III or Compound III-d, 19.5% hypromellose acetate succinate, and 0.5% sodium lauryl sulfate | 10-40 wt % |
| microcrystalline cellulose | 5-50 wt % |
| croscarmellose sodium (CCS) | 1-10 wt % | optionally magnesium stearate in an amount of 0.01 wt %-2 wt % based on the total weight of composition (c)

| Component | weight % based on the total weight of composition |
|---|---|
| crystalline Form B of a potassium salt of Compound I of claim 1 or claim 2 | 15-45 wt % |
| solid dispersion containing 80% Compound II, 20% hypromellose | 5-20 wt % |
| solid dispersion containing 80% Compound III or Compound III-d, 19.5% hypromellose acetate succinate, and 0.5% sodium lauryl sulfate | 10-40 wt % |
| microcrystalline cellulose | 5-50 wt % |
| croscarmellose sodium (CCS) | 1-10 wt % |
| magnesium stearate | 0.05-2 wt % |

(d)

| Component | weight % based on the total weight of composition |
|---|---|
| crystalline Form B of a potassium salt of Compound I of claim 1 or claim 2 | 15-35 wt % |
| solid dispersion containing 80% Compound II, 20% hypromellose | 5-20 wt % |
| solid dispersion containing 80% Compound III, 19.5% hypromellose acetate succinate, and 0.5% sodium lauryl sulfate | 20-40 wt % |
| microcrystalline cellulose | 20-40 wt % |
| croscarmellose sodium (CCS) | 1-10 wt % |
| magnesium stearate | 0.05-2 wt % |

(e)

| Component | weight % based on the total weight of composition |
|---|---|
| crystalline Form B of a potassium salt of Compound I of claim 1 or claim 2 | 20-40 wt % |
| solid dispersion containing 80% Compound II, 20% hypromellose | 5-20 wt % |
| solid dispersion containing 80% Compound III, 19.5% hypromellose acetate succinate, and 0.5% sodium lauryl sulfate | 10-25 wt % |
| microcrystalline cellulose | 20-40 wt % |
| croscarmellose sodium (CCS) | 1-10 wt % |
| magnesium stearate | 0.05-2 wt % |

(f)

| Component | weight % based on the total weight of composition |
|---|---|
| crystalline Form B of a potassium salt of Compound I of claim 1 or claim 2 | 25-35 wt % |
| solid dispersion containing 80% Compound II, 20% hypromellose | 10-20 wt % |
| solid dispersion containing 80% Compound III, 19.5% hypromellose acetate succinate, and 0.5% sodium lauryl sulfate | 15-25 wt % |
| microcrystalline cellulose | 25-35 wt % |
| croscarmellose sodium (CCS) | 2-7 wt % |
| magnesium stearate | 0.05-2 wt % |

(g)

| Component | weight % based on the total weight of composition |
|---|---|
| crystalline Form B of a potassium salt of Compound I of claim 1 or claim 2 | 27-32 wt % |
| solid dispersion containing 80% Compound II, 20% hypromellose | 12-17 wt % |
| solid dispersion containing 80% Compound III, 19.5% hypromellose acetate succinate, and 0.5% sodium lauryl sulfate | 18-23 wt % |
| microcrystalline cellulose | 25-35 wt % |
| croscarmellose sodium (CCS) | 3-6 wt % |
| magnesium stearate | 0.05-1.5 wt % |

(h)

| Component | weight % based on the total weight of composition |
|---|---|
| crystalline Form B of a potassium salt of Compound I of claim 1 or claim 2 | 25-40 wt % |
| solid dispersion containing 80% Compound II, 20% hypromellose | 7-15 wt % |
| solid dispersion containing 80% Compound III-d, 19.5% hypromellose acetate succinate, and 0.5% sodium lauryl sulfate | 15-35 wt % |
| microcrystalline cellulose | 25-35 wt % |
| croscarmellose sodium (CCS) | 2-5 wt % |
| magnesium stearate | 0.05-1.5 wt % |

(i)

| Component | weight % based on the total weight of composition |
|---|---|
| crystalline Form B of a potassium salt of Compound I of claim 1 or claim 2 | 15-40 wt % |
| solid dispersion containing 80% Compound II, 20% hypromellose | 5-20 wt % |
| solid dispersion containing 80% Compound III-d, 19.5% hypromellose acetate succinate, and 0.5% sodium lauryl sulfate | 20-40 wt % |
| microcrystalline cellulose | 10-50 wt % |
| croscarmellose sodium (CCS) | 2-7 wt % | optionally magnesium stearate in an amount of 0.01 wt %-2 wt % based on the total weight of composition (j)

| Component | weight % based on the total weight of composition |
|---|---|
| crystalline Form B of a potassium salt of Compound I of claim 1 or claim 2 | 20-30 wt % |
| solid dispersion containing 80% Compound II, 20% hypromellose | 8-18 wt % |
| solid dispersion containing 80% Compound III-d, 19.5% hypromellose acetate succinate, and 0.5% sodium lauryl sulfate | 20-30 wt % |
| microcrystalline cellulose | 20-30 wt % |
| croscarmellose sodium (CCS) | 2-5 wt % | optionally magnesium stearate in an amount of 0.01 wt %-1.5 wt % based on the total weight of composition and (k)

| Component | weight % based on the total weight of composition |
|---|---|
| crystalline Form B of a potassium salt of Compound I of claim 1 or claim 2 | 22-32 wt % |
| solid dispersion containing 80% Compound II, 20% hypromellose | 10-20 wt % |
| solid dispersion containing 80% Compound III-d, 19.5% hypromellose acetate succinate, and 0.5% sodium lauryl sulfate | 20-30 wt % |
| microcrystalline cellulose | 20-30 wt % |
| croscarmellose sodium (CCS) | 2-5 wt % | optionally magnesium stearate in an amount of 0.01 wt %-1.5 wt % based on the total weight of composition 15. The pharmaceutical composition of claim 4, wherein the composition is in the form of a single tablet comprising:
(a) 50 mg to 140 mg of a crystalline Form B of a potassium salt of Compound I of claim 1 or claim 3;
(b) 25 mg to 65 mg of a first solid dispersion comprising 80 wt % Compound II relative to the total weight of the first solid dispersion, and 20 wt % of a hypromellose relative to the total weight of the first solid dispersion; and
(c) 75 mg to 200 mg of a second solid dispersion comprising 80 wt % of Compound III relative to the total weight of the second solid dispersion, 0.5 wt % of sodium lauryl sulfate relative to the total weight of the second solid dispersion; and 19.5 wt % of a hypromellose acetate succinate to the total weight of the second solid dispersion
(d) 60 mg to 150 mg of a microcrystalline cellulose;
(e) 5 mg to 25 mg of a croscarmellose sodium; and
(f) 1 mg to 6 mg of magnesium stearate.

16. The pharmaceutical composition of claim 4, wherein the composition is in the form of a single tablet comprising:
(a) 100 mg to 250 mg of a crystalline Form B of a potassium salt of Compound I of claim 1 or claim 2;
(b) 30 mg to 65 mg of a first solid dispersion comprising 80 wt % Compound II relative to the total weight of the first solid dispersion, and 20 wt % of a hypromellose relative to the total weight of the first solid dispersion; and
(c) 75 mg to 200 mg of a second solid dispersion comprising 80 wt % of Compound III relative to the total weight of the second solid dispersion, 0.5 wt % of sodium lauryl sulfate relative to the total weight of the second solid dispersion; and 19.5 wt % of a hypromellose acetate succinate to the total weight of the second solid dispersion;
(d) 85 mg to 215 mg of a microcrystalline cellulose;
(e) 10 mg to 30 mg of a croscarmellose sodium; and
(f) 1 mg to 7 mg of magnesium stearate.

17. The pharmaceutical composition of claim 4, wherein the composition is in the form of a single tablet comprising:
(a) 100 mg to 215 mg of crystalline Form B of a potassium salt of Compound I of claim 1 or claim 3;
(b) 30 mg to 65 mg of a first solid dispersion comprising 80 wt % Compound II relative to the total weight of the first solid dispersion, and 20 wt % of a hypromellose relative to the total weight of the first solid dispersion; and
(c) 50 mg to 300 mg of a second solid dispersion comprising 80 wt % of Compound III-d relative to the total weight of the second solid dispersion, 0.5 wt % of sodium lauryl sulfate relative to the total weight of the second solid dispersion; and 19.5 wt % of a hypromellose acetate succinate to the total weight of the second solid dispersion;
(d) 85 mg to 215 mg of a microcrystalline cellulose;
(e) 10 mg to 30 mg of a croscarmellose sodium; and
(f) 1 mg to 7 mg of magnesium stearate.

18. The pharmaceutical composition of claim 4, wherein the composition is in the form of a single tablet comprising:
(a) 55 mg to 300 mg of a crystalline Form B of a potassium salt of Compound I of claim 1 or claim 2;
(b) 30 mg to 130 mg of a first solid dispersion comprising 80 wt % Compound II relative to the total weight of the first solid dispersion, and 20 wt % of a hypromellose relative to the total weight of the first solid dispersion; and
(c) 50 mg to 300 mg of a second solid dispersion comprising 80 wt % of Compound III-d relative to the total weight of the second solid dispersion, 0.5 wt % of sodium lauryl sulfate relative to the total weight of the second solid dispersion; and 19.5 wt % of a hypromellose acetate succinate to the total weight of the second solid dispersion
(d) 60 mg to 300 mg of a microcrystalline cellulose;
(e) 7 mg to 25 mg of a croscarmellose sodium; and
(f) optionally 0.05 mg to 6 mg of magnesium stearate.

19. A method of treating cystic fibrosis in a patient comprising orally administering to the patient one or more of the pharmaceutical compositions of claim 4.

20. The method of claim 19, wherein one or more of the pharmaceutical compositions are administered once daily or twice daily.

21. The method of claim 19, wherein said patient has cystic fibrosis is chosen from patients with F508del/minimal function genotypes, patients with F508del/F508del genotypes, patients with F508del/gating genotypes, and patients with F508del/residual function genotypes.

22. The pharmaceutical composition of claim 4, wherein the composition comprises:
(a) about 128 mg of crystalline Form B of a potassium salt of Compound I of claim 1 or claim 2;
(b) about 63 mg of a first solid dispersion comprising 80 wt % Compound H relative to the total weight of the first solid dispersion, and 20 wt % of a hypromellose relative to the total weight of the first solid dispersion; and
(c) about 94 mg of a second solid dispersion comprising 80 wt % of Compound III relative to the total weight of the second solid dispersion, 0.5 wt % of sodium lauryl sulfate relative to the total weight of the second solid dispersion; and 19.5 wt % of a hypromellose acetate succinate to the total weight of the second solid dispersion.

23. The pharmaceutical composition of claim 22, wherein the pharmaceutical composition is a single tablet.

* * * * *

UNITED STATES PATENT AND TRADEMARK OFFICE
CERTIFICATE OF CORRECTION

PATENT NO. : 10,654,829 B2  
APPLICATION NO. : 16/165849  
DATED : May 19, 2020  
INVENTOR(S) : Varsha Dhamankar et al.

Page 1 of 1

It is certified that error appears in the above-identified patent and that said Letters Patent is hereby corrected as shown below:

In the Claims

Claim 1, Column 181, Lines 40-42, "5.8±0.2, 8.2±0.2, 9.6±0.2, 10.2±0.2, 13.8±0.2, 15.1±0.2, 16.3±0.2, 17.2±0.2, and 19.1±0.2." should read --5.8±0.2 Å, 8.2±0.2 Å, 9.6±0.2 Å, 10.2±0.2 Å, 13.8±0.2 Å, 15.1±0.2 Å, 16.3±0.2 Å, 17.2±0.2 Å, and 19.1±0.2 Å.--.

Claim 11, Column 183, Line 51, "claim 1 or claim 3" should read --claim 1 or claim 2--.

Claim 14, Column 184, Line 27, "claim 1 or claim 3" should read --claim 1 or claim 2--.

Claim 15, Column 187, Line 4, "claim 1 or claim 3" should read --claim 1 or claim 2--.

Claim 17, Column 187, Line 42, "claim 1 or claim 3" should read --claim 1 or claim 2--.

Signed and Sealed this  
Fifteenth Day of April, 2025

Coke Morgan Stewart  
*Acting Director of the United States Patent and Trademark Office*